US010238741B2

(12) United States Patent
Creusot

(10) Patent No.: US 10,238,741 B2
(45) Date of Patent: Mar. 26, 2019

(54) NUCLEIC ACID CONSTRUCTS FOR PRESENTATION OF CD4 AND CD8 EPITOPES, CELLULAR TRANSFECTION AND USES THEREOF

(71) Applicant: Remi J. Creusot, New York, NY (US)

(72) Inventor: Remi J. Creusot, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 15/483,889

(22) Filed: Apr. 10, 2017

(65) Prior Publication Data
US 2017/0283810 A1 Oct. 5, 2017

Related U.S. Application Data

(63) Continuation-in-part of application No. PCT/US2015/055042, filed on Oct. 10, 2015.

(60) Provisional application No. 62/062,325, filed on Oct. 10, 2014, provisional application No. 62/416,080, filed on Nov. 1, 2016.

(51) Int. Cl.
| C12P 21/02 | (2006.01) |
| A61K 39/42 | (2006.01) |
| A61K 35/76 | (2015.01) |
| A61K 31/00 | (2006.01) |
| C07K 14/55 | (2006.01) |
| C07K 14/575 | (2006.01) |
| C07K 14/735 | (2006.01) |
| C07K 14/705 | (2006.01) |
| C12N 9/16 | (2006.01) |
| C12N 9/88 | (2006.01) |
| C07K 14/47 | (2006.01) |
| C12N 15/12 | (2006.01) |
| A61K 39/00 | (2006.01) |

(52) U.S. Cl.
CPC ............ *A61K 39/42* (2013.01); *A61K 31/00* (2013.01); *A61K 35/76* (2013.01); *C07K 14/55* (2013.01); *C07K 14/575* (2013.01); *C07K 14/70535* (2013.01); *C07K 14/70582* (2013.01); *C12N 9/16* (2013.01); *C12N 9/88* (2013.01); *A61K 39/00* (2013.01); *C07K 2319/01* (2013.01); *C07K 2319/50* (2013.01); *C07K 2319/74* (2013.01)

(58) Field of Classification Search
None
See application file for complete search history.

(56) References Cited

U.S. PATENT DOCUMENTS

| 6,759,234 B1 | 7/2004 | Gefter et al. |
| 2004/0248113 A1 | 12/2004 | Sette et al. |
| 2006/0216305 A1 | 9/2006 | Lal et al. |

FOREIGN PATENT DOCUMENTS

| EP | 0960119 B1 | 9/2008 |
| WO | 1997049430 A1 | 12/1997 |
| WO | 2002083714 A2 | 10/2001 |
| WO | 2003084467 A2 | 10/2003 |
| WO | 2013149167 A1 | 10/2013 |

OTHER PUBLICATIONS

Li et al., "The future of human DNA vaccines" 162 Journal of Biotechnology 171-182 (2012).*
Steimle et al., "Regulation of MHC Class II Expression by Interferon-y Mediated by the Transactivator Gene CIITA" 265 Science 106-109 (1994).*
Lee et al., "Synergistic effect of polyethylenimine and cationic liposomes in nucleic acid delivery to human cancer cells" 1611 Biochimica et Biophysica Acta 55-62 (2003).*
An, Ling-Ling, et al. "A Multivalent Minigene Vaccine, Containing B-Cell, Cytotoxic T-Lymphocyte, and Th Epitopes from Several Microbes, Induces Appropriate Responses In Vivo and Confers Protection against More than One Pathogen" Journal of Virology, Mar. 1997, vol. 71 No. 3, pp. 2292-2302.
Bar-Or, A., et al., "Induction of antigen-specific tolerance in multiple sclerosis after immunization with DNA encoding myelin basic protein in a randomized, placebo-controlled phase 1/2 trial." Archives of Neurology. 64:1407-1415, 2007.
Coppieters, K., et al., "Demonstration of islet-autoreactive CD8 T cells in insulitic lesions from recent onset and long-term type 1 diabetes patients." Journal of Experimental Medicine. 209:51-60, 2012.
Creusot, R., et al., "Early commitment of adoptively transferred CD4+ T cells following particle-mediated DNA vaccination: implications for the study of immunomodulation." Vaccine 19:1678-1687, 2001.
Creusot, R., et al., "Instruction of naive CD4+ T cells by polarized CD4+ T cells within dendritic cell clusters." European Journal of Immunology. 33:1686-1696, 2003.

(Continued)

Primary Examiner — Nancy J Leith
(74) Attorney, Agent, or Firm — Timothy H. Van Dyke; Beusse Wolter Sanks & Maire

(57) ABSTRACT

The invention relates to constructs, cells and methods for modulating the immune system that optimize presentation of CD4 and CD8 epitopes to antigen-presenting cells and transfection into cells. Epitopes to either self antigens or non-self antigens can be used to optimize either a tolerance or immunogenicity to those epitopes, respectively. Certain new constructs encode one or more dominant, disease-driving epitopes (CD4) targeted for MHCII processing within the endosomes of a cell and one or more epitopes (CD8) targeted for MHCI processing within the cytosol of the cell, to produce the maximum antigen/epitope presentation in the immune system, and further include an MHCII activator sequence. Alternatively, the new constructs encode CD4 and CD8 epitopes operably linked to a secretion signal.

29 Claims, 29 Drawing Sheets
Specification includes a Sequence Listing.

(56) References Cited

OTHER PUBLICATIONS

Creusot, R., et al., "It's Time to Bring Dendritic Cell Therapy to Type 1 Diabetes." Diabetes 63:20-30, 2014.
Creusot, R., et al., "Lymphoid-tissue-specific homing of bone-marrow-derived dendritic cells." Blood. 113:6638-6647, 2009.
Creusot, R., et al., "Tissue-targeted therapy of autoimmune diabetes using dendritic cells transduced to express IL-4 in NOD mice." Clinical Immunology. 127:176-187, 2008.
Dastagir, S., et al. "Efficient Presentation of Multiple Endogenous Epitopes to Both CD4+ and CD8+ Diabetogenic T Cells for Tolerance." Molecular Therapy: Methods & Clinical Development. 4:27-57. 2016.
Delong, T., et al., "Diabetogenic T-cell clones recognize an altered peptide of chromogranin A." Diabetes 61:3239-3246, 2012.
Dilorenzo, T.P., et al., "Translational mini-review series on type 1 diabetes: Systematic analysis of T cell epitopes in autoimmune diabetes." Clinical and Experimental Immunology. 148:1-16, 2007.
Diebold, S.S., et al., "MHC class II presentation of endogenously expressed antigens by transfected dentritic cells." Gene Therapy. 8(6):487, 2001.
Fernandes, D., et al., "Characterization of MHC class II-presented peptides generated from an antigen targeted to different endocytic compartments." European Journal of Immunology. 30(8):2333, 2000.
Giannoukakis, N., et al., "Phase I (safety) study of autologous tolerogenic dendritic cells in type 1 diabetic patients." Diabetes Care 34:2026-2032, 2011.
Giannoukakis, N., et al. "Cell therapy for Type 1 diabetes suppression." Immunotherapy 4:1063-1074, 2012.
Gordon, J., et al., "Regulatory dendritic cells for immunotherapy in immunologic diseases." Frontiers in Immunology. 5:7, 2014.
Ho, Peggy P., et al. "An Immunomodulatory GpG Oligonucleotide for the Treatment of Autoimmunity via the Innate and Adaptive Immune Systems." The Journal of Immunology, 2003; 171:4920-4926.
Kaushansky, N., et al., "Multi-epitope-targeted immune-specific therapy for a multiple sclerosis-like disease via engineered multi-epitope protein is superior to peptides." PLoS ONE 6(11):e27860 doi:10.1371/journal/pone.00027860, 2011.
Lukacs-Kornek, V., et al., "Self-antigen presentation by dendritic cells and lymphoid stroma and its implications for autoimmunity." Current Opinion on Immunology. 23:138-145. 2011.
Melhem, Nada M., et al. "Robust CD4+ and CD8+ T cell responses to SIV using mRNA-transfected DC expressing analogous viral Ag." European Journal of Immunology, 2007, 37:2164-2173.
Michels, A., et al. "Update: antigen-specific therapy in type 1 diabetes." Current Opinion on Endocrinology Diabetes Obesity. 18:235-240. 2011.
Nair, Smita, et al., "Isolation and Generation of Human Dendritic Cells." Current Protocols in Immunology. 7.32.1-7.32.23, Nov. 2012.
Nava, Sara, et al. An Optimized Method for Manufacturing a Clinical Scale Dendritic Cell-Based Vaccine for the Treatment of Glioblastoma. PLOS ONE, vol. 7, Issue 12, pp. 1-7, 2012.
Rivas, Elisa I., et al. "Targeting of a T Cell Agonist Peptide to Lysosomes by DNA Vaccination Induces Tolerance in the Nonobese Diabetic Mouse." The Journal of Immunology. 2011, 186:4078-4087.
Roep, B., et al., "Plasmid-encoded proinsulin preserves C-peptide while specifically reducing proinsulin-specific CD8 (+) T cells in type 1 diabetes." Science Translational Med. 5:191-182, 2013.
Ryden, A., et al., "Non-antigenic and antigenic interventions in type 1 diabetes." Human Vaccine and Immunotherapeutics. 10:838-846. 2014.
Sahin, Ugur, et al. "mRNA-based therapeutics—developing a new class of drugs." Nature Reviews (Drug Discovery); vol. 13, Oct. 2014, pp. 759-780.
Sanderson, S., et al., "Expression of endogenous peptide-major histocompatibility complex class II complexes derived from in variant chain-antigen fusion proteins." Proceedings of the National Academy of Sciences. USA 92 (16):7217-7221, 1995.
Sarikonda, G., et al., "Transient B-Cell Depletion with Anti-CD20 in Combination with Proinsulin DNA Vaccine or Oral Insulin: Immunologic Effect and Efficacy in NOD Mice." PLOS ONE, vol. 8, Issue 2, pp. 1-10, Feb. 6, 2013.
Solvason, N., et al., "Improved efficacy of a tolerizing DNA vaccine for reversal of hyperglycemia through enhancement of gene expression and localization to intracellular sites." J. Immunol. 181:8298-8307, 2008.
Stadinski, B., et al., "Diabetogenic T cells recognize insulin bound to IAg7 in an unexpected, weakly binding register." Proceedings of the National Academy of Sciences. USA 107:10978-10983, 2010.
Thomas, Ranjeny. "Dendritic cells and the promise of antigen-specific therapy in rheumatoid arthritis." Arthritis Research & Therapy 2013, 15:204.
Thomson, Scott A., et al., "Targeting a Polyepitope Protein Incorporating Multiple Class II-Restricted Viral Epitopes to the Secretory/Endocytic Pathway Facilitates Immune Recognition by CD4+ Cytotoxic T Lymphocytes: A Novel Approach to Vaccine Design." Journal of Virology, Mar. 1998, vol. 27, No. 3, pp. 2246-2252.
Van Nuffel, An MT, et al. "Dendritic Cells Loaded with mRNA Encoding Full-Length Tumor Antigens Prime CD4+ and CD8+ T Cells in Melanoma Patients." Molecular Therapy, May 2012, vol. 20, No. 5, pp. 1063-1074.
Velders, Markwin P., et al. "Defined Flanking Spacers and Enhanced Proteolysis Is Essential for Eradication of Established Tumors by and Epitope String DNA Vaccine." The Journal of Immunology. 2001, 166:5366-5373.

\* cited by examiner

| PEPTIDE | ANTIGEN | SEQUENCE | MHC | T CELL | TCR | MOUSE | SEQ ID NO |
|---|---|---|---|---|---|---|---|
| B:9-23 | Ins2 | SHLVEALYLVCGERG | I-A$^{g7}$ | CD4 | Vβ2 | BDC12-4.1 | 1 |
| B:15-23 | Ins2 | LYLVCGERG | K$^d$ | CD8 | Vβ6 Vα18 | G9C8 | 2 |
| B:9-23 (R22E) | MIMOTOPE | SHLVEALYLVCGEEG | I-A$^{g7}$ | CD4 | Vβ2 | BDC12-4.1 | 3 |
| WE14 | ChgA | WSRMDQLAKELTAE | I-A$^{g7}$ | CD4 | Vβ4 Vα1 | BDC2.5 | 4 |
| 1040-79 | MIMOTOPE | AVPPLWVRME | I-A$^{g7}$ | CD4 | Vβ4 Vα1 | BDC2.5 | 5 |
| 206-214 | IGRP | VYLKTNVFL | K$^d$ | CD8 | Vβ8.1 Vα1 | NY8.3 | 6 |
| 286-300 | GAD65 | KKGAAALGIGTDSVI | I-A$^{g7}$ | CD4 | Vβ1 Vα4.5 | G286 | 7 |

FIG. 5

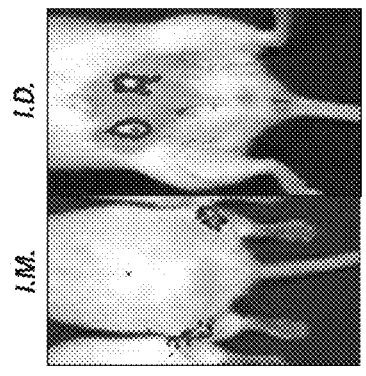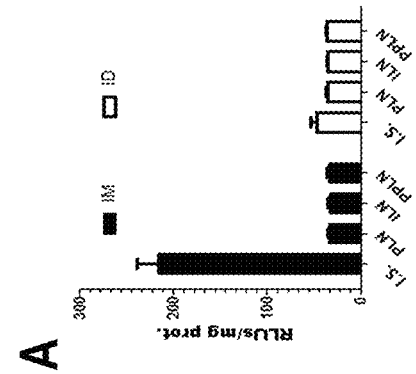
Fig. 20A  Fig. 20B  Fig. 20C

FIG. 20D
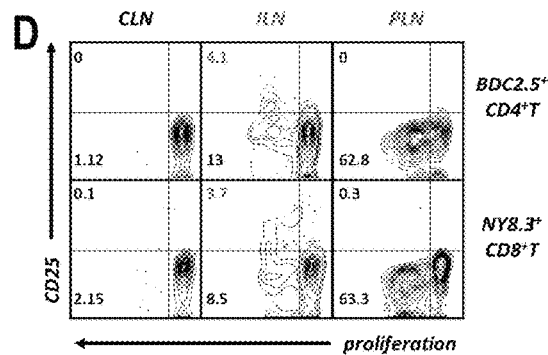
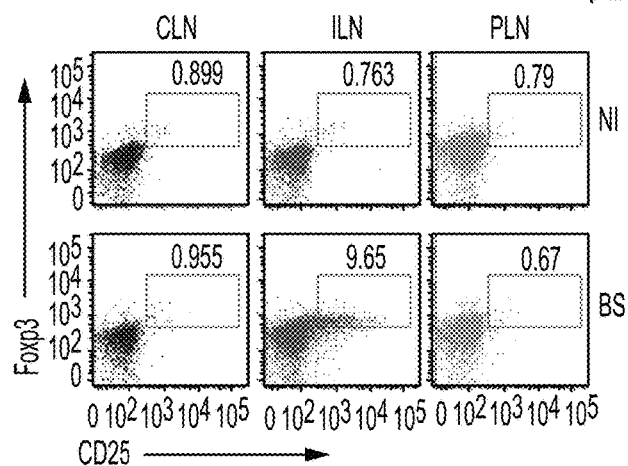
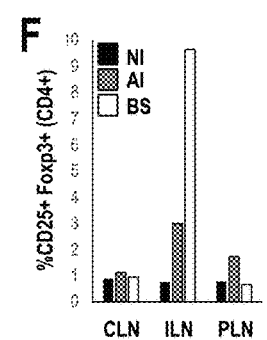
FIG. 20E
FIG. 20F
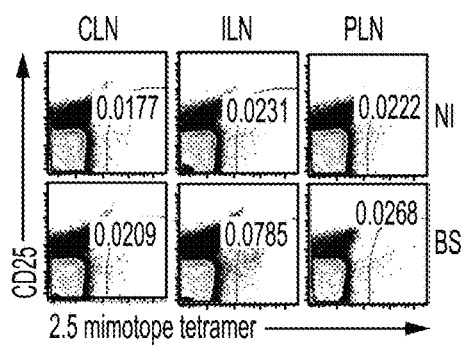
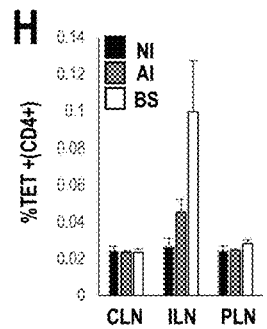
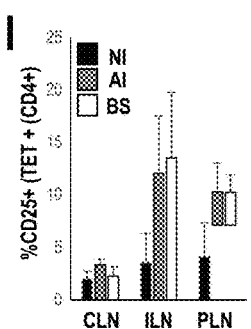
FIG. 20G
FIG. 20H
FIG. 20I

SEQUENCE LISTING

<160> NUMBER OF SEQ ID NOS: 66

<210> SEQ ID NO 1
<211> LENGTH: 15
<212> TYPE: PRT
<213> ORGANISM: Artificial Sequence
<220> FEATURE:
<223> OTHER INFORMATION: Synthetic

<400> SEQUENCE: 1

Ser His Leu Val Glu Ala Leu Tyr Leu Val Cys Gly Glu Arg Gly
1               5                   10                  15

<210> SEQ ID NO 2
<211> LENGTH: 9
<212> TYPE: PRT
<213> ORGANISM: Artificial Sequence
<220> FEATURE:
<223> OTHER INFORMATION: Synthetic

<400> SEQUENCE: 2

Leu Tyr Leu Val Cys Gly Glu Arg Gly
1               5

<210> SEQ ID NO 3
<211> LENGTH: 15
<212> TYPE: PRT
<213> ORGANISM: Artificial Sequence
<220> FEATURE:
<223> OTHER INFORMATION: Synthetic

<400> SEQUENCE: 3

Ser His Leu Val Glu Ala Leu Tyr Leu Val Cys Gly Glu Glu Gly
1               5                   10                  15

<210> SEQ ID NO 4
<211> LENGTH: 14
<212> TYPE: PRT
<213> ORGANISM: Artificial Sequence
<220> FEATURE:
<223> OTHER INFORMATION: Synthetic

<400> SEQUENCE: 4

Trp Ser Arg Met Asp Gln Leu Ala Lys Glu Leu Thr Ala Glu
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic

<400> SEQUENCE: 5

Ala Val Pro Pro Leu Trp Val Arg Met Glu
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Val Tyr Leu Lys Thr Asn Val Phe Leu
1               5

```
<210> SEQ ID NO 7
<211> LENGTH: 15
<212> TYPE: PRT
<213> ORGANISM: Artificial Sequence
<220> FEATURE:
<223> OTHER INFORMATION: Synthetic

<400> SEQUENCE: 7

Lys Lys Gly Ala Ala Ala Leu Gly Ile Gly Thr Asp Ser Val Ile
1               5                   10                  15

<210> SEQ ID NO 8
<211> LENGTH: 675
<212> TYPE: DNA
<213> ORGANISM: Artificial Sequence
<220> FEATURE:
<223> OTHER INFORMATION: Synthetic

<400> SEQUENCE: 8
actagtgcca ccatgatgga tcaagctaga tcagcattct ctaacttgtt tggtggagaa      60
ccattgtcat atcccggtt  cagcctggct cggcaagtag atggcgataa cagtcatgtg     120
gagatgaaac ttgctgtaga tgaagaagaa atgctgaca ataacacaaa ggccaatgtc     180
acaaaaccaa aaggtgtag  tggaagtatc tgctatggga ctattgctgt gatcgtcttt     240
ttcttgattg gatttatgat tggctacttg ggctattgta aagggtaga  accaaaaact     300 gagtgtgaga gactggcagg aaccgagtct ccagtgaggg aggagccagg agaggacttc     360
cctgcaccgc ggtgtggttc ccacctggtg gaggctctct acctggtgtg tggggaggag     420
ggcttcttca gcgagcagt  tcgacctcta tgggtacgta tggaaaagcg gtctctcaag     480
aagggagctg cagccttagg gattggaaca gacagtgtga ttctgattga gggcagagga     540
agtctgctaa catgcggtga cgtcgaggag aatcctggac ctgaggctct ctacctggtg     600
tgtggggagc gtggcttctt cttgagtgtg tacctgaaga ccaacgtctt cctcttcctg     660
cccgggtagg tcgac                                                     675

<210> SEQ ID NO 9
<211> LENGTH: 675
<212> TYPE: DNA
<213> ORGANISM: Artificial Sequence
<220> FEATURE:
<223> OTHER INFORMATION: Synthetic

<400> SEQUENCE: 9
actagtgcca ccatgatgga ccaagctaga tccgccttca gcaatctgtt cggaggagag      60
cccctctcct atacaagatt ctccctggcc aggcaagtgg acggcgacaa ctcccacgtc     120
gagatgaaac tcgccgtgga tgaagaggag aacgccgaca taacaccaa  ggccaacgtg     180 accaagccta gaggtgcag  cggaagcatc tgctacggca caatcgccgt gatcgtcttc     240
ttcctgatcg gattcatgat cggataccttg gctactgca agggcgtgga gcctaaaacc     300
gagtgcgaga gactcgctgg aacagagtcc cctgtcaggg aggaacctgg agaggatttc     360
cctgccccgc ggtgcggatc ccatctggtc gaagccctgt acctggtctg tggcgaggaa     420
ggattcttca gagggctgt  caggcctctg tgggtgagga tggaaagag  atccctgaaa     480 aaaggcgccg ctgccctggg aattggcacc gactccgtca ttctcatcga gggcagagga     540
tccctcctga cctgtggcga cgtggaggaa aaccccggac cgaagctctg tacctggtg      600 tgtggcgaaa ggggctttt  cctgtccgtc tacctgaaaa ccaatgtctt tctgtttctg     660
```
cccgggtagg tcgac                                                      675

<210> SEQ ID NO 10
<211> LENGTH: 218
<212> TYPE: PRT
<213> ORGANISM: Artificial Sequence
<220> FEATURE:
<223> OTHER INFORMATION: Synthetic

<400> SEQUENCE: 10

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Glu Asn Ala
        35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Pro Arg Cys Gly Ser His Leu Val Glu Ala
        115                 120                 125

Leu Tyr Leu Val Cys Gly Glu Glu Gly Phe Phe Lys Arg Ala Val Arg
    130                 135                 140

Pro Leu Trp Val Arg Met Glu Lys Arg Ser Leu Lys Lys Gly Ala Ala
145                 150                 155                 160

Ala Leu Gly Ile Gly Thr Asp Ser Val Ile Leu Ile Glu Gly Arg Gly
                165                 170                 175

Ser Leu Leu Thr Cys Gly Asp Val Glu Glu Asn Pro Gly Pro Glu Ala
            180                 185                 190

Leu Tyr Leu Val Cys Gly Glu Arg Gly Phe Phe Leu Ser Val Tyr Leu
        195                 200                 205

Lys Thr Asn Val Phe Leu Phe Leu Pro Gly
    210                 215

<210> SEQ ID NO 11
<211> LENGTH: 354
<212> TYPE: DNA
<213> ORGANISM: Artificial Sequence
<220> FEATURE:
<223> OTHER INFORMATION: Synthetic

<400> SEQUENCE: 11
atgatggatc aagctagatc agcattctct aacttgtttg gtggagaacc attgtcatat      60
acccggttca gcctggctcg gcaagtagat ggcgataaca gtcatgtgga gatgaaactt     120
gctgtagatg aagaagaaaa tgctgacaat aacacaaagg ccaatgtcac aaaaccaaaa     180
aggtgtagtg gaagtatctg ctatgggact attgctgtga tcgtcttttt cttgattgga     240
tttatgattg gctacttggg ctattgtaaa ggggtagaac caaaaactga gtgtgagaga     300
ctggcaggaa ccgagtctcc agtgagggag gagccaggag aggacttccc tgca           354

<210> SEQ ID NO 12

<211> LENGTH: 118
<212> TYPE: PRT
<213> ORGANISM: Artificial Sequence
<220> FEATURE:
<223> OTHER INFORMATION: Synthetic

<400> SEQUENCE: 12

Met Met Asp Gln Ala Arg Ser Ala Phe Ser Asn Leu Phe Gly Gly Glu
1               5                   10                  15
Pro Leu Ser Tyr Thr Arg Phe Ser Leu Ala Arg Gln Val Asp Gly Asp
            20                  25                  30
Asn Ser His Val Glu Met Lys Leu Ala Val Asp Glu Glu Asn Ala
        35                  40                  45
Asp Asn Asn Thr Lys Ala Asn Val Thr Lys Pro Lys Arg Cys Ser Gly
    50                  55                  60
Ser Ile Cys Tyr Gly Thr Ile Ala Val Ile Val Phe Phe Leu Ile Gly
65                  70                  75                  80
Phe Met Ile Gly Tyr Leu Gly Tyr Cys Lys Gly Val Glu Pro Lys Thr
                85                  90                  95
Glu Cys Glu Arg Leu Ala Gly Thr Glu Ser Pro Val Arg Glu Glu Pro
            100                 105                 110
Gly Glu Asp Phe Pro Ala
        115

<210> SEQ ID NO 13
<211> LENGTH: 240
<212> TYPE: DNA
<213> ORGANISM: Artificial Sequence
<220> FEATURE:
<223> OTHER INFORMATION: Synthetic

<400> SEQUENCE: 13
atggatgacc aacgcgacct catctctaac catgaacagt tgcccatact gggcaaccgc      60
cctagagagc cagaaaggtg cagccgtgga gctctgtaca ccggtgtctc tgtcctggtg     120
gctctgctct tggctgggca ggccaccact gcttacttcc tgtaccagca acagggccgc     180
ctagacaagc tgaccatcac ctcccagaac ctgcaactgg agagccttcg catgaagctt     240

<210> SEQ ID NO 14
<211> LENGTH: 80
<212> TYPE: PRT
<213> ORGANISM: Artificial Sequence
<220> FEATURE:
<223> OTHER INFORMATION: Synthetic

<400> SEQUENCE: 14

Met Asp Asp Gln Arg Asp Leu Ile Ser Asn His Glu Gln Leu Pro Ile
1               5                   10                  15
Leu Gly Asn Arg Pro Arg Glu Pro Glu Arg Cys Ser Arg Gly Ala Leu
            20                  25                  30
Tyr Thr Gly Val Ser Val Leu Val Ala Leu Leu Leu Ala Gly Gln Ala
        35                  40                  45
Thr Thr Ala Tyr Phe Leu Tyr Gln Gln Gln Gly Arg Leu Asp Lys Leu
    50                  55                  60
Thr Ile Thr Ser Gln Asn Leu Gln Leu Glu Ser Leu Arg Met Lys Leu
65                  70                  75                  80

<210> SEQ ID NO 15
<211> LENGTH: 642
<212> TYPE: DNA

<213> ORGANISM: Artificial Sequence
<220> FEATURE:
<223> OTHER INFORMATION: Synthetic

<400> SEQUENCE: 15

| | | | | | |
|---|---|---|---|---|---|
| atggatgacc | aacgcgacct | catctctaac | catgaacagt | tgcccatact | gggcaaccgc | 60 |
| cctagagagc | cagaaaggtg | cagccgtgga | gctctgtaca | ccggtgtctc | tgtcctggtg | 120 |
| gctctgctct | tggctgggca | ggccaccact | gcttacttcc | tgtaccagca | acagggccgc | 180 |
| ctagacaagc | tgaccatcac | ctcccagaac | ctgcaactgg | agagccttcg | catgaagctt | 240 |
| ccgaaatctg | ccaaacctgt | gagccagatg | cggatggcta | ctcccttgct | gatgcgtcca | 300 |
| atgtccatgg | ataacatgct | ccttgggcct | gtgaagaacg | ttaccaagta | cggcaacatg | 360 |
| acccaggacc | atgtgatgca | tctgctcacg | aggtctggac | ccctggagta | cccgcagctg | 420 |
| aaggggacct | tcccagagaa | tctgaagcat | cttaagaact | ccatggatgg | cgtgaactgg | 480 |
| aagatcttcg | agagctggat | gaagcagtgg | ctcttgtttg | agatgagcaa | gaactccctg | 540 |
| gaggagaaga | agcccaccga | ggctccacct | aaagagccac | tggacatgga | agacctatct | 600 |
| tctggcctgg | gagtgaccag | gcaggaactg | ggtcaagtca | cc | | 642 |

<210> SEQ ID NO 16
<211> LENGTH: 214
<212> TYPE: PRT
<213> ORGANISM: Artificial Sequence
<220> FEATURE:
<223> OTHER INFORMATION: Synthetic

<400> SEQUENCE: 16

Met Asp Asp Gln Arg Asp Leu Ile Ser Asn His Glu Gln Leu Pro Ile
1               5                   10                  15

Leu Gly Asn Arg Pro Arg Glu Pro Glu Arg Cys Ser Arg Gly Ala Leu
            20                  25                  30

Tyr Thr Gly Val Ser Val Leu Val Ala Leu Leu Leu Ala Gly Gln Ala
        35                  40                  45

Thr Thr Ala Tyr Phe Leu Tyr Gln Gln Gln Gly Arg Leu Asp Lys Leu
    50                  55                  60

Thr Ile Thr Ser Gln Asn Leu Gln Leu Glu Ser Leu Arg Met Lys Leu
65                  70                  75                  80

Pro Lys Ser Ala Lys Pro Val Ser Gln Met Arg Met Ala Thr Pro Leu
                85                  90                  95

Leu Met Arg Pro Met Ser Met Asp Asn Met Leu Leu Gly Pro Val Lys
            100                 105                 110

Asn Val Thr Lys Tyr Gly Asn Met Thr Gln Asp His Val Met His Leu
        115                 120                 125

Leu Thr Arg Ser Gly Pro Leu Glu Tyr Pro Gln Leu Lys Gly Thr Phe
    130                 135                 140

Pro Glu Asn Leu Lys His Leu Lys Asn Ser Met Asp Gly Val Asn Trp
145                 150                 155                 160

Lys Ile Phe Glu Ser Trp Met Lys Gln Trp Leu Leu Phe Glu Met Ser
                165                 170                 175

Lys Asn Ser Leu Glu Glu Lys Lys Pro Thr Glu Ala Pro Pro Lys Glu
            180                 185                 190

Pro Leu Asp Met Glu Asp Leu Ser Ser Gly Leu Gly Val Thr Arg Gln
        195                 200                 205

Glu Leu Gly Gln Val Thr
    210

<210> SEQ ID NO 17
<211> LENGTH: 69
<212> TYPE: DNA
<213> ORGANISM: Artificial Sequence
<220> FEATURE:
<223> OTHER INFORMATION: Synthetic

<400> SEQUENCE: 17

```
atgactttgg acacccagat gtttcagaat gcacactctg aagccaatg gctacttcca      60 ccactgaca                                                             69
```

<210> SEQ ID NO 18
<211> LENGTH: 23
<212> TYPE: PRT
<213> ORGANISM: Artificial Sequence
<220> FEATURE:
<223> OTHER INFORMATION: Synthetic

<400> SEQUENCE: 18

Met Thr Leu Asp Thr Gln Met Phe Gln Asn Ala His Ser Gly Ser Gln
1               5                   10                  15

Trp Leu Leu Pro Pro Leu Thr
            20

<210> SEQ ID NO 19
<211> LENGTH: 651
<212> TYPE: DNA
<213> ORGANISM: Artificial Sequence
<220> FEATURE:
<223> OTHER INFORMATION: Synthetic

<400> SEQUENCE: 19

```
gatgccacta tccaggccta cctgtcgagt ggcaacttca gcaaggaaga gacacactgc      60
acacaggatg gaccttcccc aaccactggg ccacccagcc cctcaccacc acttgtgccc     120
acaaacccca ctgtatccaa gtacaatgtt actggtaaca acggaacctg cctgctggcc     180
tctatggcac tgcaactgaa tatcacctac ctgaaaaagg acaacaagac ggtgaccaga     240
gcgttcaaca tcagcccaaa tgacacatct agtgggagtt gcggtatcaa cttggtgacc     300
ctgaaagtgg agaacaagaa cagagccctg gaattgcagt ttgggatgaa tgccagctct     360
agcctgtttt tcctgcaagg agtgcgcttg aatatgactc ttcctgatgc cctagtgccc     420
acattcagca tctccaacca ttcactgaaa gctcttcagg ccactgtggg aaactcatac     480
aagtgcaaca ctgaggaaca catctttgtc agcaagatgc tctccctcaa tgtcttcagt     540
gtgcaggtcc aggctttcaa ggtggacagt gacaggtttg ggtctgtgga agagtgtgtt     600
caggatggta acaacatgtt gatccccatt gctgtgggcg gtgccctggc a              651
```

<210> SEQ ID NO 20
<211> LENGTH: 217
<212> TYPE: PRT
<213> ORGANISM: Artificial Sequence
<220> FEATURE:
<223> OTHER INFORMATION: Synthetic

<400> SEQUENCE: 20

Asp Ala Thr Ile Gln Ala Tyr Leu Ser Ser Gly Asn Phe Ser Lys Glu
1               5                   10                  15

Glu Thr His Cys Thr Gln Asp Gly Pro Ser Pro Thr Thr Gly Pro Pro
            20                  25                  30

```
Ser Pro Ser Pro Pro Leu Val Pro Thr Asn Pro Thr Val Ser Lys Tyr
        35                  40                  45

Asn Val Thr Gly Asn Asn Gly Thr Cys Leu Leu Ala Ser Met Ala Leu
 50                  55                  60

Gln Leu Asn Ile Thr Tyr Leu Lys Lys Asp Asn Lys Thr Val Thr Arg
 65                  70                  75                  80

Ala Phe Asn Ile Ser Pro Asn Asp Thr Ser Ser Gly Ser Cys Gly Ile
                 85                  90                  95

Asn Leu Val Thr Leu Lys Val Glu Asn Lys Asn Arg Ala Leu Glu Leu
            100                 105                 110

Gln Phe Gly Met Asn Ala Ser Ser Leu Phe Phe Leu Gln Gly Val
            115                 120                 125

Arg Leu Asn Met Thr Leu Pro Asp Ala Leu Val Pro Thr Phe Ser Ile
130                 135                 140

Ser Asn His Ser Leu Lys Ala Leu Gln Ala Thr Val Gly Asn Ser Tyr
145                 150                 155                 160

Lys Cys Asn Thr Glu Glu His Ile Phe Val Ser Lys Met Leu Ser Leu
                165                 170                 175

Asn Val Phe Ser Val Gln Val Gln Ala Phe Lys Val Asp Ser Asp Arg
                180                 185                 190

Phe Gly Ser Val Glu Glu Cys Val Gln Asp Gly Asn Asn Met Leu Ile
            195                 200                 205

Pro Ile Ala Val Gly Gly Ala Leu Ala
        210                 215

<210> SEQ ID NO 21
<211> LENGTH: 57
<212> TYPE: DNA
<213> ORGANISM: Artificial Sequence
<220> FEATURE:
<223> OTHER INFORMATION: Synthetic

<400> SEQUENCE: 21
tgtggttccc acctggtgga ggctctctac ctggtgtgtg gggagcgtgg cttcttc      57

<210> SEQ ID NO 22
<211> LENGTH: 19
<212> TYPE: PRT
<213> ORGANISM: Artificial Sequence
<220> FEATURE:
<223> OTHER INFORMATION: Synthetic

<400> SEQUENCE: 22

Cys Gly Ser His Leu Val Glu Ala Leu Tyr Leu Val Cys Gly Glu Arg
  1               5                  10                  15

Gly Phe Phe

<210> SEQ ID NO 23
<211> LENGTH: 57
<212> TYPE: DNA
<213> ORGANISM: Artificial Sequence
<220> FEATURE:
<223> OTHER INFORMATION: Synthetic

<400> SEQUENCE: 23
tgtggttccc acctggtgga ggctctctac ctggtgtgtg gggaggaggg cttcttc      57

<210> SEQ ID NO 24
<211> LENGTH: 19
<212> TYPE: PRT
```

<213> ORGANISM: Artificial Sequence
<220> FEATURE:
<223> OTHER INFORMATION: Synthetic

<400> SEQUENCE: 24

Cys Gly Ser His Leu Val Glu Ala Leu Tyr Leu Val Cys Gly Glu Glu
1               5                   10                  15

Gly Phe Phe

<210> SEQ ID NO 25
<211> LENGTH: 57
<212> TYPE: DNA
<213> ORGANISM: Artificial Sequence
<220> FEATURE:
<223> OTHER INFORMATION: Synthetic

<400> SEQUENCE: 25
tgtggttccc acctggtgga ggctctctac ctggtgtgtg ggggagaggg cttcttc        57

<210> SEQ ID NO 26
<211> LENGTH: 19
<212> TYPE: PRT
<213> ORGANISM: Artificial Sequence
<220> FEATURE:
<223> OTHER INFORMATION: Synthetic

<400> SEQUENCE: 26

Cys Gly Ser His Leu Val Glu Ala Leu Tyr Leu Val Cys Gly Gly Glu
1               5                   10                  15

Gly Phe Phe

<210> SEQ ID NO 27
<211> LENGTH: 54
<212> TYPE: DNA
<213> ORGANISM: Artificial Sequence
<220> FEATURE:
<223> OTHER INFORMATION: Synthetic

<400> SEQUENCE: 27
aagcgatgga gcaggatgga ccagctggcc aaagagctga cagcagagaa gcgg            54

<210> SEQ ID NO 28
<211> LENGTH: 18
<212> TYPE: PRT
<213> ORGANISM: Artificial Sequence
<220> FEATURE:
<223> OTHER INFORMATION: Synthetic

<400> SEQUENCE: 28

Lys Arg Trp Ser Arg Met Asp Gln Leu Ala Lys Glu Leu Thr Ala Glu
1               5                   10                  15

Lys Arg

<210> SEQ ID NO 29
<211> LENGTH: 42
<212> TYPE: DNA
<213> ORGANISM: Artificial Sequence
<220> FEATURE:
<223> OTHER INFORMATION: Synthetic

<400> SEQUENCE: 29
aagcgagcag ttcgacctct atgggtacgt atggaaaagc gg                        42

<210> SEQ ID NO 30

```
<211> LENGTH: 14
<212> TYPE: PRT
<213> ORGANISM: Artificial Sequence
<220> FEATURE:
<223> OTHER INFORMATION: Synthetic

<400> SEQUENCE: 30

Lys Arg Ala Val Arg Pro Leu Trp Val Arg Met Glu Lys Arg
1               5                   10

<210> SEQ ID NO 31
<211> LENGTH: 57
<212> TYPE: DNA
<213> ORGANISM: Artificial Sequence
<220> FEATURE:
<223> OTHER INFORMATION: Synthetic

<400> SEQUENCE: 31
tctctcaaga agggagctgc agccttaggg attggaacag acagtgtgat tctgatt        57

<210> SEQ ID NO 32
<211> LENGTH: 19
<212> TYPE: PRT
<213> ORGANISM: Artificial Sequence
<220> FEATURE:
<223> OTHER INFORMATION: Synthetic

<400> SEQUENCE: 32

Ser Leu Lys Lys Gly Ala Ala Ala Leu Gly Ile Gly Thr Asp Ser Val
1               5                   10                  15

Ile Leu Ile

<210> SEQ ID NO 33
<211> LENGTH: 72
<212> TYPE: DNA
<213> ORGANISM: Artificial Sequence
<220> FEATURE:
<223> OTHER INFORMATION: Synthetic

<400> SEQUENCE: 33
agaatgagcc gcctctcaaa ggtggcgcca gtgattaaag ccagaatgat ggagtatggg      60
accacaatgg tc                                                         72

<210> SEQ ID NO 34
<211> LENGTH: 24
<212> TYPE: PRT
<213> ORGANISM: Artificial Sequence
<220> FEATURE:
<223> OTHER INFORMATION: Synthetic

<400> SEQUENCE: 34

Arg Met Ser Arg Leu Ser Lys Val Ala Pro Val Ile Lys Ala Arg Met
1               5                   10                  15

Met Glu Tyr Gly Thr Thr Met Val
            20

<210> SEQ ID NO 35
<211> LENGTH: 57
<212> TYPE: DNA
<213> ORGANISM: Porcine teschovirus-1

<400> SEQUENCE: 35
gctactaact tcagcctgct gaagcaggct ggagacgtgg aggagaaccc tggacct        57
```

```
<210> SEQ ID NO 36
<211> LENGTH: 19
<212> TYPE: PRT
<213> ORGANISM: Porcine teschovirus-1

<400> SEQUENCE: 36

Ala Thr Asn Phe Ser Leu Leu Lys Gln Ala Gly Asp Val Glu Glu Asn
1               5                   10                  15

Pro Gly Pro

<210> SEQ ID NO 37
<211> LENGTH: 54
<212> TYPE: DNA
<213> ORGANISM: Thosea asigna virus

<400> SEQUENCE: 37
gagggcagag gaagtctgct aacatgcggt gacgtcgagg agaatcctgg acct        54

<210> SEQ ID NO 38
<211> LENGTH: 18
<212> TYPE: PRT
<213> ORGANISM: Thosea asigna virus

<400> SEQUENCE: 38

Glu Gly Arg Gly Ser Leu Leu Thr Cys Gly Asp Val Glu Glu Asn Pro
1               5                   10                  15

Gly Pro

<210> SEQ ID NO 39
<211> LENGTH: 60
<212> TYPE: DNA
<213> ORGANISM: Equine rhinitis A virus

<400> SEQUENCE: 39
cagtgtacta attatgctct cttgaaattg gctggagatg ttgagagcaa ccctggacct  60

<210> SEQ ID NO 40
<211> LENGTH: 20
<212> TYPE: PRT
<213> ORGANISM: Equine rhinitis A virus

<400> SEQUENCE: 40

Gln Cys Thr Asn Tyr Ala Leu Leu Lys Leu Ala Gly Asp Val Glu Ser
1               5                   10                  15

Asn Pro Gly Pro
            20

<210> SEQ ID NO 41
<211> LENGTH: 66
<212> TYPE: DNA
<213> ORGANISM: Foot-and-mouth disease virus

<400> SEQUENCE: 41
gtgaaacaga ctttgaattt tgaccttctc aagttggcgg gagacgtgga gtccaaccct  60
ggacct                                                             66

<210> SEQ ID NO 42
<211> LENGTH: 22
<212> TYPE: PRT
<213> ORGANISM: Foot-and-mouth disease virus

<400> SEQUENCE: 42
```

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 43
<211> LENGTH: 39
<212> TYPE: DNA
<213> ORGANISM: Artificial Sequence
<220> FEATURE:
<223> OTHER INFORMATION: Synthetic

<400> SEQUENCE: 43
gaggctctct acctggtgtg tggggagcgt ggcttcttc                       39

<210> SEQ ID NO 44
<211> LENGTH: 13
<212> TYPE: PRT
<213> ORGANISM: Artificial Sequence
<220> FEATURE:
<223> OTHER INFORMATION: Synthetic

<400> SEQUENCE: 44

Glu Ala Leu Tyr Leu Val Cys Gly Glu Arg Gly Phe Phe
1               5                   10

<210> SEQ ID NO 45
<211> LENGTH: 39
<212> TYPE: DNA
<213> ORGANISM: Artificial Sequence
<220> FEATURE:
<223> OTHER INFORMATION: Synthetic

<400> SEQUENCE: 45
ttgagtgtgt acctgaagac caacgtcttc ctcttcctg                       39

<210> SEQ ID NO 46
<211> LENGTH: 13
<212> TYPE: PRT
<213> ORGANISM: Artificial Sequence
<220> FEATURE:
<223> OTHER INFORMATION: Synthetic

<400> SEQUENCE: 46

Leu Ser Val Tyr Leu Lys Thr Asn Val Phe Leu Phe Leu
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Synthetic

<400> SEQUENCE: 47

Gly Arg Lys Lys Arg Arg Gln Arg Arg Pro Gln
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Synthetic

<400> SEQUENCE: 48

Gly Asp Leu Gln Thr Leu Trp Ser Arg Met Asp
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Synthetic

<400> SEQUENCE: 49

Leu Gln Thr Leu Ala Leu Trp Ser Arg Met Asp
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthetic

<400> SEQUENCE: 50

Leu Gln Thr Leu Ala Leu Asn Ala Ala Arg Asp
1               5                   10

<210> SEQ ID NO 51
<211> LENGTH: 15
<212> TYPE: PRT
<213> ORGANISM: Artificial Sequence
<220> FEATURE:
<223> OTHER INFORMATION: Synthetic

<400> SEQUENCE: 51

Gly Gln Val Glu Leu Gly Gly Gly Ser Ser Pro Glu Thr Leu Ile
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Synthetic

<400> SEQUENCE: 52

Gly Gln Val Glu Leu Gly Gly Gly Asn Ala Val Glu Val Leu Lys
1               5                   10                  15

<210> SEQ ID NO 53
<211> LENGTH: 3553
<212> TYPE: DNA
<213> ORGANISM: Artificial Sequence
<220> FEATURE:
<223> OTHER INFORMATION: Synthetic

<400> SEQUENCE: 53
cttaagatct gccaccatgg gtaaccactt ccaggccatt ctggcccagg tgcagacact    60
gctgagcagc cagaagccta gacaagtccg agcactgctg gatggcctgc tggaagagga   120
actgctgtcc agagaatacc actgcgctct gctgcacgaa cctgatgggg atgccctggc   180
cagaaagatc agcctgactc tgctggaaaa gggcgacctg acctgacat tcctgagctg    240 ggtctgcaac tctctgcagg ccctacagt ggaaagaggc acctcttaca gagatcacgg    300
cgaccacagc ctgtgcgcta caatggatc tggcagccct gagggcagct acctggaact   360
gctcaactct gatgccgatc tctctgcatct gtaccacctg tacgaccaga tggatctggc   420

```
cggcgaggaa gagatcgagc tgtctagcga gcctgacacc gacaccatca actgcgacca    480
gttcagcaag ctgctgcagg acatggaact ggacgaggaa acaagagagg cctacgccaa    540
tatcgccgag ctggaccagt acgtgttcca ggatacacag ctggaaggcc tgagcaagga    600
cctgttcatc gagcacatcg cgctgagga aggcttcggc gagaatatcg agatccctgt     660
ggaagccgga cagaagcccc agaagagaag attccctgag gaacacgcca tggacagcaa    720
gcacagaaag ctggtgccta ccagcagaac cagcctgaac tatctggacc tgcctaccgg    780
ccacatccag attttcacca cactgcctca aggcctgtgg cagatttctg gcgctggaac    840
aggactgagc agcgtgctga tctaccacgg cgagatgcct caagtgaacc aggtgctgcc    900
tagcagctcc ctgtctatcc catctctgcc tgagagccct gacagacctg gcagcacaag    960
ccctttcaca ccttctgccg ccgacctgcc ttctatgcct gaacctgctc tgacctccag   1020
agtgaacgag acagaggaca caagcccatc tccatgccaa gagggacccg agtctagcat   1080
caagctgcct aagtggcctg aggccgtgga agatttcag cacagcctgc aggataagta    1140
caaggccctg ccacagtctc ctagaggacc tctggtggct gtggaactcg tcagagctag   1200
actggaaagg ggcagcaaca agagccaaga gagagagctg gccacacctg actggaccga   1260
aagacaactg gctcacggtg gactggctga ggtgctgcaa gtggtgtctg actgtagaag   1320
gcctggcgag acacaggtgg tggcagttct gggaaaagcc ggccagggaa agtctcactg   1380
ggctagaaca gtgtcccaca catgggcatg tggacagctc tccagtacg acttcgtgtt    1440
ctacgtgcca tgccactgcc tggatagacc tggcgacaca taccacctga gggacctgct   1500
gtgtccacct tctctgcagc ctctggccat ggatgacgag gtgctggact acatcgtgcg   1560
gcagcctgat agagtgctgc tgatcctgga cgccttcgag gaactggaag ctcaggatgg   1620
actgctgcat ggaccttgtg gatctctgag cctgagcct tgttctctga gggactgct    1680
ggccggcatc ttccagagaa agctgctgag aggctgtacc ctgctgctga cagctagacc   1740
tagaggcaga ctgccccaga gcctgtctaa ggccgatgct atcttcgagg tgcccagctt   1800
cagcaccaag caggccaaga cctacatgag acactactc gagaacagcg gcaccgccgg   1860
caatcaggat aaggcacttg gactgctcga aggccagcct ctgctgtgta gctactctca   1920
cagccctgtc gtgtgcagag ccgtgtgtca gctgtctaaa gctctgctcg aacagggcac   1980
agaggcccag ttgccttgta cactgaccgg actgtatgtg tccctgctgg acctgccgc    2040
tcaaaattct cctcctggtg ctctggtgga actggccaaa ctggcttggg aactcggaag   2100
aaggcaccag tctaccctgc aagagacaag attcagcagc gtggaagtga aacctgggc    2160
cgtgacacag ggcctgatgc agcagaccct ggaaacaaca gaagctcagc tggccttag    2220
cagcttcctg ctgcagtgtt ttctgggcgc tgtgtggctg gcccagtgta atgagatcaa   2280
ggacaaagag ctgcctcagt acctggctct gacacctaga aagaagaggc cctacgataa   2340
ctggctggaa gggtgccca gattcctggc tggactggtg tttcagccta gggctcattg    2400
tctgggagcc ctggttgaac cagctgtggc tgccgtggct gacagaaagc agaaagtgct   2460
gaccagatac ctgaagagac tgaaactggg aacactgaga gccggcagac tgctggaact   2520
cctgcactgt gctcacgaaa cacagcagcc tggcatctgg agcatgtgg cacatcagct    2580
gcctggccac ctgtcctttc tgggcacaag actgacacct ccagacgtgt acgtgctggg   2640
cagagcactg gaaaccgcct ctcaggactt tagcctggat ctgagacaga ccggcgtgga   2700
accttctgga ctgggaaatc tcgtgggcct gagctgcgtg acaagcttca gagcctctct   2760
gagcgacaca atggccctgt gggaatctct gcaacagcag ggcgaagcac agctgcttca   2820
```

```
ggccgctgaa gagaagttca ccatcgagcc cttcaaggcc aagtctccca aggacgttga    2880
ggacctggat aggctggtgc agactcagag actgagaaac cctagcgagg acgccgctaa    2940
ggatctgcct gctatcaggg acctgaagaa gctggaattc gctctgggac ccatcctggg    3000
acctcaggct tttcctacac tggctaagat cctgccagcc ttctctagcc tgcagcatct    3060
ggatctggac tccctgagcg agaacaagat cggcgataag ggcgtgtcca agctgagcgc    3120
tacattccct cagctgaagg ctctggaaac actgaatctg tcccagaaca acatcaccga    3180
cgtgggcgcc tgtaaactgg ctgaagcact gcctgctctg gccaaatctc tgctgaggct    3240
gagcctgtac aacaactgca tctgcgacaa gggcgccaag tcactggctc aggttctgcc    3300
tgacatggtg tccctgagag tgatggacgt gcagttcaac aagttcacag ccgctggcgc    3360
ccagcaactg gcatcatctc tgcagaaatg tccccaggtg gaaaccctgg ctatgtggac    3420
ccctacaatc cccttcggcg tgcaagaaca tctccagcag ctggacgcca gaatctccct    3480
gagacaattg gccaccaact tcagcctgct gaagcaggcc ggcgacgtgg aagaaaatcc    3540
tggacctggt acc                                                      3553
```

<210> SEQ ID NO 54
<211> LENGTH: 1177
<212> TYPE: PRT
<213> ORGANISM: Artificial Sequence
<220> FEATURE:
<223> OTHER INFORMATION: Synthetic

<400> SEQUENCE: 54

```
Met Gly Asn His Phe Gln Ala Ile Leu Ala Gln Val Gln Thr Leu Leu
1               5                   10                  15

Ser Ser Gln Lys Pro Arg Gln Val Arg Ala Leu Leu Asp Gly Leu Leu
            20                  25                  30

Glu Glu Glu Leu Leu Ser Arg Glu Tyr His Cys Ala Leu Leu His Glu
        35                  40                  45

Pro Asp Gly Asp Ala Leu Ala Arg Lys Ile Ser Leu Thr Leu Leu Glu
    50                  55                  60

Lys Gly Asp Leu Asp Leu Thr Phe Leu Ser Trp Val Cys Asn Ser Leu
65                  70                  75                  80

Gln Ala Pro Thr Val Glu Arg Gly Thr Ser Tyr Arg Asp His Gly Asp
                85                  90                  95

His Ser Leu Cys Ala Thr Met Asp Leu Gly Ser Pro Glu Gly Ser Tyr
            100                 105                 110

Leu Glu Leu Leu Asn Ser Asp Ala Asp Pro Leu His Leu Tyr His Leu
        115                 120                 125

Tyr Asp Gln Met Asp Leu Ala Gly Glu Glu Ile Glu Leu Ser Ser
    130                 135                 140

Glu Pro Asp Thr Asp Thr Ile Asn Cys Asp Gln Phe Ser Lys Leu Leu
145                 150                 155                 160

Gln Asp Met Glu Leu Asp Glu Glu Thr Arg Glu Ala Tyr Ala Asn Ile
                165                 170                 175

Ala Glu Leu Asp Gln Tyr Val Phe Gln Asp Thr Gln Leu Glu Gly Leu
            180                 185                 190

Ser Lys Asp Leu Phe Ile Glu His Ile Gly Ala Glu Glu Gly Phe Gly
        195                 200                 205

Glu Asn Ile Glu Ile Pro Val Glu Ala Gly Gln Lys Pro Gln Lys Arg
    210                 215                 220
```

-continued

Arg Phe Pro Glu Glu His Ala Met Asp Ser Lys His Arg Lys Leu Val
225                 230                 235                 240

Pro Thr Ser Arg Thr Ser Leu Asn Tyr Leu Asp Leu Pro Thr Gly His
            245                 250                 255

Ile Gln Ile Phe Thr Thr Leu Pro Gln Gly Leu Trp Gln Ile Ser Gly
            260                 265                 270

Ala Gly Thr Gly Leu Ser Ser Val Leu Ile Tyr His Gly Glu Met Pro
        275                 280                 285

Gln Val Asn Gln Val Leu Pro Ser Ser Ser Leu Ser Ile Pro Ser Leu
    290                 295                 300

Pro Glu Ser Pro Asp Arg Pro Gly Ser Thr Ser Pro Phe Thr Pro Ser
305                 310                 315                 320

Ala Ala Asp Leu Pro Ser Met Pro Glu Pro Ala Leu Thr Ser Arg Val
            325                 330                 335

Asn Glu Thr Glu Asp Thr Ser Pro Ser Pro Cys Gln Glu Gly Pro Glu
            340                 345                 350

Ser Ser Ile Lys Leu Pro Lys Trp Pro Glu Ala Val Glu Arg Phe Gln
        355                 360                 365

His Ser Leu Gln Asp Lys Tyr Lys Ala Leu Pro Gln Ser Pro Arg Gly
    370                 375                 380

Pro Leu Val Ala Val Glu Leu Val Arg Ala Arg Leu Glu Arg Gly Ser
385                 390                 395                 400

Asn Lys Ser Gln Glu Arg Glu Leu Ala Thr Pro Asp Trp Thr Glu Arg
            405                 410                 415

Gln Leu Ala His Gly Gly Leu Ala Glu Val Leu Gln Val Val Ser Asp
            420                 425                 430

Cys Arg Arg Pro Gly Glu Thr Gln Val Val Ala Val Leu Gly Lys Ala
        435                 440                 445

Gly Gln Gly Lys Ser His Trp Ala Arg Thr Val Ser His Thr Trp Ala
    450                 455                 460

Cys Gly Gln Leu Leu Gln Tyr Asp Phe Val Phe Tyr Val Pro Cys His
465                 470                 475                 480

Cys Leu Asp Arg Pro Gly Asp Thr Tyr His Leu Arg Asp Leu Leu Cys
            485                 490                 495

Pro Pro Ser Leu Gln Pro Leu Ala Met Asp Asp Glu Val Leu Asp Tyr
            500                 505                 510

Ile Val Arg Gln Pro Asp Arg Val Leu Leu Ile Leu Asp Ala Phe Glu
        515                 520                 525

Glu Leu Glu Ala Gln Asp Gly Leu Leu His Gly Pro Cys Gly Ser Leu
    530                 535                 540

Ser Pro Glu Pro Cys Ser Leu Arg Gly Leu Leu Ala Gly Ile Phe Gln
545                 550                 555                 560

Arg Lys Leu Leu Arg Gly Cys Thr Leu Leu Thr Ala Arg Pro Arg
            565                 570                 575

Gly Arg Leu Ala Gln Ser Leu Ser Lys Ala Asp Ala Ile Phe Glu Val
            580                 585                 590

Pro Ser Phe Ser Thr Lys Gln Ala Lys Thr Tyr Met Arg His Tyr Phe
        595                 600                 605

Glu Asn Ser Gly Thr Ala Gly Asn Gln Asp Lys Ala Leu Gly Leu Leu
    610                 615                 620

Glu Gly Gln Pro Leu Leu Cys Ser Tyr Ser His Ser Pro Val Val Cys
625                 630                 635                 640

Arg Ala Val Cys Gln Leu Ser Lys Ala Leu Leu Glu Gln Gly Thr Glu

-continued

```
            645                 650                 655
Ala Gln Leu Pro Cys Thr Leu Thr Gly Leu Tyr Val Ser Leu Leu Gly
                660                 665                 670

Pro Ala Ala Gln Asn Ser Pro Pro Gly Ala Leu Val Glu Leu Ala Lys
                675                 680                 685

Leu Ala Trp Glu Leu Gly Arg Arg His Gln Ser Thr Leu Gln Glu Thr
        690                 695                 700

Arg Phe Ser Ser Val Glu Val Lys Thr Trp Ala Val Thr Gln Gly Leu
705                 710                 715                 720

Met Gln Gln Thr Leu Glu Thr Thr Glu Ala Gln Leu Ala Phe Ser Ser
                725                 730                 735

Phe Leu Leu Gln Cys Phe Leu Gly Ala Val Trp Leu Ala Gln Cys Asn
                740                 745                 750

Glu Ile Lys Asp Lys Glu Leu Pro Gln Tyr Leu Ala Leu Thr Pro Arg
                755                 760                 765

Lys Lys Arg Pro Tyr Asp Asn Trp Leu Glu Gly Val Pro Arg Phe Leu
                770                 775                 780

Ala Gly Leu Val Phe Gln Pro Arg Ala His Cys Leu Gly Ala Leu Val
785                 790                 795                 800

Glu Pro Ala Val Ala Ala Val Ala Asp Arg Lys Gln Lys Val Leu Thr
                805                 810                 815

Arg Tyr Leu Lys Arg Leu Lys Leu Gly Thr Leu Arg Ala Gly Arg Leu
                820                 825                 830

Leu Glu Leu Leu His Cys Ala His Glu Thr Gln Gln Pro Gly Ile Trp
                835                 840                 845

Glu His Val Ala His Gln Leu Pro Gly His Leu Ser Phe Leu Gly Thr
850                 855                 860

Arg Leu Thr Pro Pro Asp Val Tyr Val Leu Gly Arg Ala Leu Glu Thr
865                 870                 875                 880

Ala Ser Gln Asp Phe Ser Leu Asp Leu Arg Gln Thr Gly Val Glu Pro
                885                 890                 895

Ser Gly Leu Gly Asn Leu Val Gly Leu Ser Cys Val Thr Ser Phe Arg
                900                 905                 910

Ala Ser Leu Ser Asp Thr Met Ala Leu Trp Glu Ser Leu Gln Gln Gln
                915                 920                 925

Gly Glu Ala Gln Leu Leu Gln Ala Ala Glu Lys Phe Thr Ile Glu
                930                 935                 940

Pro Phe Lys Ala Lys Ser Pro Lys Asp Val Glu Asp Leu Asp Arg Leu
945                 950                 955                 960

Val Gln Thr Gln Arg Leu Arg Asn Pro Ser Glu Asp Ala Ala Lys Asp
                965                 970                 975

Leu Pro Ala Ile Arg Asp Leu Lys Leu Glu Phe Ala Leu Gly Pro
                980                 985                 990

Ile Leu Gly Pro Gln Ala Phe Pro Thr Leu Ala Lys Ile Leu Pro Ala
                995                 1000                1005

Phe Ser Ser Leu Gln His Leu Asp Leu Asp Ser Leu Ser Glu Asn
        1010                1015                1020

Lys Ile Gly Asp Lys Gly Val Ser Lys Leu Ser Ala Thr Phe Pro
        1025                1030                1035

Gln Leu Lys Ala Leu Glu Thr Leu Asn Leu Ser Gln Asn Asn Ile
        1040                1045                1050

Thr Asp Val Gly Ala Cys Lys Leu Ala Glu Ala Leu Pro Ala Leu
        1055                1060                1065
```

Ala Lys Ser Leu Leu Arg Leu Ser Leu Tyr Asn Asn Cys Ile Cys
    1070            1075                1080

Asp Lys Gly Ala Lys Ser Leu Ala Gln Val Leu Pro Asp Met Val
    1085            1090                1095

Ser Leu Arg Val Met Asp Val Gln Phe Asn Lys Phe Thr Ala Ala
    1100            1105                1110

Gly Ala Gln Gln Leu Ala Ser Ser Leu Gln Lys Cys Pro Gln Val
    1115            1120                1125

Glu Thr Leu Ala Met Trp Thr Pro Thr Ile Pro Phe Gly Val Gln
    1130            1135                1140

Glu His Leu Gln Gln Leu Asp Ala Arg Ile Ser Leu Arg Gln Leu
    1145            1150                1155

Ala Thr Asn Phe Ser Leu Leu Lys Gln Ala Gly Asp Val Glu Glu
    1160            1165                1170

Asn Pro Gly Pro
    1175

<210> SEQ ID NO 55
<211> LENGTH: 69
<212> TYPE: DNA
<213> ORGANISM: Artificial Sequence
<220> FEATURE:
<223> OTHER INFORMATION: Synthetic

<400> SEQUENCE: 55
atgaagtggg taacctttct cctcctcctc ttcatctccg gttctgcctt ttctagggc      60 aagcttatg                                                              69

<210> SEQ ID NO 56
<211> LENGTH: 75
<212> TYPE: DNA
<213> ORGANISM: Artificial Sequence
<220> FEATURE:
<223> OTHER INFORMATION: Synthetic

<400> SEQUENCE: 56
atgaagtggg taacctttat tcccttctt tttctcttta gctcggctta ttccaggggt      60
gtgtttcgtc gagat                                                       75

<210> SEQ ID NO 57
<211> LENGTH: 63
<212> TYPE: DNA
<213> ORGANISM: Artificial Sequence
<220> FEATURE:
<223> OTHER INFORMATION: Synthetic

<400> SEQUENCE: 57
atggagacag acacactcct gctatgggta ctgctgctct gggttccagg ttccactggt      60
gac                                                                    63

<210> SEQ ID NO 58
<211> LENGTH: 242
<212> TYPE: PRT
<213> ORGANISM: Artificial Sequence
<220> FEATURE:
<223> OTHER INFORMATION: Synthetic

<400> SEQUENCE: 58

Met Asp Asp Gln Arg Asp Leu Ile Ser Asn His Glu Gln Leu Pro Ile
1               5                   10                  15

```
Leu Gly Asn Arg Pro Arg Glu Pro Glu Arg Cys Ser Arg Gly Ala Leu
             20                  25                  30

Tyr Thr Gly Val Ser Val Leu Val Ala Leu Leu Leu Ala Gly Gln Ala
         35                  40                  45

Thr Thr Ala Tyr Phe Leu Tyr Gln Gln Gln Gly Arg Leu Asp Lys Leu
 50                  55                  60

Thr Ile Thr Ser Gln Asn Leu Gln Leu Glu Ser Leu Arg Met Lys Leu
65                  70                  75                  80

Pro Arg Cys Gly Ser His Leu Val Glu Ala Leu Tyr Leu Val Cys Gly
                 85                  90                  95

Glu Glu Gly Phe Phe Lys Arg Ala Val Arg Pro Leu Trp Val Arg Met
            100                 105                 110

Glu Lys Arg Cys Gly Ser His Leu Val Glu Ala Leu Tyr Leu Val Cys
        115                 120                 125

Gly Glu Arg Gly Phe Phe Ser Leu Lys Lys Gly Ala Ala Ala Leu Gly
130                 135                 140

Ile Gly Thr Asp Ser Val Ile Leu Ile Cys Gly Ser His Leu Val Glu
145                 150                 155                 160

Ala Leu Tyr Leu Val Cys Gly Gly Glu Gly Phe Phe Arg Met Ser Arg
                165                 170                 175

Leu Ser Lys Val Ala Pro Val Ile Lys Ala Arg Met Met Glu Tyr Gly
            180                 185                 190

Thr Thr Met Val Glu Gly Arg Gly Ser Leu Leu Thr Cys Gly Asp Val
        195                 200                 205

Glu Glu Asn Pro Gly Pro Glu Ala Leu Tyr Leu Val Cys Gly Glu Arg
210                 215                 220

Gly Phe Phe Leu Ser Val Tyr Leu Lys Thr Asn Val Phe Leu Phe Leu
225                 230                 235                 240

Pro Gly

<210> SEQ ID NO 59
<211> LENGTH: 735
<212> TYPE: DNA
<213> ORGANISM: Artificial Sequence
<220> FEATURE:
<223> OTHER INFORMATION: Synthetic

<400> SEQUENCE: 59
gccaccatgg acgaccagag ggacctgatc agcaaccacg agcagctgcc catcctgggc      60
aacagacccc gcgagcctga gagatgtagc agaggcgctc tgtacaccgg cgtgtccgtg     120
ctggtggctc tgctgctggc tggccaggct acaaccgcct acttcctgta tcagcagcag     180
ggcagactgg acaagctgac catcaccagc cagaacctcc agctcgaaag cctgagaatg     240
aagctgccgc ggtgcggctc tcacctggtg aagctctgt acctcgtgtg cggcgaggaa      300
ggcttcttca gagggctgt gcgacccctg tgggtccgaa tggaaaagag atgcggcagc      360
cacctggtcg aggccctcta tctcgtgtgt ggggagagag cttttttcag cctgaagaag     420
ggcgctgccg ccctgggcat cggcacagac tctgtgatcc tgatctgcgg aagccatctc     480
gtcgaagcac tgtatctggt ctgcggaggc gagggcttct ccggatgag cagactgagc      540 aaggtggccc ccgtgatcaa ggccagaatg atggaatacg gcaccacaat ggtggaaggc     600
agaggcagcc tgctgacctg cggcgacgtg aagagaaacc tggccctga ggcactctac      660 ctggtctgtg gcgagcgcgg attcttcctg agcgtgtacc tcaagaccaa cgtgttcctg     720
```
ttcctgcccg ggtag                                                      735

<210> SEQ ID NO 60
<211> LENGTH: 154
<212> TYPE: PRT
<213> ORGANISM: Artificial Sequence
<220> FEATURE:
<223> OTHER INFORMATION: Synthetic

<400> SEQUENCE: 60

Met Lys Trp Val Thr Phe Leu Leu Leu Phe Ile Ser Gly Ser Ala
1               5                   10                  15

Phe Ser Arg Gly Lys Leu Met Pro Arg Cys Gly Ser His Leu Val Glu
            20                  25                  30

Ala Leu Tyr Leu Val Cys Gly Glu Glu Gly Phe Phe Lys Arg Ala Val
        35                  40                  45

Arg Pro Leu Trp Val Arg Met Glu Lys Arg Cys Gly Ser His Leu Val
    50                  55                  60

Glu Ala Leu Tyr Leu Val Cys Gly Glu Arg Gly Phe Phe Ser Leu Lys
65                  70                  75                  80

Lys Gly Ala Ala Ala Leu Gly Ile Gly Thr Asp Ser Val Ile Leu Ile
                85                  90                  95

Cys Gly Ser His Leu Val Glu Ala Leu Tyr Leu Val Cys Gly Gly Glu
            100                 105                 110

Gly Phe Phe Arg Met Ser Arg Leu Ser Lys Val Ala Pro Val Ile Lys
        115                 120                 125

Ala Arg Met Met Glu Tyr Gly Thr Thr Met Val Leu Ser Val Tyr Leu
    130                 135                 140

Lys Thr Asn Val Phe Leu Phe Leu Pro Gly
145                 150

<210> SEQ ID NO 61
<211> LENGTH: 471
<212> TYPE: DNA
<213> ORGANISM: Artificial Sequence
<220> FEATURE:
<223> OTHER INFORMATION: Synthetic

<400> SEQUENCE: 61
gccaccatga agtgggtcac ctttctgctg ctgctgttca tcagcggcag cgccttcagc      60
agaggcaagc tgatgccgcg gtgcggctct cacctggtgg aagccctgta cctcgtgtgc     120
ggcgaggaag gcttcttcaa gagggctgtg cgacccctgt gggtccgaat ggaaaagaga     180
tgcggcagcc acctggtcga ggcactctat ctcgtgtgtg gggagagagg cttttttcagc    240 ctgaagaagg gcgcagccgc cctgggcatc ggcacagact ctgtgatcct gatctgcgga     300
agccatctcg tcgaagctct gtatctggtc tgcggcggag agggcttctt tagaatgagc     360
agactgagca aggtggcccc cgtgatcaag gccagaatga tggaatacgg caccacaatg     420
gtgctgagcg tgtacctcaa gaccaacgtg ttcctgttcc tgcccgggta g              471

<210> SEQ ID NO 62
<211> LENGTH: 1421
<212> TYPE: PRT
<213> ORGANISM: Artificial Sequence
<220> FEATURE:
<223> OTHER INFORMATION: Synthetic

<400> SEQUENCE: 62

Met Gly Asn His Phe Gln Ala Ile Leu Ala Gln Val Gln Thr Leu Leu

```
  1               5                    10                   15
Ser Ser Gln Lys Pro Arg Gln Val Arg Ala Leu Leu Asp Gly Leu Leu
              20                  25                  30

Glu Glu Glu Leu Leu Ser Arg Glu Tyr His Cys Ala Leu Leu His Glu
              35                  40                  45

Pro Asp Gly Asp Ala Leu Ala Arg Lys Ile Ser Leu Thr Leu Leu Glu
 50                  55                  60

Lys Gly Asp Leu Asp Leu Thr Phe Leu Ser Trp Val Cys Asn Ser Leu
 65                  70                  75                  80

Gln Ala Pro Thr Val Glu Arg Gly Thr Ser Tyr Arg Asp His Gly Asp
                  85                  90                  95

His Ser Leu Cys Ala Thr Met Asp Leu Gly Ser Pro Glu Gly Ser Tyr
             100                 105                 110

Leu Glu Leu Leu Asn Ser Asp Ala Asp Pro Leu His Leu Tyr His Leu
             115                 120                 125

Tyr Asp Gln Met Asp Leu Ala Gly Glu Glu Ile Glu Leu Ser Ser
130                 135                 140

Glu Pro Asp Thr Asp Thr Ile Asn Cys Asp Gln Phe Ser Lys Leu Leu
145                 150                 155                 160

Gln Asp Met Glu Leu Asp Glu Glu Thr Arg Glu Ala Tyr Ala Asn Ile
             165                 170                 175

Ala Glu Leu Asp Gln Tyr Val Phe Gln Asp Thr Gln Leu Glu Gly Leu
             180                 185                 190

Ser Lys Asp Leu Phe Ile Glu His Ile Gly Ala Glu Glu Gly Phe Gly
             195                 200                 205

Glu Asn Ile Glu Ile Pro Val Glu Ala Gly Gln Lys Pro Gln Lys Arg
210                 215                 220

Arg Phe Pro Glu Glu His Ala Met Asp Ser Lys His Arg Lys Leu Val
225                 230                 235                 240

Pro Thr Ser Arg Thr Ser Leu Asn Tyr Leu Asp Leu Pro Thr Gly His
                 245                 250                 255

Ile Gln Ile Phe Thr Thr Leu Pro Gln Gly Leu Trp Gln Ile Ser Gly
             260                 265                 270

Ala Gly Thr Gly Leu Ser Ser Val Leu Ile Tyr His Gly Glu Met Pro
             275                 280                 285

Gln Val Asn Gln Val Leu Pro Ser Ser Leu Ser Ile Pro Ser Leu
             290                 295                 300

Pro Glu Ser Pro Asp Arg Pro Gly Ser Thr Ser Pro Phe Thr Pro Ser
305                 310                 315                 320

Ala Ala Asp Leu Pro Ser Met Pro Glu Pro Ala Leu Thr Ser Arg Val
                 325                 330                 335

Asn Glu Thr Glu Asp Thr Ser Pro Ser Pro Cys Gln Glu Gly Pro Glu
                 340                 345                 350

Ser Ser Ile Lys Leu Pro Lys Trp Pro Glu Ala Val Glu Arg Phe Gln
                 355                 360                 365

His Ser Leu Gln Asp Lys Tyr Lys Ala Leu Pro Gln Ser Pro Arg Gly
                 370                 375                 380

Pro Leu Val Ala Val Glu Leu Val Arg Ala Arg Leu Glu Arg Gly Ser
385                 390                 395                 400

Asn Lys Ser Gln Glu Arg Glu Leu Ala Thr Pro Asp Trp Thr Glu Arg
                 405                 410                 415

Gln Leu Ala His Gly Gly Leu Ala Glu Val Leu Gln Val Val Ser Asp
                 420                 425                 430
```

```
Cys Arg Arg Pro Gly Glu Thr Gln Val Val Ala Val Leu Gly Lys Ala
        435                 440                 445

Gly Gln Gly Lys Ser His Trp Ala Arg Thr Val Ser His Thr Trp Ala
    450                 455                 460

Cys Gly Gln Leu Leu Gln Tyr Asp Phe Val Phe Tyr Val Pro Cys His
465                 470                 475                 480

Cys Leu Asp Arg Pro Gly Asp Thr Tyr His Leu Arg Asp Leu Leu Cys
                485                 490                 495

Pro Pro Ser Leu Gln Pro Leu Ala Met Asp Asp Glu Val Leu Asp Tyr
            500                 505                 510

Ile Val Arg Gln Pro Asp Arg Val Leu Leu Ile Leu Asp Ala Phe Glu
        515                 520                 525

Glu Leu Glu Ala Gln Asp Gly Leu Leu His Gly Pro Cys Gly Ser Leu
    530                 535                 540

Ser Pro Glu Pro Cys Ser Leu Arg Gly Leu Leu Ala Gly Ile Phe Gln
545                 550                 555                 560

Arg Lys Leu Leu Arg Gly Cys Thr Leu Leu Leu Thr Ala Arg Pro Arg
                565                 570                 575

Gly Arg Leu Ala Gln Ser Leu Ser Lys Ala Asp Ala Ile Phe Glu Val
            580                 585                 590

Pro Ser Phe Ser Thr Lys Gln Ala Lys Thr Tyr Met Arg His Tyr Phe
        595                 600                 605

Glu Asn Ser Gly Thr Ala Gly Asn Gln Asp Lys Ala Leu Gly Leu Leu
    610                 615                 620

Glu Gly Gln Pro Leu Leu Cys Ser Tyr Ser His Ser Pro Val Val Cys
625                 630                 635                 640

Arg Ala Val Cys Gln Leu Ser Lys Ala Leu Leu Glu Gln Gly Thr Glu
                645                 650                 655

Ala Gln Leu Pro Cys Thr Leu Thr Gly Leu Tyr Val Ser Leu Leu Gly
            660                 665                 670

Pro Ala Ala Gln Asn Ser Pro Pro Gly Ala Leu Val Glu Leu Ala Lys
        675                 680                 685

Leu Ala Trp Glu Leu Gly Arg Arg His Gln Ser Thr Leu Gln Glu Thr
    690                 695                 700

Arg Phe Ser Ser Val Glu Val Lys Thr Trp Ala Val Thr Gln Gly Leu
705                 710                 715                 720

Met Gln Gln Thr Leu Glu Thr Thr Glu Ala Gln Leu Ala Phe Ser Ser
                725                 730                 735

Phe Leu Leu Gln Cys Phe Leu Gly Ala Val Trp Leu Ala Gln Cys Asn
            740                 745                 750

Glu Ile Lys Asp Lys Glu Leu Pro Gln Tyr Leu Ala Leu Thr Pro Arg
        755                 760                 765

Lys Lys Arg Pro Tyr Asp Asn Trp Leu Glu Gly Val Pro Arg Phe Leu
    770                 775                 780

Ala Gly Leu Val Phe Gln Pro Arg Ala His Cys Leu Gly Ala Leu Val
785                 790                 795                 800

Glu Pro Ala Val Ala Ala Val Ala Asp Arg Lys Gln Lys Val Leu Thr
                805                 810                 815

Arg Tyr Leu Lys Arg Leu Lys Leu Gly Thr Leu Arg Ala Gly Arg Leu
            820                 825                 830

Leu Glu Leu Leu His Cys Ala His Glu Thr Gln Gln Pro Gly Ile Trp
        835                 840                 845
```

-continued

Glu His Val Ala His Gln Leu Pro Gly His Leu Ser Phe Leu Gly Thr
850                     855                 860

Arg Leu Thr Pro Pro Asp Val Tyr Val Leu Gly Arg Ala Leu Glu Thr
865                 870                  875                 880

Ala Ser Gln Asp Phe Ser Leu Asp Leu Arg Gln Thr Gly Val Glu Pro
            885                 890                 895

Ser Gly Leu Gly Asn Leu Val Gly Leu Ser Cys Val Thr Ser Phe Arg
            900                 905                 910

Ala Ser Leu Ser Asp Thr Met Ala Leu Trp Glu Ser Leu Gln Gln Gln
            915                 920                 925

Gly Glu Ala Gln Leu Leu Gln Ala Ala Glu Lys Phe Thr Ile Glu
930                 935                 940

Pro Phe Lys Ala Lys Ser Pro Lys Asp Val Glu Asp Leu Asp Arg Leu
945                 950                 955                 960

Val Gln Thr Gln Arg Leu Arg Asn Pro Ser Glu Asp Ala Ala Lys Asp
                965                 970                 975

Leu Pro Ala Ile Arg Asp Leu Lys Lys Leu Glu Phe Ala Leu Gly Pro
            980                 985                 990

Ile Leu Gly Pro Gln Ala Phe Pro  Thr Leu Ala Lys Ile  Leu Pro Ala
            995                 1000                1005

Phe Ser  Ser Leu Gln His Leu  Asp Leu Asp Ser Leu  Ser Glu Asn
1010                 1015                1020

Lys Ile  Gly Asp Lys Gly Val  Ser Lys Leu Ser Ala  Thr Phe Pro
1025                 1030                1035

Gln Leu  Lys Ala Leu Glu Thr  Leu Asn Leu Ser Gln  Asn Asn Ile
1040                 1045                1050

Thr Asp  Val Gly Ala Cys Lys  Leu Ala Glu Ala Leu  Pro Ala Leu
1055                 1060                1065

Ala Lys  Ser Leu Leu Arg Leu  Ser Leu Tyr Asn Asn  Cys Ile Cys
1070                 1075                1080

Asp Lys  Gly Ala Lys Ser Leu  Ala Gln Val Leu Pro  Asp Met Val
1085                 1090                1095

Ser Leu  Arg Val Met Asp Val  Gln Phe Asn Lys Phe  Thr Ala Ala
1100                 1105                1110

Gly Ala  Gln Gln Leu Ala Ser  Ser Leu Gln Lys Cys  Pro Gln Val
1115                 1120                1125

Glu Thr  Leu Ala Met Trp Thr  Pro Thr Ile Pro Phe  Gly Val Gln
1130                 1135                1140

Glu His  Leu Gln Gln Leu Asp  Ala Arg Ile Ser Leu  Arg Gln Leu
1145                 1150                1155

Ala Thr  Asn Phe Ser Leu Leu  Lys Gln Ala Gly  Asp Val Glu Glu
1160                 1165                1170

Asn Pro  Gly Pro Gly Thr Met  Asp Asp Gln Arg Asp  Leu Ile Ser
1175                 1180                1185

Asn His  Glu Gln Leu Pro Ile  Leu Gly Asn Arg Pro  Arg Glu Pro
1190                 1195                1200

Glu Arg  Cys Ser Arg Gly Ala  Leu Tyr Thr Gly Val  Ser Val Leu
1205                 1210                1215

Val Ala  Leu Leu Leu Ala Gly  Gln Ala Thr Thr Ala  Tyr Phe Leu
1220                 1225                1230

Tyr Gln  Gln Gln Gly Arg Leu  Asp Lys Leu Thr Ile  Thr Ser Gln
1235                 1240                1245

Asn Leu  Gln Leu Glu Ser Leu  Arg Met Lys Leu Pro  Arg Cys Gly

| | | | | |
|---|---|---|---|---|
| Ser His Leu Val Glu Ala Leu Tyr Leu Val Cys Gly Glu Glu Gly | | | | |
| 1265 | | 1270 | | 1275 |
| Phe Phe Lys Arg Ala Val Arg Pro Leu Trp Val Arg Met Glu Lys | | | | |
| 1280 | | 1285 | | 1290 |
| Arg Cys Gly Ser His Leu Val Glu Ala Leu Tyr Leu Val Cys Gly | | | | |
| 1295 | | 1300 | | 1305 |
| Glu Arg Gly Phe Phe Ser Leu Lys Lys Gly Ala Ala Ala Leu Gly | | | | |
| 1310 | | 1315 | | 1320 |
| Ile Gly Thr Asp Ser Val Ile Leu Ile Cys Gly Ser His Leu Val | | | | |
| 1325 | | 1330 | | 1335 |
| Glu Ala Leu Tyr Leu Val Cys Gly Gly Glu Gly Phe Phe Arg Met | | | | |
| 1340 | | 1345 | | 1350 |
| Ser Arg Leu Ser Lys Val Ala Pro Val Ile Lys Ala Arg Met Met | | | | |
| 1355 | | 1360 | | 1365 |
| Glu Tyr Gly Thr Thr Met Val Glu Gly Arg Gly Ser Leu Leu Thr | | | | |
| 1370 | | 1375 | | 1380 |
| Cys Gly Asp Val Glu Glu Asn Pro Gly Pro Glu Ala Leu Tyr Leu | | | | |
| 1385 | | 1390 | | 1395 |
| Val Cys Gly Glu Arg Gly Phe Phe Leu Ser Val Tyr Leu Lys Thr | | | | |
| 1400 | | 1405 | | 1410 |
| Asn Val Phe Leu Phe Leu Pro Gly | | | | |
| 1415 | | 1420 | | |

<210> SEQ ID NO 63
<211> LENGTH: 4272
<212> TYPE: DNA
<213> ORGANISM: Artificial Sequence
<220> FEATURE:
<223> OTHER INFORMATION: Synthetic

<400> SEQUENCE: 63

```
gccaccatgg gtaaccactt ccaggccatt ctggcccagg tgcagacact gctgagcagc      60
cagaagccta gacaagtccg agcactgctg gatggcctgc tggaagagga actgctgtcc     120
agagaatacc actgcgctct gctgcacgaa cctgatgggg atgccctggc cagaaagatc     180
agcctgactc tgctggaaaa gggcgacctg gacctgacat tcctgagctg ggtctgcaac     240
tctctgcagg cccctacagt ggaaagaggc acctcttaca gagatcacgg cgaccacagc     300
ctgtgcgcta caatggatct tggcagccct gagggcagct acctggaact gctcaactct     360
gatgccgatc tctgcatct gtaccacctg tacgaccaga tggatctggc cggcgaggaa      420
gagatcgagc tgtctagcga gcctgacacc gacaccatca actgcgacca gttcagcaag     480
ctgctgcagg acatggaact ggacgaggaa acaagagagg cctacgccaa tatcgccgag     540
ctggaccagt acgtgttcca ggatacacag ctggaaggcc tgagcaagga cctgttcatc     600
gagcacatcg cgctgagga aggcttcggc gagaatatcg atccctgt ggaagccgga       660
cagaagcccc agaagagaag attccctgag gaacacgcca tggacagcaa gcacagaaag     720
ctggtgccta ccagcagaac cagcctgaac tatctggacc tgcctaccgg ccacatccag     780
attttcacca cactgcctca aggcctgtgg cagatttctg cgctggaac aggactgagc     840
agcgtgctga tctaccacgg cgagatgcct caagtgaacc aggtgctgcc tagcagctcc     900
ctgtctatcc catctctgcc tgagagccct gacagacctg cagcacaag ccctttcaca     960
ccttctgccg ccgacctgcc ttctatgcct gaacctgctc tgacctccag agtgaacgag    1020
```

```
acagaggaca caagcccatc tccatgccaa gagggacccg agtctagcat caagctgcct    1080
aagtggcctg aggccgtgga aagatttcag cacagcctgc aggataagta caaggccctg    1140
ccacagtctc ctagaggacc tctggtggct gtggaactcg tcagagctag actggaaagg    1200
ggcagcaaca agagccaaga gagagagctg gccacacctg actggaccga agacaactg     1260 gctcacggtg gactggctga ggtgctgcaa gtggtgtctg actgtagaag gcctggcgag    1320
acacaggtgg tggcagttct gggaaaagcc ggccagggaa agtctcactg gctagaaca    1380 gtgtcccaca catgggcatg tggacagctg ctccagtacg acttcgtgtt ctacgtgcca    1440
tgccactgcc tggatagacc tggcgacaca taccacctga gggacctgct gtgtccacct    1500
tctctgcagc ctctggccat ggatgacgag gtgctggact acatcgtgcg gcagcctgat    1560
agagtgctgc tgatcctgga cgccttcgag gaactggaag ctcaggatgg actgctgcat    1620
ggaccttgtg gatctctgag ccctgagcct tgttctctga gaggactgct ggccggcatc    1680
ttccagagaa agctgctgag aggctgtacc ctgctgctga cagctagacc tagaggcaga    1740
ctggcccaga gcctgtctaa ggccgatgct atcttcgagg tgcccagctt cagcaccaag    1800
caggccaaga cctacatgag acactacttc gagaacagcg gcaccgccgg caatcaggat    1860
aaggcacttg gactgctcga aggccagcct ctgctgtgta gctactctca cagccctgtc    1920
gtgtgcagag ccgtgtgtca gctgtctaaa gctctgctcg aacagggcac agaggcccag    1980
ttgccttgta cactgaccgg actgtatgtg ccctgctgg gacctgccgc tcaaaattct     2040
cctcctggtg ctctggtgga actggccaaa ctggcttggg aactcggaag aaggcaccag    2100
tctaccctgc aagagacaag attcagcagc gtggaagtga aaacctgggc cgtgacacag    2160
ggcctgatgc agcagaccct ggaaacaaca gaagctcagc tggcctttag cagcttcctg    2220
ctgcagtgtt ttctgggcgc tgtgtggctg gcccagtgta atgagatcaa ggacaaagag    2280
ctgcctcagt acctggctct gacacctaga aagaagaggc cctacgataa ctggctggaa    2340
ggggtgccca gattcctggc tggactggtg tttcagccta gggctcattg tctgggagcc    2400
ctggttgaac cagctgtggc tgccgtggct gacagaaagc agaaagtgct gaccagatac    2460
ctgaagagac tgaaactggg aacactgaga gccggcagac tgctggaact cctgcactgt    2520
gctcacgaaa cacagcagcc tggcatctgg gagcatgtgg cacatcagct gcctggccac    2580
ctgtcctttc tgggcacaag actgacacct ccagacgtgt acgtgctggg cagagcactg    2640
gaaaccgcct tcaggactt tagcctggat ctgagacaga ccggcgtgga accttctgga    2700
ctgggaaatc tcgtgggcct gagctgcgtg acaagcttca gagcctctct gagcgacaca    2760
atggccctgt gggaatctct gcaacagcag ggcgaagcac agctgcttca ggccgctgaa    2820
gagaagttca ccatcgagcc cttcaaggcc aagtctccca aggacgttga ggacctggat    2880
aggctggtgc agactcagag actgagaaac cctagcgagg acgccgctaa ggatctgcct    2940
gctatcaggg acctgaagaa gctggaattc gctctgggac ccatcctggg acctcaggct    3000
tttcctacac tggctaagat cctgccagcc ttctctagcc tgcagcatct ggatctggac    3060
tccctgagcg agaacaagat cggcgataag ggcgtgtcca agctgagcgc tacattccct    3120
cagctgaagg ctctggaaac actgaatctg tcccagaaca acatcaccga cgtgggcgcc    3180
tgtaaactgg ctgaagcact gctgctctg gccaaatctc tgctgaggct gagcctgtac    3240
aacaactgca tctgcgacaa gggcgccaag tcactggctc aggttctgcc tgacatggtg    3300
tccctgagag tgatggacgt gcagttcaac aagttcacag ccgctggcgc ccagcaactg    3360
gcatcatctc tgcagaaatg tccccaggtg gaaaccctgg ctatgtggac ccctacaatc    3420
```

-continued

```
cccttcggcg tgcaagaaca tctccagcag ctggacgcca gaatctccct gagacaattg    3480
gccaccaact tcagcctgct gaagcaggcc ggcgacgtgg aagaaaatcc tggacctggt    3540
accatggacg accagaggga cctgatcagc aaccacgagc agctgcccat cctgggcaac    3600 agacccccgcg agcctgagag atgtagcaga ggcgctctgt acaccggcgt gtccgtgctg    3660
gtggctctgc tgctggctgg ccaggctaca accgcctact tcctgtatca gcagcagggc    3720
agactggaca agctgaccat caccagccag aacctccagc tcgaaagcct gagaatgaag    3780
ctgccgcggt gcggctctca cctggtggaa gctctgtacc tcgtgtgcgg cgaggaaggc    3840
ttcttcaaga gggctgtgcg acccctgtgg gtccgaatgg aaaagagatg cggcagccac    3900
ctggtcgagg ccctctatct cgtgtgtggg gagagaggct ttttcagcct gaagaagggc    3960
gctgccgccc tgggcatcgg cacagactct gtgatcctga tctgcggaag ccatctcgtc    4020
gaagcactgt atctggtctg cggaggcgag ggcttcttcc ggatgagcag actgagcaag    4080
gtggcccccg tgatcaaggc cagaatgatg aatacggca ccacaatggt ggaaggcaga    4140
ggcagcctgc tgacctgcgg cgacgtggaa gagaaccctg gccctgaggc actctacctg    4200
gtctgtggcg agcgcggatt cttcctgagc gtgtacctca agaccaacgt gttcctgttc    4260
ctgcccgggt ag                                                         4272
```

```
<210> SEQ ID NO 64
<211> LENGTH: 15
<212> TYPE: PRT
<213> ORGANISM: Artificial Sequence
<220> FEATURE:
<223> OTHER INFORMATION: Synthetic

<400> SEQUENCE: 64

Ser His Leu Val Glu Ala Leu Tyr Leu Val Cys Gly Gly Glu Gly
1               5                   10                  15

<210> SEQ ID NO 65
<211> LENGTH: 10
<212> TYPE: PRT
<213> ORGANISM: Artificial Sequence
<220> FEATURE:
<223> OTHER INFORMATION: Synthetic

<400> SEQUENCE: 65

Ala Val Arg Pro Leu Trp Val Arg Met Glu
1               5                   10

<210> SEQ ID NO 66
<211> LENGTH: 20
<212> TYPE: PRT
<213> ORGANISM: Artificial Sequence
<220> FEATURE:
<223> OTHER INFORMATION: Synthetic

<400> SEQUENCE: 66

Ser Arg Leu Ser Lys Val Ala Pro Val Ile Lys Ala Arg Met Met Glu
1               5                   10                  15
Tyr Gly Thr Thr
            20
```

NUCLEIC ACID CONSTRUCTS FOR PRESENTATION OF CD4 AND CD8 EPITOPES, CELLULAR TRANSFECTION AND USES THEREOF

CROSS-REFERENCE TO RELATED APPLICATIONS

This application is a continuation in part of PCT application No. PCT/US15/55042 filed Oct. 10, 2015 to which priority is claimed under 35 U.S.C. § 120 and claims benefit of priority under 35 U.S.C. § 119(e) to Provisional Application Ser. No. 62/062,325, filed on Oct. 10, 2014. This application also claims benefit of priority under 35 U.S.C. § 119(e) to Provisional Application Ser. No. 62/416,080, filed Nov. 1, 2016 the entire contents of which is hereby incorporated by reference as if fully set forth herein.

STATEMENT OF GOVERNMENTAL INTEREST

This invention was made with government support under DK063608 awarded by the National Institutes of Health. The government has certain rights in the invention.

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "20170407_15003-324US1_ST25.txt" created on Apr. 7, 2017 and is 61 KB in size. The sequence listing contained in this .txt file is part of the specification and is hereby incorporated by reference herein in its entirety.

BACKGROUND OF THE INVENTION

Self-recognition or immune tolerance is mediated by several mechanisms including presentation of a "self" peptide to a CD4+ or CD8+ T cell, eliminating, inhibiting, or converting autoreactive (self-reactive) T cells that would potentially attack a cell producing the autoantigen (self-protein) from which the particular epitope (peptide) is derived. Autoimmune diseases such as Type 1 diabetes (T1D), rheumatoid arthritis (RA), multiple sclerosis (MS), psoriasis, systemic lupus erythematosus (SLE), and inflammatory bowel disease (IBD) can develop when this process is deficient or altered, and the immune system inappropriately attacks the body's own tissues. The National Institutes of Health estimates that 23.5 million Americans suffer from an autoimmune disease. Due to the complexity of these diseases (resulting from a combination of multiple genes and environmental factors), it has been difficult to apply drugs or biologics targeting one or a few pathways to restore tolerance efficiently and durably.

Current therapies for autoimmune disorders concentrate on symptomatic response and on mitigating the immune system as a whole, which has the inherent drawback of increasing susceptibility to infections and otherwise controlled malignancies. Antigen-specific therapy has recently emerged as a potential long-term solution to autoimmune disorders, but eliciting appropriate immune responses (i.e. tolerance-inducing or tolerogenic) and targeting sufficient numbers of disease-driving T cells has proven difficult. Immune tolerance, which prevents an immunogenic response from developing upon self-recognition, is mediated by several mechanisms, primarily involving the presentation of "self" peptides to CD4+ or CD8+ T cells in a manner that results in the elimination, inhibition, or conversion of the autoreactive T cells that otherwise would potentially attack cells and tissues that are the source of autoantigens and/or support the production by B cells of antibodies that react against these autoantigens. Under normal conditions (in absence of inflammation or infection), the presentation of epitopes (peptides or regions of a protein antigen that are recognized by immune cells) by specialized antigen-presenting cells (APCs) typically instructs the immune cells not to attack cells and tissues bearing these particular autoantigens. APCs that acquire antigens exogenously (from their milieu) more effectively engage CD4+ T cells, whereas those producing antigens endogenously present epitopes mainly to CD8+ T cells. However, both CD4+ and CD8+ self-reactive T cells should be silenced in order to prevent autoimmunity.

APCs include "professional" hematopoietic cells, primarily dendritic cells (DCs) but also macrophages and B cells, and "non-professional" non-hematopoietic cells, primarily lymph node stromal cells that have most contact with immune cells. Only professional APCs have the ability to elicit a productive immune response in the presence of recognized inflammatory signals and pathogen elements. Absent such signals, professional APCs tend to induce tolerance to presented antigens, while non-professional APCs, which do not upregulate the costimulatory ligands required for full activation are by default robustly tolerogenic. Stromal cells express lower MHC levels, and some do not express MHC class II (MHCII). They also have more limited endocytosis compared to professional antigens. Thus, stromal cells primarily present endogenously expressed antigens on MHC class I (MHCI), and a specific subset of epithelial cells in the thymus expresses high levels of MHCII and is able to present endogenous antigens on MHCII via autophagy.

Stromal Cells (SCs) are non-professional APCs that inherently lack the accessory molecules needed to stimulate effector T cell responses and have limited ability to acquire exogenous antigens and present them. Lymph node stromal cells (LNSCs) are constantly in contact with circulating T cells. They can present endogenously expressed peptides to naïve CD8+ T cells, leading to their deletion or anergy (Cohen, et al. *J Exp Med* 207: 681-688; Fletcher et al. (2010), *J Exp Med* 207: 689-697; and Cire, et al. (2016) *Mol Ther*.). They also participate in the maintenance of Tregs (Baptista et al. (2014) *eLife* 3) although their MHC-II expression is limited to some subsets or transferred from DCs (Dubrot et al. (2014), *J Exp Med* 211: 1153-1166). SCs and parenchymal cells are more readily transfected by DNA vaccines and other non-viral vectors than DCs (Yin et al. (2014), *Nature reviews Genetics* 15: 541-555.). After the death of SCs, a limited quantity of antigens may be passed onto DCs, but the majority of endogenously expressed antigens are only presented as peptides on MHC-I to CD8+ T cells. Indeed, DNA vaccines can lead to a reduction of antigen-specific CD8+ T cells in T1D patients and delayed loss of C-peptide secretion without notable adverse effect (Roep et al. (2013), *Science translational medicine* 5: 191ra182). However, engagement of CD4+ T cells by endogenous antigens expressed from DNA vaccines is inefficient. When targeted to MHC-II using a lysosome-targeting signal, a single endogenously expressed peptide allowed engagement of diabetogenic CD4+ T cells and reduce disease incidence (Rivas et al. (2011) *J Immunol* 186: 4078-4087). However, multiple treatments (≥3) were required to achieve a measurable immunological response, yet without evidence for antigen-specific Treg induction (Rivas et al. 2011).

Although antigen-specific immunotherapy (ASIT) using a single antigen or epitope may achieve partial protection, they are likely not as effective as if diabetogenic T cells specific to multiple β cell Antigens (involved via epitope spreading) were targeted. Furthermore, MHC-II is absent or very low on most SC subsets, which restricts direct presentation to CD4+ T cells. While SCs do not readily migrate to the draining lymph nodes to engage T cells, there are reports of stromal cells trafficking from the peritoneum or adjacent adipose tissue into the local lymph nodes (Jalili et al. (2016) *PloS one* 11: e0146970; and Benezech et al. (2012) *Immunity* 37: 721-734).

Current antigen-specific therapies use either exogenously provided whole antigens or peptides delivered orally, intranasally or intravenously, which tend to be mostly processed onto major histocompatibility (MHC) class II molecules (MHCII) and presented as peptides to CD4+ T cells, or endogenously expressed proteins or peptides delivered by injection of DNA plasmids or viral vectors, which results mainly in MHC class I (MHCI) presentation to CD8+ T cells. These strategies, which cause the antigen to be presented primarily on MHCII (to CD4+ T cells) or on MHCI (to CD8+ T cells), have met with limited success.

A strategy and method for eliciting a broad tolerogenic response in autoreactive (self-reactive) T cells using antigen-specific therapy, which specifically targets the pathogenic T cells to modulate or prevent autoimmune disorders is needed in the art. The invention described herein addresses these needs.

SUMMARY OF THE INVENTION

The invention relates to nucleic acid constructs for optimal presentation of CD4 and CD8 epitopes and uses thereof in which a series of selected epitopes from multiple antigens are expressed, whereby the epitopes can be differentially targeted to the proper intracellular processing machinery for MHC class I (via proteasome) or class II (via endosome) presentation, respectively, and affect CD8+ or CD4+ cells, respectively. In addition, where tolerance rather than active immunity is desired, constructs can be co-expressed to produce inhibitory ligands or cytokines, which can interfere with the ability of the APC to activate T cells.

Methods to enable MHCII expression in other stromal cells and improve presentation of endogenous antigens on MHCII has been lacking in the development of more efficient tolerogenic DNA vaccines. Certain embodiments provided herein relate to new nucleic acid constructs that are designed to include a MHCII activator sequence that equips SCs with the ability to process and present CD4 epitopes on MHCII. Other embodiments pertain to new nucleic acid constructs that are designed for transfection into APCs and secrete epitopes out of the cell. Further, the new nucleic acid constructs may be complexed with polycationic molecules that further enhance their uptake into nonprofessional APCs.

One embodiment relates to an isolated nucleic acid construct encoding a polypeptide which comprises (a) a first sequence comprising an MHCII targeting sequence and one or more different epitope sequences intended for processing in endosomes; (b) a second sequence comprising one or more different epitope sequences intended for processing by cytoplasmic proteasomes; and (c) a cytosolic protease cleavage site located between the first and second sequences. Preferably, the epitope sequences in the first sequence are processed in endosomes for presentation to CD4+ T cells and the epitope sequences in the second sequence are processed in cytoplasmic proteasomes for presentation to CD8+ T cells. The construct may be complexed with at least one polycationic molecule to enhance transfection and processing once in the cell.

Typically, the nucleic acid construct further comprises (a) one or more endosomal proteolytic cleavage sites flanking the one or more epitope sequences of the first sequence; (b) one or more cytoplasmic proteolytic cleavage sites flanking the one or more epitope sequences of the second sequence; or (c) both (a) and (b). In some embodiments, the MHC class II targeting sequence is operably linked to the one or more different epitope sequences intended for processing in endosomes.

Another embodiment relates to an isolated nucleic acid construct encoding a polypeptide which comprises (a) a first sequence comprising an MHCII targeting sequence and one or more different epitope sequences intended for processing in endosomes; (b) a second sequence comprising one or more different epitope sequences intended for processing by cytoplasmic proteasomes; (c) a first cytosolic protease cleavage site located between the first and second sequences; (d) a third sequence comprising a MHC II expression activator sequence; and (e) a second cytosolic protease cleavage site located between the third sequence and either the first sequence or second sequence, or both. The epitope sequences in the first sequence are processed in endosomes for presentation to CD4+ T cells and the epitope sequences in the second sequence are processed in cytoplasmic proteasomes for presentation to CD8+ T cells. The construct may be complexed with at least one polycationic molecule to enhance transfection and processing once in the cell.

In some embodiments, the nucleic acid construct is DNA, or mRNA. The invention also includes an expression vector comprising the nucleic acid construct described above, which can be a viral vector.

In some embodiments the sequences of the nucleic acid construct are in the order, from 5' to 3': (a) the first sequence; (b) the cleavage site; (c) the second sequence.

In certain embodiments, the MHCII targeting sequence of the nucleic acid construct is selected from the group consisting of an upstream transferrin receptor domain 1-118; an upstream invariant chain domain 1-80; an upstream invariant chain domain 1-214; an upstream CD16 domain 1-23 and a downstream LAMP-1 domain 166-382; a downstream LIMP-2 domain 459-478; downstream a CD1a-d cytoplasmic tail; and a downstream PMEL domain 506-575.

The invention includes nucleic acid constructs wherein at least one epitope in the first sequence or the second sequences is from a self antigen, which preferably is a self antigen recognized in an autoimmune disease condition, This self antigen can be selected from the group consisting of type 1 diabetes, rheumatoid arthritis, multiple sclerosis, psoriasis, lupus, Crohn's disease and ulcerative colitis.

In certain embodiments, the cleavage site as described above is recognized and cleaved by a cytosolic protease. This cleavage site preferably is selected from the group consisting of a T2A cleavage site, a P2A cleavage site, an E2A cleavage site, and an F2A cleavage site.

Another embodiment pertains to a nucleic acid construct comprising (a) a first nucleic acid sequence comprising one or more different epitope sequences; and (b) a second nucleic acid sequence comprising a cell secretion signal sequence, wherein the second nucleic acid sequence is operably linked to the first nucleic acid sequence so as to promote cell secretion of the expressed one or more epitope sequences. This construct may also be complexed with at least one polycationic molecule.

In certain embodiments, the nucleic acid constructs described above are comprised of DNA, or mRNA. Related embodiments also includes an expression vector comprising the nucleic acid construct described above, which can be a viral vector.

Further embodiments include a tolerogenic DNA vaccine comprising the nucleic acid constructs as described above. In certain embodiments, the tolerogenic DNA vaccine has CpG motifs removed from the backbone of the DNA and optionally replaced by GpG motifs.

The nucleic acid constructs designed for secretion of epitopes harbor epitopes of a non-self antigen, for example an infectious disease antigen, preferably an antigen from a pathogen selected from the group consisting of a virus, bacteria, fungus, or parasite, or a cancer antigen. Other embodiments include an immunogenic DNA vaccine comprising the secretory nucleic acid construct as described above. The immunogenic DNA vaccine may have CpG motifs that are maintained in the backbone of the DNA or optionally added to it.

In some embodiments of the invention, at least one of the epitopes harbored on the construct is a mimotope.

In certain embodiments, the nucleic acid constructs are codon-optimized.

Further embodiments pertain to an isolated antigen-presenting cell that expresses the nucleic acid construct of any of the above-mentioned embodiments. The antigen presenting cell preferably is a dendritic cell, a macrophage, a B cell, a mesenchymal stromal cell, an epithelial cell, an endothelial cell and a fibroblastic cell.

Additional embodiments pertain to a peptide encoded by the nucleic acid construct described as any of the above embodiments, and a pharmaceutical composition comprising any of the nucleic acid constructs described above or any of the peptides encoded by these nucleic acid constructs or any of the cells containing the peptides or nucleic acid constructs. Such pharmaceutical compositions preferably also contain a pharmaceutically acceptable carrier.

Also disclosed herein is a method of inactivating a self-reactive T cell in a subject in need, comprising administering to the subject any of the described nucleic acid constructs or any of the cells that express the described nucleic acid constructs, where the epitope sequences comprise an epitope to which the subject is self-reactive, for example a diabetogenic antigen epitope.

Further, disclosed is a method of treating a subject suffering from an autoimmune disease, comprising administering to the subject any of the described nucleic acid constructs or any of the cells that express the described nucleic acid constructs. Examples of autoimmune diseases that are treated are selected from the group consisting of type 1 diabetes, rheumatoid arthritis, multiple sclerosis, psoriasis, Crohn's disease and ulcerative colitis.

Certain method embodiments disclosed herein inactivating a self-reactive T cell or treating an autoimmune disease may comprise further administering to the subject an immunosuppressive compound, which can be selected from the group consisting transforming growth factor beta (TGF-β), interleukin 10 (IL-10), interleukin 1 receptor antagonist (IL-1RA), interleukin 4 (IL-4), interleukin 27 (IL-27), interleukin 34 (IL-34), interleukin 35 (IL-35), programmed death-ligand 1 (PD-L1), inducible T-cell co-stimulator ligand (ICOSL), B7-H3, B7-H4, ILT3, ILT4, HVEM, VISTA, CD39, CD73, FAS, FAS-IL, indoleamine 2,3-dioxygenase 1 (IDO1), indoleamine 2,3-dioxygenase 2 (IDO2), acetaldehyde dehydrogenase 1 (ALDH1)/retinaldehyde dehydrogenase (RALDH), arginase 1 (ARG1), arginase 2 (ARG2), nitrous oxide synthase (NOS2), HMOX1, galectin-1, galectin-9, semaphorin 4A, and any combination thereof.

In specific method embodiments, the nucleic acid constructs comprise an epitope from an antigen selected from the group consisting of proinsulin, insulin, insulin B:9-23, R22E, E21G/R22E, glutamate decarboxylase 65 (GAD 65), insulinoma-associated protein 2 (IA-2), insulinoma-associated protein 2 beta (IA-2b heat shock protein 60, islet-specific glucose-6-phosphate catalytic subunit-related protein (IGRP), chromogranin A (ChgA), zinc transporter 8 (ZnT8), islet amyloid polypeptide (IAPP), regenerating islet 3A (REG3A), hybrid insulin peptide (HIP), REGII, ZnT8, Vitamin D binding protein (VDBP) and islet cell autoantigen 69 (ICA69).

Certain method embodiments pertain to a method for treating an autoimmune disease, comprising administering to a subject in need an isolated antigen-presenting cell of claim that expresses any of the nucleic acid constructs described herein or the tolerogenic DNA vaccines described herein.

Alternative method embodiments for treating an infectious disease comprise administering to a subject in need an isolated antigen-presenting cell as described herein that expresses any of the secretory nucleic acid constructs described herein.

BRIEF DESCRIPTION OF THE DRAWINGS

The present invention is illustrated by way of example, and not by way of limitation, in the figures of the accompanying drawings.

The following figures are illustrative only, and are not intended to be limiting.

FIG. 1 is a schematic drawing showing four alternate embodiments (FIG. 1A, FIG. 1B, FIG. 1C and FIG. 1D) of the inventive construct. Rectangles indicate epitope sequences, of which there can be one or more per each of the first and second sequences. n=an integer from 0 to 12. Circles represent the proteolytic cleavage site between the first and second sequences. The boxes marked "T" indicate an MHC class II targeting sequence.

FIG. 4A shows five exemplary constructs, which can contain natural peptides only, or some or all of the natural epitopes, such as the Ins2 and ChgA peptides, can be replaced with their mimotope counterpart. The MHC class II pathway-targeting sequences are shown in blue. FIG. 4B is a cartoon presenting the mechanism of peptide production intracellularly.

FIG. 5 (SEQ ID NOs: 1-7) is a table showing a selection of epitopes relevant to T1D, including sequences and characteristics of autoreactive T cells that have been previously isolated as reacting against these epitopes.

FIG. 7A is a series of graphs showing how transduced DCs were sorted based on intermediate GFP expression levels to correct for variations in transduction efficiencies and normalize expression of epitopes between groups. Data are representative of two experiments. The constructs used are depicted in FIG. 6, except for the superior IET4T construct (containing rearranged epitopes and T2A cleavage site), which is depicted on FIG. 2. FIG. 7B is a graph showing GFP MFI for the indicated cells, including All GFP+ (triangle) and sorted GFP+ (circle), from the work shown in FIG. 7A.

FIG. 8A is a series of plots showing FACS results of stimulation of ChgA-specific BDC2.5 CD4+ T cells. FIG. 8B is a graph showing the percent divided for the NO series (native epitope) and the NM series (mimotopes) of these experiments. Data are representative of two experiments, and show that these CD4+ T cells only respond to the mimotope and require a targeting signal for maximal response.

FIG. 9A is a series of plots showing FACS results of stimulation of Ins-specific BDC12-4.1 CD4+ T cells. FIG. 9B is a graph showing the percent divided for the NO series (native epitope) and the NM series (mimotopes) of these experiments. Data are representative of two experiments, and show that these CD4+ T cells respond better to the mimotope and require a targeting signal for maximal response.

FIG. 10A is a series of FACS plots showing cell sorting results after stimulation of Ins-specific G9C8 CD8+ T cells (TCR alpha-/- background). FIG. 10B is a graph presenting data for the NO series (native epitope only) and NM series (mimotopes included) constructs. Data are combined from two experiments, with the second experiment using frozen T cells. The results show that these CD8+ T cells only respond to the native epitope and respond better if the epitope is not diverted to the endosomal pathway.

FIG. 11A is a series of FACS plots showing cell sorting results after stimulation of IGRP-specific NY8.3 CD8+ T cells. FIG. 11B and FIG. 11C are graphs presenting data for the NO series (native epitope only) and NM series (mimotopes included) constructs. Data are representative of at least two experiments, and show that these CD8+ T cells respond best if the epitope is not diverted to the endosomal pathway (no mimotope available for this T cell clone, the response is already very strong to the native peptide).

FIG. 17 presents data on the stimulation of ChgA-reactive CD4+ T cells in vivo and in vitro using DCs electroporated with IET4T mRNA, with or without TGF-β mRNA. FIG. 17A is a series of plots showing FACS data for CD4+ CD25- T cells isolated from BDC2.5.GFP-Foxp3 mice, labeled with Violet Cell Proliferation Dye (VCPD) and stimulated for 3 days in vitro±exogenous TGF-β or in vivo in NOD Thy1.1 mice. FIG. 17B and FIG. 17C are graphs showing the data for divisions of the cells in vivo (FIG. 17B) and in vitro (FIG. 17C). FIG. 17D presents data for the % GFP-Foxp3 induced in vitro for the indicated cells/constructs. Arrows indicate exogenous TGF-β. FIG. 17E shows % GFP-Foxp3 induced in divided CD4+ T cells in vivo for the indicated cells/constructs. These data indicate that DCs expressing IET4T can efficiently engage ChgA-reactive T cells, but in vivo, the proliferation of these responding T cells is inhibited by co-expression of TGF-β, which is accompanied by an increase of Foxp3+ regulatory T cells, a desired outcome in the treatment of autoimmune diseases.

FIG. 18A Response of BDC2.5 CD4$^+$ T cells to WE14 peptide or 2.5 mimotope expressed and presented by DAPg7 fibroblasts from mixed (MIX) or segregated epitopes (SEG/AI), whereby TFR and Ii short are endosome-targeting signals (ETS). FIG. 18B Response of BDC12-4.1 CD4$^+$ T cells to native or mimotope (R22E) InsB(9-23) peptides expressed and presented by DAPg7 fibroblasts from mixed (MIX) or segregated epitopes (SEG/

AI). FIG. 18C Response of NY8.3 CD8+ T cells to IGRP (206-214) peptide expressed and presented by PCRC-5 lymph node stromal cells from mixed (MIX) or segregated epitopes (SEG/AI). FIG. 18D Expression of Foxp3 and CD25 by BDC2.5 CD4+ T cells stimulated by DAPg7 cells pulsed with exogenous peptide or transduced with endogenous epitope (construct AI). FIG. 18E Examples of constructs expressing epitopes from insulin, IGRP, GAD65 and ChgA, and also containing CIITA (AIC) or albumin secretion signal (BS).

FIG. 19A Luciferase signal from DNA vaccine given 'naked', or formulated with cell penetrating peptides (Polyplex), JetPrime (Polyplus) or Lipofectamine transfection reagents in bone marrow-derived DCs and the LNSC line PCRC-5 (SCs). FIG. 19B, FIG. 19C Response of BDC2.5 CD4+ T cells in the ILNs and PLNs 3 days after transfer in NOD.Thy1.1 mice and intradermal injection of AI or BS constructs (50 ug). FIG. 19D Tetramer identification of endogenous 2.5 mimotope-specific CD4+ T cells in NOD mice 3 days after intradermal injection of AI or BS constructs.

FIGS. 20A-20I. T cell responses to epitopes delivered by DNA. Expression of luciferase in excised tissues (FIG. 20A) and in live mice (FIG. 20B) 24 h after intramuscular (IM) and intradermal (ID) delivery. Proliferative response of adoptively transferred antigen-specific CD4+ T cells (FIG. 20C-20D; note that for FIG. 20C the groups of bar graphs represents, from left to right, CLM, ILN, PALN and PLN, with the PLN group showing a dramatic proliferation increase) and CD8+ T cells (FIG. 20D) 2.5 days after IM or ID vaccination. Expression of CD25 (FIGS. 20D-20F) and Foxp3 (FIGS. 20E-F) on adoptively transferred T cells. Expansion of endogenous CD4+ T cell specific for the 2.5 mimotope expressed among other epitopes in our DNA vaccines (FIGS. 20G-20I) 2.5 days after a single injection of DNA vaccine. Abbreviations: IS injection site; LN lymph nodes (PLN pancreatic, ILN inguinal, PPLN popliteal, CLN cervical, PALN periaortic); NI non-immunized.

DETAILED DESCRIPTION OF THE INVENTION

1. Introduction

Figure 1A:
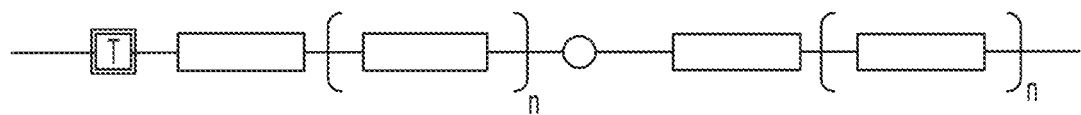
FIGS. 1A-1D.
Figure 1B:
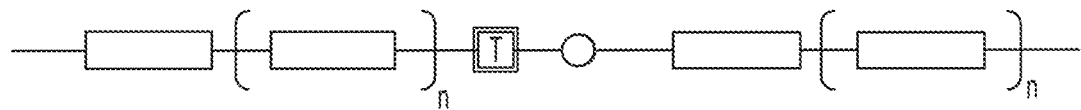
Figure 1C:
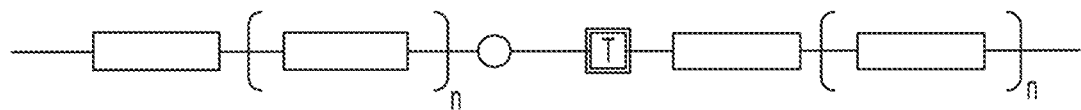
Figure 1D:
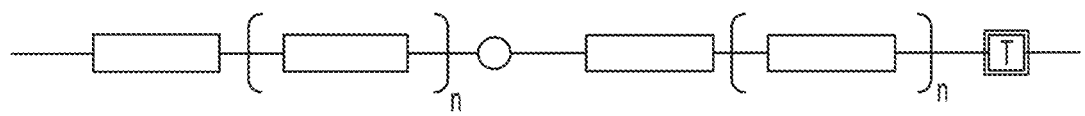

The invention relates to constructs, cells and methods for modulating the immune system that optimize presentation of CD4 and CD8 nonself- or self-epitopes to antigen-presenting cells, and in so doing optimize either tolerance or immunogenicity to those respective epitopes. The new constructs referred to as tandem epitope constructs (TEC), encode one or more dominant, disease-driving epitopes targeted for MHC class II processing within the endosomes of a cell and one or more epitopes targeted for MHC class I processing within the cytosol of the cell, to achieve maximum antigen/epitope presentation in the immune system. The two types of epitopes (CD4 and CD8) are separated from one another on the construct and grouped together for optimum processing in the cell. The invention can be used to either increase immune tolerance as is needed in autoimmune disease treatment by including a plurality of relevant epitopes from self antigens in the construct, or to increase an immune response (immune stimulation) for example to treat infectious diseases whereby several non-self epitopes are included in the construct. The TEC optimize presentation of both CD4 and CD8 epitopes to achieve a strong tolerogenic (including tolerance, ignorance or suppression of a response to the epitope(s)) or immunogenic response to both groups of epitopes by optimizing antigen/epitope presentation. By "optimizing" is meant increasing epitope presentation and engagement of a T cell, regardless of the eventual outcome of the engagement.

It has now been discovered that multiple relevant dominant, disease-driving epitopes can be administered to the subject without administering each protein individually. Instead, selected epitopes from different antigen proteins can be co-expressed as an artificial protein in a single construct in such a way that they are efficiently processed and presented on their appropriate MHC molecules. In one embodiment, this artificial protein construct is referred to as a "tandem epitope construct (TEC)." In an exemplary embodiment, the TEC includes a series of epitopes or mimotopes that are processed in endosomes for presentation on MHC class II to CD4+ T cells, and a series of epitopes or mimotopes processed by the proteasome in the cytoplasm for presentation on MHC class I for CD8+ T cells. The mimotopes in the TEC can optimally include analog peptides (also referred to by some as altered peptide ligands APL), but are not limited to them. Mimotopes that are rationally designed typically differ from the native epitope by a few amino acids, whereas those that are identified via a screening system may have a more substantial dissimilarity.

Insufficient induction of tolerance to self antigens from particular tissues is the major cause for tissue-specific autoimmune diseases. Under normal conditions, these tissue-specific antigens are presented by tolerance-inducing (tolerogenic) cells, which program T cells to not respond to these antigens. However, in autoimmune diseases, these antigens are presented improperly, instructing specific T cells to respond instead. Previous studies using antigen-specific immunotherapy have shown that administering certain antigens known to be involved in a particular autoimmune disease, systematically or via the mucosa, was effective in reinstating tolerance in animal models at least in part through the generation of suppressor T cells able to counteract improperly activated pathogenic T cells. However, many autoimmune diseases, and particularly the most common types of tissue-specific autoimmune diseases, involve multiple epitopes, a large number of which have been identified (DiLorenzo 2007) and continue being identified. Using the current methods, each protein comprising a relevant epitope(s) has to be administered to the subject to induce tolerance, and in contrast to animals, this led to poor efficacy in patients. Without being bound by any theory, this may be because a single antigen was chosen and/or because the native protein cannot produce the modified epitopes produced during the course of disease which can be better simulated by mimotopes. Finally, whole native antigens are delivered in these methods, either as protein (which is mostly acquired and processed to MHC class II in vivo) or as a DNA vaccine (which is mostly processed to MHC class I, unless the expressed product is secreted).

Thus, in an embodiment the TEC consists of (a) a first sequence comprising an MHC class II targeting sequence operably linked to one or more different epitope sequences (which epitopes are processed in the endosomes for CD4+ T cells); (b) a second sequence comprising one or more different epitope sequences (these epitopes are processed in the cytoplasm where the construct itself is originally delivered and therefore does not need to have any MHC targeting sequence); and (c) a cleavage site located between the first and second sequences to separate the two polypeptides and allow their differential targeting within the cell.

In this embodiment the epitopes are arranged into two groups: a first group of CD4 epitopes (for association with MHC class II) are included in a first sequence of the TEC to be targeted to the endosomes by using an appropriate MHC class II targeting sequence, and a second group of CD8 epitopes (for association with MHC class I) included in a second sequence of the TEC destined for processing in the cytoplasm and presentation on the surface in the context of class I. The position of the MHC class II targeting sequence with respect to the CD4 epitopes on the first sequence is either upstream or downstream of the epitopes, depending on the choice of MHC class II targeting sequence. See FIG. 1. This approach not only permits the expression of multiple disease-driving epitopes in a single construct but also results in each group of epitopes being optimally processed and presented onto their respective MHC molecules (class II for CD4 and class I for CD8).

Also deAntigens delivered exogenously rely primarily on dendritic cells (DCs) for presentation, some of which may be immunogenic. Also, disclosed herein are constructs intended to facilitate a greater involvement of stromal cells (SCs) to effectively engage and reprogram self-reactive T cells to achieve or reinstate tolerance. Particularly exemplified herein is endogenous delivery of epitope-expressing constructs in the form of DNA or RNA vaccines to non-professional APCs, such as SCs. The new embodiments disclosed herein involve nucleic acid constructs similar to the tandem expression construct (TEC) described above and shown in FIG. 1 except that they further include an MHCII activation sequence, which equips SCs with accessory molecules to enable MHCII processing and presentation of CD4 epitopes. Other new nucleic acid construct embodiments described herein include targeting signals that allow epitope-containing polypeptides to be secreted from transfected APCs, such as SCs, in which they are contained. In addition, it has been discovered that complexing the nucleic acid constructs with polycationic molecules enhances selective in vivo delivery to SCs over DCs. SCs tend to produce tolerogenic responses while DCs can produce tolerogenic or immunogenic responses depending on the signals received from their environment. Thus, other improvements to the nucleic acid constructs involve those that are packaged with such polycationic molecules.

Delivery of both CD4 and CD8 epitopes in the same construct ensures that each APC will acquire and express both or secrete both together. The only way to ensure that (and get optimal linked cooperation between CD4+ and CD8+ T cells) is that if all epitopes are delivered under the same construct. Linked cooperation is a natural process whereby a helper CD4+ T cell helps a CD8+ T cell to become activated. This requires the APC to bridge the two cells thereby presenting both epitopes. T cell help can be direct from the CD4+ T cell to a CD8+ T cell that is brought in close proximity via bridging APC, or the CD4+ T cell boosts the APC's immunogenicity, and the APC in turn becomes a better stimulator for the CD8+ T cell. If CD4 and CD8 epitopes are delivered on different constructs, there is no way to be sure that the CD4 and CD8 epitopes are co-expressed in the same APC, and thus that linked cooperation occurs. In the case of tolerance, the CD4+ T cells can be regulatory T cells (so-called "Tregs") that, instead of boosting the immunogenicity of APCs, dampen the APC's function and ensure that both autoreactive CD4+ and autoreactive CD8+ T cells receive tolerogenic signals. In the context of tolerance, Treg cells also can directly suppress the activation of autoreactive T cells upon concomitant interaction with APCs due to the close proximity. This process, known as linked suppression, equally relies on co-expression of both CD4 and CD8 epitopes by the same APC (Cobbold et al., $Immunol$ $Rev.$ 2010 July; 236:203-18).

Minicircle.

DNA vectors, devoid of bacterial components, are known to achieve much longer expression than conventional plasmids, and are likely small enough to facilitate drainage to lymph nodes for direct lymph node stromal cell (LNSC) targeting. Of interest, particular routes of injection (intraperitoneal) are suitable for drainage of particulate antigens to pancreatic lymph nodes (PLNs) (Turley, S, Lee, J, Dutton-Swain, N, Mathis, D, and Benoist, C (2005). Endocrine self and gut non-self intersect in the pancreatic lymph nodes. $Proc$ $Natl$ $Acad$ $Sci$ $USA$ 102: 17729-17733), where many diabetogenic T cells get activated. If LNSCs in the PLNs can be more efficiently targeted to present relevant antigens, their tolerogenic potential should not be adversely affected by the local proinflammatory environment that cause DCs to be immunogenic. Accordingly, disclosed herein are several innovative avenues to improve overall antigen delivery by DNA or RNA for safer and more effective antigen specific immune therapy, and more particularly to selectively transfect SCs, and exploit them to induce formation of tolerogenic APCs.

Tolerogenic Vaccines

TEC with MHCII Activator.

In certain embodiments, the nucleic acid constructs are similar to the modified tandem epitope constructs (TEC) set forth in the '986 publication are modified to include additional epitopes and features that further promote greater uptake and MHCII presentation by stromal cells. As described in more detail herein, stromal cells do not typically express MHCII molecules and consequently are not capable of processing and presenting CD4 epitopes. Nucleic acid constructs are disclosed that further incorporate an MHCII activator sequence in addition to both CD4 and CD8 epitope sequences. Similar to the tandem expression construct (TEC) described in the '986 publication, the CD4 and CD8 epitopes are separated by a protease cleavage site, and an endosome targeting sequence (ETS) is operably linked to the CD4 epitope(s). These new constructs when transfected into SCs equip the SCs with the cell machinery required for MHCII processing and presentation of CD4 epitope(s). SCs already can express MHCI and present CD8 epitope(s) thus SCs transfected with these nucleic acid constructs will be able present both CD4 and CD8 epitope(s).

Accordingly, one embodiment pertains to a nucleic acid construct that includes (a) a first sequence having an MHCII targeting sequence and one or more different epitope sequences intended for processing in endosomes; (b) a second sequence comprising one or more different epitope sequences intended for processing by cytoplasmic proteasomes and presentation onto MHCI; (c) a first cytosolic protease cleavage site located between the first and second sequences; (d) a third sequence comprising a MHCII expression activator sequence; and (e) a second cytosolic protease cleavage site located between the third sequence and either the first sequence or second sequence. It has been determined that stromal cells, along with certain parenchymal cells, are primarily transfected by DNA or RNA vaccines, but since they do not typically present CD4 epitopes, they have not been able to participate in the advantages of tandem epitope expression. Equipping stromal cells the ability to present both CD4 and CD8 epitopes by adding the MHC2 activator dramatically increases the tolerogenic potential of DNA vaccines.

Secretory Constructs.

It has been discovered that nucleic acid based vaccines can be engineered to secrete CD4 and/or CD8 epitope(s). Embodiments of these new constructs incorporate a secretion signal sequence that is operably linked to the CD4 and CD8 epitopes which directs secretion of these epitopes from the transfected cells. The secreted epitopes can then by endocytosed by surrounding APCs to initiate tolerance.

Accordingly, a further embodiment disclosed herein pertains to a nucleic acid construct that promotes secretion of epitopes that includes (a) a first nucleic acid sequence having one or more different epitope sequences; and (b) a second nucleic acid sequence having a secretion signal sequence, wherein the second nucleic acid sequence is operably linked to the first nucleic acid sequence so as to promote cell secretion of the expressed one or more epitope sequences from the transfected cell. The majority of cells transfected with DNA or RNA vaccines are stromal and parenchymal cells, which are typically located in regions where surrounding professional APCs are tolerogenic by default. Stromal Cells transfected with a new secretory nucleic acid construct will be able to secrete both CD4 and CD8 epitopes such that they can be endocytosed by surrounding tolerogenic APCs thereby inducing a tolerogenic immune response. These secretory nucleic acid constructs do not need an endosome targeting sequence (ETS), because the secreted epitopes will be endocytosed by the other cells and therefore localize in endosome. The ETS is only required for cytoplasmic/endogenous antigens to get to the endosomes. Also, there is no signal to transfer the endocytosed epitopes from the endosome to the cytoplasm, so there is no need for the other features added to the TEC described such as a proteolytic cleavage site to separate CD4 and CD8 epitopes or an MHCII activator sequence to promote expression of MHCII in the case of SCs. Though endocytosis by the professional APCs typically only results in presentation of CD4 epitopes, some of professional APCs have "cross-presentation" abilities thereby allowing them to process endocytosed epitopes for presentation on MHCI as well.

As explained, the TECs with MHCII activator construct or the secretory nucleic acid construct embodiments provided herein are well-suited for inducing tolerogenic immune responses. This is because they are tailored to transfect non-professional APCs, such as SCs, that naturally induce tolerogenic responses. However, it is contemplated that the secretory constructs could also be adapted to induce an immunogenic immune response after they are secreted by the APCs. In this context, the secretory nucleic acid constructs are engineered to include epitopes from non-self antigens such as bacterial or viral epitopes. These non-self antigen epitope containing secretory nucleic acid constructs are co-administered with an adjuvant. Use of the adjuvant increases the likelihood that APCs surrounding those transfected with the secretory nucleic acid construct are primed to be immunogenic such that when they endocytose the secreted epitopes they initiate an immunogenic response against such epitopes.

Complexing

The TEC constructs with an MHCII activator sequence or the secretory nucleic acid constructs described herein may also be complexed with polycationic molecules that enhance cell transfection. However, such complexes tend to be rapidly degraded in professional APCs such as DCs, thus productive transfection is more successful in stromal cells.

As explained above, presentation of dual CF4 and CD8 epitopes by stromal cells, or secretion of these epitopes by stromal cells increases the likelihood of inducing a tolerogenic response to such epitopes. Complexing nucleic acid constructs with polycationic molecules increases their tolerogenic potential because the polycationic molecules enhance their uptake by SCs over DCs. Examples of polycationic molecules include, but are not limited to, positively charged cell-penetrating peptides (such as polyarginine, polylysine or HIV Tat peptide), used in conjunction with calcium or not, or positively charged polymer molecules (such as polyethylenimine) The polycationic molecules associate with negative charges on the nucleic acid construct so as to fold and condense the construct. This condensing makes the construct smaller, which in turn facilitates migration of the construct and easier uptake into cells.

Further Uses and Delivery of Tolerogenic and Immunogenic Vaccines

In other embodiments, tolerogenic nucleic acid construct embodiments harboring self-antigen epitope sequences are delivered directly to tolerogenic APCs (or alternatively immunogenic nucleic acid construct embodiments harboring non-self antigen epitope sequences are delivered to immunogenic APCs) ex vivo using viral vectors or mRNA electroporation or other vector, or delivered directly in vivo in the form of tolerogenic DNA or RNA (or immunogenic) vaccines and the like. In some embodiments, the nucleic acid constructs are co-expression or co-administered with agents known to be immunosuppressive, such as TGF-β, IL-10, IL-1RA, IL-4, IL-27, IL-34, IL-35, PD-L1, ICOSL, B7-H3, B7-H4, ILT3, ILT4, HVEM, VISTA, CD39, CD73, FAS, FAS-L, IDO1, IDO2, ALDH1/RALDH, ARG1, ARG2, NOS2, HMOX1, galectin-1, galectin-9, semaphorin 4A, and any combination thereof can help APCs to reprogram autoreactive T cells into tolerant cells.

The tolerogenic or immunogenic ex vivo transfected APCs are then inoculated into subjects for therapy of autoimmune or infectious diseases, respectively. The use of mRNA in the constructs provides the option of co-delivering other mRNAs encoding tolerogenic ligands or immunosuppressive cytokines in the case of tolerogenic cells, and immunogenic ligands in the case of an infectious disease or other disease where an immune response to one or more particular epitopes is needed. It is expected that, when delivered to the appropriate tolerogenic cells or via a suitable route, this construct will allow reprogramming of many self-reactive T cells into programmed cell death, a state of unresponsiveness or suppressor cells. Regardless of the method of construct delivery (DNA vaccine, lentivirus, mRNA), all epitopes would be presented by the same APCs, allowing processes such as linked suppression and infectious tolerance whereby preexisting suppressor CD4+ cells specific to a particular (CD4) epitope can suppress self-reactive CD4+ or CD8+ T cells recognizing other epitopes from the expressed set of antigens, and reprogrammed CD4+ T cells can in turn become suppressor cells. Alternatively, immunogenic nucleic acid constructs carrying epitopes from non-self antigens such as bacterial epitopes can be delivered into immunogenic (immune-stimulating) APCs ex vivo that are then inoculated into subjects to fight certain infections or malignancies.

2. Definitions

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention. Moreover, it should also be understood that as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary. Hence, where appropriate to the invention and as understood by those of skill in the art, it is proper to describe the various aspects of the invention using approximate or relative terms and terms of degree commonly employed in patent applications, such as: so dimensioned, about, approximately, substantially, essentially, consisting essentially of, comprising, and effective amount.

Generally, nomenclature used in connection with, and techniques of, cell and tissue culture, molecular biology, immunology, microbiology, genetics, protein, and nucleic acid chemistry and hybridization described herein are those well-known and commonly used in the art. The methods and techniques of the present invention generally are performed according to conventional methods well known in the art and as described in various general and more specific references, unless otherwise indicated. See, e.g., Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Principles of Neural Science, 4th ed., Eric R. Kandel, James H. Schwartz, Thomas M. Jessell editors. McGraw-Hill/Appleton & Lange: New York, N.Y. (2000). Unless defined otherwise, all technical and scientific terms used herein have the same meaning as commonly understood by one of ordinary skill in the art.

As used herein and in the appended claims, the singular forms "a," "an," and "the" include plural references unless the content clearly dictates otherwise.

As used herein, the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

As used herein, an "adjuvant" is a compound that enhances or prolongs the antigen-specific immunostimulatory response produced by a vaccine. In the context of a DNA vaccine, there are three types of adjuvants that can be considered for use: (1) the adjuvant properties of the DNA vector itself, for example the presence and abundance of unmethylated CpG motifs, which act as an adjuvant by stimulation through the TLR-9 receptor, (2) genetic adjuvants, which are proteins expressed alongside antigen by the same or another co-administered DNA vector, including inflammatory cytokines and immunomodulatory cytokines that support specific subsets of T cells, and (3) conventional adjuvants, which can be co-injected with the DNA vectors, and include alum-based adjuvants, saponin-based adjuvants, certain bacterial elements known in the art, immunostimulatory complexes, and mineral oil-based adjuvants (Petrovsky and Aguilar, Vaccine adjuvants: current state and future trends. Immunol. Cell. Biol. 84:488-496, 2004. These are considered to be an adjuvant in the context of this invention. Genetic adjuvant plasmids and conventional adjuvants (such as aluminum salts, oil-based adjuvants, virosomes or squalene adjuvants), as known in the art also are contemplated for use with the invention.]

An "antigen," or "Ag" as the term used herein, is a structural substance, often a protein, that is recognized by the immune system and serves as a target for an immune response. A "self antigen" or "autoantigen" is an antigen derived from an organism which under normal circumstances is not recognized by the immune system of that organism, but which may become a target of immune attack, resulting in an autoimmune disease. A "cancer antigen" is an antigen present on cells of a tumor or other malignancy which is overexpressed or mutated in the tumor or other malignancy and so advantageously can be targeted as a non-self antigen for immune attack.

"Antigen-presenting cells" as used herein refer to any cell that can present, or can be induced to present, antigens in the context of MHCII and/or MHCI. Professional antigen-presenting cells (APCs) known in the art express high levels of MHCI and MHCII and can be highly immunogenic in the context of inflammation and infection. These cells, which typically include dendritic cell subsets, and to some extent macrophages and B-cells, can also be tolerogenic under steady-state conditions and other contexts. Non-professional APCs express MHCI and some inducible levels of MHCII, are typically tolerogenic and consist of stromal cells that include certain epithelial cells, fibroblastic cells and endothelial cells.

"Autoimmune diseases" are caused by an abnormal immune responses against self antigens, wherein the immune system attacks normal tissues or organs. Type 1 diabetes is an autoimmune disease where cells that recognize insulin or other beta-cell antigens have become activated and destroy pancreatic beta cells, leading to diabetes.

A "CD4 epitope," as used herein, refers to an epitope that is processed by or designed to be processed by the MHCII pathway and presented in the context of MHCII to CD4+ T cells.

A "CD8 epitope," as used herein, refers to an epitope that is processed by or designed to be processed by the MHCI pathway and presented in the context of MHCI to CD8+ T cells.

A "cleavage site," as used herein, is a short sequence of peptides within a sequence which is susceptible to proteolytic cleavage by one or more proteases, or by the translation machinery in the case of "2A" sites. The nucleic acid sequence encoding a cleavage site also is referred to as a cleavage site.

As used herein, the terms "codon-optimized" and "codon optimization" refer to a technique for improving protein expression in a cell, increasing translational efficiency of the gene, by using codons preferentially used in the system expressing the DNA. For example, bacteria use some codons rarely used by humans, therefore if the bacterial codon for a particular amino acid is substituted with the codon preferentially used by human cells, the protein will be translated more efficiently. Therefore, codon optimization refers to a method of using the codons most used in the species of interest for expression of foreign proteins or peptides.

The term "construct," as used herein, refers to an artificially synthesized sequence of nucleic acid which encodes a protein or peptide of interest, and generally contains promoters for expression of that protein or peptide in a cell.

A "cytosolic proteolytic cleavage site," as used herein, is a proteolytic cleavage site that is acted upon by a protease located in the cytosol, generally but not necessarily in association with a proteasome such that the site is cleaved in the cytosol. Thus, the terms "cytosolic proteolytic cleavage," "cytoplasmic proteolytic cleavage," and "proteasomal proteolytic cleavage" and their cognates are used interchangeably herein.

"Diabetogenic T cells" are beta-cell antigen-reactive T cells (self-reactive T cells) that have eluded tolerance mechanisms and eventually cause the destruction of beta-cells, leading to Type 1 diabetes.

A "DNA vaccine," in general terms, is DNA in the form of an expression plasmid for administration to a subject, which DNA contains the sequence of one or more antigens to which it is desired to produce an immune reaction in that subject. The desired reaction includes the opposite effects of increasing tolerance to the antigens, such as self antigens, or to stimulate an immune response, such as a response against microbial epitopes.

An "endosomal proteolytic cleavage site," as used herein, is a proteolytic cleavage site that is acted upon, preferably selectively acted upon, by a protease located in the endosome, such that the site is not cleaved appreciably until arrival in the endosome.

An "epitope," (also referred to as an "antigenic determinant") as the term is used herein, is the part of an antigen which is specifically recognized by the immune system. Epitopes are either in the form of peptides presented by MHC molecules and recognized by T cell through their T cell receptor, or correspond to exposed regions of a complete antigen that are recognized by B cells through their B cell receptor, and later by antibodies that these B cells produce. The term epitope is interpreted to include mimotopes unless indicated otherwise or if the context of the reference implies that only natural epitopes are being described.

"Epitope spreading" occurs when the immune reaction targets epitopes beyond the primary epitope or antigen. Responses can spread from one epitope to another epitope within the same antigen (intramolecular) or from an epitope of one antigen to an epitope of another antigen (intermolecular). Responses to autoantigens tend to become more diverse as the disease progresses. This also is referred to as "determinant spreading" or "antigen spreading," or diversification of the autoimmune response."

As used herein, the terms "expressing" or "expression" is intended to mean the transcription and translation of a nucleic acid by a cell. Expression can be, for example, constitutive or regulated such as by an inducible promoter or a tissue or cell specific promoter.

"Immune response" or "immunity" refers to a coordinated response by the immune system to defend an organism against infection or a disease, such as cancer.

"Immune tolerance" as used herein is the mechanism of non-self discrimination which allows the immune system to recognize foreign antigens, but not self antigens. Under normal conditions, tissue-specific self antigens are presented by tolerance-inducing (tolerogenic) cells, which program T cells to not respond to these antigens. Autoimmune disease results when these self antigens are not tolerized.

As used herein, a "immunogenic DNA (or RNA) vaccine" or a "immunostimulatory DNA (or RNA) vaccine" refers to a DNA or RNA vaccine designed to stimulate an immune response to the antigen(s) in the subject, thereby promoting the rejection of the antigen-expressing pathogens, infected cells or tumors. Typically, the antigens of an immunogenic DNA or RNA vaccine are non-self.

The term "MHCII activator sequence" refers to a sequence that induces production of MHCII molecules when expressed in a cell. One non-limiting example of an MHCII activator sequence is the Class II TransActivator (CIITA) sequence (see Kim et al., J Immunol 2008; 180:7019-7027).

As used herein, a "mimotope" is a molecule that mimics the three-dimensional structure of an epitope, and therefore has the same or a highly similar binding specificity, but may or may not have a different affinity or avidity. A "mimotope" causes an antibody response similar to that elicited by the epitope which it mimics. An antibody elicited against a particular epitope (antigen) recognizes a mimotope of that particular epitope, and a mimotope of a particular epitope can elicit an antibody response which binds that particular epitope. Therefore, one or more mimotopes can be used as a vaccine. A mimotope may be, as are most epitopes, a portion of a macromolecule, such as a protein, nucleic acid or polysaccharide. Preferably, it is a protein or a portion of a protein, and may be a peptide typically about 9 to about 20 amino acids in length. Mimotopes are either obtained by screening phage-display or peptide libraries, or by directed mutagenesis aimed at altering the binding properties of the peptide, according to methods known in the art.

"Minicircle DNA" as used herein refers small (2-4 kb) circular plasmid derivatives that have been freed from all prokaryotic vector parts. Since minicircle DNA vectors contain no bacterial DNA sequences, they are less likely to be perceived as foreign and destroyed. (Typical transgene delivery methods involve plasmids, which contain foreign DNA.) As a result, these vectors can be expressed for longer periods of time (in order of weeks or months) compared to conventional plasmids (days to weeks) (Minicircle DNA vectors devoid of bacterial DNA result in persistent and high-level transgene expression in vivo. Chen Z Y, He C Y, Ehrhardt A, Kay M A. Mol Ther. 2003 September; 8(3):495-500 and Minicircle DNA vectors achieve sustained expression reflected by active chromatin and transcriptional level. Gracey Maniar L E, Maniar J M, Chen Z Y, Lu J, Fire A Z, Kay M A. Mol Ther. 2013 January; 21(1):131-8. The smaller size of minicircles also facilitates their delivery into cells.

As used herein, the term "naked," with respect to naked DNA or naked RNA, refers to purified, histone-free DNA or RNA, without associated proteins and free of agents that promote transfection.

As used herein, the term "operably linked" or "operable link," and their cognates, has its usual meaning of an arrangement in which a genetic control sequence, e.g. a promoter, enhancer or terminator, is capable of exerting its function with regard to a polynucleotide being operably linked to it, for example a polynucleotide encoding a polypeptide. It has a further meaning for the purpose of this invention wherein it means that the MHCII targeting sequence in the first sequence of the TEC is located in a position that is in sufficient proximity to one or more epitope sequences in the first sequence of embodiments of the invention so as to target the group of expressed epitopes to the endosomes for processing by MHCII. The targeting sequence can be upstream or downstream, or can be composed of sequences placed both upstream and downstream of the DNA sequence to be targeted depending on the particular targeting sequence selected. The term operably linked also has a further meaning with respect to implementation of a secretion signal sequence, wherein it means that a secretion signal sequence is in sufficient proximity to a sequence encoding one or more epitope sequences such that the expressed one or more epitope sequences are secreted as a polypeptide from the cell in which they are expressed.

"Polycationic molecule," as used herein, refers to a positively charged molecule that when complexed to a nucleic acid construct induces its condensation into a more compact macromolecule and increases capture by cells. Transfection can be achieved in all types of cells, though at variable efficiency. Stromal cells and certain parenchymal cells that are replicate more frequently tend to be transfected a lot more efficiently than professional APCs, which tend to degrade DNA complexes before the DNA has a chance to escape from endosomes to cytosol. Polycationic molecules include small non-immunogenic peptides comprised of positively charged amino acids, such as polyarginine, poly-L-lysine and the HIV-based Tat peptide (GRKKRRQRRRPQ) (SEQ ID NO: 47). These peptides are typically referred to as cell-penetrating peptides (CPP). Other polycationic molecules include positively charged polymers such as polyethylenimine (PEI) and polyamidoamine (PAMAM). These polycationic molecules are described in more details elsewhere (Non-viral vectors for gene-based therapy. Yin H, Kanasty R L, Eltoukhy A A, Vegas A J, Dorkin J R, Anderson D G. *Nat Rev Genet.* 2014 August; 15(8):541-55). Upon endocytosis of the complexed nucleic acid construct, where there is a low pH inside the endosome, protons neutralize the negative charges of the nucleic acid sequence, and the polycationic molecules detach and can disrupt the membrane of the endosome.

A "protease" is an enzyme that cleaves protein sequences. A cytosolic protease is located in the cytosol of a cell; an endosomal protease is located in the endosomes of a cell.

Proteasomes are protein complexes inside all eukaryotes and archaea, and in some bacteria. In eukaryotes, they are located in the nucleus and the cytoplasm. The main function of the proteasome is to degrade unneeded or damaged proteins by proteolysis, a chemical reaction that breaks peptide bonds. The proteasomes referred to herein for processing of the TEC are cytoplasmic.

"Regulatory T cells" (Tregs) secrete regulatory cytokines (such as IL-10, IL-35 or TGF-β) and/or present inhibitory ligands (such as CTLA-4, LAG-3) that suppress immune responses. As a result, Tregs can inactivate T cells in a contact-independent manner (via suppressive cytokines) and/or via contact-dependent manner (via inhibitory receptors). Finally, Tregs dampen the immunogenic function of APCs, and can potentially render them tolerogenic. Tregs are involved in preventing autoimmune diseases and preventing tissue damage from excessive immune responses.

As used herein, the term "secretion" or "secreted" is intended to mean expression of a gene product into the extracellular space. Secreted peptides employ a leader sequence or signal sequence that directs the propeptide through the cell membrane. In eukaryotic cells, for example, the leader sequence is cleaved off in the rough endoplasmic reticulum to produce a mature polypeptide and the mature peptide is trafficked to the cell surface via vesicles. Construction of chimeric gene constructs containing leader sequences operatively linked to a coding region to effect the expression and secretion of mature peptide is well known in the art.

"Secretion signal" is a peptide that when operably linked to one or more epitopes directs secretion of the one or more epitopes out of the cells in which they are expressed.

"Secretion signal sequence" as used herein, is a nucleic acid sequence that encodes a secretion signal. One non-limiting example of a secretion signal sequence is a nucleic acid sequence that encodes an albumin secretion signal (see Maeda, Y, Soda, M, Ito, K, and Sato, K (1997). Efficient production of active TNF-alpha by albumin signal peptide. *Biochem Mol Biol Int* 42: 825-832). There are many signal sequences for various localizations (see links to cryst-.bbk.ac.uk/pps97/assignments/projects/dulai/signal.html#nocl or signalpeptide.de, for example), some of which are cleaved off and others remain attached to the targeted peptide. The albumin secretion signal is an example of a signal peptide that is both efficient and short, the latter being important in keeping the construct as small as possible for best transfection.

"Secretory nucleic acid construct" is a nucleic acid construct that is engineered to cause transfected cells to secrete CD4 and/or CD8 epitopes. Secretory nucleic acid constructs incorporate a secretion signal sequence that is operably linked to the CD4 and/or CD8 epitopes which directs secretion of these epitopes from the transfected cells. The secreted epitopes can then be endocytosed by surrounding APCs to initiate tolerance or immunogenicity.

A "sequence," as used herein, refers to the primary structure of a biological macromolecule or oligomolecule, or the ordering of monomers (nucleotides or peptides, for example) covalently linked within a biopolymer. A "targeting sequence" refers to a sequence of nucleotides within a sequence that causes targeting to a particular location or compartment of the cell, for example endosomes or the extracellular space.

"Stromal cells" (SCs) as used herein refers to cells that are part of the stroma. SCs are connective tissue cells of an organ and support the function of the parenchymal cells of that organ. SCs can include fibroblasts and pericytes, their precursors mesenchymal stromal cells, as well as certain types of endothelial and epithelial cells. In certain embodiments, stromal cells are lymph node stromal cells (LNSCs).

"T cells" are a type of lymphocytes. T helper cells (CD4+ T cells) become activated when they are presented with peptide antigens by MHCII molecules on the surface of antigen-presenting cells. Once activated, T helper cells divide and secrete cytokines that stimulate an active immune response. Cytotoxic T cells (CD8+ T cells) are activated by binding to antigen associated with MHCI molecules on the surface of antigen-presenting cells, and destroy virus-infected cells and tumor cells. These cytotoxic T cells also are implicated in transplant rejection. A self-reactive (or autoreactive) T cell is a CD4+ or CD8+ T cell that is or has been activated by a self antigen (or autoantigen).

A "tandem epitope construct" (TEC), as used herein, refers to a nucleic acid construct that contains multiple linked epitopes, which once expressed as one or two polypeptides, can be processed into peptides depending on the compartment where it is located and proteases present in that compartment, and presented onto MHC molecules as epitopes. The linked epitopes may not be naturally linked as they may originate from different antigens. In certain embodiments, TECs can contain two groups of such linked epitopes, where the groups are separated from each other by a proteolytic cleavage site, and where one group of epitopes destined for processing in the MHCII pathway for presentation to CD4+ T cells is operably linked to an endosomal targeting sequence and the other group of epitopes destined for processing in the MHCI pathway for presentation to CD8+ T cells does not. After cleavage at the proteolytic cleavage site, the two groups of epitopes in the tandem epitope construct are separated so that each group undergoes separate processing within the cell, one onto MHCII and the other one onto MHCI. Each epitope in each of the two groups may be separated by a proteolytic cleavage site so that once in the appropriate cellular compartment for processing, each epitope is cleaved from the other epitopes in the group. Experiments described in the examples use TEC designed to induce immune tolerance to the epitopes carried by the construct, although a TEC also can be designed in such a way as to increase an immune response to certain epitopes, for example those from bacterial antigens.

As used herein, "therapeutically effective amount" or "an effective amount" have the standard meanings known in the art and are used interchangeably herein to mean an amount sufficient to treat a subject afflicted with a disease (e.g., diabetes) or to alleviate a symptom or a complication associated with the disease.

A "tolerogenic DNA vaccine" refers to a DNA vaccine designed to produce tolerance or anergy to the antigen(s), or to achieve reprogramming of CD4+ T cells reactive to the antigen(s) to antigen-tolerant and suppressive "Tregs" in the subject, thereby preventing rejection of autoantigen-expressing cells and tissues.

As used herein, "treating" and "treatment" have the standard meaning known in the art to mean slowing, stopping or reversing the progression of diabetes or other autoimmune diseases, or conversely to mean enhancing or accelerating an immune response meant to eradicate an unwanted pathogen or tumor. "Treatment," thus, for example, covers any treatment of diabetes in a mammal, particularly in a human.

A "vector" generally refers to a DNA molecule used as a vehicle used to carry foreign genetic material into a cell, where it can be expressed. As used herein, the term refers to any means for inserting a nucleic acid into a cell, and includes mRNA, plasmids, viral vectors, cosmids, artificial chromosomes, expression constructs and the like.

3. Overview

Presenting immune cells to a part of a "self" antigen, or epitope, typically instructs the immune cell not to attack cells bearing that peptide. In autoimmune disorders, often this presentation is deficient or occurs in a context that promotes T cell activation rather than inactivation. Epitopes produced ex vivo and injected into a patient as part of proteins, or produced from the hosts' own cellular machinery following delivery of DNA has been shown to initiate immune tolerance in animal models and some patients with autoimmune disease. However, exogenous proteins mostly results in presentation of epitopes that are seen by CD4+ T cells, whereas endogenously produced epitopes are mainly recognized by CD8+ T cells, both of which cell types are implicated in autoimmune responses and are important for robust immunological response. Therefore, neither previously known approach is optimal for the treatment for autoimmune disease.

In addition another challenge of many tissue-specific diseases (such as T1D, MS, RA) is that the autoimmune response targets an increasing number of antigens from the same target tissue (epitope spreading), such that subsequent induction of tolerance to one antigen may not completely block the disease. Tolerance induction to multiple antigens is more difficult to achieve when so many antigens all need to be administered or expressed to achieve immune tolerance.

Exogenous delivery of antigens generally leads to uptake by professional APCs, the tolerogenic function of which may become compromised under inflammatory conditions. In addition, these antigens are primarily presented on MHCII to CD4+ T cells, while CD8+ T cells represent the predominant islet-infiltrating lymphocyte population in human T1D, for example. Endogenous delivery of antigens, as with DNA vaccines, can achieve expression in a wide range of cells, including non-professional APCs. Non-professional APCs, such as fibroblastic and endothelial cells, can mediate CD8+ T cell tolerance and cannot become immunogenic (Lukacs-Kornek & Turley, 2011, Curr. Opin. Immunol, 23:138). For example, a ProIns DNA vaccine reduced the frequency of insulin-reactive CD8+ T cells in T1D patients, but the effect on CD4+ T cells remains unclear (Roep et al., 2013, Sci. Transl. Med, 5(191):191ra82). Furthermore, the same treatment in NOD mice, although therapeutically beneficial, did not significantly promote active tolerance that is typically mediated by regulatory CD4+ T cells (Solvason, J. Immunol, 181(12):8298-307, 2008). However, when applied to multiple sclerosis patients, this treatment dramatically reduced myelin antigen-specific CD4+ T cells (Bar-Or, Arch. Neurol. 64(10):1407-15, 2007). Systemic delivery of peptides provides the advantage of direct binding to both MHCI and MHCII on many cell types with evidence of Treg cell induction, but the half-life of these peptides is very short and the effect more diluted.

With the recent findings that autoreactive T cells can be more responsive to peptides bound to MHC in an uncommon conformation (Stadinski et al., PNAS, 107(24):10978-83, 2010) or to post-translationally modified peptides (DeLong et al., 61(12):3239-46, 2012; van Lummel et al., Curr. Opin. Endocrinol. Diabetes Obes. 20(4):299-306, 2013), it has become clear that mimotopes are beneficial in targeting such T cells. For example, the mimotope that mimics InsB:9-23 bound to I-Ag7 on register #3 (one of the position in which the peptide can fit in the MHC groove) was found to be greatly superior to the corresponding native epitope in preventing T1D and inducing Treg cells in NOD mice (Daniel et al., J. Exp. Med. 208(7):1501-10, 2011) and humanized mice (Type 1 diabetes vaccine candidates promote human Foxp3(+)Treg induction in humanized mice. Serr I, Fürst R W, Achenbach P, Scherm M G, Gökmen F, Haupt F, Sedlmeier E M, Knopff A, Shultz L, Willis R A, Ziegler A G, Daniel C. Nat Commun. 2016 Mar. 15; 7:10991). Furthermore, more of such insulin mimotope-specific T cells can be found circulating in T1D patients, and they have a more proinflammatory phenotype (Regulatory vs. inflammatory cytokine T-cell responses to mutated insulin peptides in healthy and type 1 diabetic subjects. Nakayama M, McDaniel K, Fitzgerald-Miller L, Kiekhaefer C, Snell-Bergeon J K, Davidson H W, Rewers M, Yu L, Gottlieb P, Kappler J W, Michels A. *Proc Natl Acad Sci USA.* 2015 Apr. 7; 112(14):4429-34.

Antigen-specific therapies aimed at increasing tolerance to self antigens currently use methods that target either MHCI or MHCII pathways, but not both optimally. This has extremely limited success, especially in autoimmune diseases where epitope spreading occurs (T1D, MS, RA). In such diseases, both the T cell and antibody responses diversify against an increasing number of antigens from the target tissue. In T1D, there is solid evidence that insulin is one of the major driving antigens, if not the initial one, for the disease (Nakayama, Diabetes Metab. Res. Rev. 27(8):773-7, 2011). Antigen-specific therapies in preclinical and clinical studies for diabetes so far have involved administering proinsulin, insulin, glutamate decarboxylase 65 (GAD65) or heat shock protein 60 (HSP60) one at a time, however, although encouraging there has been only limited success in humans. See Lernmark & Larsson, Nat. Rev. Endocrinol. 9:92-103, 2013; Ryden et al., Hum. Vaccines Immunother. 10, 2013; Coppieters et al., Clin. Immunol. 149:345-355, 2013; See Michels & von Herrath, Current Opinion in Endocrinology, Diabetes & Obesity, 2011. It has been hypothesized that the failure to induce robust tolerance in diabetics using this method is a result of introducing only one or a very few disease-driving antigens at a time, which may not be sufficient to counteract the widely diversified immune responses evident in the advance stages of disease.

Prior methods have reported the delivery of multiple antigens via either exogenous delivery of mixed recombinant proteins or endogenous expression from DNA vaccine vectors or mRNA. The use of different MHCII targeting sequences to direct antigens to the endosome or lysosome for MHCII processing has also been reported for full proteins (Fernandez et al., Eur. J. Immunol., 2000; Diebold et al., Gene Therapy, 2001, etc) and peptide (Targeting of a T cell agonist peptide to lysosomes by DNA vaccination induces tolerance in the nonobese diabetic mouse. Rivas E I, Driver J P, Garabatos N, Presa M, Mora C, Rodriguez F, Serreze D V, Stratmann T. *J Immunol.* 2011 Apr. 1; 186(7): 4078-87). Known methods include targeting antigens to either the cytoplasm, favoring processing of epitopes onto MHCI, or the extracellular milieu from which endocytosed antigens end up in the endosome or lysosome for processing onto MHCII, but not both. Although subsets of APCs have the capability of cross-presentation (channeling some exogenous antigens to MHCI) and/or autophagy (redirecting some endogenous antigens to endosomes, which may be processed onto MHCII), this property can be greatly generalized and amplified by the present invention. Immune response strategies are discussed, for example, in Diebold et al., Gene Therapy 8:487-493, 2001; Sanderson et al., P.N.A.S. USA 92(16):7217-7221, 1995; U.S. Pat. No. 6,759,234; EP 0 960 119; and WO 1997/049430. Delivery to the cytoplasm and endosomes differentially affects how epitopes are presented to CD4+ or CD8+ T cells, except in a minority of cells capable of cross-presentation. Thus, antigen-specific therapies targeting multiple antigens would benefit from approaches which permit the processing of each antigen through the appropriate presentation pathways within the same cell. Herein are proposed constructs that address this therapeutic need.

4. Summary of the Results

Currently, there is no cure for the most complex, multifactorial autoimmune diseases such as T1D, RA or MS, but studies in animal models suggest that these diseases may be prevented or treated through successful restoration of antigen-specific immune tolerance, by exposing target T cells to a broad panel of relevant self antigens while imposing potent tolerance-inducing (tolerogenic) signals and dampening inflammation. Using the inventive methods, several constructs, containing several CD4/CD8 epitopes and various endosome-targeting signals and/or cleavage sites, were expressed in dendritic cells, which were used to stimulate purified T cell receptor transgenic T cells specific for these epitopes. When available, mimotopes were compared with native peptides.

The inventive constructs are called "tandem epitope constructs (TEC)" and contain two groups of epitopes, one group that is intended for processing in cytoplasmic proteasomes for MHC class I presentation to CD8 cells, and one group intended for processing in the endosome for MHC class II presentation to CD8 cells. It was discovered that including an MHC class II targeting signal operably linked to the group of epitopes intended for presentation to CD4+ T cells but allowing the epitopes intended for presentation to CD8+ T cells to remain in the cytoplasm has enabled proper targeting and improved interaction with the immune system using only one nucleic acid coding sequence for the epitopes. The result is improved engagement of target T cells.

Figure 2:
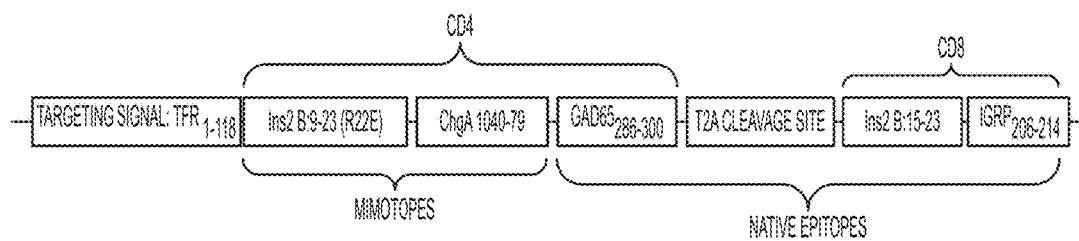
FIG. 2 is a more detailed schematic showing an embodiment of the inventive nucleic acid construct, with the indicated epitopes and mimotopes. The figure shows a representative construct (IET4T) according to some embodiments of the invention, comprising an MHC class II targeting sequence, a string of epitopes and mimotopes for processing to CD4+ T cells, a T2A cleavage site, and a string of epitopes for processing to CD8+ T cells.

The inventors here have found that adding an MHC class II targeting sequence to antigens which are intended for processing to both compartments improved stimulation of CD4+ T cells, but diminished that of CD8+ T cells. This is because the MHC class II targeting sequence also caused the CD8 epitopes as well as the CD4 epitopes to bypass cytoplasmic processing and presentation to CD8+ T cells. Superior engagement of both CD4+ and CD8+ T cell clones was obtained using constructs in which CD4 and CD8 epitopes were grouped together and physically separated by a proteolytic cleavage site which is cleaved in the cell after translation to detach the CD8 epitopes from the CD4 epitopes prior to transport of the targeted sequence to the endosome for MHC class II processing. FIG. 1 and FIG. 2 show a TEC in which two groups or strings of epitopes were joined in one sequence, but separated by a proteolytic cleavage site so that one group, having a targeting sequence for endosomal delivery and class II processing was processed and presented to CD4+ T cells in endosomes, while the other group without an added target sequence, was processed and presented to CD8+ cells in the cytoplasm.

The methods of culture, transduction, electroporation, and the like, of dendritic cells were confirmed not to harm the cells (A short pulse of IL-4 delivered by DCs electroporated with modified mRNA can both prevent and treat autoimmune diabetes in NOD mice. (Creusot et al., Mol. Ther. 18 (12):2112-2120, 2010).

The new TECs increased presentation of multiple epitopes by both pathways. Autoimmune cells such as diabetogenic T cells can now be targeted by endogenous delivery of a plurality of selected epitopes arranged in such a way that both CD4 and CD8 epitopes can be targeted optimally for proper presentation on MHC class II and class I, respectively. Furthermore, the data presented here show that substitution of certain native epitopes by mimotopes enhances engagement of particular T cell clones. Mimotopes typically allowed for better engagement of target CD4+ T cells than native epitopes, which were poorly or not at all recognized. For example, the native insulin B:9-23 epitope can bind to MHC class II in three different conformations called registers. The register that is recognized by diabetogenic T cells is one that is uncommon because of weak binding. By a single mutation, the binding in the desired conformation can be favored so that diabetogenic can be more efficiently engaged by the APC (Stadinski et al., Proc. Natl. Acad. Sci. USA. 107 (24):10978-10983, 2010). Another example is an epitope from another beta cell antigen, chromagranin A (ChgA). A well-known diabetogenic CD4+ T cell clone is incapable of reacting to the native peptide, but if the latter is post-translationally modified by the enzyme transglutaminase, it becomes strongly recognized (Delong et al., Diabetes 61(12):3239-3246, 2010). Mimotopes have been identified by screening peptide libraries that are able to efficiently stimulate those T cells, thus in a way simulating those modified antigens (Judkowski et al., J. Immunol. 166 (2):908-917, 2001; You et al., J. Immunol. 170(8):4011-4020, 2003). Of interest, the insulin B:9-23 CD4 epitope, recognized by the BDC12-4.1 CD4+ T cell clone contains the B:15-23 CD8 epitope recognized by the G9C8 CD8+ T cell clone. While the R22E mutation (mimotope) enhanced the stimulation of the CD4+ T clone, it abrogated recognition by the CD8+ T clone, indicating a benefit of including multiple variants for each epitope, as done in some embodiments of the TECs (see FIG. 2 and FIG. 15).

DNA constructs have been produced that express major epitopes from multiple β cell antigens, whereby CD4 and CD8 epitopes (or mimotopes) are both optimally presented by SCs (and DCs) after endogenous delivery (FIG. 18). Presentation of CD4 epitopes by MHC-II+ SCs after endogenous delivery can generate a high frequency of Foxp3+ T cells among the stimulated CD4+ T cells in vitro (FIG. 18D).

Figure 19A:
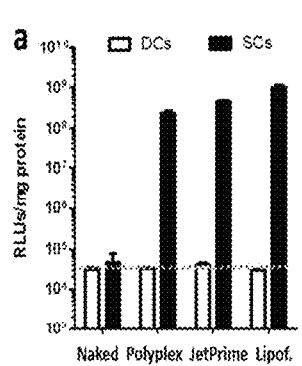
FIGS. 19A-19D.

A luciferase-expressing DNA vaccine complexed with positively-charged cell-penetrating peptides (CPPs, small non-immunogenic, polylysine) or PEI polymer (Polyplus JetPrime) lead to high levels of transfection and expression in SCs but not in DCs in vitro, confirming that SCs will be more likely targets of DNA vaccines complexed with polycationic molecules (FIG. 19A).

Figure 19B:
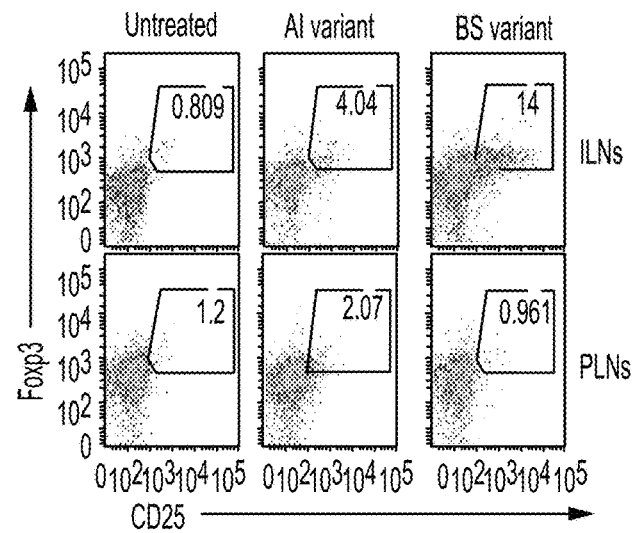
Figure 19C:
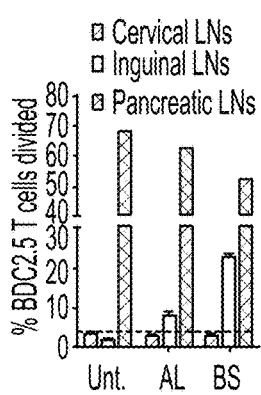
Figure 19D:
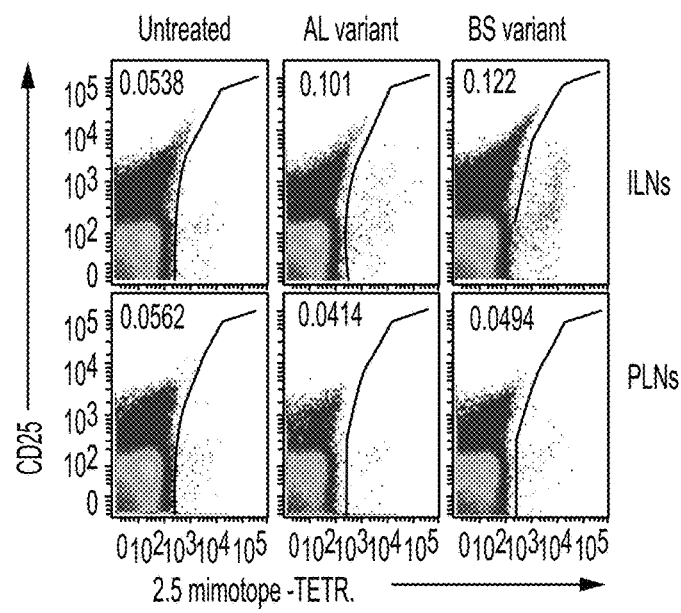

In adoptive transfer experiments, DNA vaccine containing nucleic acid constructs described herein in 'naked' form generated an encouraging response in the draining (inguinal) lymph nodes after a single intradermal injection, with a substantial proportion of CD25+ Foxp3+ Tregs and moderate proliferation (FIGS. 19B-19C). In contrast, the same CD4+ T cells proliferated extensively to endogenous antigens in the PLNs, without CD25 or Foxp3 upregulation (FIGS. 19B-19C). Responding endogenous T cells were also observed after a single treatment (FIG. 19D). Based on this in vitro data, even more pronounced responses with complexed DNA are expected.

Figure 18A:
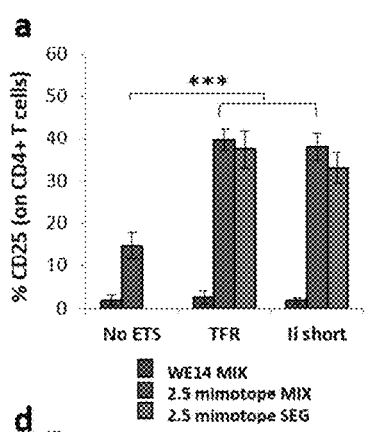
FIGS. 18A-18E.
Figure 18B:
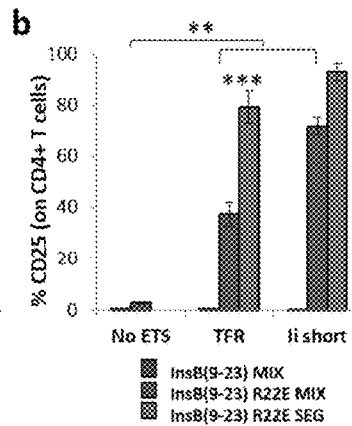
Figure 18C:
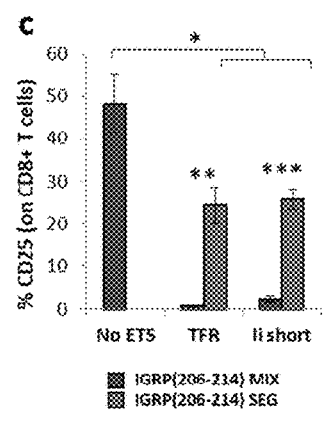
Figure 18D:
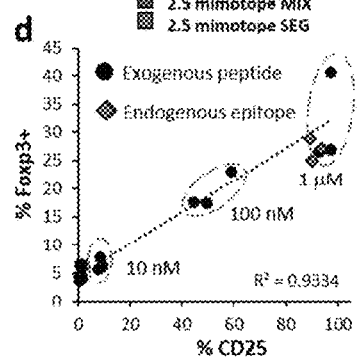
Figure 18E:
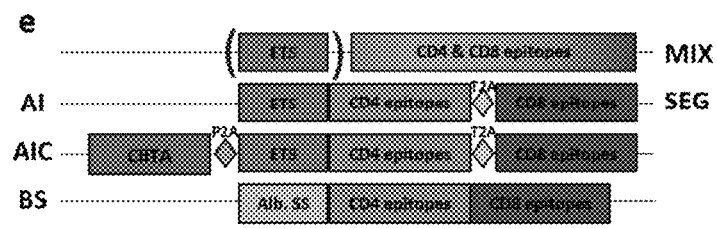

A variant of the DNA vaccine construct described above and shown in FIG. 1 (see AI construct of FIG. 18E) has been produced whereby CIITA (a transcription factor known to induce expression of MHCII molecules) is co-expressed with the epitopes (see AIC construct in FIG. 18E). This AIC construct enables robust MHC-II expression in a wide range of transfected SCs[14-18].

5. Detailed Description of Embodiments

Certain embodiments of this invention are directed primarily to tolerogenic nucleic acid constructs carrying a fusion peptide sequence encoding a operably linked endosomal MHCII targeting sequence followed by one or more epitope sequences for CD4+ T cells (presented on MHCII), a series of one or more CD8 epitope sequences (presented on MHCI), with a cleavable linker separating the two epitope sequences and an MHCII activator sequence operably linked to the one or more epitope sequences. This new construct enables delivery into a single cells of multiple disease-driving epitopes expressed by a single nucleic acid-based (DNA or RNA) construct or multiple mRNA molecules in the same complex that initiates immune tolerance to both autoreactive CD4+ and CD8+ T cells through optimized antigen presentation and processing and equips transfected stromal cells with the ability to present CD4 epitopes on MHCII. While the nucleic acid constructs carry an MHCII targeting sequence operably linked to the CD4 epitopes intended for processing in endosomes, it is not necessary to include an MHCI targeting sequence for CD8 epitopes because the construct is delivered to the cytoplasm where these epitopes will be processed via proteasomes, according to the normal cellular process.

The two major groups of epitopes are separated by a cleavage site allowing the CD8 epitope section to be cleaved off and remain cytoplasmic for processing in cytoplasmic proteasomes, while the CD4 epitope section is targeted to the endosomes using an appropriate MHCII targeting sequence. Thus, the invention provides a highly customizable fusion peptide with epitopes for presentation to non-professional antigen-presenting cells that can be delivered via a DNA tolerogenic or immunogenic vaccine, lentivirus, mRNA, or any other appropriate vector to carry two series of epitopes, for example from self or non-self antigens, to ensure each group of epitopes reaches the appropriate cellular compartment for proper presentation to both CD8+ (cytoplasm) and CD4+ T cells (endosomes) and are presented on MHCI and MHCII molecules.

Typically, each epitope is flanked on each side by at least two amino acids corresponding to their natural flanking amino acid residues in the native protein. The epitopes are naturally processed and generated in the cell using these natural sequences. This creates a "spacer" of at least 4 amino acid residues between each epitope, that also acts as a proteolytic cleavage site. As a general rule, residues that flank CD4 epitopes contain natural endosomal proteolytic cleavage sites, whereas those that flank CD8 epitopes contain natural proteosomal cleavage sites. Using artificial flanking sequences carries unknown risks that some epitopes may not be processed properly or bind properly on the MHC. For mimotopes, flanking sites of the corresponding native peptides can be used and may be compared with artificial flanking residues or spacers. Embodiments of the nucleic acid constructs comprise the natural flanking sequences that flank the epitope in the whole protein, instead of artificial flanking sequences. This is useful because it is known that these epitopes are naturally processed and generated in the cell using these natural sequences. Artificial flanking sequences increase the risk that adjacent amino acids will affect the binding on MHC. For mimotopes, flanking sites of the respective native peptides are used.

Other embodiments are directed to nucleic acid constructs that include one or more epitope sequences, typically at least one CD4 epitope sequence and one CD8 epitope sequence, that are operably linked with a secretion signal sequence. In a specific embodiment, the nucleic acid construct includes (a) a first nucleic acid sequence having one or more different epitope sequences; and (b) a second nucleic acid sequence having a secretion signal sequence, wherein the second nucleic acid sequence is operably linked to the first nucleic acid sequence so as to promote cell secretion of the expressed one or more epitope sequences. As noted above, the majority of cells productively transfected with the nucleic acid constructs are stromal cells. Stromal cells are typically located in regions whereby surrounding professional APCs are tolerogenic. Stromal cells transfected with this nucleic acid construct will not present the expressed epitopes but will secrete them such that they can be endocytosed by these tolerogenic APCs thereby inducing a tolerogenic immune response. An ETS is not required when the epitopes are secreted, because the secreted epitopes will be endocytosed by the other cells and therefore localize in endosomes. The ETS is only required for cytoplasmic antigens to get to the endosomes and extracellular antigens end up there automatically upon endocytosis. Also, there is no signal to transfer the endocytosed epitopes from the endosome to the cytoplasm, so there is no need for a proteolytic cleavage site to separate CD4 and CD8 epitopes. Though endocytosis by the professional APCs typically only results in presentation of CD4 epitopes, some of professional APCs have "cross-presentation" abilities thereby allowing them to process both CD4 and CD8 endocytosed epitopes.

The nucleic acid constructs may be codon-optimized for the species in which the construct is used. Codon optimization may include nucleotide changes that reduce or enhance the immunogenicity of the vector without altering the amino acid sequence.

Further, methods of producing a robust immune response using immunogenic nucleic acid constructs which comprise non-self pathogenic epitopes are provided. For example in the case of infectious disease or cancer (where the problematic organisms or tumor cells need to be destroyed) where the pathogen or tumor displays several antigens comprising CD4 and CD8 epitopes, vaccination would need to overcome the same difficulties regarding suboptimal epitope presentation as discussed above in the context of tolerance. Many vaccines only produce a predominant CD4 or CD8 T cell response, but not both. Therefore mixing CD4 and CD8 epitopes in the immunogenic nucleic acid construct, combined with appropriate adjuvants or APC modification to promote immunogenicity, generates a stronger and more balanced immune response. Typically, and preferably, vaccines designed to promote immune stimulation with respect to the antigen(s) incorporate use of adjuvants to induce the necessary signals to promote immunogenicity. Antigens without adjuvant tend to promote tolerance. Such adjuvants are taught in the art, for example by Sasaki et al., Methods, 31(3):243-254, 2003. Any of these adjuvants and adjuvant methods are contemplated for use with the invention.

The TEC nucleic acid constructs that include an MHCII activator sequence contains appropriate targeting signals to allow the cells' natural machinery to deliver and process peptides to endosomes for greater efficiency of MHCII processing. In the case of DNA/RNA-mediated endogenous delivery to tolerogenic APCs, this feature ensures robust presentation to CD4+ T cells, many of which can acquire immune suppression properties. The TEC type constructs further optionally contain appropriate proteolytic cleavage sites flanking each epitope that permits them to be separated easily into individual peptide epitopes once the translated polypeptide has been cleaved between the sections in the cytoplasm and arrived at the appropriate compartment (endosome for class II or proteasome for class I). This arrangement allows each group of epitopes to be optimally processed and presented onto their respective MHC molecules. In an embodiment for treatment of diabetes, for example, the TEC allows targeting of both CD4+ and CD8+ diabetogenic T cells for deletion or suppression across multiple beta-cell antigens, using the herein-described tolerogenic DNA vaccination strategy that has a good safety profile in T1D patients (Roep et al., 2013). In another embodiment, the TEC can be introduced into tolerogenic APCs by transfection or transduction of DNA/RNA material for cell therapy. For example, tolerogenic dendritic cell therapy has been is well-tolerated in T1D patients (Giannoukakis et al., Diabetes Care, 34:2026-2032, 2011). In another embodiment, the TEC is designed to carry bacterial or viral epitopes or cancer epitopes, for example, to create an immunogenic DNA vaccine to increase immune stimulation of both CD4+ and CD8+ T cells that attack infecting organisms, or tumor cells, respectively.

The antigens encoded by the nucleic acid constructs can be customized not only for various diseases requiring either immune tolerance such as autoimmune diseases or immune stimulation such as infectious diseases, but can also be customized for individual patients to elicit the greatest tolerance response or the greatest immune response. Various immunoassays exist to determine whether some immune cells circulating in the blood in a given patient develop an immune response to particular peptides tested. Alternatively, the antigens selected can be based on the most common reactivity seen in a class of patients. Because it is customizable, native peptides may be mutated for better targeting of specific types of self-reactive T cells (those requiring post-translational modifications or an uncommon MHC binding register). The nucleic acid constructs provide a way to ensure endogenous expression of dominant disease epitopes (including modified neoepitopes) that cannot be achieved with simple administration of combined exogenous proteins. Because only the important selected disease epitopes are included in the nucleic acid construct, a single construct suffices to present a plurality of epitopes from multiple protein antigens to both or either CD4+ and CD8+ T cells, enabling a balanced expression of both CD4 and CD8 epitopes. In previous approaches, constructs needed to include the sequence of each entire protein, which is problematic because the capacity of constructs and vehicles to deliver nucleic acids is limited.

For immune tolerance, the DNA/RNA vehicles that carry the nucleic acid construct can be modified to remove certain motifs that are immunogenic, for example CpG motifs, which can be replaced with GpG motifs. Conversely, for immune stimulation, immunogenic motifs (for example CpG motifs) can be added to the DNA to serve as internal adjuvant. The nucleic acid construct can be combined with external standard adjuvants known in the art to promote strong immunogenicity.

It will be recognized that one or more features of any embodiment disclosed herein may be combined and/or rearranged within the scope of the invention to produce further embodiments that are also within the scope of the invention.

Immunological Principles a. Epitope Processing

The region of the genome that plays a central role in regulation of the adaptive immune response is referred to as the major histocompatibility complex ("MHC"). A subgroup of more than a hundred genes in this region encodes MHC molecules that bind peptide fragments derived from pathogens (and also from environmental antigens and self-antigens), and display them on the surface of APCs in the form of peptides embedded in MHC molecules for recognition by the appropriate CD4+ or CD8+ T cells. Typically this results in killing of pathogen- or virus-infected cells, activation of macrophages to kill bacteria, and activation of B cells to produce antibodies. The interaction between the MHC/peptide and the T cell receptor plays a key role in the ability of the CD4+ T cell or CD8+ T cell to recognize an infectious organism, or the products of these pathogens, as foreign.

Two major types of foreign pathogens include: (i) viruses that take over the replicative machinery of a cell, and (ii) bacteria that replicate in different ways. These two types of pathogens present very different challenges to the immune system. A cytotoxic CD8+ T cell kills a cell containing a virus whereas a bacterium can be eliminated by a phagocyte that has been activated by a CD4+ helper T cell or neutralized by antibodies produced by B cells with the help of CD4+ T cells. The necessity of distinguishing between whether the presence of a pathogen peptide should elicit a killer or helper T cell receptor response is presumed to be the reason for the creation of two specialized forms of MHC molecules: class I and class II. Both class I and class II responses are necessary for a fully functioning immune system.

MHCI molecules are found on almost all tissues of the body, and they play an important role in alerting the immune system to virally infected cells. MHCI molecules are expressed on the cell surface of all nucleated cells and present peptide fragments derived from intracellular proteins. These peptides are normally derived from the cell's own proteins. However, in a virally infected cell, peptides derived from viral proteins may also be presented. MHCI molecules fold and assemble in the endoplasmic reticulum. Antigens for presentation in the context of MHCI are typically processed into short peptides in the proteasome, peptides which are then translocated into the lumen of the endoplasmic reticulum, where the peptide antigens (epitopes) are loaded onto the MHCI molecule. CD8+ T cells can recognize these presented peptides that we refer to as CD8 epitopes.

On the other hand, MHCII molecules are found at high levels only on professional antigen-presenting cells. MHCII molecules present antigens acquired from an exogenous source, which can be a self-tissue or a pathogen. Antigenic molecules enter the cell by endocytosis/phagocytosis and are digested in lysosomes and/or endosomes. The resulting peptide fragments, slightly longer than CD8 epitopes, are loaded onto MHCII molecules in the endosomal compartment prior to migration to the cell surface for presentation. The MHCII molecule complexed with the antigenic peptide is then recognized by CD4+ T cells; these peptides are therefore referred to as CD4 epitopes.

b. Immune Tolerance

Immune tolerance is the mechanism by which potentially harmful self-reactive T cells are eliminated, inhibited or converted into a protective type of cells. Insufficient induction of tolerance to self antigens from particular tissues is the major cause for tissue-specific autoimmune diseases. Under normal conditions, these tissue-specific self antigens are presented by tolerance-inducing (tolerogenic) cells, which program any reactive T cells to undergo cell death, unresponsiveness or conversion to a type of Treg. In autoimmune diseases, these same self antigens are either not presented sufficiently, which limit engagement of autoreactive T cells for instruction, or presented improperly, instructing specific T cells to mount an immune response instead of tolerating the antigen as self. Antigen-specific therapies that deliver these self antigens to potent tolerogenic cells, systematically or via the mucosa are partially able to reinstate tolerance in part through the generation of suppressor T cells able to counteract improperly activated pathogenic T cells.

c. Autoimmune Diseases

Insufficient induction of tolerance to antigens from particular tissues is the major cause for tissue-specific autoimmune diseases. Deficits in central or peripheral tolerance cause cells of the immune system to inappropriately mount an immune response to self antigens, resulting in syndromes such as SLE, RA, T1D, MS, autoimmune polyendocrine syndrome type 1 (APS-1) and immunodysregulation polyendocrinopathy enteropathy X-linked syndrome (IPEX), and potentially contribute to asthma, and IBD. Central tolerance refer to instruction of T cells in the thymus as they develop from precursors to mature T cells, whereas peripheral tolerance relates to instruction of mature T cells in secondary lymphoid tissues (spleen, lymph nodes) after their release from the thymus.

Autoimmune diseases such as T1D, MS, RA, SLE, and IBD can develop when this process is deficient or altered. APCs that acquire antigens exogenously (from their milieu) more effectively engage CD4+ T cells, whereas those producing antigens endogenously present epitopes mainly to CD8+ T cells. However, both CD4+ and CD8+ self-reactive T cells should be silenced in order to prevent autoimmunity. Current antigen-specific therapies aimed at inducing regulatory T cell responses use either exogenously provided whole antigens or peptides delivered orally, intranasally or intravenously, which tend to be mostly processed onto MHCII and presented as peptides to CD4+ T cells, or endogenously expressed proteins or peptides delivered by injection of DNA plasmids or viral vectors, which results mainly in MHCI presentation to CD8+ T cells. Presentation of peptides from exogenous antigens on MHCI and vice versa is possible through mechanisms called "cross-presentation" and "autophagy" respectively, but this unique capacity is limited to few types of antigen-presenting cells only.

Currently there is no cure for the most complex (polygenic) tissue-specific autoimmune diseases such as T1D, RA or MS, however animal studies have suggested that restoration of antigen-specific immune tolerance may prevent or treat the disease. Without being bound by theory, targeting multiple islet antigens (in the case of T1D) can allow a broader and more robust induction of tolerance that will improve current antigen-specific approaches. Furthermore, in some embodiments, presentation of particular epitopes will be enhanced when these are most optimally processed and presented (i.e. CD4 epitopes onto MHCII and CD8 epitopes onto MHCI) and targeting of certain diabetogenic T cells will be improved when certain mutated epitopes (mimotopes) are included to mimic certain post-translational epitope modifications or favor particular MHC binding registers.

d. Other Diseases

Because the construct embodiments disclosed herein can be designed to hold a plurality of any epitopes, the invention can be used to cause any epitope to be presented. Thus, other diseases where it would be desirable to tolerize a subject to particular antigens comprising both CD4 and CD8 epitopes can be treated using the invention. Prior to transplanting a tissue or an organ into a subject, the subject can be treated according to the invention using antigens from the prospective transplant so that the subject can be tolerized. Thus, pre-exposing transplant patients to epitopes present on donor organs can condition their immune system not to respond to these epitopes, increasing the chance of transplant success.

In certain embodiments, the constructs of the invention can be used to induce immune responses against pathogens or tumors, where multiple epitopes that include both CD4 and CD8 epitopes need to be targeted. If a stimulated immune response is desired, the construct should be administered in a manner that prime antigen-presenting cells to be immunogenic, typically with the help of adjuvant administration. Furthermore, an immunogenic DNA vaccine or a vector carrying an immunogenic TEC can be engineered to include immunostimulatory motifs such as CpG, or in the contrary, to remove them (and optionally replace them with GpG motifs) when tolerance is desired.

Diseases where stimulation of the immune response is preferred included infectious diseases, such as influenza and HIV, where antigenic shift (reassortment of antigens) is a problem or multiple epitopes are known. Some viruses such as hepatitis B and C viruses can cause chronic infection by exhausting T cells. Eradication of many viruses rely heavily on optimal cytotoxic T cell responses and B cell-mediated antibody neutralization, both of which depends on robust CD4+ T cell help. Many viral and bacterial pathogens are well characterized in terms of the CD4 and CD8 epitopes recognized in most patients. Better eradication of these infections may depend on a better stimulation of as many epitopes as possible. Alternatively, hyperproliferative diseases such as cancer can be treated using tumor antigens, to increase killing of the tumor cells. Preferred cancers for use with the invention include, but are not limited to melanomas and carcinomas that are characterized by multiple antigens mutated or overexpressed.

Exemplary Nucleic Acid Constructs

The tandem epitope construct of the invention is depicted in its most simplistic form in FIG. 1. The rectangular boxes represent individual epitope sequences, of which there are one or more in each group. Therefore, preferably n=0-24 in the figure (allowing for 1-25 individual epitope sequences in each group) including for example, n=1-5, 5-10, 10-15 or 15-25. The square box marked "T" indicates a targeting sequence which enables delivery of the epitopes in that group to the endosome for MHC class II processing for CD4+ T cells. The circle represents a proteolytic cleavage site to separate the two groups of epitopes from each other, allowing one group to be targeted to MHC class I and the other to MHC class II processing. As can be seen from the differences between FIG. 1A, FIG. 1B, FIG. 1C and FIG. 1D, the group of epitopes operably linked to a targeting region can be positioned at either end of the construct. Each of the two sequences, to be targeted to MHC class I or class II pathways and joined to form a tandem construct separated by a protease cleavage site, contains at least one epitope. To an extent, the number of epitopes depends on the number of nucleic acids any given vector can accommodate. The number will depend on the size of the epitopes and the vector being used, and can be determined by one of skill in the art. The epitopes generally are about 7-25 amino acids in length, and preferably 8 or 9 to about 15 or 20 amino acids. A construct of 1,000 to 2,000 bp can easily be expressed by mRNA, DNA plasmid or a viral vector. Including the targeting sequence (80-240 amino acids or 240-720 bp), 2A cleavage site (18-22 amino acids or 54-66 bp), and flanking amino acids (2-3 amino acids on each side of each epitopes or a total of 12-18 bp per epitope), it is theoretically possible to express at least 50 epitopes without issue.

The construct contains two strings of epitopes, separated by a site for proteolytic cleavage which can separate the two strings of epitopes from each other. See FIG. 2 for an embodiment of the construct in schematic form, showing the epitopes, mimotopes, targeting sequence and cleavage site.

Other examples of nucleic acid constructs of the present invention are depicted in FIG. 18E. The AI construct pertains to the TEC construct disclosed in FIG. 1. The AIC construct contains two strings of epitopes (boxes labeled as CD4 epitopes and CD8 epitopes), separated by a site for proteolytic cleavage (diamond labeled T2A) which can separate the two strings of epitopes from each other. Each epitope in the string optionally can be flanked by native sequences that assist in processing (cleaving) of the individual epitopes (to replicate natural processing of the whole antigen), or in some cases, flanked by specific amino acids, for example lysines, which define good proteasomal cleavage sites. In addition, the AIC construct includes an MHCII activator sequence (CIITA) that is provided upstream of the ETS sequence and is separated from the ETS sequence by a proteolytic cleavage site (diamond labeled P2A). The MHCII activator sequence is cleaved in the cytoplasm and taken into the nucleus where it upregulates transcription of the MHCII gene. Alternatively, the MHCII activator sequence could be located downstream of either the CD4 or CD8 epitope sequences, or both so long as a proteolytic cleavage site is included to cleave out the MHCII activator sequence from the epitope sequences. Any of the individual native epitopes can be substituted with a mimotope to improve binding and recognition of the epitope by the appropriate T cell. The sequence of a mimotope can be obtained based on "rational design" or from peptide screening studies. The existence of mimotopes or modified antigens is usually known in each field. Modification of beta cell antigens can result from enzymes induced upon beta cell stress in T1D, including transglutaminases (Delong et al., 2012). Citrullination is well-known epitope modification that affects various antigens in RA.

The BS construct shown in FIG. 18E pertains to a nucleic acid construct that is tailored to secrete epitopes from the cells in which they are expressed. The BS construct includes epitope sequences (boxes labeled CD4 epitopes and CD8 epitopes) that are operably linked to a secretory peptide sequence (box labeled Alb. SS).

Numerous disease conditions can be treated to advantage using the invention described here. The nucleic acid construct, vectors, and cells containing them can be used to induce either immune tolerance or to increase an immune response to certain epitopes. Where the tandem construct and vector for administration are designed to produce tolerance or conversion of a reactive T cell to a regulatory T cell, diseases such as autoimmune diseases can be treated; and where the tandem construct and vector for administration are designed to induce immunity or an immune reaction, diseases such as infectious diseases and malignancies can be treated.

The autoimmune diseases that can benefit most from the invention are those autoimmune diseases characterized by multiple protein antigens targeted by the immune system (epitope spreading), in which the antigenic epitopes are known or can be discovered, and in which the epitopes comprise both CD4 and CD8 epitopes. Should there be a disease in which only CD4 or CD8 epitope processing is needed, the construct can be so designed. Persons of skill are aware of diseases of this type and any of these are contemplated as part of the invention. Such autoimmune diseases include, but are not limited to type 1 diabetes (T1D), multiple sclerosis (MS), rheumatoid arthritis (RA), psoriasis, inflammatory bowel syndrome (IBS; including Crohn's disease and ulcerative colitis), autoimmune hepatitis, lupus, vitiligo, and celiac disease. Other autoimmune disorders which involve limited numbers of epitopes can be used with the invention as well, but will not receive the maximum benefits of the invention and hence are not preferred.

Below is a list of antigens that are known for certain diseases. Epitopes from these antigens can be included in the nucleic acid construct for treatment of the respective diseases. For an overview, see Di Lorenzo et al., Clin. Exp. Immunol. 148(1):1-16, 2007.

Exemplary Autoantigens in T1D

Major Antigens:

Proinsulin/insulin (gene: INS): extensive CD4+ T cell responses in NOD mice and T1D patients, extensive CD8+ T cell in T1D patients, some CD8+ T cell in NOD mice, autoantibodies in NOD mouse and T1D patients.

GAD65 (glutamic acid decarboxylase, gene: GAD2): extensive CD4+ T cell responses in NOD mice and T1D patients, some CD8+ T cell responses in NOD mice and T1D patients, autoantibodies in T1D patients.

IA-2 (insulinoma-associated protein 2, or protein tyrosine phosphatase, receptor type, N, gene: PTPRN): extensive CD4+ T cell responses in NOD mice and T1D patients (Peakman et al., J. Clin. Invest. 104(10):1449-1457, 1999), some CD8+ T cell responses in T1D patients, autoantibodies in T1D patients (Bonifacio et al., J. Immunol. 155(11):5419-5426, 1995).

IGRP (islet-specific glucose-6-phosphatase catalytic subunit-related protein; gene: G6PC2): some CD4+ T cell responses in NOD mice and T1D patients (Jarchum et al., Clin Immunol, 127(3):359-365, 2008), some CD8+ T cell responses in T1D patients, extensive CD8+ T cell responses in NOD mice.

Minor Antigens:

Chromogranin A (gene: CHGA): CD4+ T cell responses in NOD mice (Stadinski et al., Proc. Natl. Acad. Sci. USA 107:10978-10983, 2010; Delong et al., Diabetes 61:3239-3246, 2012); CD8+ T cell responses in humanized NOD mice and T1D patients (Gottlieb et al., J. Autoimmun, 50:38-41, 2014); (Li et al., Clin Immunol, 159(1):63-71, 2015).

IAPP (islet amyloid polypeptide; gene: IAPP): CD4+ T cell responses in NOD mice see Baker et al., J. Immunol, 191(8):3990-3994, 2013; some CD8+ T cell responses in T1D patients.

ZnT8 (zinc transporter 8; gene: SLC30A8): autoantibodies in T1D patients, evidence of T cell responses in NOD mice (Dang et al., J. Immunol, 186(10):6056-6063. 2011); (Nayak et al., Diabetes, 63(10):3438-3448, 2014).

ICA69 (islet cell autoantigen; gene: ICA1): some CD4+ T cell responses in NOD mice and T1D patients.

IA-2β (insulinoma-associated protein 2 beta or phogrin or protein tyrosine phosphatase, receptor type, N polypeptide 2; gene: PTPRN2): some CD4+ T cell responses in NOD mice and T1D patients.

RegII (regenerating islet II, gene: REG3A): T cell responses in NOD mice (Gurr et al., Diabetes, 51(2):339-346, 2002); (Gurr et al., Diabetes, 56(1):34-40, 2007).

GPR78 (G protein-coupled receptor 78, when citrullinated; gene: GPR78): T cell responses and autoantibodies against citrullinated GPR78 in NOD mice (Rondas et al., Diabetes, 64(2):573-586, 2015).

HSP60

HSP70

Hybrid insulin peptides (HIPs) that are fusions between insulin peptides and peptides from other beta-cell antigens, including ChgA, IAPP1, IAPP2 and amylin (Delong, T, Wiles, T A, Baker, R L, Bradley, B, Barbour, G, Reisdorph, R, et al. (2016). Pathogenic CD4 T cells in type 1 diabetes recognize epitopes formed by peptide fusion. *Science* 351: 711-714). Examples of such peptides that can be included in our constructs include GDLQTLWSRMD (SEQ ID NO: 48), LQTLALWSRMD (SEQ ID NO: 49) and LQTLAL-NAARD (SEQ ID NO: 50). Similar HIPs identified from T1D patients include GQVELGGGSSPETLI (SEQ ID NO: 51) and GQVELGGGNAVEVLK (SEQ ID NO: 52) (Delong et al.). More peptide fusion may be produced between insulin and ChgA by transpeptidation that can stimulate diabetogenic T cell clones (Jin, N, Wang, Y, Crawford, F, White, J, Marrack, P, Dai, S, et al. (2015). N-terminal additions to the WE14 peptide of chromogranin A create strong autoantigen agonists in type 1 diabetes. *Proc Natl Acad Sci USA* 112: 13318-13323).

REGII,

ZnT8,

Vitamin D binding protein (VDBP)

Autoantigens in MS

For an overview, see Riedhammer et al., Immunol. 17; 6: 322, 2015. Each of these antigens can elicit CD4+ or CD8+ T cell responses, or both.

Major Antigens:

Myelin basic protein (MBP; gene: MBP)

Proteolipid protein (PLP; gene: PLP1)

Myelin oligodendrocyte glycoprotein (MOG; gene: MOG)

Minor Antigens:

Myelin-associated antigen (MAG; gene: MAG)

Myelin-associated oligodendrocyte basic protein (MOBP; gene: MOBP)

2', 3'-cyclic-nucleotide 3'-phosphodiesterase (CNPase; gene: CNP)

S100β transaldolase.

Autoantigens in RA

See Hueber et al., Proteomic biomarkers for autoimmune disease, Proteomics, 6(14):4100-105, 2006, and Riedhammer et al., Antigen Presentation, Autoantigens, and Immune Regulation in Multiple Sclerosis and Other Autoimmune Diseases, Front. Immunol. 6:322, 2015.

Major Antigens:

Collagen (type II): T cell responses and antibodies

Cartilage glycoprotein 39 (Chitinase 3-like 1; gene: CHI3L1) (Verheijden et al., Arthritis Rheum, 40(6):1115-1125, 1997)

Aggrecan G1 (cartilage-specific proteoglycan core protein, domain G1; gene ACAN) (Li et al., Cell Res, 10(1): 39-49, 2000)

Autoantibody Responses:

Rheumatoid factor (autoantibodies to Fc portions of IgG)

Citrullinated peptides from fibrinogen, vimentin, fillaggrin, keratin, clusterin, biglycan, apolipoprotein E (Goronzy et al., Arthritis Res. Ther. 11(5):249, 2009; (Sakkas et al., Autoimmun Rev. 13(11):1114-1120, 2014) and (Wagner et al., Ann. Rheum. Dis. 74(3):579-586, 2015).

Carbamylated antigens (Shi et al., Autoimmun Rev. 3(3): 225-30, 2014)

PAD4 and BRAF (Auger et al., Autoimmun Rev. 11(11): 801-803, 2012).

HSP65

Autoantigens in Other Autoimmune Disorders

Psoriasis and Other Skin Conditions:

Basement membrane laminin (McFadden et al., Scand J. Immunol. 10.1111-12384, 2015).

LL37 (T cell responses) (Lande et al., Nat Commun, 5:5621, 2014).

Progranulin (autoantibodies) (Thurner et al., J. Autoimmun, 42:29-38, 2013).

Desmoglein 3 (T cells and autoantibodies) (Nishimoto, J. Immunol, 191(6):3065-3072, 2013).

Pso p27 (Iversen et al., Autoimmunity, 44(3):229-234, 2011).

Ezrin, maspin, peroxiredoxin 2, HSP27 (Besgen et al., J. Immunol, 184(9):5392-5402, 2010).

Collagen type XVII (Inokuma et al., Br. J. Dermatol, 160(2):451-454, 2009).

Keratin 13, hnRNP-A1 and FLJ00294 (Jones et al., J. Invest. Dermatol, 123(1):93-100, 2004).

hnRNP-C1/C2

SCG, GLCDAC05, alpha-endosulfine, NOL8, GFGR3, dematin, signal recognition particle subunit 14 and EPF as alopecia areata autoantigens (Lueking et al., Mol. Cell. Proteomics, 4(9):1382-1390, 2005).

Inflammatory Bowel Disease (Crohn's Disease and Ulcerative Colitis):

Glycoproteins CUZD1 and GP2 (Roggenbuck et al., Gut, 58(12):1620-1628, 2009; Komorowski et al., J. Crohns Colitis, 7(10):780-90, 2013).

HMGB1/HMGB2, ASCA autoantibodies

FAM84A (Vermeulen et al., Inflamm Bowel Dis, 17(6): 1291-1300, 2011).

Collagen type VII (Chen et al., J. Invest. Dermatol, 118(6):1059-1064, 2002), (Hundorfean et al., J. Cell Mol Med, 14(10):2393-2403, 2010).

Complement C3 (Lundgren et al., Eur J. Gastroenterol Hepatol, 22(4):429-436, 2010).

Ubiquitination factor e4A (UBE4A) (Sakiyama et al., Inflamm Bowel Dis, 14(3):310-7, 2008).

CBir1 flagellin autoantibodies (Targan et al., Gastroenterology, 128(7):2020-2028, 2005).

Alpha 3(IV)NC1 and BP180 autoantibodies (Plaisier et al., Am J. Kidney Dis, 40(3):649-654, 2002).

Galectin-3 autoantibodies (Jensen-Jarolim et al., J. Clin Immunol, 21(5):348-356, 2001).

Catalase and alpha-enolase (Roozendaal et al., Clin Exp Immunol, 112(1):10-6, 1998).

Lactoferrin autoantibodies (Roozendaal et al., Adv Exp Med Biol, 443:313-319, 1998).

The tandem epitope construct also can be used to treat and produce immune reaction to infectious diseases characterized by multiple protein antigens (conserved antigens) to be targeted by the immune system, for where the immune response benefits from being composed of both CD4+ T cell and CD8+ T cell responses, and for which antigenic epitopes are known or predicted. Examples of such diseases are influenza, HIV, HBV, and HCV.

Hyperproliferative disorders, including malignancies, also can have more than one antigen useful for targeting the tumor cells (i.e. mutated or overexpressed antigens). In these cases, the inventive methods can be used to target epitopes from a plurality of the known antigens at the same time for optimal results.

Any known epitope to which one would like to induce tolerance or stimulate an immune reaction in a subject is contemplated for use with the invention. The choice of epitopes is determined based on those most often targeted in the patient population or personalized to individual patients based on diagnostic tests. Because it is customizable, native peptides may be mutated for better targeting of specific types of self-reactive T cells (those requiring post-translational modifications or uncommon MHC binding register). Preferably, the construct encodes a balance of both CD4 and CD8 epitopes so that tolerance or alternatively a robust immune response is stimulated for both MHCI and MHCII antigens at the same time. Preferred antigens for making a tolerogenic nucleic acid construct include any of those specifically discussed or provided herein, or any epitopes from diabetogenic or autoimmune antigens. Cancer antigens, pathogens and the like also are contemplated for use with a nucleic acid construct designed to induce a strong immune response to those antigens/epitopes. Thus far, three antigens have been evaluated individually in T1D clinical trials (proinsulin/insulin, GAD65 and HSP60 p277) using a variety of delivery methods. Overall, these antigen-specific therapies were well-tolerated, but poorly efficacious. Other antigens are targeted in T1D, including but not limited to IA-2, IGRP, ChgA and ZnT8. Given the extent of epitope spreading occurring in T1D (as in other major tissue-specific autoimmune diseases), achieving tolerance against a single antigen or epitope appears to be insufficient for durable tolerance induction and may in part explain the relative failure of previous clinical trials. In addition to targeting multiple antigen specificities, efficient tolerogenic presentation to both CD4+ and CD8+ T cells, further enhanced by using mimotopes when available, increases efficiency and exploits all mechanisms of tolerance induction (or alternatively specific immune stimulation). Preclinical assessment of these new parameters is required in order to optimize current strategies.

A large number of epitopes from β cell antigens are now known to be targeted by diabetogenic CD4+ or CD8+ T cells in both NOD mice and T1D patients, as reported in 2007 by DiLorenzo et al., with many more identified since then (see for example Delong et al. 2016, and Wang et al. 2015). The review by DiLorenzo et al. (Clin. Exp. Immunol. 147:doi: 10.1111/j.11365-2249.2007.03328.x (2007)) provides sequences, examples and discussion concerning many useful T cell epitopes for autoimmune diabetes and many examples of T cell epitopes. The data presented are based on epitopes targeted in the NOD mouse model of T1D, and include Ins2 B:15-23 and IGRP$_{206-214}$ for CD8 epitopes, and Ins2 B:9-23, Ins2 B:9-23 (R22E), Ins2 B:9-23 (R22E)(E21G), ChgA1040-79, GAD65$_{286-300}$, GAD65$_{524-543}$ for CD4 epitopes/mimotopes. Some of these epitopes have been chosen for proof of principle experiments because tools and reagents exist to assess the T cell responses to these particular epitopes, such as T cell receptor transgenic mice and tetramer reagents. For humans, key epitopes include those known in the field from insulin, GAD65, and IA-2. A smaller number of epitopes have been identified for other antigens, including IGRP, ChgA, ZnT8, IAPP and ICA69 as well as a number of newly discovered hybrid insulin peptides (Delong et al. 2016). Epitopes from HSP60/70 proteins are also targeted although those are not beta cell-specific. A widely recognized important epitope for T1D is the CD4 epitope insulin B:9-23, which is targeted in both NOD mice and T1D patients. In NOD mice, this epitope is involved in initiation of disease (Nakayama et al., Nature. 35(7039):220-3, 2005). There are various mimotopes designed for this epitope, which are efficacious both in mice (Daniel et al.), humanized mice (Serr et al.) and in humans (Nakayama et al., Proc. Natl. Acad. Sci. USA 112(14):4429-34, 2015). Epitopes and mimotopes continue to be identified in a regular basis for T1D and other autoimmune diseases, and will therefore complete the arsenal of epitopes already existing. As more epitopes become known, and sensitive assays that help determine which epitopes need to be targeted in particular disease or even in a particular individual, constructs and methods can be designed accordingly.

Other autoantigens, in diseases such as MS, RA, IBD, and psoriasis, some of which are listed herein, and others also known in the art, are contemplated for use with the invention. Because of the phenomenon of epitope spreading, the numbers of known autoimmune epitopes are growing. Any self antigens, and antigens from an organ or tissue to be transplanted, are also contemplated. Thus, any epitopes that become known in the future also are contemplated for use with the invention. Mimotopes can be substituted for any epitope when available. Any of the mimotopes to relevant antigens/epitopes which are known in the art can be used.

Because immunogenic nucleic acid constructs can also be made to induce an immune response, any antigen on an invading pathogen, such as a viral antigen, bacterial antigen, fungal antigen, parasitic antigen and the like can be used. Preferred pathogen antigens are viral antigens such as influenza antigens and HIV antigens, however any antigen which is known to produce an immune response can take advantage of the compositions and methods of this invention. In addition, specific tumor antigens or antigens mutated or overexpressed in tumors can be used with the invention and for treatment of hyperproliferative disorders. Persons of skill in the art are aware of such antigens which may be important in various disease conditions and can choose appropriate epitopes (or design mimotopes) as a matter of routine.

Any tumor antigens which are overexpressed in tumors or which are mutated in cells to be destroyed can be used. Preferably, when treating a tumor, the epitopes used are those which will not affect normal tissues bearing the same epitope but are confined to or mostly confined to the tumor. For immune stimulation purposes, pathogen epitopes such as viral nucleic acid sequences and the like can be used. The invention may be used with or comprise expression vectors. Such vectors are known per se in the art and are designed as a mode of delivery of a nucleic acid, or to produce endogenous expression of a peptide encoded by a nucleic acid. Any vector which is convenient can be used, including "naked" DNA vaccines, viral vectors, including lentiviral vectors, and the like, depending on the subject, the disease being treated and whether the treatment is designed to produce immunity or tolerance to the antigen(s). The person of skill is aware of how to select and use such vectors.

Vectors for delivering nucleic acids can be viral, non-viral, or physical. See, for example, Rosenberg et al., Science, 242:1575-1578, 1988, and Wolff et al., Proc. Natl. Acad. Sci. USA 86:9011-9014 (1989). Discussion of methods and compositions for use in gene therapy include Eck et al., in Goodman & Gilman's The Pharmacological Basis of Therapeutics, Ninth Edition, Hardman et al., eds., McGraw-Hill, New York, (1996), Chapter 5, pp. 77-101; Wilson, Clin. Exp. Immunol. 107 (Suppl. 1):31-32, 1997; Wivel et al., Hematology/Oncology Clinics of North America, Gene Therapy, S. L. Eck, ed., 12(3):483-501, 1998; Romano et al., Stem Cells, 18:19-39, 2000, and the references cited therein. U.S. Pat. No. 6,080,728 also provides a discussion of a wide variety of gene delivery methods and compositions. The routes of delivery include, for example, systemic administration and administration in situ. Well-known viral delivery techniques include the use of adenovirus, retrovirus, lentivirus, foamy virus, herpes simplex virus, vaccinia virus and adeno-associated virus vectors.

Viral Vectors

Preferred viral vectors are based on non-cytopathic eukaryotic viruses in which non-essential genes have been replaced with the nucleic acid construct carrying the nucleic acid sequences encoding the epitopes and targeting sequences of interest. Preferred viruses for certain embodiments of the invention are the adenoviruses and adeno-associated (AAV) viruses, which are double-stranded DNA viruses that have already been approved for human use in gene therapy. In addition, preferred vectors for tolerizing do not include immune-stimulating sequences.

1. Adenovirus Vectors

One illustrative method for in vivo delivery of one or more nucleic acid sequences involves the use of an adenovirus expression vector. "Adenovirus expression vector" is meant to include those constructs containing adenovirus sequences sufficient to (a) support packaging of the construct and (b) to express a polynucleotide that has been cloned therein in a sense or antisense orientation. Of course, in the context of an antisense construct, expression does not require that the gene product be synthesized. In a specific embodiment, the delivery vector pertains to commercially available ORF of cytochrome b5 reductase 3 (CYB5R3), transcript variant 1 in adenoviral vector pAd, with C terminal Flag and His tag, (Vigene Biosciences Product code AH889428). WIPO Patent Application WO/2015/050364 also teaches vectors with expression constructs including a Cyb5r3 gene.

Adenoviral vectors are highly immunogenic and therefore are less preferred for administration to induce tolerance by presenting antigens, or in the case of autoimmune diseases. These vectors can be used, however to induce immunity, for example in treatment of infectious diseases and the like, include, for example, influenza, HBV, HCV and HIV.

2. Adeno-Associated Virus Vectors (AAV)

AAV is a good choice of delivery vehicles due to its safety, i.e., genetically engineered (recombinant) does not integrate into the host genome. Likewise, AAV is not pathogenic and not associated with any disease. The removal of viral coding sequences minimizes immune reactions to viral gene expression, and therefore, rAAV does not evoke an inflammatory response. According to a specific embodiment, an AAV vector containing an epitope sequence containing nucleic acid construct described herein is useful for transducing APCs.

Typically, viral vectors containing an epitope containing nucleic acid construct are assembled from polynucleotides encoding the desired epitopes, suitable regulatory elements and elements necessary for epitope expression which mediate cell transduction. In one embodiment, adeno-associated viral (AAV) vectors are employed. In a more specific embodiment, the AAV vector is an AAV1, AAV6, or AAV8.

The AAV expression vector which harbors the DNA molecule of interest bounded by AAV ITRs, can be constructed by directly inserting the selected sequence(s) into an AAV genome which has had the major AAV open reading frames ("ORFs") excised therefrom. Examples of constitutive promoters which may be included in the AAV of this invention include, without limitation, the exemplified CMV immediate early enhancer/chicken β-actin (CBA) promoter.

For eukaryotic cells, expression control sequences typically include a promoter, an enhancer, such as one derived from an immunoglobulin gene, SV40, cytomegalovirus, etc., and a polyadenylation sequence which may include splice donor and acceptor sites. The polyadenylation sequence generally is inserted following the transgene sequences and before the 3' ITR sequence. In one embodiment, the bovine growth hormone polyA may be used.

Selection of these and other common vector and regulatory elements are conventional and many such sequences are available. See, e.g., Sambrook et al., and references cited therein at, for example, pages 3.18-3.26 and 16.17-16.27 and Ausubel et al., Current Protocols in Molecular Biology, John Wiley & Sons, New York, 1989). Of course, not all vectors and expression control sequences will function equally well to express all of the transgenes of this invention. However, one of skill in the art may make a selection among these expression control sequences without departing from the scope of this invention. Suitable promoter/enhancer sequences may be selected by one of skill in the art using the guidance provided by this application. Such selection is a routine matter and is not a limitation of the molecule or construct.

3. Retrovirus Vectors

In a certain embodiments, the viral vector may be a retroviral vector. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are known to those of skill in the art.

The retroviral genome contains three genes, gag, pol, and env that code for capsid proteins, polymerase enzyme, and envelope components, respectively. A sequence found upstream from the gag gene contains a signal for packaging of the genome into virions. Retroviral vectors are gene transfer plasmids wherein the heterologous nucleic acid resides between two retroviral LTRs. Retroviral vectors typically contain appropriate packaging signals that enable the retroviral vector, or RNA transcribed using the retroviral vector as a template, to be packaged into a viral virion in an appropriate packaging cell line (see, e.g., U.S. Pat. No. 4,650,764). These two long terminal repeat (LTR) sequences are present at the 5' and 3' ends of the viral genome. These contain strong promoter and enhancer sequences and are also required for integration in the host cell genome (Coffin, 1990). In order to construct a retroviral vector, a nucleic acid encoding one or more oligonucleotide or polynucleotide sequences of interest is inserted into the viral genome in the place of certain viral sequences to produce a virus that is replication-defective. Also included are episomal or non-integrating forms of retroviral vectors based on lentiviruses (e.g., a type of retrovirus).

Lentiviral vectors are useful when stable expression is needed, but lentiviral vectors can be immunogenic, and possibly have other undesirable effects. Therefore, although lentiviral vectors are convenient for research, care should be taken when using them for human administration, particularly where it is desired to induce tolerance rather than immunity. Lentiviruses are suitable for engineering T cells or dendritic cells or other antigen presenting cells ex vivo for cancer therapy, although mRNA electroporation is more safe. However, two recent advances have made the use of lentiviruses safer and more clinically translatable. First, the coexpression of a suicide gene along with the antigens whose products become functional when a drug is administered. A typical example is Herpes simplex virus thymidine kinase (HSV-Tk). Cells that express these genes can metabolize the drug ganciclovir into a cytotoxic product that induces cell death. Thus, in case some transduced cells become malignant, they can be eradicated. About a dozen such systems exist (Duarte et al., Cancer Letters, 324:160-170, 2012). Second, there are now non-integrating lentiviral vectors being developed that are therefore non-oncogenic (Nightingale et al., 2006, Mol. Ther., 13:1121-1132). These methods can be used with the invention according to the judgement of the person of skill in the art.

Suitable retroviral vectors for use herein are described, for example, in U.S. Pat. Nos. 5,399,346 and 5,252,479; and in WIPO publications WO 92/07573, WO 90/06997, WO 89/05345, WO 92/05266 and WO 92/14829, which provide a description of methods for efficiently introducing nucleic acids into human cells using such retroviral vectors. Other retroviral vectors include, for example, mouse mammary tumor virus vectors (e.g., Shackleford et al., Proc. Natl. Acad. Sci. U.S.A. 85:9655-9659, 1998), lentiviruses, and the like. An exemplary viral vector is plentilox-IRES-GFP.

4. Other Viral Vectors as Expression Constructs

Other viral vectors may be employed as expression constructs in the present invention for the delivery of oligo-nucleotide or polynucleotide sequences to a host cell. Vectors derived from viruses such as vaccinia virus, polioviruses and herpes viruses may be employed. They offer several attractive features for various mammalian cells. Also included are hepatitis B viruses.

Promoters

Constitutive promoters are active in any cell type in which it is introduced, although the activity varies from cell to cell. Some promoters generate higher levels of expression than others, some promoters become silenced over time, and others have a very stable expression. The most common promoters include the CMV promoter (from cytomegalovirus), the composite CAG promoter (CMV early enhancer, chicken beta actin promoter, rabbit beta globin splice acceptor), the ubiquitin C promoter, the PGK promoter (phosphoglycerate kinase 1), the EF1-alpha promoter (elongation factor 1-alpha), the SV40 promoter, the MSCV promoter (from murine stem cell virus), and the composite MND promoter (MPSV LTR, NCR deleted, and d/587 PBS). Any of these are contemplated for use with the invention, but any convenient promoter can be chosen by the person of skill in the art, depending on the system being used.

Tissue-specific promoters are promoters that are only active in certain cell types such as the dendritic cell-specific CD11c promoter, the hepatocyte-specific ET and albumin promoters, the endothelial cell-specific ICAM-2 promoter or the epithelial cell-specific Cytokeratin 18 promoter (Papadakis et al., Current Gene Therapy, 4:89-113, 2004).

mRNA does not depend on a promoter as it is already transcribed. It is rapidly translated in any cell, whether it is picked up in vivo or introduced ex vivo by transfection methods such as electroporation.

Non-Viral Vectors

1. Plasmid Vectors

Other vectors include plasmid vectors. Plasmid vectors have been extensively described in the art and are well known to those of skill in the art. See e.g. Sambrook et al., 1989, cited above. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide epitope encoded by nucleic acid within the plasmid. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

Thus, in one aspect, a plasmid is provided for expression of the epitope containing nucleic acid construct which includes an expression cassette; also referred to as a transcription unit. When a plasmid is placed in an environment suitable for epitope expression, the transcriptional unit will express the polynucleotide including a sequence encoding the epitopes, ETS and MHCII activator sequence, or sequence encoding the epitopes and secretion signal sequence, and anything else encoded in the construct. The transcription unit includes a transcriptional control sequence, which is transcriptionally linked with a cellular immune response element coding sequence. Transcriptional control sequence may include promoter/enhancer sequences such as cytomegalovirus (CMV) promoter/enhancer sequences. However, those skilled in the art will recognize that a variety of other promoter sequences suitable for expression in eukaryotic cells are known and can similarly be used in the constructs disclosed herein. The level of expression of the nucleic acid product will depend on the associated promoter and the presence and activation of an associated enhancer element.

In certain embodiments, a sequence encoding the desired epitopes and targeting sequence can be cloned into an expression plasmid which contains the regulatory elements for transcription, translation, RNA stability and replication (i.e., including a transcriptional control sequence). Such expression plasmids are well known in the art and one of ordinary skill would be capable of designing an appropriate expression construct with a polynucleotide including a sequence encoding a cellular immune response element or fragment thereof in such a manner that the cellular immune response element is expressible. There are numerous examples of suitable expression plasmids into which a polynucleotide including a sequence could be cloned such as pCI-neo, pUMVC or pcDNA3.

Large quantities of a bacterial host harboring a plasmid for expression of cellular immune response element or fragment thereof may be fermented and the plasmid can be purified for subsequent use. Current human clinical trials using plasmids utilize this approach. Recombinant DNA Advisory Committee Data Management Report, Human Gene Therapy 6: 535-548, 1994. Current DNA isolation methods known in the art include removal of lipopolysaccharides (endotoxins) that are contaminants from the bacteria used to propagate the plasmids. This step is most preferably taken for use of tolerogenic DNA vaccines as endotoxins act as strong adjuvants and can produce undesired immune stimulation.

The purpose of the plasmid is the efficient delivery of nucleic acid sequences to and expression of therapeutic epitopes in a cell or tissue. In particular, the purpose of the plasmid may be to achieve high copy number, avoid potential causes of plasmid instability and provide a means for plasmid selection. As for expression, the nucleic acid cassette contains the necessary elements for expression of the nucleic acid within the cassette. Expression includes the efficient transcription of an inserted gene, nucleic acid sequence, or nucleic acid cassette with the plasmid. Expression products may be proteins, polypeptides or RNA. The nucleic acid sequence can be contained in a nucleic acid cassette. Expression of the nucleic acid can be continuous or regulated.

Minicircle

Embodiments of nucleic acid constructs described herein may be processed in the form of minicircle DNA. Minicircle DNA pertains to small (2-4 kb) circular plasmid derivatives that have been freed from all prokaryotic vector parts. Since minicircle DNA vectors contain no bacterial DNA sequences, they are less likely to be perceived as foreign and destroyed. (Typical transgene delivery methods involve plasmids, which contain foreign DNA.) As a result, these vectors can be expressed for longer periods of time (in order of weeks or months) compared to conventional plasmids (days to weeks). The smaller size of minicircles also extends their cloning capacity and facilitates their delivery into cells. Kits for producing minicircle DNA are known in the art and are commercially available (System Biosciences, Inc., Palo Alto, Calif.). Information on minicircle DNA is provided in Dietz et al., Vector Engineering and Delivery *Molecular Therapy* (2013); 21 8, 1526-1535 and Hou et al., *Molecular Therapy—Methods & Clinical Development*, Article number: 14062 (2015) doi:10.1038/mtm.2014.62. More information on Minicircles is provided in Chen Z Y, He C Y, Ehrhardt A, Kay M A. *Mol Ther.* 2003 September; 8(3):495-500 and Minicircle DNA vectors achieve sustained expression reflected by active chromatin and transcriptional level. Gracey Maniar L E, Maniar J M, Chen Z Y, Lu J, Fire A Z, Kay M A. *Mol Ther.* 2013 January; 21(1):131-8

As an initial step in the process of ultimately obtaining expression of a product encoded by a nucleic acid, is to effect the uptake of the nucleic acid by cells. Uptake of nucleic acid by cells is dependent on a number of factors, one of which is the length of time during which a nucleic acid is in proximity to a cellular surface. For instance, after intramuscular (i.m.) administration of plasmid DNA in buffer, a marked reduction in gene expression was observed if the muscle is massaged, presumably due to DNA leakage out of the muscle either directly or via lymphatic vessels (Human Gene Therapy 4:151-159; 1993). Accordingly, it may be desirable to formulate nucleic acids with compounds which would retard the rate at which nucleic acids diffuse or are carried away from a site at which cellular uptake of the nucleic acid is desired. Further, these compounds could be suitable for administration to an organism by means such as injection while maintaining or regaining the physical characteristics necessary to increase cellular uptake of nucleic acids.

In order to effect expression of oligonucleotide or polynucleotide sequences, the expression construct must be delivered into a cell. In certain embodiments of the invention, an expression construct comprising one or more oligonucleotide or polynucleotide sequences may simply consist of naked recombinant DNA or plasmids.

To prime immunity, DNA vaccine vectors of any type preferably are engineered to be CpG-rich (to stimulate TLR9 on immune cells) or conversely are engineered to remove CpG, and when possible, replace CpG motifs with GpG motifs (Ho et al., J. Immunol. 71(9):4920-6, 2003; Ho et al., J. Immunol. 175(9):6226-34, 2005). DNA vaccines can be engineered to contain the antigen(s)/epitope(s), and also can contain additional genes for co-expression with the antigens to act as adjuvants or immunomodulators (multiple promoter vectors. These DNA vaccines have been found to be safe clinically, for example in T1D patients (Roep et al., Sci. Transl. Med. 5(191):191ra82, 2013).

2. Mechanical Delivery Systems

Additional non-viral delivery methods include but are not limited to mechanical delivery systems that can be used in vitro such as the approach described in Woffendin et al., Proc. Natl. Acad. Sci. USA 91(24):11581, 1994; deposition of photopolymerized hydrogel materials or use of ionizing radiation (see, e.g., U.S. Pat. No. 5,206,152 and WO 92/11033); the use of a hand-held gene transfer particle gun (see, e.g., U.S. Pat. No. 5,149,655); and the use of ionizing radiation for activating transferred gene (see, e.g., U.S. Pat. No. 5,206,152 and WO 92/11033). Delivery devices can also be biocompatible, and may also be biodegradable. The formulation preferably provides a relatively constant level of active component release. On the other hand, a more rapid rate of release immediately upon administration may be desired. The formulation of such compositions is well within the level of ordinary skill in the art using known techniques.

Physical methods to enhance delivery include electroporation (where short pulses of high voltage carries the nucleic acid across the membrane), a gene gun (where DNA is loaded onto gold particles and forced to achieve penetration of the DNA into the cells), sonoporation, magnetofection, hydrodynamic delivery and the like, all of which are known to those of skill in the art. DNA also can be encapsulated in liposomes, preferably cationic liposomes, or polymersomes (synthetic liposomes) which can interact with the cell membrane and fuse or undergo endocytosis to effect DNA transfer into the cell. The DNA also can be formed into complexes with polymers (polyplexes) or with dendrimers which can directly release there load into the cytoplasm of a cell.

Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active agent contained within a sustained release formulation depends upon the site of implantation, the rate and expected duration of release and the nature of the condition to be treated or prevented.

Biodegradable microspheres (e.g., polylactate polyglycolate) may be employed as carriers for compositions. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Modified hepatitis B core protein carrier systems such as described in WO/99 40934, and references cited therein, will also be useful for many applications. Another illustrative carrier/delivery system employs a carrier comprising particulate-protein complexes, such as those described in U.S. Pat. No. 5,928,647, which are capable of inducing an MHCI-restricted cytotoxic T lymphocyte responses in a host.

Biodegradable polymeric nanoparticles facilitate nonviral nucleic acid transfer to cells. Small (approximately 200 nm), positively charged (approximately 10 mV) particles are formed by the self-assembly of cationic, hydrolytically degradable poly(beta-amino esters) and plasmid DNA.

Polynucleotides may also be administered to cells by direct microinjection, temporary cell permeabilizations (e.g., co-administration of repressor and/or activator with a cell permeabilizing agent), fusion to membrane translocating peptides, and the like.

3. mRNA mRNA can be used to modify dendritic cells (DC) or other antigen presenting cells for cell therapy of cancer, and are contemplated for use with the invention (Lee J, Boczkowski D, Nair, Methods Mol. Biol. 969:111-25, 2013). mRNA is less immunogenic than DNA in DCs differentiated in vitro, and possibly is the least immunogenic of all vectors (See Creusot et al., Mol. Ther. 18(12):2112-2120, 2012, and U.S. Pat. No. 8,513,208 B2 for more information on these vectors and their use, particularly for cell therapy for autoimmunity). Although it has a short window of expression, its lower immunogenicity nevertheless makes mRNA vectors suitable vector for use as described herein. mRNA electroporation offers many advantages over traditional viral techniques used for DC manipulation, including ability to co-express many genes in a per cell basis, high transfection efficiency, good viability, minimal DC maturation (which would otherwise render them more immunogenic) and absence of genetic disruption.

Naked RNA also can be used as a vaccine to administer the treatment of the invention, as well, although it is unstable, particularly outside cells (Challenges and advances towards the rational design of mRNA vaccines. (Pollard et al., J. Trends Mol. Med. 19(12):705-13, 2013). Although less immunogenic than most viral vectors and unmodified plasmid DNA, RNA has nonetheless some immunogenic properties that can be reduced or abrogated with certain modification, for example as described in Karikó et al., "Suppression of RNA recognition by Toll-like receptors: the impact of nucleoside modification and the evolutionary origin of RNA." Immunity August; 23(2):165-75, 2005; Karikó et al., "Incorporation of pseudouridine into mRNA yields superior nonimmunogenic vector with increased translational capacity and biological stability." Mol. Ther. 16(11):1833-1840, 2008; and Anderson et al., "Incorporation of pseudouridine into mRNA enhances translation by diminishing PKR activation." Nucleic Acids Res. 38(17): 5884-5892, 2010. These methods are well known to the skilled artisan. Briefly they involve producing mRNA by in vitro transcription (IVT) using uncommon nucleotides such as methyl-cytidin or pseudouridin. In most embodiments, the IVT mRNA is delivered into a patient's cells ex vivo prior to the cells administered back into the patient, or direct delivered by various routes of inoculation. In order to be recognized by the cell as a normal mature mRNA, ready for transcription, the mRNA usually is constructed to have a 5' cap and a poly-A tail, correct start and stop codons, and flanking untranslated regions. See Sahin et al., "mRNA-based therapeutics—developing a new class of drugs." Nature Reviews 13:759-780, 2014, for a review of methods and techniques known in the art for using mRNA and maximizing their usefulness.

Electroporation is a preferred method for introducing mRNA into a cell. This well-known method has been shown to be safe in patients with cancer and is contemplated for use here. Delivery of naked mRNA to the subject also can be used and has been shown to induce immune responses in other contexts.

Certain vectors suitable for use when inducing tolerance include (1) mRNA and plasmid DNA modified for minimal immunogenicity for direct inoculation, (2) mRNA electroporation into tolerogenic APCs ex vivo which are then re-infused, and also (3) non-integrating lentiviral vectors used to infect tolerogenic APCs ex vivo or directly inoculated, Viral vectors with tissue-specific promoters are preferred, such as those described for gene therapy of T1D (Insulin B chain 9-23 gene transfer to hepatocytes protects from type 1 diabetes by inducing Ag-specific FoxP3+ Tregs. Akbarpour et al., Sci. Transl. Med. 7(289):289ra81, 2015). Long-term expression is seen as favorable for maintenance of tolerance, although most vectors do not achieve long-term expression without certain risks (e.g., integrating vectors). Vectors that are non-immunogenic and have limited integration sites like AAV have an advantage at this level.

Preferred vectors for use when inducing an active immune response are viral vectors, mRNA or DNA plasmids non-devoid of immunostimulatory motifs and combined with adjuvants that are known in the art. However, vectors that confer long-term expression may not be favorable or should include a shutdown mechanism for after the pathogens or tumor has been eradicated.

Polycationic Molecules for Complexing with Nucleic Construct Embodiments

The nucleic acid constructs disclosed herein may be associated with polycationic molecules that serve to enhance uptake into cells. Complexing the nucleic acid construct with polycationic molecules also helps in packaging the construct such their size is reduced, which is believed to assist with cellular uptake. Once in the endosome, the complex dissociates due to the lower pH, and the polycationic molecules can disrupt the endosome's membrane to facilitate DNA escape into the cytoplasm before it can be degraded. Preliminary data shows that the nucleic acid construct embodiments had enhanced uptake into SCs over DCs when complexed with the polycationic molecules polylysine or polyethyleneimine.

One example of polycationic molecules useful for complexing with nucleic acid constructs includes cell penetrating peptides (CPP), examples include polylysine (described above), polyarginine and Tat peptides. Cell penetrating peptides (CPP) are small peptides which can bind to DNA and, once released, penetrate cell membranes to facilitate escape of the DNA from the endosome to the cytoplasm. Another example of a CPP pertains to a 27 residue chimeric peptide, termed MPG, was shown some time ago to bind ss- and ds-oligonucleotides in a stable manner, resulting in a non-covalent complex that protected the nucleic acids from degradation by DNase and effectively delivered oligonucleotides to cells in vitro (Mahapatro A, et al., *J Nanobiotechnol*, 2011, 9:55). The complex formed small particles of approximately 150 nm to 1 um when different peptide:DNA ratios were examined, and the 10:1 and 5:1 ratios (150 nm and 1 um respectively). Another CPP pertains to a modified tetrapeptide [tetralysine containing guanidinocarbonylpyrrole (GCP) groups (TL-GCP)], which was reported to bind with high affinity to a 6.2 kb plasmid DNA resulting in a positive charged aggregate of 700-900 nm Li et al., Agnew Chem Int Ed Enl 2015; 54(10):2941-4). RNA can also be complexed by such polycationic molecules for in vivo delivery (see review by Yin & Anderson).

Other examples of polycationic molecules that may be complexed with the nucleic acid constructs described herein include polycationic polymers commercially available as JETPRIME® and In Vivo JET (Polypus-transfection, S.A., Illkirch, France).

MHCII Activator Sequences

Certain nucleic acid construct embodiments include implementation of an MHCII activator sequence. The CIITA sequence has been well studied and has been shown to bind and activate the promoter encoding MHCII. Constructs implemented with MHCII activator sequences such as CIITA are preferably located on the construct upstream or downstream of epitope sequences and are separated by a protease cleavage site such that they are cleaved and taken into the nucleus. Information on CIITA is provided in Kim et al., *J Immunol* 2008; 180:7019-7027.

Provided below is a sequence of a murine CIITA sequence that is fully optimized. All internal restriction sites within CIITA (NheI, KpnI, AflII, BglII, XhoI(2), ApaI(3) and XmaI/SmaI(3)) have been removed. IET5AI has been previously codon-optimized.

Features: 1-AflII, 2-BglII, 3-KOZAR, 4-CIITA, 5-MfeI, 6-P2A, 7-KpnI, (SEQ ID NO: 53)

CTTAAGATCT[1]GCCACC[3]ATG[4]GGT[3]AACCACTTCCAGGCCATTCTGGCC
CAGGTGCAGACACTGCTGAGCAGCCAGAAGCCTAGACAAGTCCGAGCACT
GCTGGATGGCCTGCTGGAAGAGGAACTGCTGTCCAGAGAATACCACTGCG
CTCTGCTGCACGAACCTGATGGGGATGCCCTGGCCAGAAAGATCAGCCTG
ACTCTGCTGGAAAAGGGCGACCTGGACCTGACATTCCTGAGCTGGGTCTG
CAACTCTCTGCAGGCCCCTACAGTGGAAAGAGGCACCTCTTACAGAGATC
ACGGCGACCACAGCCTGTGCGCTACAATGGATCTTGGCAGCCCTGAGGGC
AGCTACCTGGAACTGCTCAACTCTGATGCCGATCCTCTGCATCTGTACCA
CCTGTACGACCAGATGGATCTGGCCGGCGAGGAAGAGATCGAGCTGTCTA
GCGAGCCTGACACCGACACCATCAACTGCGACCAGTTCAGCAAGCTGCTG
CAGGACATGGAACTGGACGAGGAAACAAGAGAGGCCTACGCCAATATCGC
CGAGCTGGACCAGTACGTGTTCCAGGATACACAGCTGGAAGGCCTGAGCA
AGGACCTGTTCATCGAGCACATCGGCGCTGAGGAAGGCTTCGGCGAGAAT
ATCGAGATCCCTGTGGAAGCCGGACAGAAGCCCCAGAAGAGAAGATTCCC
TGAGGAACACGCCATGGACAGCAAGCACAGAAAGCTGGTGCCTACCAGCA
GAACCAGCCTGAACTATCTGGACCTGCCTACCGGCCACATCCAGATTTTC
ACCACACTGCCTCAAGGCCTGTGGCAGATTTCTGGCGCTGGAACAGGACT
GAGCAGCGTGCTGATCTACCACGGCGAGATGCCTCAAGTGAACCAGGTGC
TGCCTAGCAGCTCCCTGTCTATCCATCTCTGCCTGAGAGCCCTGACAGA
CCTGGCAGCACAAGCCCTTTCACACCTTCTGCCGCCGACCTGCCTTCTAT
GCCTGAACCTGCTCTGACCTCCAGAGTGAACGAGACAGAGGACACAAGCC
CATCTCCATGCCAAGAGGGACCCGAGTCTAGCATCAAGCTGCCTAAGTGG
CCTGAGGCCGTGGAAAGATTTCAGCACAGCCTGCAGGATAAGTACAAGGC
CCTGCCACAGTCTCCTAGAGGACCTCTGGTGGCTGTGGAACTCGTCAGAG
CTAGACTGGAAAGGGGCAGCAACAAGAGCCAAGAGAGAGAGCTGGCCACA
CCTGACTGGACCGAAAGACAACTGGCTCACGGTGGACTGGCTGAGGTGCT
GCAAGTGGTGTCTGACTGTAGAAGGCCTGGCGAGACACAGGTGGTGGCAG
TTCTGGGAAAAGCCGGCCAGGGAAAGTCTCACTGGGCTAGAACAGTGTCC
CACACATGGGCATGTGGACAGCTGCTCCAGTACGACTTCGTGTTCTACGT
GCCATGCCACTGCCTGGATAGACCTGGCGACACATACCACCTGAGGGACC
TGCTGTGTCCACCTTCTCTGCAGCCTCTGGCCATGGATGACGAGGTGCTG
GACTACATCGTGCGGCAGCCTGATAGAGTGCTGCTGATCCTGGACGCCTT
CGAGGAACTGGAAGCTCAGGATGGACTGCTGCATGGACCTTGTGGATCTC
TGAGCCCTGAGCCTTGTTCTCTGAGAGGACTGCTGGCCGGCATCTTCCAG
AGAAAGCTGCTGAGAGGCTGTACCCTGCTGCTGACAGCTAGACCTAGAGG
CAGACTGGCCCAGAGCCTGTCTAAGGCCGATGCTATCTTCGAGGTGCCCA
GCTTCAGCACCAAGCAGGCCAAGACCTACATGAGACACTACTTCGAGAAC
AGCGGCACCGCCGGCAATCAGGATAAGGCACTTGGACTGCTCGAAGGCCA
GCCTCTGCTGTGTAGCTACTCTCACAGCCCTGTCGTGTGCAGAGCCGTGT

-continued
GTCAGCTGTCTAAAGCTCTGCTCGAACAGGGCACAGAGGCCCAGTTGCCT
TGTACACTGACCGGACTGTATGTGTCCCTGCTGGGACCTGCCGCTCAAAA
TTCTCCTCCTGGTGCTCTGGTGGAACTGGCCAAACTGGCTTGGGAACTCG
GAAGAAGGCACCAGTCTACCCTGCAAGAGACAAGATTCAGCAGCGTGGAA
GTGAAAACCTGGGCCGTGACACAGGGCCTGATGCAGCAGACCCTGGAAAC
AACAGAAGCTCAGCTGGCCTTTAGCAGCTTCCTGCTGCAGTGTTTTCTGG
GCGCTGTGTGGCTGGCCCAGTGTAATGAGATCAAGGACAAAGAGCTGCCT
CAGTACCTGGCTCTGACACCTAGAAAGAAGAGGCCCTACGATAACTGGCT
GGAAGGGGTGCCCAGATTCCTGGCTGGACTGGTGTTTCAGCCTAGGGCTC
ATTGTCTGGGAGCCCTGGTTGAACCAGCTGTGGCTGCCGTGGCTGACAGA
AAGCAGAAAGTGCTGACCAGATACCTGAAGAGACTGAAACTGGGAACACT
GAGAGCCGGCAGACTGCTGGAACTCCTGCACTGTGCTCACGAAACACAGC
AGCCTGGCATCTGGGAGCATGTGGCACATCAGCTGCCTGGCCACCTGTCC
TTTCTGGGCACAAGACTGACACCTCCAGACGTGTACGTGCTGGGCAGAGC
ACTGGAAACCGCCTCTCAGGACTTTAGCCTGGATCTGAGACAGACCGGCG
TGGAACCTTCTGGACTGGGAAATCTCGTGGGCCTGAGCTGCGTGACAAGC
TTCAGAGCCTCTCTGAGCGACACAATGGCCCTGTGGGAATCTCTGCAACA
GCAGGGCGAAGCACAGCTGCTTCAGGCCGCTGAAGAGAAGTTCACCATCG
AGCCCTTCAAGGCCAAGTCTCCCAAGGACGTTGAGGACCTGGATAGGCTG
GTGCAGACTCAGAGACTGAGAAACCCTAGCGAGGACGCCGCTAAGGATCT
GCCTGCTATCAGGGACCTGAAGAAGCTGGAATTCGCTCTGGGACCCATCC
TGGGACCTCAGGCTTTTCCTACACTGGCTAAGATCCTGCCAGCCTTCTCT
AGCCTGCAGCATCTGGATCTGGACTCCCTGAGCGAGAACAAGATCGGCGA
TAAGGGCGTGTCCAAGCTGAGCGCTACATTCCCTCAGCTGAAGGCTCTGG
AAACACTGAATCTGTCCCAGAACAACATCACCGACGTGGGCGCCTGTAAA
CTGGCTGAAGCACTGCCTGCTCTGGCCAAATCTCTGCTGAGGCTGAGCCT
GTACAACAACTGCATCTGCGACAAGGGCGCCAAGTCACTGGCTCAGGTTC
TGCCTGACATGGTGTCCCTGAGAGTGATGGACGTGCAGTTCAACAAGTTC
ACAGCCGCTGGCGCCCAGCAACTGGCATCATCTCTGCAGAAATGTCCCCA
GGTGGAAACCCTGGCTATGTGGACCCCTACAATCCCCTTCGGCGTGCAAG
AACATCTCCAGCAGCTGGACGCCAGAATCTCCCTGAGA[4]CAATTG[2]GCCA
CCAACTTCAGCCTGCTGAAGCAGGCCGGCGACGTGGAAGAAAATCCTGGA
CCT[6]GGTACC[5]

Translated protein:
(SEQ ID NO: 54)
MGNHFQAILAQVQTLLSSQKPRQVRALLDGLLEEELLSREYHCALLHEPD
GDALARKISLTLLEKGDLDLTFLSWVCNSLQAPTVERGTSYRDHGDHSLC
ATMDLGSPEGSYLELLNSDADPLHLYHLYDQMDLAGEEEIELSSEPDTDT
INCDQFSKLLQDMELDEETREAYANIAELDQYVFQDTQLEGLSKDLFIEH
IGAEEGFGENIEIPVEAGQKPQKRRFPEEHAMDSKHRKLVPTSRTSLNYL
DLPTGHIQIFTTLPQGLWQISGAGTGLSSVLIYHGEMPQVNQVLPSSSLS
IPSLPESPDRPGSTSPFTPSAADLPSMPEPALTSRVNETEDTSPSPCQEG -continued
PESSIKLPKWPEAVERFQHSLQDKYKALPQSPRGPLVAVELVRARLERGS
NKSQERELATPDWTERQLAHGGLAEVLQVVSDCRRPGETQVVAVLGKAGQ
GKSHWARTVSHTWACGQLLQYDFVFYVPCHCLDRPGDTYHLRDLLCPPSL
QPLAMDDEVLDYIVRQPDRVLLILDAFEELEAQDGLLHGPCGSLSPEPCS
LRGLLAGIFQRKLLRGCTLLLTARPRGRLAQSLSKADAIFEVPSFSTKQA
KTYMRHYFENSGTAGNQDKALGLLEGQPLLCSYSHSPVVCRAVCQLSKAL
LEQGTEAQLPCTLTGLYVSLLGPAAQNSPPGALVELAKLAWELGRRHQST
LQETRFSSVEVKTWAVTQGLMQQTLETTEAQLAFSSFLLQCFLGAVWLAQ
CNEIKDKELPQYLALTPRKKRPYDNWLEGVPRFLAGLVFQPRAHCLGALV
EPAVAAVADRKQKVLTRYLKRLKLGTLRAGRLLELLHCAHETQQPGIWEH
VAHQLPGHLSFLGTRLTPPDVYVLGRALETASQDFSLDLRQTGVEPSGLG
NLVGLSCVTSFRASLSDTMALWESLQQQGEAQLLQAAEEKFTIEPFKAKS
PKDVEDLDRLVQTQRLRNPSEDAAKDLPAIRDLKKLEFALGPILGPQAFP
TLAKILPAFSSLQHLDLDSLSENKIGDKGVSKLSATFPQLKALETLNLSQ
NNITDVGACKLAEALPALAKSLLRLSLYNNCICDKGAKSLAQVLPDMVSL
RVMDVQFNKFTAAGAQQLASSLQKCPQVETLAMWTPTIPFGVQEHLQQLD
ARISLRQLATNFSLLKQAGDVEENPGP

Secretion Signal

Certain embodiments of the nucleic acid constructs may implement a secretion signal sequence for secreting the one or epitopes from the transfected cell. An example of a secretion signal sequence pertains to a codon-optimized albumin secretion signal:

(SEQ ID NO: 55)
ATGAAGTGGGTAACCTTTCTCCTCCTCCTCTTCATCTCCGGTTCTGCCTT
TTCTAGGGGCAAGCTTATG

Those skilled in the art will appreciate that other known secretion signal sequences may be implemented in the nucleic acid constructs. A secretory signal sequence can be obtained from other eukaryotic polypeptides that are known to be secreted. With the cloning and sequencing of numerous genomes, including human, there exists a wide variety of eukaryotic secretion signal sequences that can be employed. Ideally, the secretion signal sequence is selected from a species from transfection of cells is intended, or codon-optimized for that species. In addition to the codon-optimized albumin secretion signal provided above, other examples include an albumin leader having the sequence ATG AAG TGG GTA ACC TTT ATT TCC CTT CTT TTT CTC TTT AGC TCG GCT TAT TCC AGG GGT GTG TTT CGT CGA GAT (SEQ ID NO: 56) and an immunoglobulin kappa (Ig κ)-chain leader having the sequence ATG GAG ACA GAC ACA CTC CTG CTA TGG GTA CTG CTG CTC TGG GTT CCA GGT TCC ACT GGT GAC (SEQ ID NO: 57). See also U.S. Pat. No. 9,157,085 and WO/2014/177826 for other examples that may be adapted for use with nucleic acid construct embodiments.

Cells

Antigen-presenting cells (APCs) are cells that can, or can be induced to, present antigens on their surface in the context of MHCI or MHCII. Dendritic cells, macrophages, and B cells, are considered in the art to be "professional APCs." These cells, and any other "non-professional" APCs that are able to present antigen with MHCI (and to some extent with MHCII) are defined here as APCs. Any APC can be used with the invention and are contemplated for administration to subjects as described.

Dendritic cells have considerable clinical benefits for reprogramming immune cells because of their ability to target specific T cells, ability to preferentially migrate to tissues of interest, ease of ex vivo expansion and manipulation, and good safety records. Dendritic cells and their use are well known in the art. These cells are discussed in Creusot et al., Blood 113:6638-6647, 2009 and Creusot et al. Diabetes 63(1):20-30, 2014, as well as methods for handling and culturing the cells and using these cells for presentation of antigen, and a discussion of homing and trafficking of dendritic cells. The work of Giannoukakis et al., in Diabetes Care 34(9):2026-32, 2011 has shown that dendritic cells are safely tolerated in T1D patients. Dendritic cells have also been used in a large number of cancer therapy trials (Dendritic-cell-based therapeutic cancer vaccines. Palucka K, Banchereau J. Immunity. 25; 39(1):38-48, 2013).

To obtain human dendritic cells, blood can be harvested from a subject according to methods well-known in the art, from which monocytes can be isolated and differentiated in vitro over one week of culture in presence of granulocyte-macrophage colony-stimulating factor (GM-CSF) and IL-4. Phenotype can be analyzed and confirmed by FACS according to well-known methods in the art. For suitable methods, see Nava et al., "An optimized method for manufacturing a clinical scale dendritic cell-based vaccine for the treatment of glioblastoma. PloS ONE 7(12):e52301. Doi10.1371/journal.pone.052301, 2012; Nair et al., "Isolation and Generation of Human Dendritic Cells," Curr. Protoc. Immunol. 99:7.32.1-7.32.23, 2012.

Tolerogenic (tolerance-inducing) antigen-presenting cells (APCs) are naturally found throughout lymphoid tissues and function to present self antigens to potential autoreactive T cells and instruct these T cells to undergo apoptosis (deletion), inactivation (anergy) or conversion into regulatory T cells (Tregs) via tolerogenic signals. Different subsets of tolerogenic APCs exist within the dendritic cell and stromal cell populations. Each subset displays its own combination of antigens, acquired exogenously or through endogenous expression, and surface-expressed or secreted molecules (tolerogenic signals). Thus, a single tolerogenic cell can simultaneously provide antigenic and multiple tolerogenic signals that can be optimally integrated and interpreted by the target T cells. Immature (non-immunogenic) DCs can be modified to co-express antigens and multiple tolerogenic products, for example by mRNA electroporation.

Immunogenic DCs have been tested as therapeutic vaccines in cancer patients for nearly a decade, culminating with the FDA approval of Provenge®. The application of tolerogenic DCs to autoimmune diseases and transplantation has been more recent, leading to the first clinical trials for T1D (Giannoukakis et al., Diabetes Care, 2011) and RA (AutoDECRA trial in UK, Rheumavax trial in Australia: Citrullinated peptide dendritic cell immunotherapy in HLA risk genotype-positive rheumatoid arthritis patients. Benham et al., Sci. Transl. Med. 7(290):290ra87, 2015). With the emergence of these new personalized therapies comes a need for increased specificity, efficiency and safety, which can be addressed by strategic manipulation of the therapeutic DCs to display appropriate epitopes alongside tolerogenic signals that specifically engage target T cells through multiple signals that can be integrated for efficient reprogramming.

Figure 3:
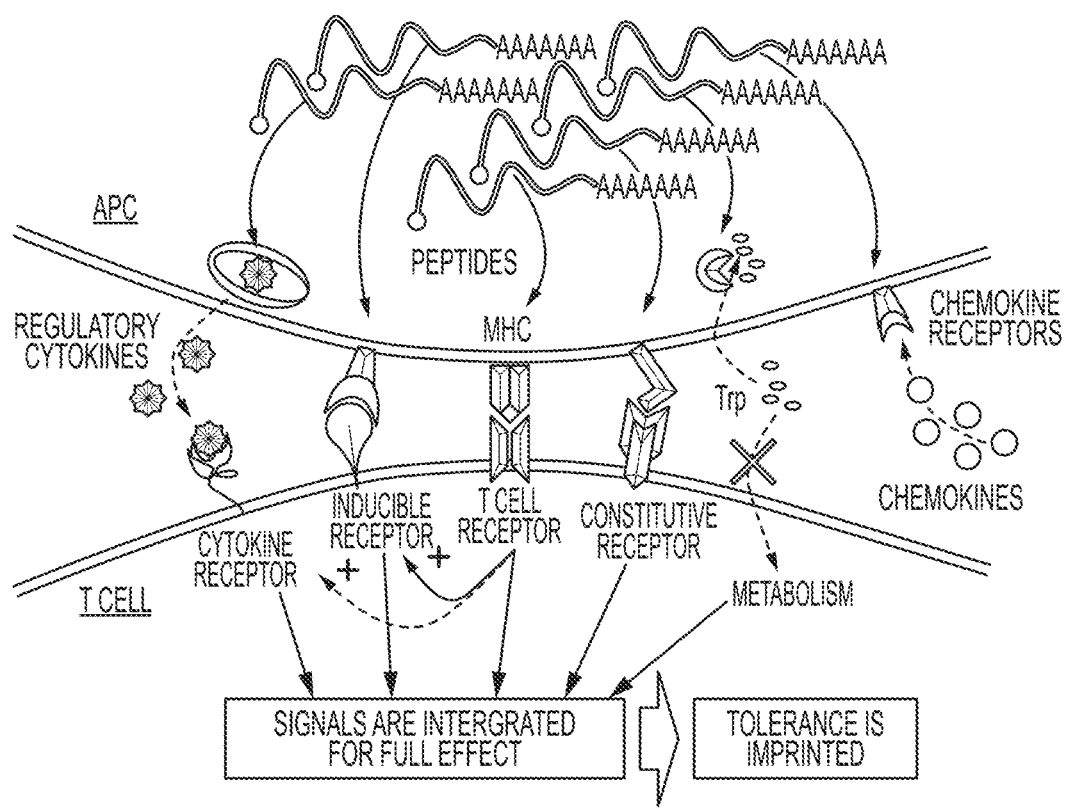
FIG. 3 is a cartoon showing the interactions which are part of the strategy for achieving tolerance using the inventive methods. Tolerogenic interfaces can comprise several of the following: (i) MHC/peptide complexes, (ii) inhibitory ligands displayed on the cell surface, (iii) secreted molecules that regulate T cells, and (iv) enzymes that influence the metabolism of the T cells (e.g. Tryptophan deprivation by IDO or retinoic acid production by ALDH1). Optimal tolerance induction may require integration of all antigenic and tolerogenic signals by the targeted T cells. Thus, these signals must be concomitant. Such interfaces can be created by providing mRNAs coding for all the needed components to antigen-presenting cells serving as the tolerogenic interface.

Because different tolerogenic signals may be found naturally segregated between subsets of tolerogenic dendritic or stromal cells, there is much potential in creating novel and elaborate tolerogenic "interfaces" combining antigens and tolerogenic signals (FIG. 3) that would more efficiently engage multiple biological pathways in T cells in order to address the limitations of conventional drugs and biologics that lack specificity and cannot assure that combined signals to T cells are concomitant and integrated.

Compositions, Administration, Routes, and Doses.

The nucleic constructs of the invention are contemplated for administration to a subject in need, and can be administered by any convenient method known to the person of skill in the art. Administration can be by any route, including but not limited to local and systemic methods, for example aerosols for delivery to the lung, oral, rectal, vaginal, buccal, transmucosal, intranodal, transdermal, intravenous, subcutaneous, intradermal, intratracheal, intramuscular, intraarterial, intraperitoneal, intracranial (e.g., intrathecal or intraventricular) or any known and convenient route. Preferred routes of administration are intravenous, intraperitoneal, oral/nasal and direct injection into the affected organ, tissue, area of infection or tumor, or specific lymph nodes. The form of the administration can determine how the active agent is formulated, and this is easily determined by the skilled artisan. Nucleic acid drugs generally are delivered in nano-sized drug formulations into the blood stream, and these well-known formulations and methods of administration are preferred. An exemplary nanocarrier is described in Pujol-Autonell et al., "Use of autoantigen-loaded phosphatidyl-serine-liposomes to arrest autoimmunity in type 1 diabetes." PloS one 10, e0127057 (2015).

Compositions of the present invention therefore can include, but are not limited to, solid preparations for oral administration, solid preparations to be dissolved in a liquid carrier for oral or parenteral administration, solutions, suspensions, emulsions, oils, creams, ointments, lotions, gels, powders, granules, cells in suspension, and liposome-containing formulations, and the like, or any convenient form known in the art. These compositions may be generated from a variety of components that include, but are not limited to, preformed liquids, self-emulsifying solids and self-emulsifying semisolids.

Solutions or suspensions used for parenteral, intradermal, subcutaneous or other injection can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylene diamine tetra acetic acid; buffers such as acetates, citrates or phosphates; and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Compositions suitable for injectable use include sterile aqueous solutions (where the therapeutic agents are water soluble) or dispersions and sterile powders for the extemporaneous preparation of sterile injectable solutions or dispersion. For intravenous administration, suitable carriers include physiological saline, bacteriostatic water, Cremophor EL® (BASF, Parsippany, N.J.) or phosphate buffered saline (PBS). In all cases, the composition must be sterile and should be fluid to the extent that they can pass through a syringe and needle easily enough for administration. It should be stable under the conditions of manufacture and storage and should be preserved against the contaminating action of microorganisms such as bacteria and fungi. All solutions used to solubilize DNA or RNA should also be DNase-free and RNase-free.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active agent in the required amount in an appropriate solvent with one or a combination of the ingredients enumerated above, as required, followed by filter sterilization. Generally, dispersions are prepared by incorporating the active agent into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. The skilled person is aware of how to use these dried preparations for injection.

Oral compositions generally include an inert diluent or an edible carrier. They can be enclosed in gelatin capsules or compressed into tablets. Depending on the specific conditions being treated, pharmaceutical compositions of the present invention for treatment of atherosclerosis or the other elements of metabolic syndrome can be formulated and administered systemically or locally. Techniques for formulation and administration can be found in "Remington: The Science and Practice of Pharmacy" (20th edition, Gennaro (ed.) and Gennaro, Lippincott, Williams & Wilkins, 2000). For oral administration, the agent can be contained in enteric forms to survive the stomach or further coated or mixed to be released in a particular region of the GI tract by known methods. For the purpose of oral therapeutic administration, the active agent can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL® or corn starch; a lubricant such as magnesium stearate or STEROTES®; a glidant such as colloidal silicon dioxide; a sweetening agent such as sucrose or saccharin; or a flavoring agent such as peppermint, methyl salicylate, or orange flavoring.

Systemic administration can also be by transmucosal means to the intestinal or colon, such as by suppository or enema, for example. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active agents are formulated into ointments, salves, gels, or creams as generally known in the art.

Figure 21:
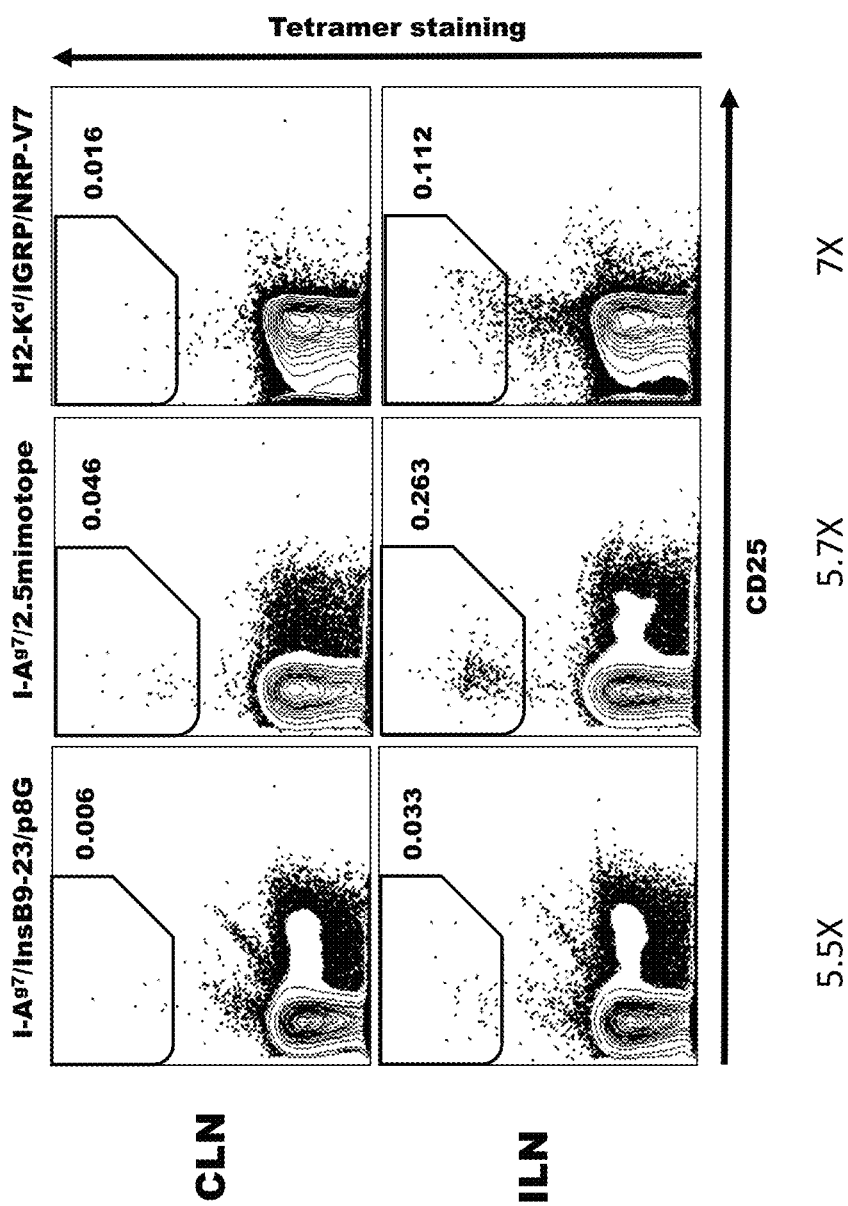
FIG. 21. In vivo expansion (5-7x) of antigen-specific T cells identified by MHC tetramer staining in control CLNs and skin-draining ILNs 2.5 days after ID injection of DNA vaccines (BS) expressing all relevant epitopes and mimotopes.

Homing of dendritic cells and the effects of different modes of administration of these cells are discussed in Creusot et al., Blood 113:6638-6647, 2009. Preferred administration sites include those that target the lymph nodes draining the site of infection, tumor or autoimmune attack. Persons of skill are aware of those locations and can select an appropriate route of administration for each patient or disease state. For example, pancreatic lymph nodes are targeted efficiently by dendritic cells after intraperitoneal and intravenous administration. See Creusot et al. Blood 113:6638-6647, 2009. In a specific embodiment, the nucleic acid constructs are administered intramuscularly, intradermally, intraperitoneally or intranodally (intralymphatically). Without being bound to any theory, it is believed that intraperitoneal administration may be particularly suitable for administration of tolerogenic nucleic acid constructs as they stand a greater chance of migrating to pancreatic lymph nodes, which harbor a larger population of diabetogenic self-reactive T-cells. Intradermal and intramuscular, most commonly used with DNA vaccines, lead to antigen presentation in other draining lymph nodes where autoreactive may also circulate and be engaged (see FIG. 21C). Transfection of lymph node stromal cells or tolerogenic professional APCs located in the pancreatic lymph nodes may provide a greater potential of inactivating T cells primarily involved in T1D, by directly counteracting the stimulation provided by immunogenic DCs in those lymph nodes that drained a tissue under inflammation.

In several embodiments, the active agents are prepared with carriers that will protect the compound against rapid elimination from the body, such as a controlled release or delayed formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to particular cells with, e.g., monoclonal antibodies) can also be used as pharmaceutically acceptable carriers. These can be prepared according to methods known to those skilled in the art.

Formulations designed to provide extended or delayed release also are contemplated for use with the invention. The following United States patents contain representative teachings concerning the preparation of uptake, distribution and/or absorption assisting formulations: U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756. Such compositions are contemplated for use with the invention.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product. The active agents described herein also can be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Such methods for creating liquid, solid, semi-solid, gel, powder or inhalable formulations and the like are known in the art. Techniques for formulation and administration can be found in "Remington: The Science and Practice of Pharmacy" (20th edition, Gennaro (ed.) and Gennaro, Lippincott, Williams & Wilkins, 2000). Alternatively, the inventive compounds can be fused to microspheres in suspension for intravenous injection.

Dosages and regimens for administration are determined by the person of skill, including physicians. Administration of compositions, including the nucleic acid, peptide, composition and cells of the invention can be performed a single time, or repeated at intervals, such as by continuous infusion over a period of time, four times daily, twice daily, daily, every other day, weekly, monthly, or any interval to be determined by the skilled artisan based on the subject involved. Treatment can involve administration over a period of one day only, a week, a month, several months, years, or over a lifetime. Regimens and duration can vary according to any system known in the art, as is known to the skilled person.

Cells expressing a DNA or an mRNA, or naked DNA or RNA in a nanocarrier-type pharmaceutical vehicle, can be injected into a patient, intravenously or into the tissues and/or organs affected by the disease condition to be treated. Current cell vehicles available for human therapy include tolerogenic or immunogenic dendritic cells, and stromal cells. Dendritic cells are typically differentiated in vitro from blood precursors, but may also be derived from bone marrow precursors. Precursors of certain types of stromal cells (mesenchymal stromal cells or mesenchymal stem cells) may be derived from bone marrow or adipose tissue. The nanocarrier vehicle can be a liposome, a nanoparticle or microparticle, which can be taken up by APCs in vivo.

Doses of the inventive nucleic acid construct, peptide and cells can be determined by the skilled artisan based on the condition of the subject and the route of administration to be used, but are expected to range from about 100 µg to about 10 mg, preferably from about 500 µg to about 10 mg, or about 1 mg to about 10 mg, or about 1 mg to about 5 mg or about 5 mg to about 10 mg and most preferably from about 1 mg to about 5 mg. Optimization/pharmacokinetics can make lower doses effective, therefore even lower doses are contemplated for use with the invention, for example about 10 µg to about 100 µg.

Treatment

The constructs of the invention can be delivered in situ as plasmid or minicircle DNA (naked DNA vaccines with or without nanoparticle-mediated delivery) or mRNA vaccine, or ex vivo into tolerogenic DCs (or other tolerogenic APCs as they become available) as viral vector (transduction) or mRNA (electroporation).

In contexts where tolerance is sought, the invention leads to the elimination or inactivation of self-reactive T cells, and the induction of stable regulatory T cells (Tregs), which is most important for long-term tolerance. Targeting T cells with relevant antigen specificity and focusing the intervention on relevant tissues are advantageous to avert systemic immune suppression and adverse effects. T1D patients, for example, vary in the risk alleles that they possess, the antigens that are targeted and the rate of disease progression. Thus, therapies preferably impact multiple biological pathways while targeting only specific T cell populations. For producing tolerance or inactivation of self-reactive T cells, a construct according to the invention is produced and introduced into an APC, preferably a dendritic cell, in vivo or ex vivo, using a lentivirus or other viral vector, a naked DNA or RNA transfection method, mRNA electroporation, or any of the methods discussed above. If the introduction of the construct is performed ex vivo, the modified cell is administered to a subject in need by an appropriate route of administration, preferably intravenously.

For use in methods of treatment, mRNA electroporation is preferred due to its combinatorial versatility which allows combined expression of more products than is possible using other common methods of modification such as viral vectors. Other interesting properties of an mRNA approach include the high transfection efficiency and absence of maturity induction relative to viral methods. Despite the transient expression of mRNA therapeutic products, rapid and durable effects can be achieved, including induction of protective T cell populations that sustain tolerance long after expression in DCs is lost, resulting in significant delay, reduced incidence, and even reversal of disease in non-obese diabetic (NOD) mice (Creusot et al., Mo. Ther. 18:2112-2190, 2010). This approach adds another clinical safety aspect since mRNA cannot disrupt the genome nor lead to prolonged expression of the encoded nucleic acids, as this may not necessarily be desirable where producing immune stimulation. Production of antigen-specific Tregs that are more suppressive and more stable can be achieved.

Changing the mode of antigen presentation (from tolerogenic to immunogenic) may enhance immune responses in cases where destruction of a cell is desired, such as, e.g., cancer, viral and bacterial infections. This mode of antigen delivery would favor efficient priming of CD4+ and CD8+ T cells that target multiple epitopes while enabling cooperation between the activated T cells. In methods where it is desired to produce tolerance, anergy, or a conversion of auto-reactive T cells to Tregs, the following steps preferably are performed: single or multiple treatments with a nucleic acid construct embodiment of choice with or without other tolerogenic products or administration of a tolerogenic APC modified by a nucleic acid construct embodiment of choice to express TEC with or without other tolerogenic products. In methods where it is desired to produce immune stimulation against a tumor, pathogen, or the like, the following steps preferably are performed: single or multiple treatments with a nucleic acid construct embodiment of choice with or without adjuvants to enhance immunogenicity or administration of an immunogenic APC modified by a nucleic acid construct embodiment of choice and activated with immunogenic compounds such as TLR ligands.

In some embodiments of the invention, immunosuppressive compounds can be co-administered with a tolerogenic nucleic acid construct embodiment. Such compounds include, but are not limited to immunosuppressive compounds selected from the group consisting of TGF-β, IL-10, IL-1RA, IL-4, IL-27, IL-34, IL-35, PD-L1, ICOSL, B7-H3, B7-H4, ILT3, ILT4, HVEM, VISTA, CD39, CD73, FAS, FAS-L, IDO1, IDO2, ALDH1/RALDH, ARG1, ARG2, NOS2, HMOX1, galectin-1, galectin-9, semaphorin 4A, or any combination thereof. These can be coadministered, for example, by administration of the compound itself, or by administration of an mRNA encoding the compound, with appropriate sequences necessary for expression of the compound.

The inventive nucleic acid constructs and approaches of administering epitopes by engaging multiple pathways in antigen-specific T cells as part of a single encounter with an engineered APC can be used in research to design better cell-based therapies, and can be used to develop rational combinations of small drugs and/or biologics that simultaneously impact these pathways. Because DC manipulation with mRNA allows for co-expression of additional products, homing molecules that would enhance the in vivo targeting of tolerogenic DCs, or inhibitory molecules that dampen the immune system can be used with the invention, mRNA methods are preferred.

6. Examples

This invention is not limited to the particular processes, compositions, or methodologies described or exemplified, as these may vary. Although any methods and materials similar or equivalent to those described herein can be used in the practice or testing of embodiments of the present invention, the preferred methods, devices, and materials are described. It will, however, be evident that various modifications and changes may be made thereto without departing from the broader spirit and scope of the invention. Examples are provided below to facilitate a more complete understanding of the invention. The following examples illustrate the exemplary modes of making and practicing the invention, however, the scope of the invention is not limited to specific embodiments disclosed in these Examples, which are for purposes of illustration only. Those skilled in the art will recognize, or be able to ascertain, using no more than routine experimentation, numerous equivalents to the specific embodiments described herein. Such equivalents are considered to be within the scope of this invention.

Example 1. Methods

A. Testing of In Vivo Stimulation of Diabetogenic T Cells

Presentation of epitopes can be tested in vitro using T cell clones from T cell receptor transgenic mice such as BDC2.5, BDC12-4.1, NY8.3, G9C8 and G286. Spleen and pooled lymph nodes from these mice are produced into single cell suspensions and antigen-specific CD4+ CD25− or CD8+ T cells are purified and injected into recipient NOD or NOD-.Thy1.1 mice. The recipient mice are treated on the same day or the day after with TEC or DCs modified by lentiviral vector or mRNA to express TEC. Spleen and lymph nodes can be isolated 3 days later to measure stimulation of adoptively transferred T cell clones, and induction of regulatory T cells expressing Foxp3 or IL-10 for example. As an alternative to these T cell clones, antigen-specific T cells reactive to specific epitopes expressed by TECs, can be identified by tetramer staining for phenotype analysis. Many such reagents are available, for example from the NIH Tetramer Core Facility.

B. Production of Dendritic Cells

Bone marrow from mice or humans is harvested according to methods well-known in the art, and then depleted of T cells, B cells, and granulocytes by magnetic separation using biotinylated anti-CD3, anti-B220 and anti-Gr-1, and anti-biotin microbeads. Blood from human subjects is enriched for monocytes using Ficoll and/or magnetic separation methods. In both cases, the isolated cells are cultured for approximately 1 week in the presence of complete recombinant mouse granulocyte-macrophage colony-stimulating factor (GM-CSF) and IL-4 (mouse or human) The phenotype of the generated DCs is analyzed by FACS according to well-known methods in the art.

C. Transduction

If a viral vector is used to transduce dendritic cells, preferably a multiplicity of infection (MOI; estimated number of. viral particles in suspension) of about 10 MOI to about 100 MOI is used, more preferably an MOI of about 15-20 If transduction proves difficult, an MOI of up to about 200 can be used.

C. DNA Vectors

DNA plasmids (vectors) containing TEC are produced in large scale using combined endotoxin-free maxiprep or gigaprep kits and are solubilized in DNase-free saline. For testing in mouse models, 100 µg of the plasmids/vectors can be injected per mouse per day intramuscularly (50 µg per quadriceps). For human patients, between 300 ug and 6 mg of GMP-grade DNA plasmid can be administered by intramuscular injection (weekly for 12 weeks) (Roep et al., Sci. Transl. Med., 2013). Typically the high end of this range is most effective, therefore preferred doses range from about 100 micrograms to about 10 milligrams per dose. Other routes of inoculation remain to be evaluated as the optimal route of treatment will vary from disease to disease, however any convenient method known to the skilled person can be used.

E. Electroporation

For dendritic cell electroporation, a preferred method is to use about 30 µg mRNA per 5 million cells in a 0.4 cuvette using optimized parameters described by Creusot et al., Mol. Ther., 2010. Cells and mRNA are mixed in serum-free medium, and placed back in complete medium after electroporation. The method is essentially the same between mouse and human dendritic cells, although GMP-grade mRNA must be used for human patients. IVT mRNA, including GMP-grade, can be produced custom-made by commercial entities.

To transduce cells, in vitro, the cells generally are saturated with mRNA. This usually is accomplished by adding about 30-40 micrograms of mRNA per 5 million cells. As the skilled person in the art is aware, the amount used can be from about 1 µg to about 40 µg. Although any known and convenient method can be used, it is typical to electroporate about 1 million cells at a time.

Example 2. Preliminary Constructs for Targeting Class II

Figure 4B:
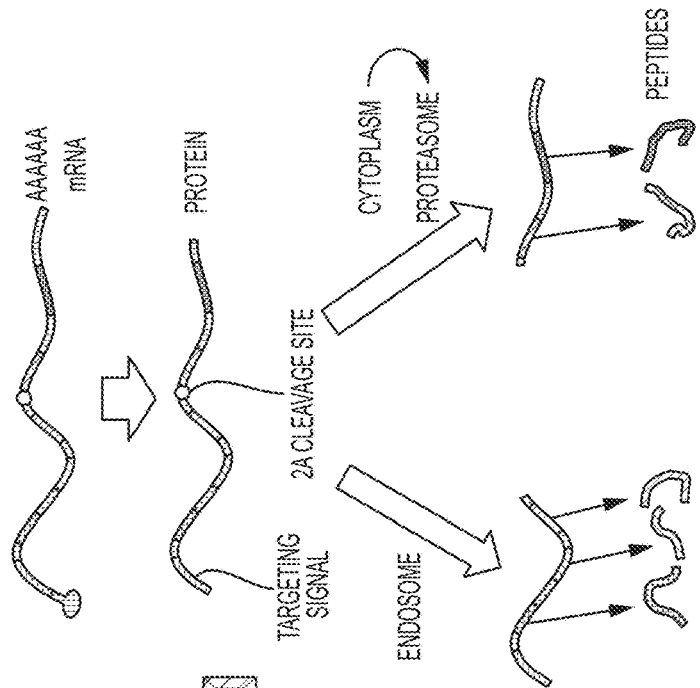
FIG. 4A and FIG. 4B are schematic drawings of exemplary constructs (4A) and the mechanism of peptide cleavage (4B) for those constructs.
Figure 4A:
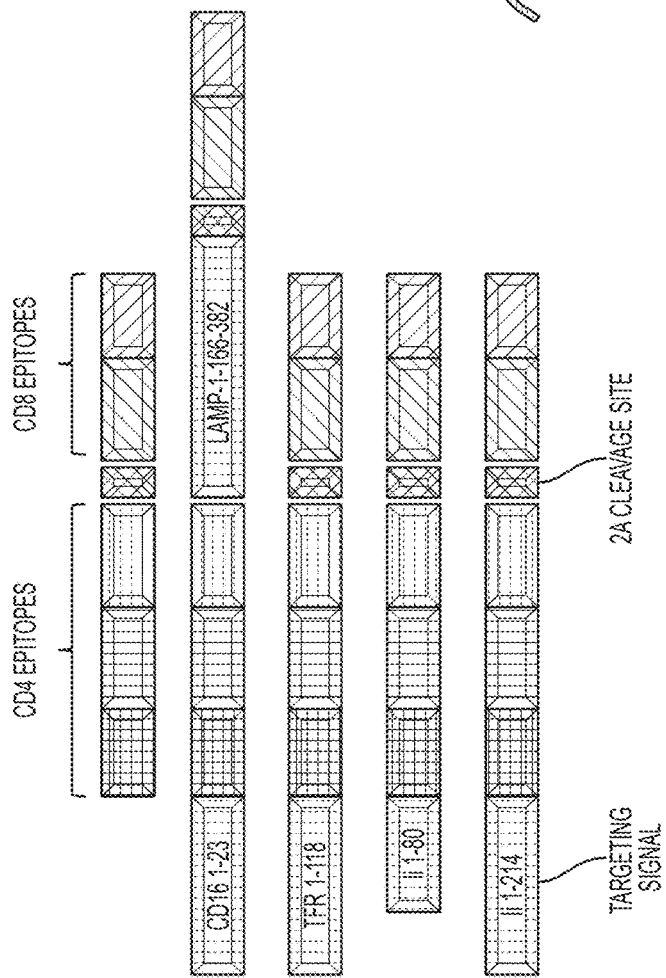

Epitopes can be delivered to DCs as a single construct or mRNA molecule with the appropriate targeting signal, and are naturally processed inside the DCs and presented onto MHC class I molecules at least (see FIG. 4A, which shows a construct designed to target for class II processing). Variants of these constructs with leader peptides can be used for their ability to target the polypeptides more efficiently to the endosomes for MHC class II presentation (see FIG. 4B). The leader sequences of these exemplary constructs include fragments from CD16 and lysosome-associated membrane protein-1 (LAMP-1) combined transferrin receptor (TFR) or invariant chain (Ii). These constructs have been codon-optimized. After lentiviral transduction of DCs, for example, purified TCR transgenic T cells or T cell clones, as listed in FIG. 5 can be used to determine the degree of presentation of the epitopes on both MHC class I and class II molecules. Depending on the clone, stimulation can be assessed by a cell proliferation dye dilution or IL-2 or IFN-γ production.

Example 3. Alternative Constructs

Figure 6:
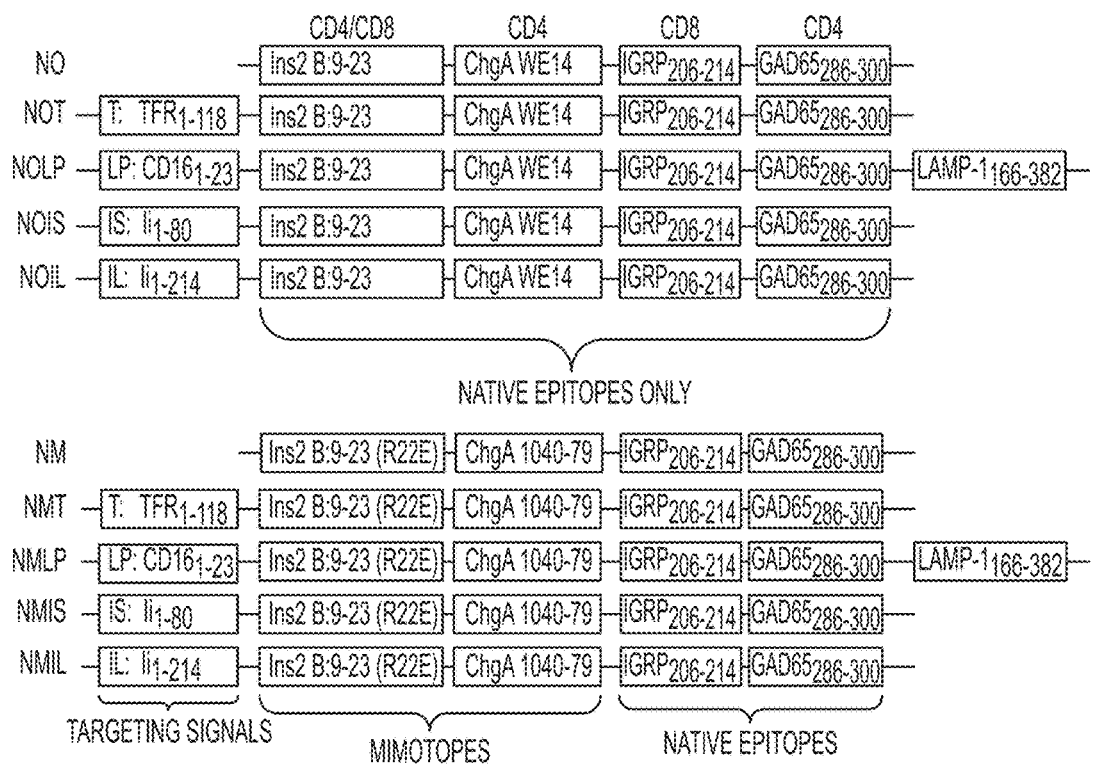
FIG. 6 is a schematic showing ten constructs, using native sequence epitopes only (NO) or some mimotope substitution (NM), that have been tested and compared upon introduction into dendritic cells by lentiviral transduction using GFP as reporter gene, whereby the expression of GFP is proportional to the expression of the epitopes.
Figure 7A:
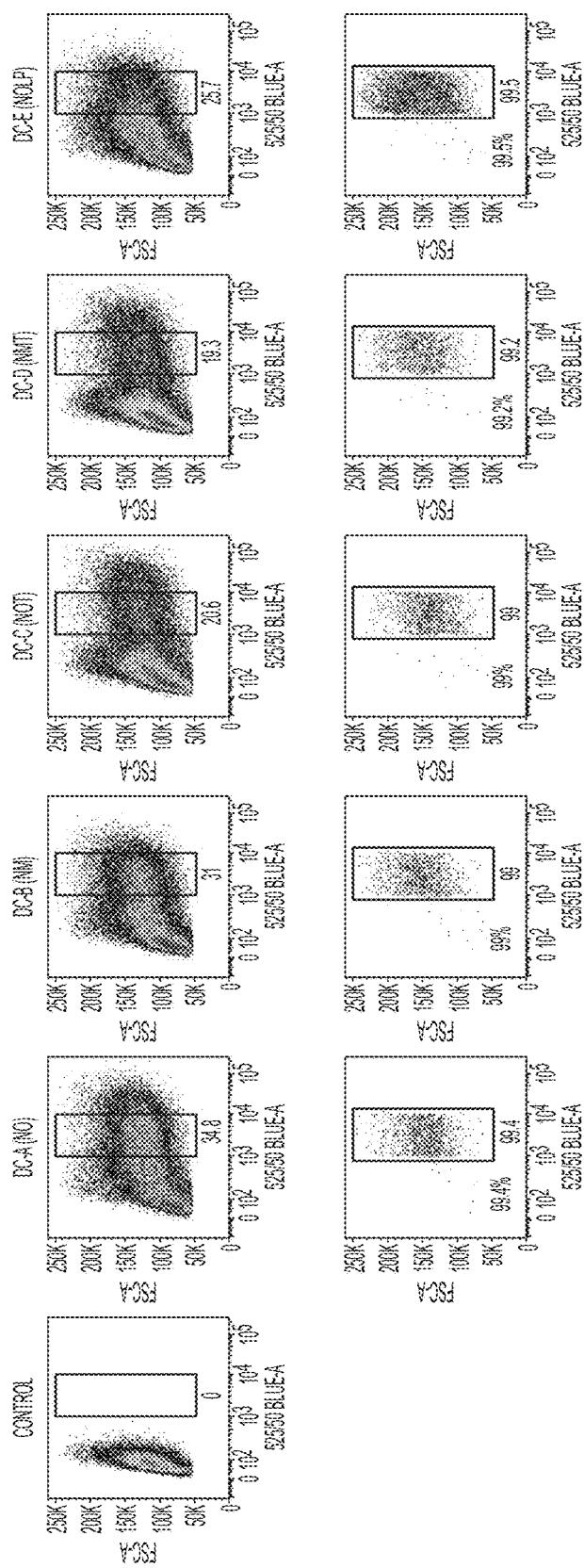
FIGS. 7A-7B.
Figure 7A:
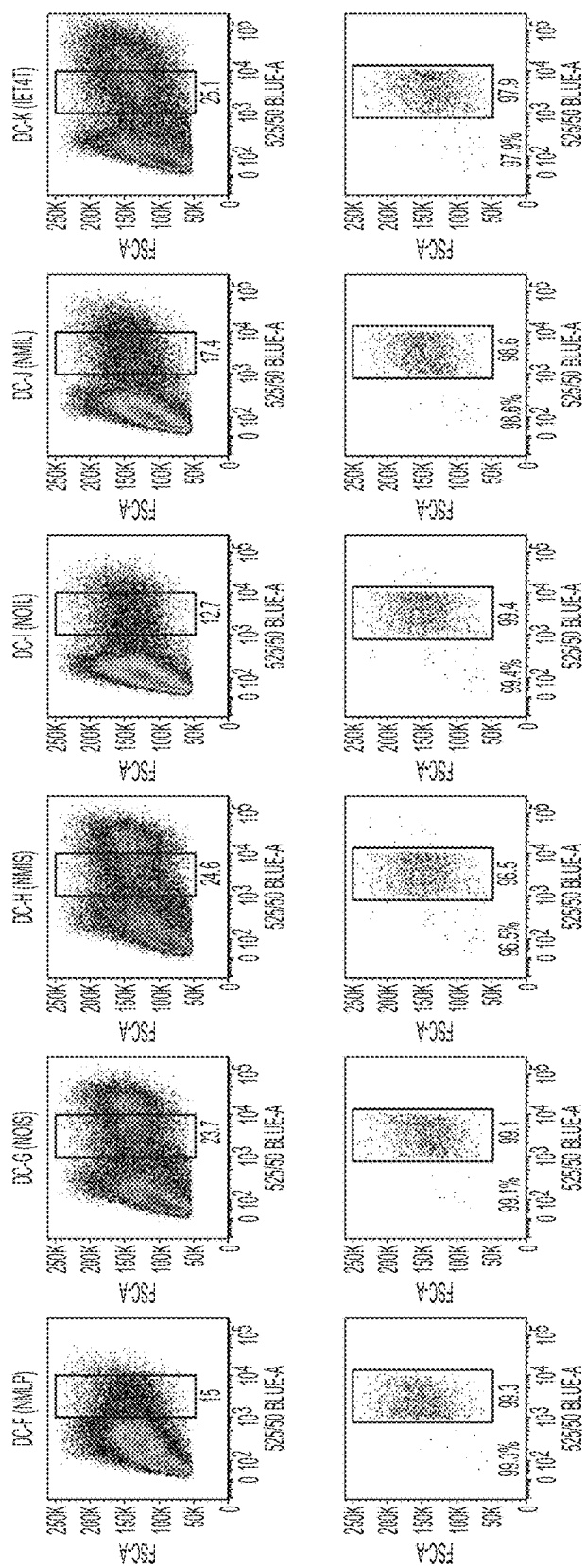
Figure 7B:
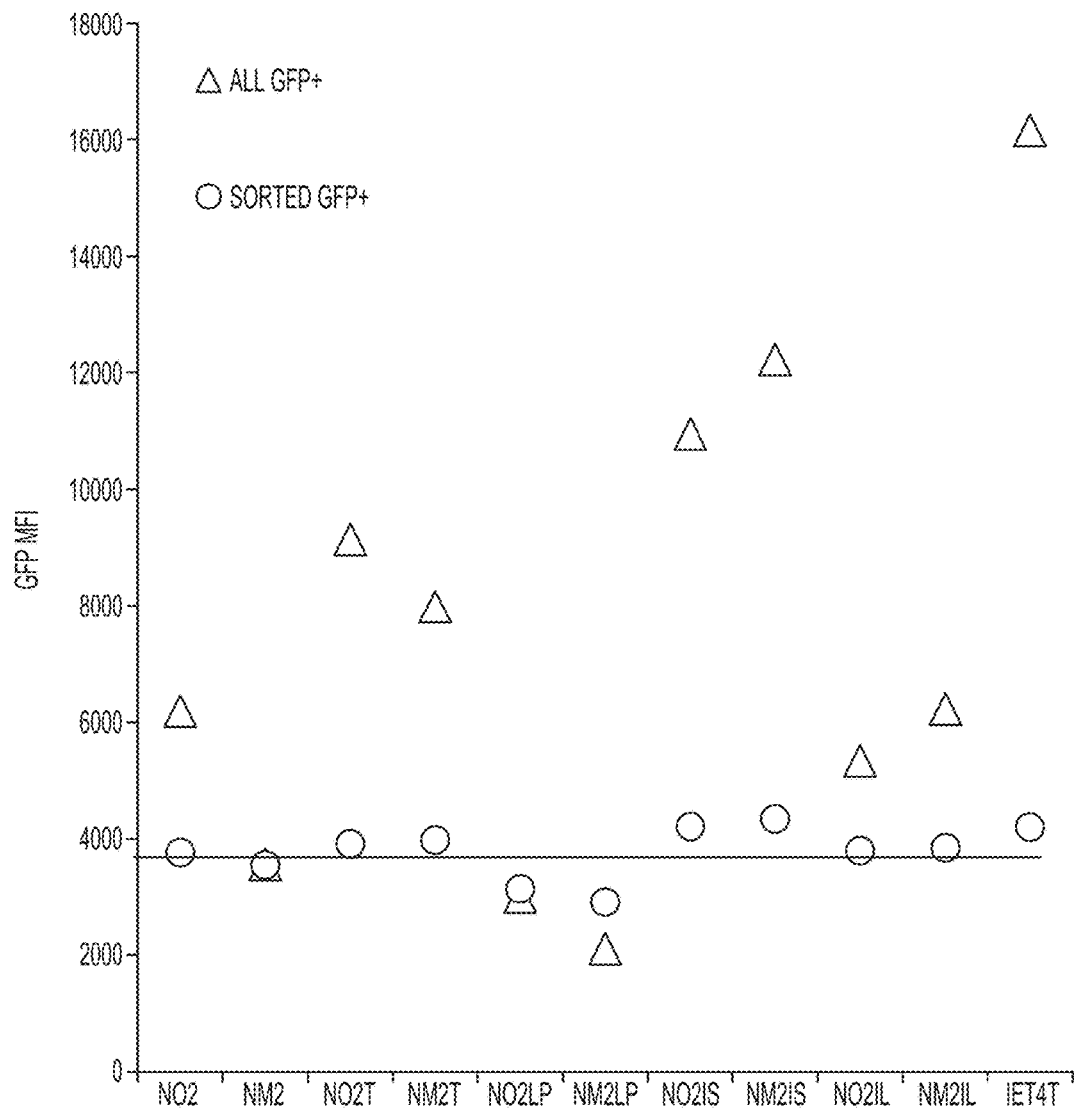
Figure 14:
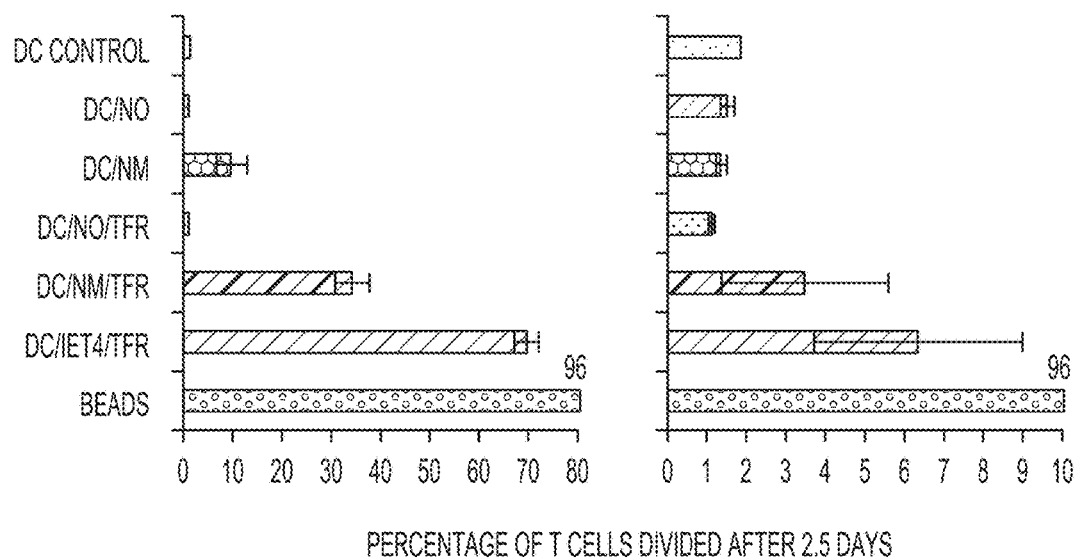
FIG. 14 shows the percentage of T cells divided after 2.5 days from the indicated mice administered DCs transduced by lentivirus with the indicated constructs. "Beads" indicate a positive control where maximal stimulation is provided. The DC control contains no construct. TFR indicates the presence of one of the MHC class II targeting sequence tested. These results show that CD4+ T cell responses are best with targeting sequences, that CD8+ T cell responses are best without targeting sequences, and that a construct representative of the invention (IET4T) is best for both CD4+ and CD8+ T cells.
Figure 14:
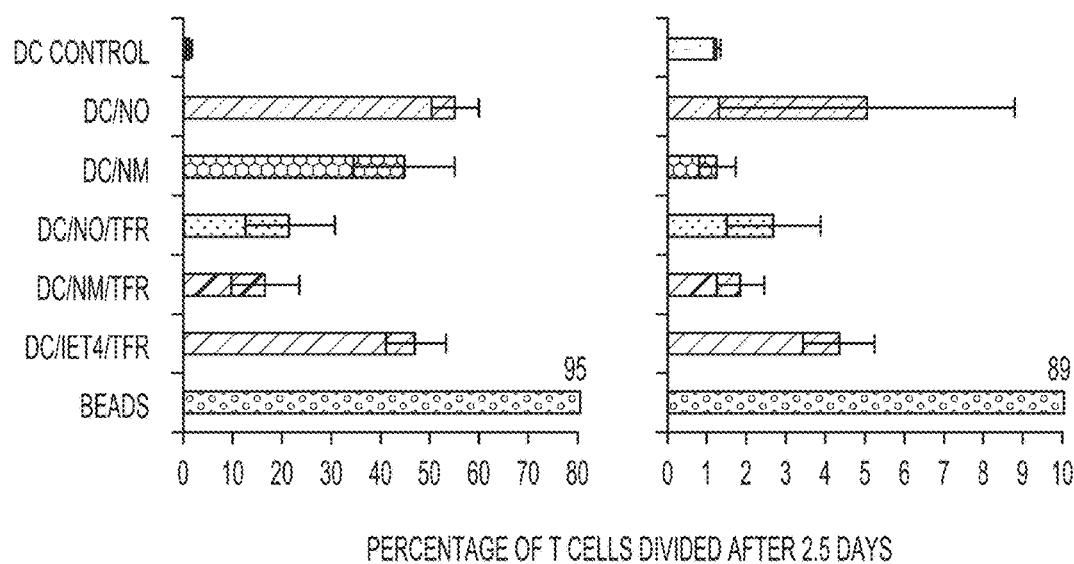

FIG. 14 shows results for antigens and antigen-reactive T cells used in the methods discussed here. The stimulation of various TCR-tg (TCR-transgenic) T cells (purified CD4+ CD25− or CD8+) was tested by dilution of a cell proliferation dye in response to the different constructs expressed in DCs. Bone marrow-derived dendritic cells from NOD mice were generated over 7 days in the presence of GM-CSF and IL-4. They were transduced on day 5 with the various antigen-expressing lentiviral constructs shown in FIG. 2 and FIG. 6, and sorted (FACS) on day 7, prior to culture with purified antigen-specific TCR-transgenic T cells. Four endosomal targeting signals (TS) from transferrin receptor (TFR), LAMP-1 and the invariant chain (Ii) were tested. See FIG. 6. All constructs co-expressed GFP and DCs were sorted at intermediate GFP expression levels to correct for variations in transduction efficiencies and normalize median fluorescence intensity (MFI) (FIG. 7).

Figure 8A:
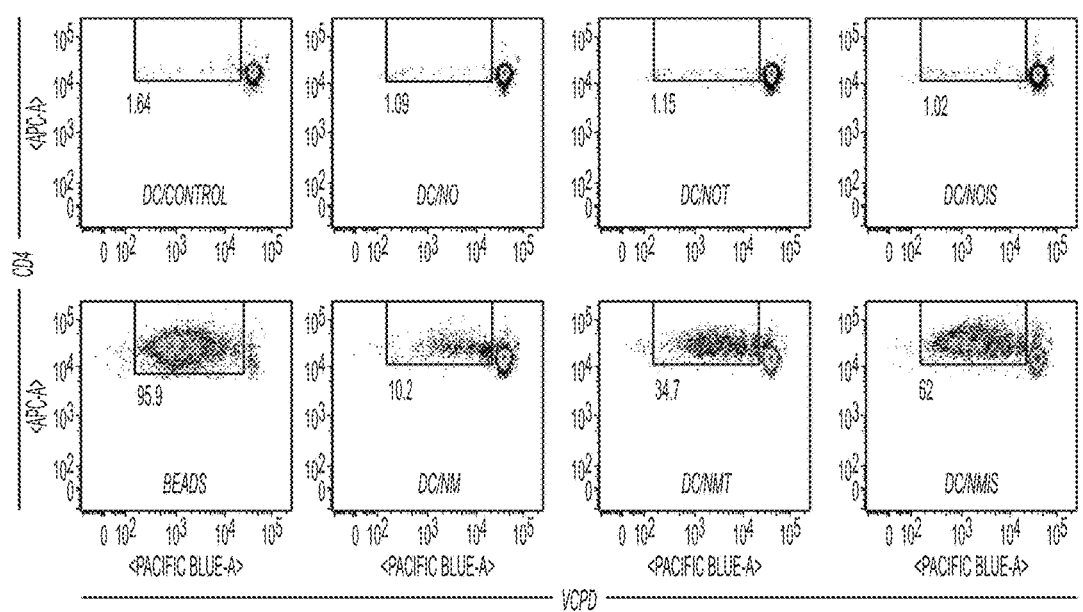
FIGS. 8A-8B.
Figure 8B:
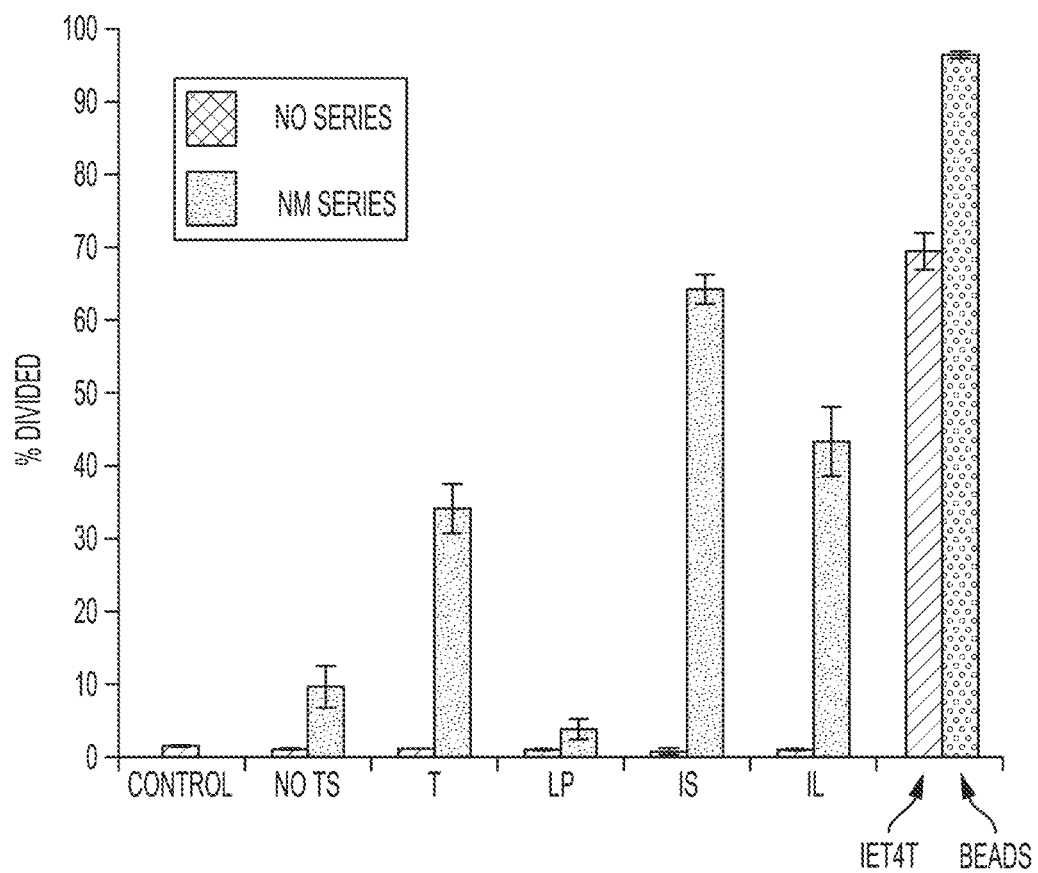
Figure 9A:
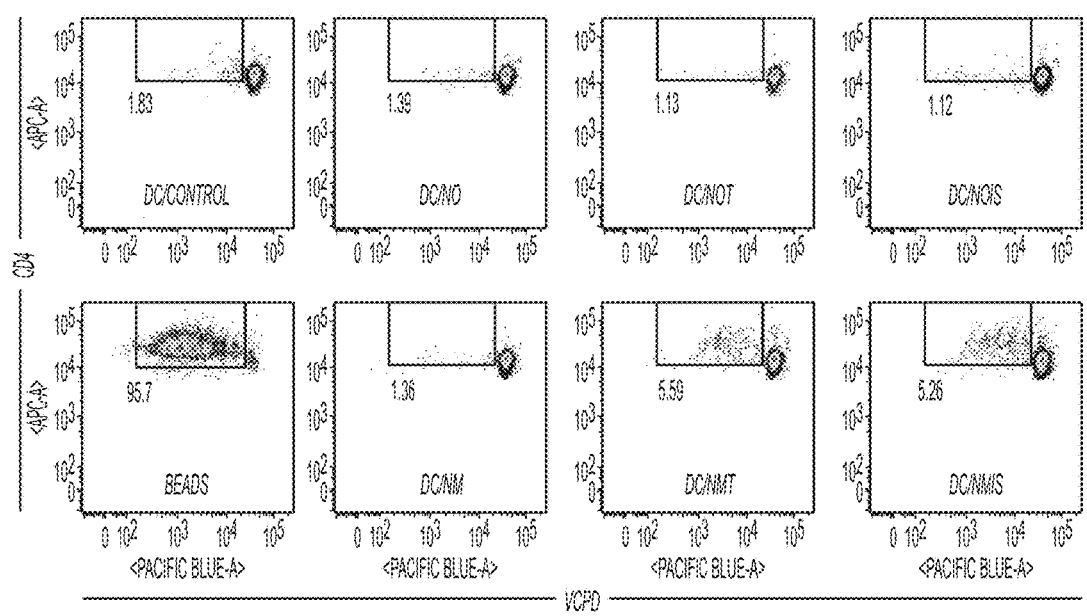
FIGS. 9A-9B.
Figure 9B:
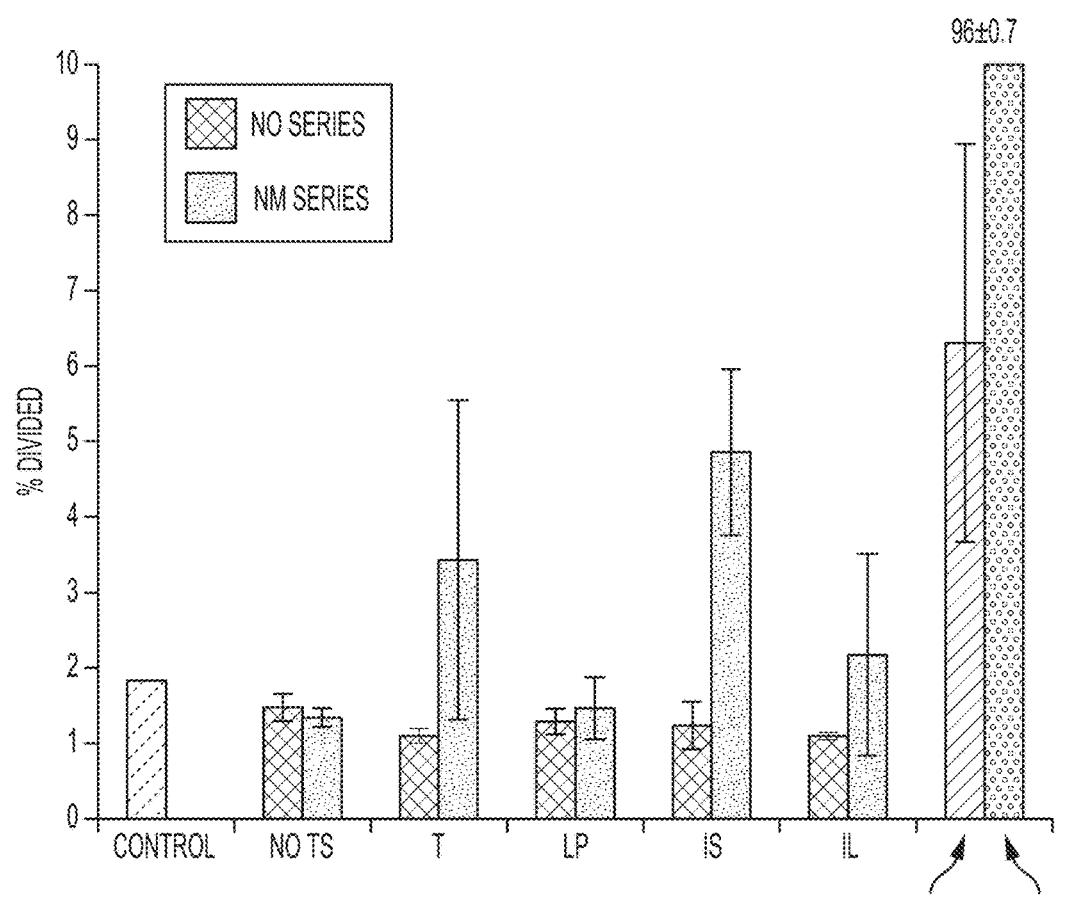
Figure 10A:
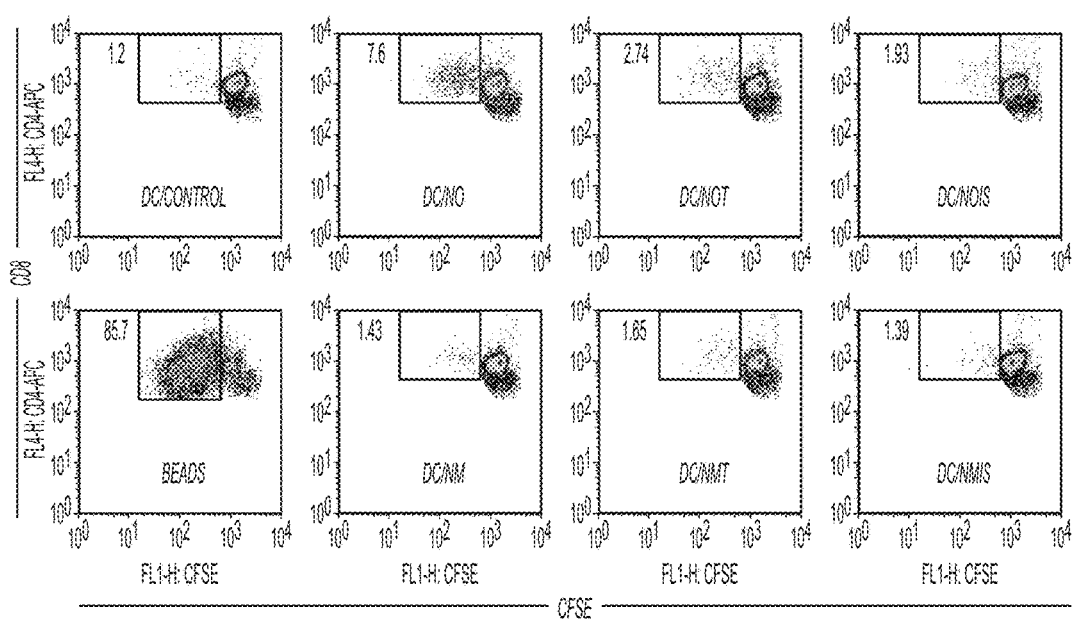
FIGS. 10A-10B.
Figure 10B:
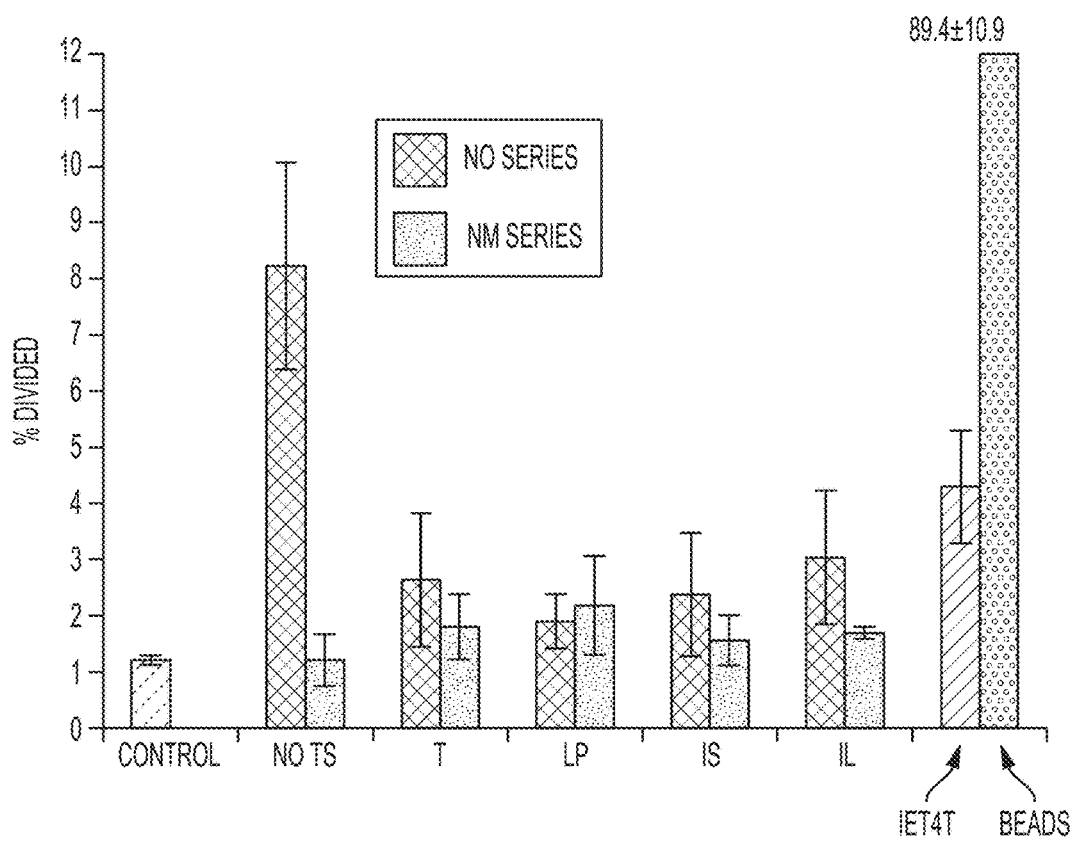
Figure 11A:
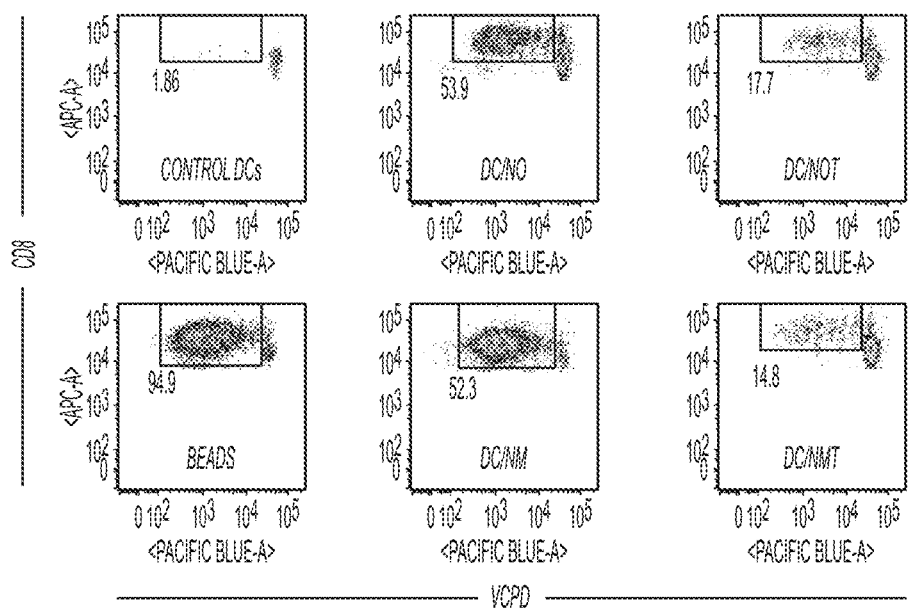
FIGS. 11A-11C.
Figures 11B, 11C:
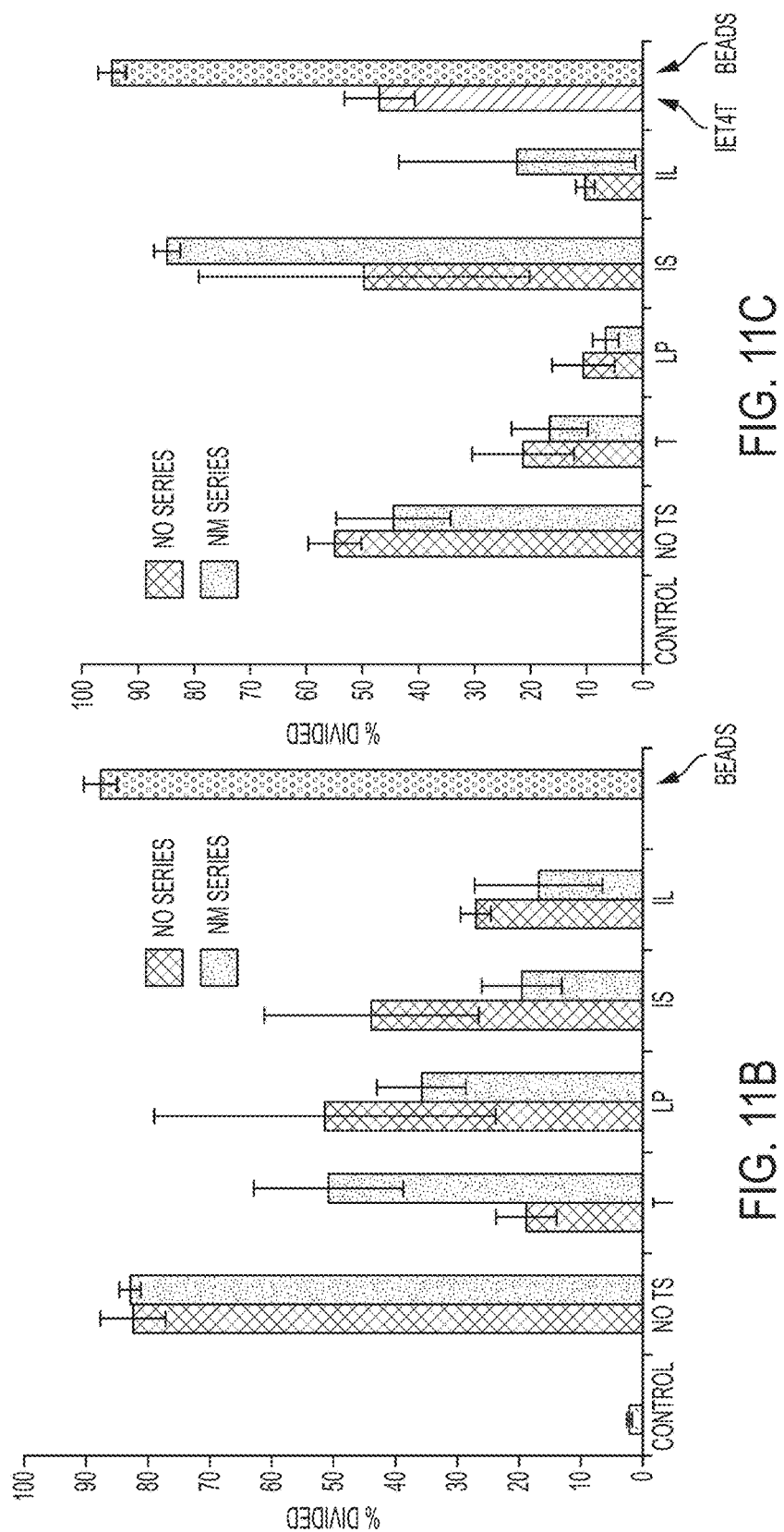
Figure 12:
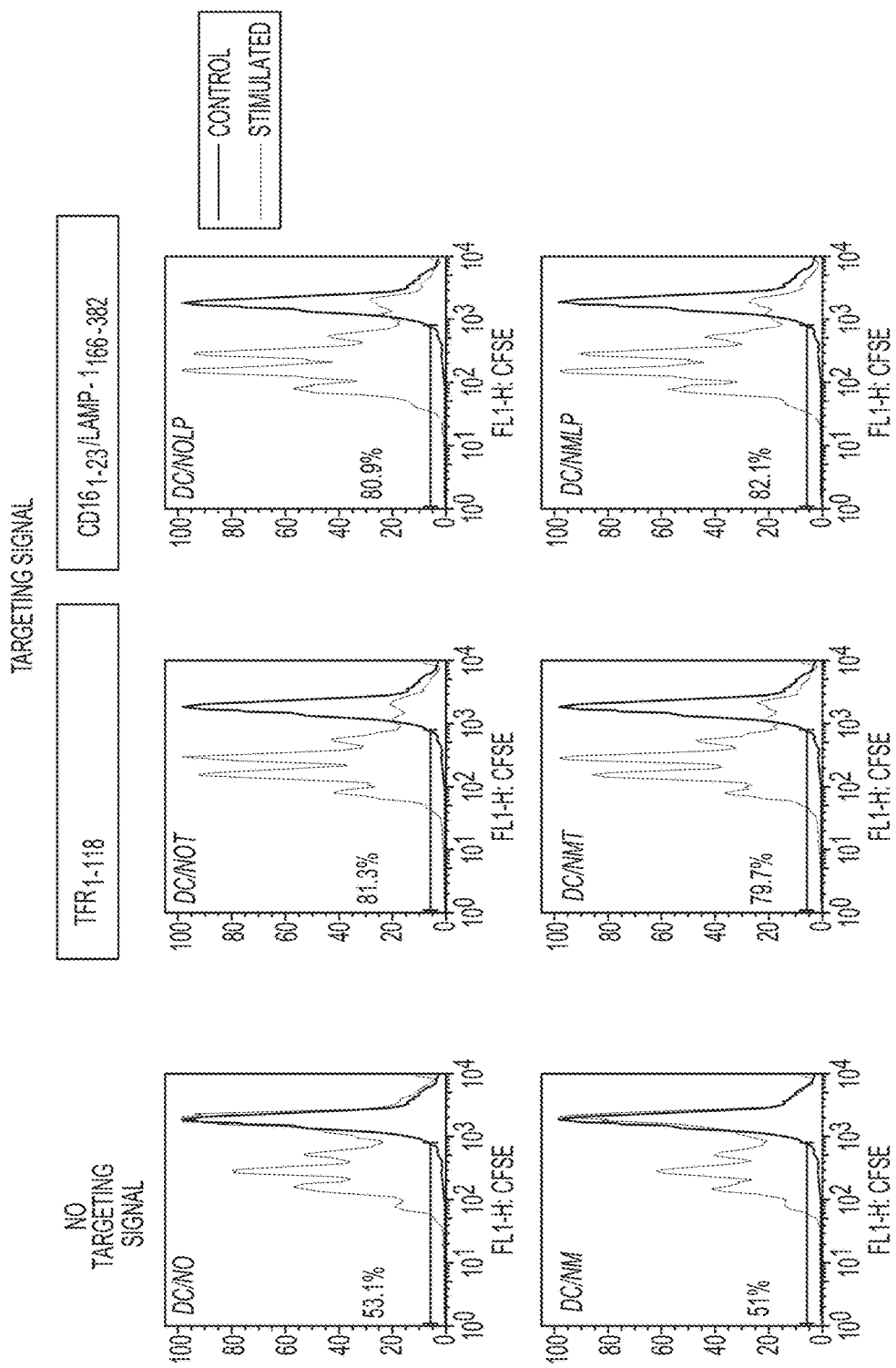
FIG. 12 is a series of FACS plots showing cell sorting results after stimulation of GAD65-specific G286 CD4+ T cells. Stimulation of cell proliferation dye-labeled T cells after 3 days in culture with transduced DCs is shown. The data show a reduced stimulation for constructs lacking a class II targeting sequence (first column) compared to constructs containing one such sequence (TFR or CD16/LAMP1; second and third column) Because there is no mimotope for this epitope, the sequence is the same between NO and NM series, and the response is the same also.
Figure 13:
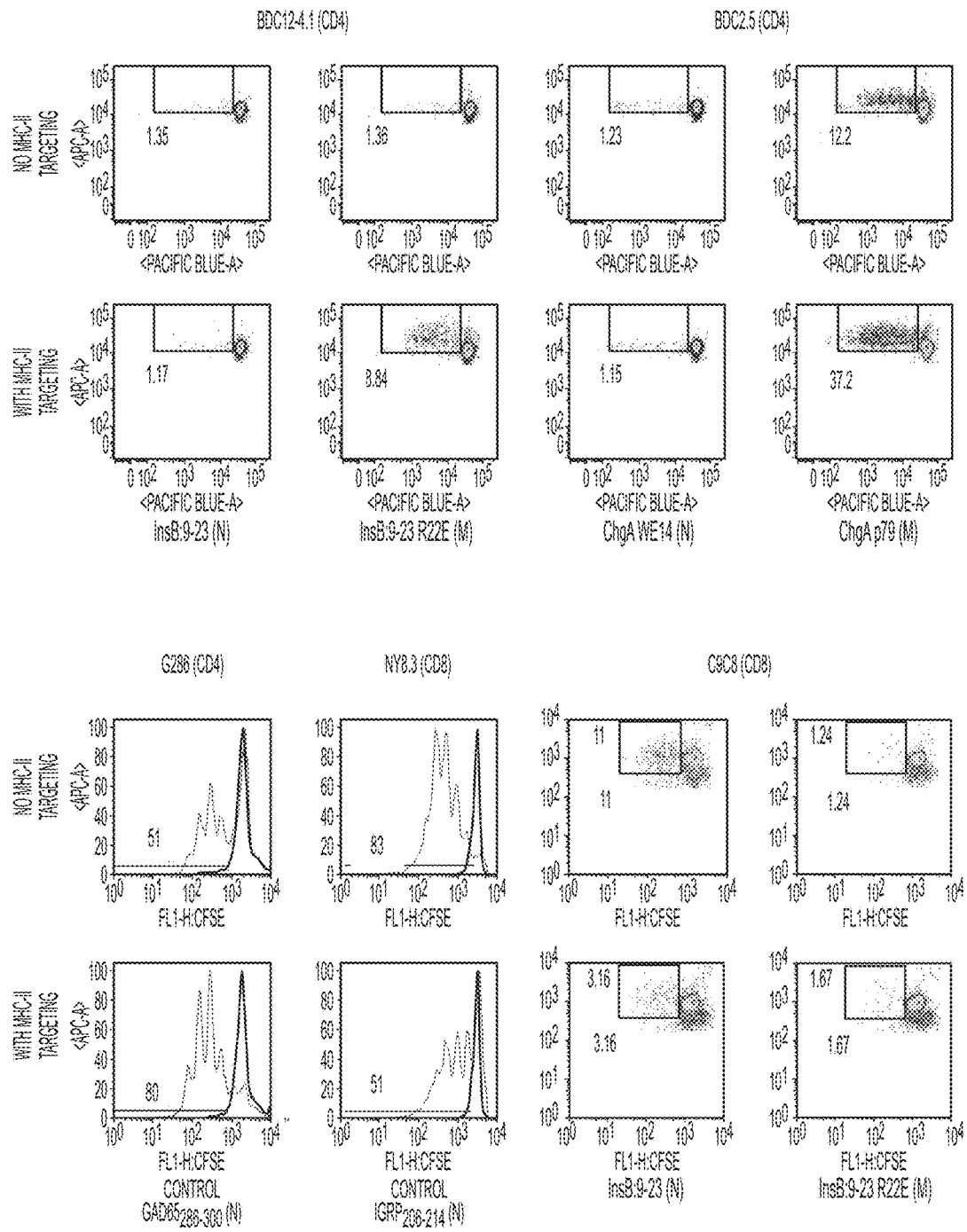
FIG. 13 is a series of plots showing FACS results summarizing the response (measured by dilution of a cell proliferation dye) of 5 different autoreactive diabetogenic T cell clones responding to 5 different epitopes, depending on whether native epitopes (N) or mimotopes (M) are used (here again, presented by transduced bone marrow-derived dendritic cells), and whether MHCII-targeting sequences are used (in this case with a domain from the transferrin receptor). Insulin-reactive T cells from BDC12-4.1 and G9C8 are low affinity and weak responders.

FIGS. 8, 9 and 12 show that CD4+ T cells benefited from their epitopes being targeted to endosomes/MHC class II, particularly with TFR1-118 and Ii1-80 (compare DC/NO and DC/NM to the results for targeted epitopes). FIGS. 10 and 11 show that CD8+ T cells were less efficiently stimulated if their epitopes were preceded by these targeting signals, suggesting that these signals divert epitopes away from the endogenous proteasome (MHC class I) pathway. BDC2.5 CD4+ T cells responded only to the mimotope (the native epitopes appear to require post-translational modifications, such as that mediated by transglutaminase, to be stimulatory). The CD4 mimotope is more efficient than the native Ins2 peptide, however the Ins2 CD8 epitope (B:15-23) contained within the Ins2 CD4 epitope (B:9-23) is no longer stimulatory if it is mutated in the mimotope (R22E).

Mimotopes can allow better targeting of CD4+ T cells than the native epitopes. ChgA-specific BDC2.5 CD4+ T cells (FIG. 8) and Ins-specific BDC12-4.1 T cells (FIG. 9) were stimulated as described above and evaluated by flow cytometry. BDC2.5 CD4+ T cells do not respond at all to the native epitope (see FIG. 8). On a Rag1−/− background, BDC12-4.1 T cells respond to both native epitope and mimotope, but better with the latter (not shown).

All three CD4+ T cells (BDC2.5, BDC12-4.1, G286) were more efficiently targeted using the endosomal targeting signals, with TFR1-118 and Ii1-80 being the best overall (see FIGS. 8, 9, and 12). However, the GAD65$_{288-300}$ peptide was less dependent on such signals (FIG. 12). Presentation of CD8 epitopes was generally more efficient in the absence of endosomal targeting signals (see FIG. 10 and FIG. 11), suggesting that these signals were diverting them away from the proteasome.

Based on these observations, a construct was designed, as depicted in FIG. 2, so that CD4 epitopes can be targeted to the endosome for MHC class II processing while CD8 epitopes can be cleaved off and left behind for MHC class I processing. This construct (termed IET4T) improved the response of all clones tested (see bars marked IE4T, in FIG. 8, FIG. 9, FIG. 10, FIG. 11 and FIG. 14). See FIG. 5 for sequence information.

Example 4. Testing of Constructs Expressing Pancreatic Islet Antigens

Constructs that express selected epitopes from different islet antigens arranged in tandem were designed (see FIG. 2). The epitopes were flanked with native amino acids that foster proper proteolytic cleavage within the endosome or proteasome (not shown in the schematic drawing). The epitopes in this construct are targeted by diabetogenic T cells in non-obese diabetic (NOD) mice. Epitopes that can be recognized by TCR-transgenic T cells were selected for validation (FIG. 5). (Many more epitopes may be included and their presentation validated using alternative tools such as, e.g., T cell lines, T cell hybridomas, or antigen-specific T cells identified using tetramers.)

Using several of these vectors, presentation of 5 epitopes from 4 islet antigens (insulin, GAD65, chromogranin A and IGRP, known to be targeted in T1D) was confirmed. Different endosomal targeting signals (for enhanced presentation of CD4-processed epitopes) and several mimotopes were tested and compared using in vitro stimulation assays. All of the epitopes were shown to be processed and presented to antigen-specific T cells when the construct is introduced into antigen presenting cells. See FIG. 13, which shows responsiveness (dilution of CFSE or equivalent) of diabetogenic T cells to native epitopes (N) or mimotopes (M) presented by transduced bone marrow-derived dendritic cells. Epitopes are expressed with (bottom row) or without (top row) MHC class II targeting (transferrin receptor domain in this case). Four endosome targeting signals were compared in total, all of which enhanced presentation of the targeted epitopes to CD4+ T cells but reduced presentation to CD8+ T cells (see data from $6^{th}$ and $7^{th}$ column of FIG. 13).

Generally, CD4 epitopes were more poorly presented in absence of targeting signals, while CD8 epitopes were most efficiently expressed in these conditions. The native insulin CD4 epitope (B:9-23) internally contains a CD8 epitope (B:15-23). However, when it is replaced by the R22E mutant, the CD4+ T cells respond better while the CD8+ T cells are no longer stimulated. Thus, it is advantageous to express the CD4 mimotope and the CD8 native epitope of insulin separately. In the light of these data, a construct like the one depicted on FIG. 2 was designed in which the epitopes have been rearranged and the CD8 epitopes may be cleaved off the CD4 epitopes and remain in the cytosol for proteasome processing while the CD4 epitopes are sent to the endosomal pathway. This strategy allows for optimal presentation of all epitopes targeting diabetogenic T cells.

Example 5. Constructs for the Presentation of Epitopes, and Sequences Thereof

Constructs for presentation of multiple epitopes contain an endosome (MHC class II)-targeting sequence, such as transferrin receptor $TFR_{1-118}$, invariant chain $Ii_{1-80}$ or $Ii_{1-214}$, a plurality of native epitopes or corresponding mimotopes known to be recognized by mouse or human CD4+ T cells downstream of this targeting sequence, a plurality of native epitopes or corresponding mimotopes known to be recognized by mouse or human CD8+ T cells, and a cleavage site, such as P2A, T2A, E2A and F2A, located between the group of CD4− and the group of CD8 epitopes. See FIG. 1 and FIG. 2. The CD4 epitopes for MHC class II processing and the CD8 epitopes for MHC class I processing can originate from multiple antigens from a given tissue that is targeted by an autoimmune response, or from multiple antigens from a pathogen or a tumor, and the like, as discussed herein. In some embodiments, each epitope (native or mimotope) is flanked by additional amino acids, e.g., 2 amino acids, from the corresponding native protein in order to facilitate processing of the peptide antigens in each targeted cellular compartment.

The construct IET4T (675 bp) is an exemplary construct according to the invention. A schematic diagram of the construct is given in FIG. 2. This "Islet Epitope Tandem" construct contains a transferrin receptor (TFR) signal (IET4T) and expresses mimotopes for an insulin CD4 epitope and a chromogranin A CD4 epitope, a native GAD65 CD4 epitope, and native insulin and IGRP CD8 epitopes. All these epitopes are recognized by known diabetogenic T cells, and therefore can target them for reprogramming.

The original DNA sequence of this construct is below (SEQ ID NO: 8). Internal sites (SacII and XmaI) flanking the epitopes allow for convenient swapping of epitopes without touching the endosome-targeting sequence.

```
                                              (SEQ ID NO: 8)
ACTAGTGCCA CCATGATGGA TCAAGCTAGA TCAGCATTCT

CTAACTTGTT TGGTGGAGAA CCATTGTCAT ATACCCGGTT

CAGCCTGGCT CGGCAAGTAG ATGGCGATAA CAGTCATGTG

GAGATGAAAC TTGCTGTAGA TGAAGAAGAA AATGCTGACA

ATAACACAAA GGCCAATGTC ACAAAACCAA AAAGGTGTAG

TGGAAGTATC TGCTATGGGA CTATTGCTGT GATCGTCTTT

TTCTTGATTG GATTTATGAT TGGCTACTTG GGCTATTGTA

AAGGGGTAGA ACCAAAAACT GAGTGTGAGA GACTGGCAGG

AACCGAGTCT CCAGTGAGGG AGGAGCCAGG AGAGGACTTC

CCTGCACCGC GGTGTGGTTC CCACCTGGTG GAGGCTCTCT

ACCTGGTGTG TGGGGAGGAG GGCTTCTTCA AGCGAGCAGT

TCGACCTCTA TGGGTACGTA TGGAAAAGCG GTCTCTCAAG

AAGGGAGCTG CAGCCTTAGG GATTGGAACA GACAGTGTGA

TTCTGATTGA GGGCAGAGGA AGTCTGCTAA CATGCGGTGA

CGTCGAGGAG AATCCTGGAC CTGAGGCTCT CTACCTGGTG

TGTGGGGAGC GTGGCTTCTT CTTGAGTGTG TACCTGAAGA

CCAACGTCTT CCTCTTCCTG CCCGGGTAGG TCGAC
```

TABLE 1

| Sequence Name | Sequence Location |
|---|---|
| Kozak sequence | 7-12 |
| Start codon | 13-15 |
| endosome-targeting sequence (TFR1-118) | 16-356 |
| Ins2B: 9-23 R22E mimotope | 379-423 |
| ChgA 1040-79 mimotope | 436-465 |
| GAD65286-300 native peptide | 478-522 |
| cleavage site (T2A) | 529-582 |
| Ins2B: 15-23 native peptide | 589-615 |
| IGRP206-214 native peptide | 628-654 |
| stop codon | 667-669 |

Restriction sites are underlined

The codon-optimized sequence of this tandem epitope construct is below (SEQ ID NO: 9).

```
                                              (SEQ ID NO: 9)
ACTAGTGCCA CCATGATGGA CCAAGCTAGA TCCGCCTTCA

GCAATCTGTT CGGAGGAGAG CCCCTCTCCT ATACAAGATT

CTCCCTGGCC AGGCAAGTGG ACGGCGACAA CTCCCACGTC

GAGATGAAAC TCGCCGTGGA TGAAGAGGAG AACGCCGACA

ATAACACCAA GGCCAACGTG ACCAAGCCTA AGAGGTGCAG

CGGAAGCATC TGCTACGGCA CAATCGCCGT GATCGTCTTC

TTCCTGATCG GATTCATGAT CGGATACCTG GGCTACTGCA

AGGGCGTGGA GCCTAAAACC GAGTGCGAGA GACTCGCTGG

AACAGAGTCC CCTGTCAGGG AGGAACCTGG AGAGGATTTC

CCTGCCCCGC GGTGCGGATC CCATCTGGTC GAAGCCCTGT

ACCTGGTCTG TGGCGAGGAA GGATTCTTCA AGAGGGCTGT

CAGGCCTCTG TGGGTGAGGA TGGAAAAGAG ATCCCTGAAA

AAAGGCGCCG CTGCCCTGGG AATTGGCACC GACTCCGTCA

TTCTCATCGA GGGCAGAGGA TCCCTCCTGA CCTGTGGCGA

CGTGGAGGAA AACCCCGGAC CCGAAGCTCT GTACCTGGTG

TGTGGCGAAA GGGGCTTTTT CCTGTCCGTC TACCTGAAAA

CCAATGTCTT TCTGTTTCTG CCCGGGTAGG TCGAC
```

The protein sequence for this construct is below (218 aa; SEQ ID NO: 10).

```
                                             (SEQ ID NO: 10)
MMDQARSAFSNLFGGEPLSYTRFSLARQVDGDNSHVEMKLAVDEEENADN

NTKANVTKPKRCSGSICYGTIAVIVFFLIGFMIGYLGYCKGVEPKTECER

LAGTESPVREEPGEDFPAPRCGSHLVEALYLVCGEEGFFKRAVRPLWVRM

EKRSLKKGAAALGIGTDSVILIEGRGSLLTCGDVEENPGPEALYLVCGER

GFFLSVYLKTNVFLFLPG
```

TABLE 2

| Sequence Name | Sequence Location |
|---|---|
| endosome-targeting sequence (TFR1-118) | 1-118 |
| Ins2B: 9-23 R22E mimotope | 123-137 |
| ChgA 1040-79 mimotope | 142-151 |
| GAD65286-300 native peptide | 156-170 |
| cleavage site (T2A) | 173-190 |
| Ins2B: 15-23 native peptide | 193-201 |
| IGRP206-214 native peptide | 206-214 |

Additional sequences are provided below.

TFR$_{1-118}$
```
ATGATGGATCAAGCTAGATCAGCATTCTCTAACTTGTTTGGTGGAGAACC

ATTGTCATATACCCGGTTCAGCCTGGCTCGGCAAGTAGATGGCGATAACA

GTCATGTGGAGATGAAACTTGCTGTAGATGAAGAAGAAAATGCTGACAAT

AACACAAAGGCCAATGTCACAAAACCAAAAAGGTGTAGTGGAAGTATCTG
```

-continued
CTATGGACTATTGCTGTGATCGTCTTTTTCTTGATTGGATTTATGATTG

GCTACTTGGGCTATTGTAAAGGGGTAGAACCAAAAACTGAGTGTGAGAGA

CTGGCAGGAACCGAGTCTCCAGTGAGGGAGGAGCCAGGAGAGGACTTCCC

TGCA (SEQ ID NO: 11)

MMDQARSAFSNLFGGEPLSYTRFSLARQVDGDNSHVEMKLAVDEEENADN

NTKANVTKPKRCSGSICYGTIAVIVFFLIGFMIGYLGYCKGVEPKTECER

LAGTESPVREEPGEDFPA (SEQ ID NO: 12)

Ii$_{1-80}$
ATGGATGACCAACGCGACCTCATCTCTAACCATGAACAGTTGCCCATACT

GGGCAACCGCCCTAGAGAGCCAGAAAGGTGCAGCCGTGGAGCTCTGTACA

CCGGTGTCTCTGTCCTGGTGGCTCTGCTCTTGGCTGGGCAGGCCACCACT

GCTTACTTCCTGTACCAGCAACAGGGCCGCCTAGACAAGCTGACCATCAC

CTCCCAGAACCTGCAACTGGAGAGCCTTCGCATGAAGCTT (SEQ ID

NO: 13)

MDDQRDLISNHEQLPILGNRPREPERCSRGALYTGVSVLVALLLAGQATT

AYFLYQQQGRLDKLTITSQNLQLESLRMKL (SEQ ID NO: 14)

Ii$_{1-214}$
ATGGATGACCAACGCGACCTCATCTCTAACCATGAACAGTTGCCCATACT

GGGCAACCGCCCTAGAGAGCCAGAAAGGTGCAGCCGTGGAGCTCTGTACA

CCGGTGTCTCTGTCCTGGTGGCTCTGCTCTTGGCTGGGCAGGCCACCACT

GCTTACTTCCTGTACCAGCAACAGGGCCGCCTAGACAAGCTGACCATCAC

CTCCCAGAACCTGCAACTGGAGAGCCTTCGCATGAAGCTTCCGAAATCTG

CCAAACCTGTGAGCCAGATGCGGATGGCTACTCCCTTGCTGATGCGTCCA

ATGTCCATGGATAACATGCTCCTTGGGCCTGTGAAGAACGTTACCAAGTA

CGGCAACATGACCCAGGACCATGTGATGCATCTGCTCACGAGGTCTGGAC

CCCTGGAGTACCCGCAGCTGAAGGGGACCTTCCCAGAGAATCTGAAGCAT

CTTAAGAACTCCATGGATGGCGTGAACTGGAAGATCTTCGAGAGCTGGAT

GAAGCAGTGGCTCTTGTTTGAGATGAGCAAGAACTCCCTGGAGGAGAAGA

AGCCCACCGAGGCTCCACCTAAAGAGCCACTGGACATGGAAGACCTATCT

TCTGGCCTGGGAGTGACCAGGCAGGAACTGGGTCAAGTCACC (SEQ ID

NO: 15)

MDDQRDLISNHEQLPILGNRPREPERCSRGALYTGVSVLVALLLAGQATT

AYFLYQQQGRLDKLTITSQNLQLESLRMKLPKSAKPVSQMRMATPLLMRP

MSMDNMLLGPVKNVTKYGNMTQDHVMHLLTRSGPLEYPQLKGTFPENLKH

LKNSMDGVNWKIFESWMKQWLLFEMSKNSLEEKKPTEAPPKEPLDMEDLS

SGLGVTRQELGQVT (SEQ ID NO: 16)

CD16/LAMP1
ATGACTTTGGACACCCAGATGTTTCAGAATGCACACTCTGGAAGCCAATG

GCTACTTCCACCACTGACA (CD16$_{1-23}$; SEQ ID NO: 17)

MTLDTQMFQNAHSGSQWLLPPLT (CD16$_{1-23}$; SEQ ID NO: 18)

GATGCCACTATCCAGGCCTACCTGTCGAGTGGCAACTTCAGCAAGGAAGA

GACACACTGCACACAGGATGGACCTTCCCCAACCACTGGGCCACCCAGCC

CCTCACCACCACTTGTGCCCACAAACCCCACTGTATCCAAGTACAATGTT

ACTGGTAACAACGGAACCTGCCTGCTGGCCTCTATGGCACTGCAACTGAA

TATCACCTACCTGAAAAAGGACAACAAGACGGTGACCAGAGCGTTCAACA

TCAGCCCAAATGACACATCTAGTGGGAGTTGCGGTATCAACTTGGTGACC

CTGAAAGTGGAGAACAAGAACAGAGCCCTGGAATTGCAGTTTGGGATGAA

TGCCAGCTCTAGCCTGTTTTTCCTGCAAGGAGTGCGCTTGAATATGACTC

TTCCTGATGCCCTAGTGCCCACATTCAGCATCTCCAACCATTCACTGAAA

GCTCTTCAGGCCACTGTGGGAAACTCATACAAGTGCAACACTGAGGAACA

CATCTTTGTCAGCAAGATGCTCTCCCTCAATGTCTTCAGTGTGCAGGTCC

AGGCTTTCAAGGTGGACAGTGACAGGTTTGGGTCTGTGGAAGAGTGTGTT

CAGGATGGTAACAACATGTTGATCCCCATTGCTGTGGGCGGTGCCCTGGC

A (LAMP1$_{166-382}$; SEQ ID NO: 19)

DATIQAYLSSGNFSKEETHCTQDGPSPTTGPPSPSPPLVPTNPTVSKYNV

TGNNGTCLLASMALQLNITYLKKDNKTVTRAFNISPNDTSSGSCGINLVT

LKVENKNRALELQFGMNASSSLFFLQGVRLNMTLPDALVPTFSISNHSLK

ALQATVGNSYKCNTEEHIFVSKMLSLNVFSVQVQAFKVDSDRFGSVEECV

QDGNNMLIPIAVGGALA (LAMP1$_{166-382}$; SEQ ID NO: 20)

Exemplary Epitope Sequences:

Ins2B:9-23
TGTGGTTCCCACCTGGTGGAGGCTCTCTACCTGGTGTGTGGGGAGCGTGG

CTTCTTC (SEQ ID NO: 21; epitope underlined)

CGSHLVEALYLVCGERGFF (SEQ ID NO: 22; epitope underlined)

Ins2B:9-23 R22E
TGTGGTTCCCACCTGGTGGAGGCTCTCTACCTGGTGTGTGGGGAGGAGGG

CTTCTTC (SEQ ID NO: 23; epitope underlined)

CGSHLVEALYLVCGEEGFF (SEQ ID NO:24; epitope underlined)

Ins2B:9-23 E21G/R22E (in IET5T, FIG. 15)
TGTGGTTCCCACCTGGTGGAGGCTCTCTACCTGGTGTGTGGGGAGAGGG

CTTCTTC (SEQ ID NO: 25)

CGSHLVEALYLVCGEGGFF (SEQ ID NO: 26; epitope underlined)

ChgA WE14
AAGCGATGGAGCAGGATGGACCAGCTGGCCAAAGAGCTGACAGCAGAGAA

GCGG (SEQ ID NO: 27; epitope underlined)

KRWSRMDQLAKELTAEKR (SEQ ID NO: 28; epitope underlined)

ChgA 1040-79
AAGCGAGCAGTTCGACCTCTATGGGTACGTATGGAAAAGCGG (SEQ ID

NO:29; epitope underlined)

KRAVRPLWVRMEKR (SEQ ID NO: 30; epitope underlined)

-continued

GAD65₂₈₆₋₃₀₀
TCTCTCAAGAAGGGAGCTGCAGCCTTAGGGATTGGAACAGACAGTGTGAT

TCTGATT (SEQ ID NO: 31; epitope underlined)

SLKKGAAALGIGTDSVILI (SEQ ID NO: 32; epitope underlined)

GAD65₅₂₄₋₅₄₃ (in IET5T, FIG. 15)
AGAATGAGCCGCCTCTCAAAGGTGGCGCCAGTGATTAAAGCCAGAATGAT

GGAGTATGGGACCACAATGGTC (SEQ ID NO: 33)

RMSRLSKVAPVIKARMMEYGTTMV (SEQ ID NO: 34; epitope underlined)

P2A (from porcine teschovirus-1)
GCTACTAACTTCAGCCTGCTGAAGCAGGCTGGAGACGTGGAGGAGAACCC

TGGACCT (SEQ ID NO: 35)

ATNFSLLKQAGDVEENPGP (SEQ ID NO: 36)

T2A (from Thosea asigna virus)
GAGGGCAGAGGAAGTCTGCTAACATGCGGTGACGTCGAGGAGAATCCTGG

ACCT (SEQ ID NO: 37)

EGRGSLLTCGDVEENPGP (SEQ ID NO: 38)

E2A (from equine rhinitis A virus)
CAGTGTACTAATTATGCTCTCTTGAAATTGGCTGGAGATGTTGAGAGCAA

CCCTGGACCT (SEQ ID NO: 39)

QCTNYALLKLAGDVESNPGP (SEQ ID NO: 40)

F2A (from Foot-and-mouth disease virus)
GTGAAACAGACTTTGAATTTTGACCTTCTCAAGTTGGCGGGAGACGTGGA

GTCCAACCCTGGACCT (SEQ ID NO: 41)

VKQTLNFDLLKLAGDVESNPGP (SEQ ID NO: 42)

Ins2B:15-23
GAGGCTCTCTACCTGGTGTGTGGGGAGCGTGGCTTCTTC (SEQ ID

NO: 43; epitope underlined)

EALYLVCGERGFF (SEQ ID NO: 44; epitope underlined)

IGRP₂₀₆₋₂₁₄
TTGAGTGTGTACCTGAAGACCAACGTCTTCCTCTTCCTG (SEQ ID

NO:45; epitope underlined)

LSVYLKTNVFLFL (SEQ ID NO: 46; epitope underlined)

Example 6. Stimulation of TCR Transgenic T Cells with Epitope-Expressing Construct The constructs indicated in FIG. 14 were delivered into DCs by lentiviral transduction and co-cultured with several purified diabetogenic clones labeled with a proliferation dye. In the figure, NO indicates that all the expressed epitopes are native epitopes; NM indicates that some of the native epitopes are replaced with mimotopes when available (Ins and ChgA). The construct labeled TFR have the transferrin receptor 1-118 targeting signal. Constructs labeled NO and NM do not have the 2A cleavage site, whereas IET4T (depicted on FIG. 2) has both a targeting signal and a cleavage site. Beads coated with anti-CD3 and anti-CD28 were used as positive control ("Beads"); DC control indicates no transduction.

The data show the percentage of T cells divided after 2.5 days. For CD4+ T cells, the best response was achieved with mimotopes and endosome (MHC class II)-targeting signals such as TFR1-118. See FIG. 14. For CD8+ T cells the response was diminished with targeting signals, indicating the need to segregate CD8 epitopes such that they are not targeted to endosomes with CD4 epitopes. Ins-reactive G9C8 CD8+ T cells respond poorly to the native peptide (InsB:15-23), but do not recognize the Ins R22E mimotope, indicating a need to use separate epitopes in this case (mimotope for CD4 and native for CD8). A construct that satisfies these requirements for optimal and differential targeting of both CD4 and CD8 epitopes was produced as IET4/TFR and demonstrated a superior ability to engage both CD4+ and CD8+ diabetogenic T cells. See FIG. 14.

Example 7. Alternative Constructs

Figure 15:
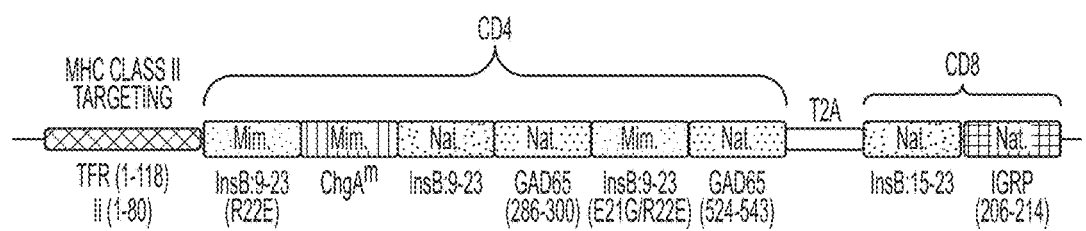
FIG. 15 is a schematic drawing of an alternative nucleic acid construct (IET5T) depicting additional epitopes for broader targeting of diabetogenic CD4+ and CD8+ T cells according to the invention.

FIG. 15 is a schematic drawing of additional nucleic acid constructs. Construct IET5 (see FIG. 15) contains more epitopes and mimotopes for extended coverage. Although more epitopes can be added, these were chosen because tools and reagents exist to assess the T cell response to these epitopes in vivo, either through adoptively transferred T cell receptor transgenic T cells or MHC tetramer reagents. An example of identification of diabetogenic T cells by tetramer staining and their response to dendritic cells expressing TEC (IET4T in this case) is shown on FIGS. 16, 19D, 20G-H and 21. These TECs will also be cloned into the DNA vaccine vector BHT-568, which has been engineered to promote tolerance rather than immunity by substitution of CpG by GpG motifs.

Example 8. Stimulation of BDC2.5 CD4+ T Cells with DCs Electroporated with IET4T mRNA, with or without TGF-β mRNA IET4T (with TFR signal) mRNA was combined with codon-optimized TGF-β mRNA to electroporate DCs (5 μg IET4T mRNA/5×10⁶ DCs with or without TGF-β mRNA 20 ug/5×10⁶ DCs). Electroporated DCs were used to stimulate BDC2.5 CD4+ CD25− GFP-Foxp3 T cells in vitro and in vivo (after adoptive transfer of 1×10⁶ T cells/mouse i.p.). See FIG. 16.

CD4+ CD25− T cells were isolated from BDC2.5.GFP-Foxp3 mice, labeled with Violet Cell Proliferation Dye (VCPD) and stimulated for 3 days in vitro±exogenous TGF-β (FIG. 17A lower panels and FIG. 17C) or in vivo (in NOD.Thy1.1 mice) (FIG. 17A upper panels and 17B) with control or electroporated DCs (eDCs). Panels A-C show proliferation, while panels D-E show GFP-Foxp3 induction (gated on divided cells, as non-stimulated cells do not upregulate Foxp3). Data shown are from gated CD4+ VCPD+ T cells. Arrows in FIG. 17D indicate exogenous TGF-β. Cells analyzed ex vivo from PLNs were further gated on Thy1.2+ cells.

Figure 17A:
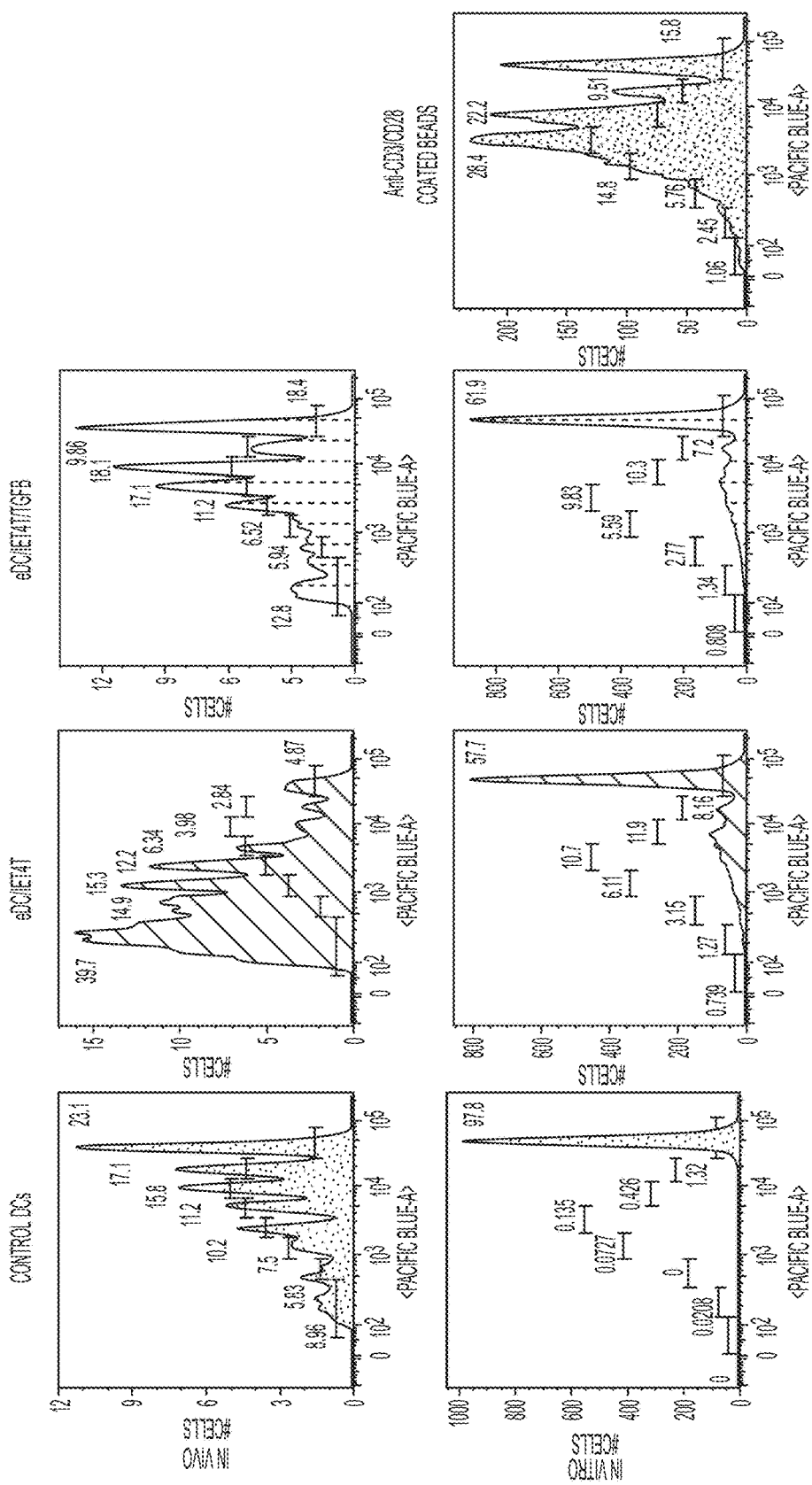
FIGS. 17A-17E.
Figure 17B:
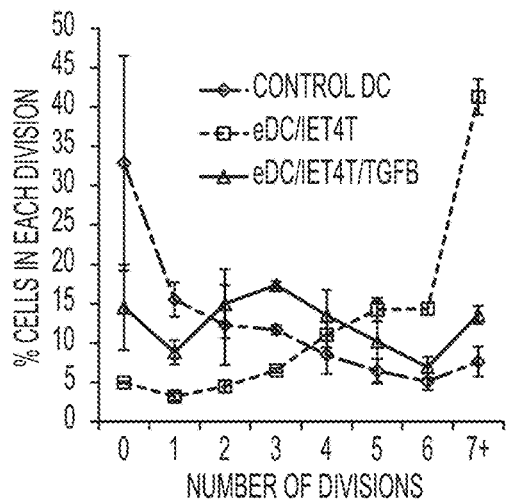
Figure 17C:
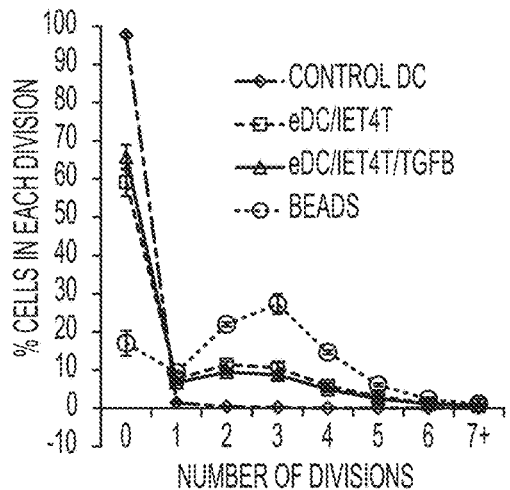
Figure 17D:
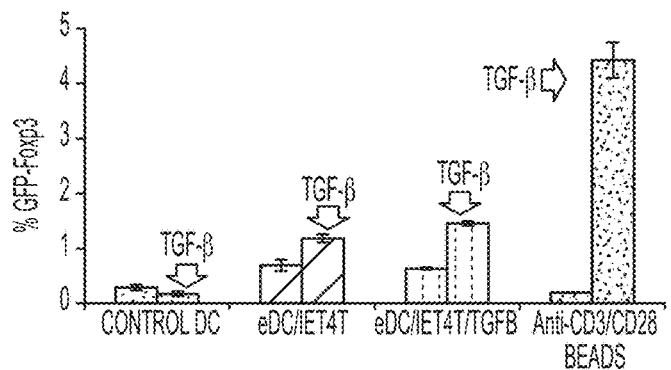
Figure 17E:
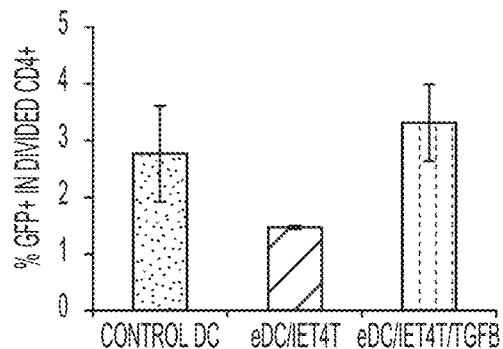

In the absence of antigens expressed in DCs, the transferred T cells are stimulated to a limited extent in vivo by endogenous DCs in the pancreatic lymph nodes (PLNs) (FIG. 17A top left panel). However, exogenous IET4T-DCs elicited a very strong recognition by the transferred T cells (FIG. 17A top middle panel), which was largely inhibited by TGF-β co-expression (FIG. 17A top right panel). In vitro, the proliferation was identical with or without TGF-β (FIG. 17A, bottom middle and right panels), indicating that the reduced proliferation with TGF-β in vivo was not due to a reduced expression of IET4T antigens, itself resulting from an excess of TGF-β mRNA competing for cell entry during electroporation. Co-expressed TGF-β mRNA, however, had no effect in vitro, which is likely due in absence of extracellular matrix needed to activate the TGF-β protein. Only exogenous TFG-β added to the culture was able to increase the % of GFP-Foxp3+ cells (FIG. 17D). However, in vivo where the co-expressed TGF-β mRNA is active, we see a doubling of the percentage of GFP-Foxp3 Treg cells (FIG. 17E), suggesting that TEC mRNA combined with immunoregulatory cytokines such as TGF-β can help reprogram diabetogenic T cells in an antigen-specific manner.

Figure 16:
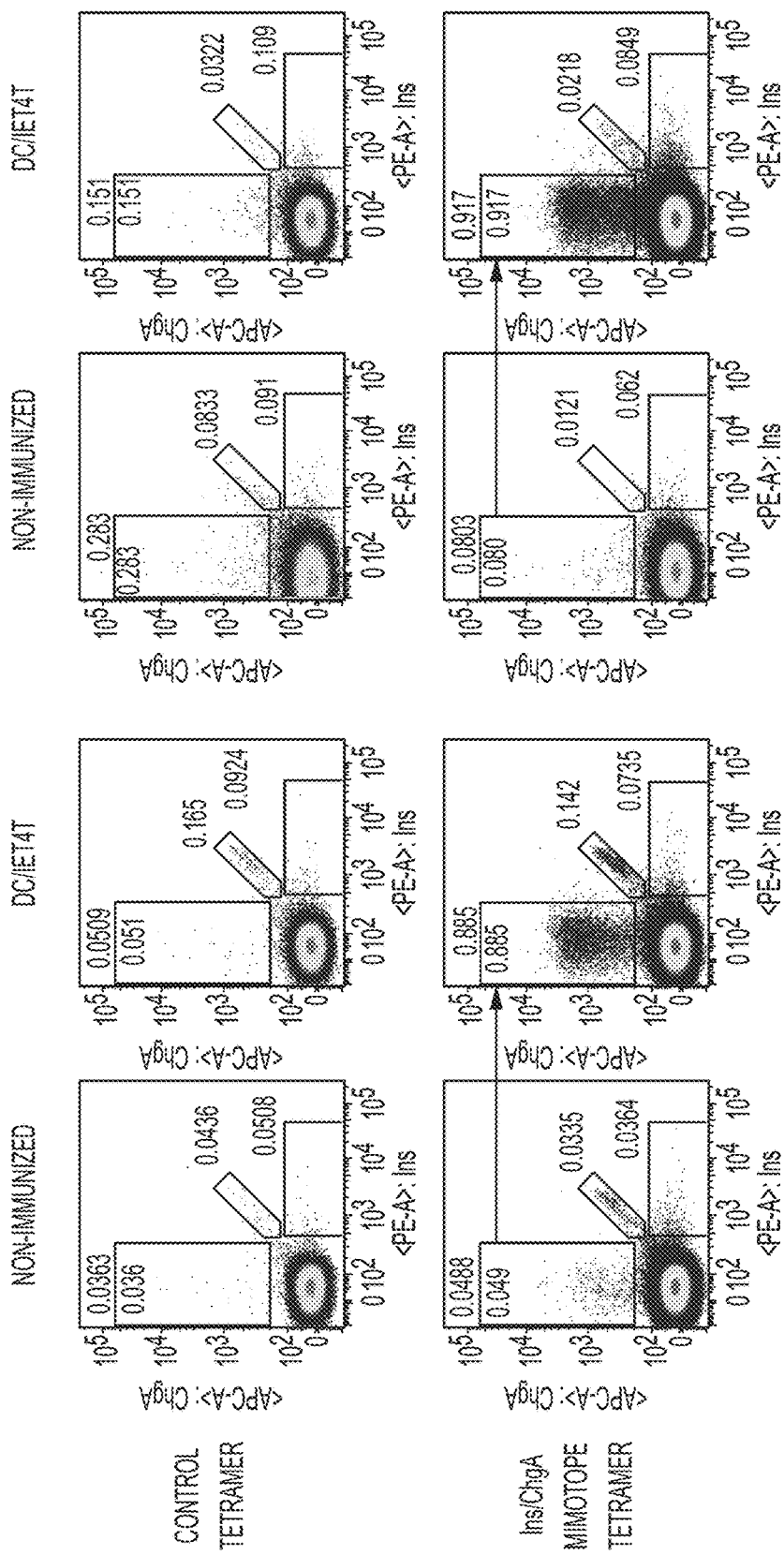
FIG. 16 shows flow cytometry data on stimulation of polyclonal ChgA-reactive T cells in vivo (in non-obese diabetic (NOD) mice). The polyclonal CD4+ T cells recognizing the ChgA mimotope were identified by tetramer staining, and these data confirm the previously shown responses using specific clones obtained from T cell receptor-transgenic mice. The left group of four plots are spleen cells; the right group of four plots are pancreatic lymph node cells.

These T cells were relatively resistant to Foxp3 induction (less than 5% GFP+) in vivo and in vitro, even with exogenous bioactive TGF-β. Other experiments indicated that using lower antigen dose may result in a higher proportion of Foxp3+ T cells within stimulated cells Example 9. Assays for T Cell Reprogramming To assess the different DC modifications in reprogramming diabetogenic T cells using TEC combined with other mRNAs encoding immunoregulatory cytokines, two CD4+ T cell clones from TCR-Tg GFP-Foxp3 mice are used (BDC2.5 and BDC12-4.1, FIG. 5). Purified CD4+ CD25− GFP− T cells from lymph nodes and spleen are labeled with GFP-compatible VCPD. For in vitro assays, T cells ($5 \times 10^4$/well) are co-cultured with electroporated DCs ($1-2 \times 10^4$/well, with <10% effectively co-localizing with T cells at the bottom of the well) for ~3 days. For in vivo assays, T cells are injected in congenic NOD.Thy1.1 female mice ($1 \times 10^6$/clone/mouse intravenously, 5 mice per group) one day before inoculation of electroporated DCs ($1 \times 10^6$/mouse intraperitoneally, which target DCs to the PLNs). After ~3 days, PLNs and inguinal lymph nodes (no stimulation control) are collected. Transferred T cells are identified as CD4+ Thy1.2+ and Vβ2+ (BDC12-4.1) or Vβ4+ (BDC2.5). DCs electroporated with GFP mRNA (no antigen) or with TEC mRNA only are used for control groups. Induction of GFP-Foxp3, CTLA-4, PD-1, ICOS and Nrp-1 is measured on day 3 and compared to baseline levels on day 0. Expression of IL-10 and LAP/TGF-β also is measured in T cells on day 3 by intracellular staining. The goal of these assays is to identify combinations that induce the highest frequency of Foxp3+, IL-10+ and/or TGF-β+ T cells. In addition to adoptively transferred T cells, the response of endogenous diabetogenic CD4+ T cells is assessed, using I-A$^{g7}$ tetramers with Ins or ChgA mimotopes or GAD65$_{286-300}$ peptide (FIG. 16).

Example 10. Assays for T Cell Suppressive Function and Stability

Selected Specific conditions will be further evaluated for Treg stability in vitro using scaled up cultures for "Treg-Demethylated Region" assays (using EpigenDx or Epiontis platform). To evaluate the ability of induced Tregs to suppress third-party T cells, we will co-transfer diabetogenic CD8+ T cells from NY8.3 mice, which are readily stimulated by endogenous DCs in the PLNs and by TEC constructs. If injected DCs induce functional Tregs, the overall proliferation of CD4+ and CD8+ T cells in the PLNs is expected to be reduced (as seen in FIGS. 17A-B). To determine the persistence of these induced Tregs, in vitro-activated BDC2.5 or NY8.3 T cells (or LPS-treated antigen-presenting DCs) are transferred two weeks after initial DC treatment and then glycemia is measured weekly to determine whether induced Tregs can delay or block the subsequent induction of disease by the in vitro activated diabetogenic T cells (transferred DCs are no longer present by then).

Example 11. Functional Tolerance of Diabetogenic T Cells by DNA Vaccine

To test the response of different T cell clones to multiple antigens/epitopes delivery by tolerogenic DNA vaccine, T cell receptor-transgenic (TCR-tg) T cells (CD4+ or CD8+) are used as traceable antigen-specific T cells reactive to specific β-cell antigens after transfer into congenic NOD-.Thy1.1 mice, or responding antigen-specific T cells can be identified by MHC tetramer staining (FIGS. 16 19D, 20G-H and 21). After 1 or 4 weekly treatments with saline or one of the TEC-containing DNA vaccine, the fate of individual responding diabetogenic T cell clones (e.g., deletion or shift from effector (IFN-γ) to regulatory (Foxp3, IL-10) function) is assessed. These studies inform the art on the possible mechanisms of action of this therapeutic approach on different types of autoreactive T cells.

Example 12. Evaluation of DNA Vaccines

Two cohorts of mice are used to reflect the most challenging conditions for prevention and treatment of T1D in this model, either advanced peri-insulitis or overt hyperglycemia. A first cohort of female NOD mice (12 weeks of age and euglycemic) are divided into groups according to the DNA vector tested: mice receive either saline (group a), pBHT-568 (encoding ProIns) only (group b), a mix of pBHT expressing ProIns, ChgA, GAD65 and IGRP (25% of total mass each) (group c), or pBHT expressing the IET5 constructs AI and BS (FIG. 2) intramuscularly (25 μg DNA or saline in 50 μL per quadricep; 50 μg and 100 μL total per mouse) (group d) (n=10-15/group) and treated weekly for 8 weeks. Mice may also be treated intradermally (total of 50 ug per mouse, 25 ug on each side of the abdomen). Glycemia is monitored every week up to 30 weeks of age. Mice with glycemia above 250 mg/dl over two consecutive measurements will be euthanized.

In a second cohort of mice (monitored for glycemia starting at 10 weeks of age), each mouse is treated as soon as it reaches blood glucose levels between 250 and 350 mg/ml with one of the above treatment weekly for 8 weeks until at least 10 mice in each group have been treated. Glycemia will be measured weekly up to 30 weeks of age and mice with glycemia over 400 mg/dl on two consecutive measurements (3 days apart) will be euthanized. If significant protection is observed (Log Rank survival test applied), additional mice will be treated in order to compare the degree of islet infiltration by histology (H&E staining).

It is expected that both professional and non-professional APCs will take up a fraction of the administered DNA and present expressed antigens in a tolerogenic fashion, leading to reduced frequencies of antigen-specific T cells relative to saline control, and/or reduced effector functions and increased regulatory function among antigen-specific diabetogenic responders. Furthermore, the mimotopes expressed in group d are expected to drive a better response among CD4+ responders than native antigens expressed in groups b and c.

Example 13. Incidence of Disease after Tolerogenic DNA Vaccine Treatment

To determine the incidence of disease after tolerogenic DNA vaccine (also called a reverse DNA vaccine) treatment of NOD mice at different stages of disease, the efficacy of various DNA vaccine treatments (containing whole proteins as traditionally done in the art or TECs) in preventing the onset of T1D in NOD mice treated during early or late stage of disease (5 versus 10 weeks of age) is assessed. In both cases, mice are treated for 8 weeks and monitored weekly for glycemia. These studies will provide valuable insights on parameters to be considered for the presentation of endogenously expressed antigens for tolerance induction.

To determine the incidence of disease after reverse DNA vaccine treatment of NOD mice at different stages of disease, two cohorts of mice are used to reflect either an early or advanced stage of peri-insulitis. One young cohort of 60 female NOD mice (5 weeks of age) are treated using one of the above treatments (groups a, b, c or d as described in Example 10; n=15/group) weekly for 8 weeks (from 5 to 12 weeks of age). Glycemia is monitored every 2 weeks from 6 to 10 weeks, and then weekly thereafter up to 30 weeks of age (Expt 2A). An older cohort of 60 female NOD mice (10 weeks of age) also are treated using one of the above treatments (groups a, b, c or d as described in Example 10; n=15/group) weekly for 8 weeks (from 10 to 17 weeks of age). Glycemia is measured weekly from 10 weeks up to 30 weeks of age (Expt 2B). Each treatment includes a total of 50 µg DNA and 100 µL total per injection per mouse as described above.

The tolerance induction with multiple antigens (groups c/d) is anticipated to provide greater protection than ProIns only (group b), especially in older mice in which epitope spreading may be more extensive. Furthermore, whether mimotopes expressed in group d provide greater therapeutic benefit and whether expression of more epitopes (full protein, groups b/c) is more advantageous than using selected epitopes (group d) will be addressed.

Example 14. Analysis of Antigen-Specific Immune Responses to Tolerogenic DCs In Vivo Bone marrow-derived DCs (CD11c+ CD11b+) from female NOD mice are generated over 6 days in the presence of GM-CSF and IL-4 and used for electroporation with several mRNA constructs. All mRNA reagents are custom-made by TriLink Biotechnologies and are codon-optimized to improve translation and modified with 5-methylcytidine and pseudouridine to reduce immune stimulation. Two types of tolerogenic DCs are evaluated: (i) DCs treated in vitro with compounds shown to augment and stabilize the regulatory properties of both murine and human DCs, such as IL-10, vitamin D3 or rapamycin, and then electroporated with antigen mRNA only; and (ii) DCs electroporated with mixtures of mRNA encoding antigens and tolerogenic products, such as (TGF-β+IL-2), IL-10 or PD-L1. The amount of mRNA used, per $5 \times 10^6$ DCs, will vary between 1 and 5 µg for antigen mRNA (intracellular IET5, see FIG. 16), and between 15 and 30 µg for tolerogenic products to be overexpressed in DCs (up to 2 genes, minimum 15 µg per gene). Modified DCs then are injected intravenously or intraperitoneally ($10^6$/mouse) into recipient NOD.Thy1.1 mice that will have received an intravenous transfer of labeled TCR-tg T cells as described in Example 6. For the testing of pharmacologically treated DCs, three different groups (n≥5/group) for each type of tolerogenic DC are compared: (a1) saline, (b1) eDC/GFP mRNA control, (c1) eDCs/IET5 mRNA and (d1) non-treated (non-tolerogenic) eDC/IET5. For the testing of DCs entirely engineered by mRNA, the conditions are: (a2) saline, (b2) eDC/GFP, (c2) eDC/IET5, (d2) eDC/IET5/TGF-β/IL-2, (e2) eDC/IL-10, (f2) eDC/PD-L1 and (g2) a mixture of (d2+e2+f2). The response and phenotype of antigen-specific T cells 3 days or 2 weeks later is analyzed as described herein. Treg induction is determined by intracellular staining of Foxp3 and IL-10, and if significant, the suppressive function is confirmed by transfer of splenocytes and lymph node cells from treated mice into NOD.SCID mice. Deletion is assessed by disappearance of antigen-specific T cells after two weeks, following possible expansion on day 3 post-treatment. Anergy is assessed by production of IL-2 upon restimulation ex vivo with specific peptides on both time points.

Example 15. Therapeutic Efficacy of Antigen-Presenting Tolerogenic DCs

The two cohorts of NOD mice described in Example 8 are used for prevention and treatment (reversal) of diabetes. Because monitoring of treated mice is a lengthy process (from 10 to 30 weeks of age), only groups of DCs that show promising results in their mechanisms of action, along with controls (saline, eDC/GFP, eDC/IET5) are tested. For prevention, euglycemic 12-wk old female NOD mice are treated with a single intravenous injection of $10^6$ DCs (of one type or a mixture). For disease reversal, aliquots of $2 \times 10^6$ DCs for each group (one aliquot per mouse) are prepared and frozen. Mice are followed weekly for glycemia and treated with thawed DCs upon onset of hyperglycemia (250-350 mg/ml). The animals are monitored weekly for glucose blood levels until 30 weeks of age.

Example 16. Combination Strategies for TECs with Tolerogenic Signals

Titrations of antigen mRNA, combined with cytokine mRNAs (TGF-β or IL-35 for Foxp3+ Tregs, IL-10 or IL-27 for Tr1) are performed to determine the conditions leading to highest induction of Foxp3 or IL-10. The expression of inducible receptors for costimulatory ligands (CTLA-4, Nrp-1, ICOS, PD-1) are measured as well, since these can contribute to enhancement of the regulatory phenotype upon additional signaling. Immature DCs, TNFα-stimulated semi-mature DCs and cluster-disrupted DCs are compared.

Antigen/cytokine mRNA is compared with expression of cell surface ligands (PD-L1, B7-H4, ICOS-L, Sema4A) that have also been implicated in the induction or boosting of Tregs (PD-L1 and Sema4A for Foxp3 Tregs through PD-1 and Nrp-1, ICOS-L and B7-H4 for Tr1 through ICOS and an unknown receptor). Using the unique combinatorial advantage of mRNA, whether additive, synergistic or antagonistic effects exist between these different biological pathways is addressed. Metabolism-modifying enzymes (IDO, CD39/CD73, ALDH1, etc.) represent another category of tolerogenic factors with a proven role in Treg induction and function, and that may later be evaluated in our system.

The TEC expressing the aforementioned epitopes and targeting sequences are synthesized after codon optimization for higher expression levels. These nucleic acids then are in vitro-transcribed into mRNA with anti-reverse cap analog and polyadenylation for enhanced stability. The DNA constructs for certain genes IL-10, IL-27, IL-35 and Sema4A have already been synthesized. IL-27 and IL-35 are composed of two chains (IL27p28/EBI3 and IL12p35/EBI3 respectively), which are expressed on the same mRNA molecule with a cleavable P2A site between the two chains. For each candidate epitope in the TEC listed above, the level of expression in DCs is assessed with or without overexpression by mRNA (up to 30 µg per $5 \times 10^6$ DCs), and the duration of expression over multiple time points (ranging from 4 to 72 h) by flow cytometry or ELISA. If "overexpressed" levels are not substantially increased over background, the DCs are considered sufficient for this product.

Example 17. TEC Constructs with MHCII Activator and Secretory Nucleic Acid Constructs Another nucleic acid construct designed for reprogramming diabetogenic T cells is the exemplary construct shown in FIG. 18(e) (AIC construct) that includes a CIITA sequence upstream of the CD4 and CD8 epitope sequences and includes a proteolytic cleavage site between the CIITA sequence and the epitopes sequences. Data involving the constructs described in FIG. 1, IET4T (with TFR endosome-targeting signal or ETS) and IET4IS (with short invariant chain ETS), is also presented in FIGS. 18A-D.

Methods

FIG. 18A: BDC2.5 CD4+ CD25− T cells cultured with DAPg7 fibroblasts transduced to express different constructs with the native ChgA$_{358-371}$ (WE14) epitope or the 2.5 mimotope (1040-79), without ETS, with TFR ETS or short invariant chain (Ii short) ETS. IET4T and IET4IS are the lighter gray bars. Stimulation of the T cells was determined based on CD25 up-regulation after 3 days of culture.

FIG. 18B: BDC12-4.1 CD4+ CD25− T cells cultured with DAPg7 fibroblasts transduced to express different constructs the native InsB$_{9-23}$ epitope or the InsB$_{9-23}$ R22E mimotope, without ETS, with TFR ETS or short invariant chain (Ii short) ETS. IET4T and IET4IS are the lighter gray bars. Stimulation of the T cells was determined based on CD25 up-regulation after 3 days of culture.

FIG. 18C: NY8.3 CD8+ T cells cultured with PCRC-5 fibroblastic lymph node stromal cells transduced to express different constructs the IGRP$_{206-214}$ epitope, without ETS, with TFR ETS or short invariant chain (Ii short) ETS. IET4T and IET4IS are the lighter gray bars. Stimulation of the T cells was determined based on CD25 up-regulation after 3 days of culture.

Constructs IET4T and IET4IS generated a good response to both CD4 and CD8 T cells in different stromal cells (same results with transduced dendritic cells). FIG. 18D: BDC2.5 CD4+ CD25− Foxp3/GFP T cells cultured with DAPg7 fibroblasts transduced to express IET4T or with DAPg7 cells pulsed with different concentrations of the 2.5 mimotope. Stimulation of the T cells was determined based on CD25 up-regulation and Foxp3 (GFP) after 3 days of culture. The transduced cells induced as much Foxp3 and CD25 expression as the highest concentration of exogenous peptide tested. Upregulation of Foxp3 is a desirable outcome when attempting to induce tolerance.

FIG. 18E: The top construct has the CD4 and CD8 epitopes mixed. If all epitopes are native, the results are those shown in FIGS. 18A-C (WE14 MIX, InsB(9-23) MIX, and IGRP(206-214) MIX) depending on the ETS. If some native epitopes are replaced by the more efficiently recognized epitopes, the results are those shown in FIGS. 18A-C (2.5 mimotope MIX, InsB(9-23) and R22E MIX), depending on the ETS. Construct AI is the kind that is shown with light gray bars in FIGS. 18A-C (2.5 mimotope SEG, InsB ((-23) R22E SEG, and IGRP(206-214) SEG), whereby CD4 and CD8 epitopes can be segregated by T2A site. Construct AIC is the same as AI, but preceded by the mouse CIITA sequence and separated by a P2A site. Construct BS has all epitopes secreted as a single polypeptide, which can then be endocytosed by other cells.

The constructs used in the DNA vaccine is the next generation and includes more epitopes. IET5AI is the equivalent of IET4IS, with the same ETS (invariant chain) but more epitopes (see sequences below). IET5BS is the secreted version of IET5.

IET5AI protein:
(SEQ ID NO: 58)
MDDQRDLISNHEQLPILGNRPREPERCSRGALYTGVSVLVALLLAGQATT

AYFLYQQQGRLDKLTITSQNLQLESLRMKL[1]PRCGSHLVEALYLVCGEE

G[2]FFKRAVRPLWVRME[3]KRCGSHLVEALYLVCGERG[4]FFSLKKGAAALGI

GTDSVI[5]LICGSHLVEALYLVCGGEG[6]FFRMSRLSKVAPVIKARMMEYGT

T[7]MVEGRGSLLTCGDVEENPGP[8]EALYLVCGERG[9]FFLSVYLKTNVFL[10]

FLPG

Key for the IET5AI Protein Superscript Annotations:

1-Ii(1-80) ETS, 2-InsB(9-23) R22E, 3-1040-79 (2.5 mimotope), 4-InsB(9-23), 5-GAD65(286-300), 6-InsB(9-23) E21G/R22E, 7-GAD65(524-543), 8-T2A cleavage site, 9-InsB(15-23), 10-IGRP(206-214)

IET5AI DNA sequence (codon-optimized):
(SEQ ID NO: 59)
GCCACCATGGACGACCAGAGGGACCTGATCAGCAACCACGAGCAGCTGCC

CATCCTGGGCAACAGACCCCGCGAGCCTGAGAGATGTAGCAGAGGCGCTC

TGTACACCGGCGTGTCCGTGCTGGTGGCTCTGCTGCTGGCTGGCCAGGCT

ACAACCGCCTACTTCCTGTATCAGCAGCAGGGCAGACTGGACAAGCTGAC

CATCACCAGCCAGAACCTCCAGCTCGAAAGCCTGAGAATGAAGCTGCCGC

GGTGCGGCTCTCACCTGGTGGAAGCTCTGTACCTCGTGTGCGGCGAGGAA

GGCTTCTTCAAGAGGGCTGTGCGACCCCTGTGGGTCCGAATGGAAAAGAG

ATGCGGCAGCCACCTGGTCGAGGCCCTCTATCTCGTGTGTGGGGAGAGAG

GCTTTTTCAGCCTGAAGAAGGGCGCTGCCGCCCTGGGCATCGGCACAGAC

TCTGTGATCCTGATCTGCGGAAGCCATCTCGTCGAAGCACTGTATCTGGT

CTGCGGAGGCGAGGGCTTCTTCCGGATGAGCAGACTGAGCAAGGTGGCCC

CCGTGATCAAGGCCAGAATGATGGAATACGGCACCACAATGGTGGAAGGC

AGAGGCAGCCTGCTGACCTGCGGCGACGTGGAAGAGAACCCTGGCCCTGA

GGCACTCTACCTGGTCTGTGGCGAGCGCGGATTCTTCCTGAGCGTGTACC

TCAAGACCAACGTGTTCCTGTTCCTGCCCGGGTAG

IET5BS protein:
(SEQ ID NO: 60)
MKWVTFLLLLFISGSAFSRGKLM[1]PRCGSHLVEALYLVCGEEG[2]FFKRAV

RPLWVRME[3]KRCGSHLVEALYLVCGERG[4]FFSLKKGAAALGIGTDSVI[5]L

ICGSHLVEALYLVCGGEG[6]FFRMSRLSKVAPVIKARMMEYGTT[7]MVLSVY

LKTNVFL[8]FLPG

Key for IET5BS Protein Superscript Annotations:

1-Albumin Secretion Signal, 2-InsB(9-23) R22E, 3-1040-79 (2.5 mimotope), 4-InsB(9-23), 5-GAD65(286-300), 6-InsB(9-23) E21G/R22E, 7-GAD65(524-543), 8-IGRP (206-214)

IET5BS DNA sequence (codon-optimized):
(SEQ ID NO: 61)
GCCACCATGAAGTGGGTCACCTTTCTGCTGCTGCTGTTCATCAGCGGCAG
CGCCTTCAGCAGAGGCAAGCTGATGCCGCGGTGCGGCTCTCACCTGGTGG
AAGCCCTGTACCTCGTGTGCGGCGAGGAAGGCTTCTTCAAGAGGGCTGTG
CGACCCCTGTGGGTCCGAATGGAAAGAGATGCGGCAGCCACCTGGTCGA
GGCACTCTATCTCGTGTGTGGGAGAGAGGCTTTTTCAGCCTGAAGAAGG
GCGCAGCCGCCCTGGGCATCGGCACAGACTCTGTGATCCTGATCTGCGGA
AGCCATCTCGTCGAAGCTCTGTATCTGGTCTGCGGCGGAGAGGGCTTCTT
TAGAATGAGCAGACTGAGCAAGGTGGCCCCCGTGATCAAGGCCAGAATGA
TGGAATACGGCACCACAATGGTGCTGAGCGTGTACCTCAAGACCAACGTG
TTCCTGTTCCTGCCCGGGTAG IET5AIC protein:
(SEQ ID NO: 62)
MGNHFQAILAQVQTLLSSQKPRQVRALLDGLLEEELLSREYHCALLHEPD
GDALARKISLTLLEKGDLDLTFLSWVCNSLQAPTVERGTSYRDHGDHSLC
ATMDLGSPEGSYLELLNSDADPLHLYHLYDQMDLAGEEEIELSSEPDTDT
INCDQFSKLLQDMELDEETREAYANIAELDQYVFQDTQLEGLSKDLFIEH
IGAEEGFGENIEIPVEAGQKPQKRRFPEEHAMDSKHRKLVPTSRTSLNYL
DLPTGHIQIFTTLPQGLWQISGAGTGLSSVLIYHGEMPQVNQVLPSSSLS
IPSLPESPDRPGSTSPFTPSAADLPSMPEPALTSRVNETEDTSPSPCQEG
PESSIKLPKWPEAVERFQHSLQDKYKALPQSPRGPLVAVELVRARLERGS
NKSQERELATPDWTERQLAHGGLAEVLQVVSDCRRPGETQVVAVLGKAGQ
GKSHWARTVSHTWACGQLLQYDFVFYVPCHCLDRPGDTYHLRDLLCPPSL
QPLAMDDEVLDYIVRQPDRVLLILDAFEELEAQDGLLHGPCGSLSPEPCS
LRGLLAGIFQRKLLRGCTLLLTARPRGRLAQSLSKADAIFEVPSFSTKQA
KTYMRHYFENSGTAGNQDKALGLLEGQPLLCSYSHSPVVCRAVCQLSKAL
LEQGTEAQLPCTLTGLYVSLLGPAAQNSPPGALVELAKLAWELGRRHQST
LQETRFSSVEVKTWAVTQGLMQQTLETTEAQLAFSSFLLQCFLGAVWLAQ
CNEIKDKELPQYLALTPRKKRPYDNWLEGVPRFLAGLVFQPRAHCLGALV
EPAVAAVADRKQKVLTRYLKRLKLGTLRAGRLLELLHCAHETQQPGIWEH
VAHQLPGHLSFLGTRLTPPDVYVLGRALETASQDFSLDLRQTGVEPSGLG
NLVGLSCVTSFRASLSDTMALWESLQQQGEAQLLQAAEEKFTIEPFKAKS
PKDVEDLDRLVQTQRLRNPSEDAAKDLPAIRDLKKLEFALGPILGPQAFP
TLAKILPAFSSLQHLDLDSLSENKIGDKGVSKLSATFPQLKALETLNLSQ
NNITDVGACKLAEALPALAKSLLRLSLYNNCICDKGAKSLAQVLPDMVSL
RVMDVQFNKFTAAGAQQLASSLQKCPQVETLAMWTPTIPFGVQEHLQQLD
ARISLR[1]QLATNFSLLKQAGDVEENPGP[2]GTMDDQRDLISNHEQLPILGN
RPREPERCSRGALYTGVSVLVALLLAGQATTAYFLYQQQGRLDKLTITSQ
NLQLESLRMKL[3]PRCGSHLVEALYLVCGEEGFFKRAVRPLWVRMEKRCGS
HLVEALYLVCGERGFFSLKKGAAALGIGTDSVILICGSHLVEALYLVCGG
EGFFRMSRLSKVAPVIKARMMEYGTTMV[4]EGRGSLLTCGDVEENPGP[5]EA
LYLVCGERGFFLSVYLKTNVFLFL[6]PG Key for the IET5BS DNA Sequence Superscript Annotations:
1-CIITA, 2-P2A 3-Ii(1-80), 4-CD4 epitopes, 5-T2A, 6-CD8 epitopes IET5AIC DNA sequence (codon-optimized):
(SEQ ID NO: 63)
GCCACCATGGGTAACCACTTCCAGGCCATTCTGGCCCAGGTGCAGACACT
GCTGAGCAGCCAGAAGCCTAGACAAGTCCGAGCACTGCTGGATGGCCTGC
TGGAAGAGGAACTGCTGTCCAGAGAATACCACTGCGCTCTGCTGCACGAA
CCTGATGGGGATGCCCTGGCCAGAAAGATCAGCCTGACTCTGCTGGAAAA
GGGCGACCTGGACCTGACATTCCTGAGCTGGGTCTGCAACTCTCTGCAGG
CCCCTACAGTGGAAAGAGGCACCTCTTACAGAGATCACGGCGACCACAGC
CTGTGCGCTACAATGGATCTTGGCAGCCCTGAGGGCAGCTACCTGGAACT
GCTCAACTCTGATGCCGATCCTCTGCATCTGTACCACCTGTACGACCAGA
TGGATCTGGCCGGCGAGGAAGAGATCGAGCTGTCTAGCGAGCCTGACACC
GACACCATCAACTGCGACCAGTTCAGCAAGCTGCTGCAGGACATGGAACT
GGACGAGGAAACAAGAGAGGCCTACGCCAATATCGCCGAGCTGGACCAGT
ACGTGTTCCAGGATACACAGCTGGAAGGCCTGAGCAAGGACCTGTTCATC
GAGCACATCGGCGCTGAGGAAGGCTTCGGCGAGAATATCGAGATCCCTGT
GGAAGCCGGACAGAAGCCCCAGAAGAGAAGATTCCCTGAGGAACACGCCA
TGGACAGCAAGCACAGAAAGCTGGTGCCTACCAGCAGAACCAGCCTGAAC
TATCTGGACCTGCCTACCGGCCACATCCAGATTTTCACCACACTGCCTCA
AGGCCTGTGGCAGATTTCTGGCGCTGGAACAGGACTGAGCAGCGTGCTGA
TCTACCACGGCGAGATGCCTCAAGTGAACCAGGTGCTGCCTAGCAGCTCC
CTGTCTATCCCATCTCTGCCTGAGAGCCCTGACAGACCTGGCAGCACAAG
CCCTTTCACACCTTCTGCCGCCGACCTGCCTTCTATGCCTGAACCTGCTC
TGACCTCCAGAGTGAACGAGACAGAGGACACAAGCCCATCTCCATGCCAA
GAGGGACCCGAGTCTAGCATCAAGCTGCCTAAGTGGCCTGAGGCCGTGGA
AAGATTTCAGCACAGCCTGCAGGATAAGTACAAGGCCCTGCCACAGTCTC
CTAGAGGACCTCTGGTGGCTGTGGAACTCGTCAGAGCTAGACTGGAAAGG
GGCAGCAACAAGAGCCAAGAGAGAGAGCTGGCCACACCTGACTGGACCGA
AAGACAACTGGCTCACGGTGGACTGGCTGAGGTGCTGCAAGTGGTGTCTG
ACTGTAGAAGGCCTGGCGAGACAGGTGGTGGCAGTTCTGGGAAAAGCC
GGCCAGGGAAAGTCTCACTGGGCTAGAACAGTGTCCCACACATGGGCATG
TGGACAGCTGCTCCAGTACGACTTCGTGTTCTACGTGCCATGCCACTGCC
TGGATAGACCTGGCGACACATACCACCTGAGGGACCTGCTGTGTCCACCT
TCTCTGCAGCCTCTGGCCATGGATGACGAGGTGCTGGACTACATCGTGCG
GCAGCCTGATAGAGTGCTGCTGATCCTGGACGCCTTCGAGGAACTGGAAG
CTCAGGATGGACTGCTGCATGGACCTTGTGGATCTCTGAGCCCTGAGCCT
TGTTCTCTGAGAGGACTGCTGGCCGGCATCTTCCAGAGAAAGCTGCTGAG AGGCTGTACCCTGCTGCTGACAGCTAGACCTAGAGGCAGACTGGCCCAGA
GCCTGTCTAAGGCCGATGCTATCTTCGAGGTGCCCAGCTTCAGCACCAAG
CAGGCCAAGACCTACATGAGACACTACTTCGAGAACAGCGGCACCGCCGG
CAATCAGGATAAGGCACTTGGACTGCTCGAAGGCCAGCCTCTGCTGTGTA
GCTACTCTCACAGCCCTGTCGTGTGCAGAGCCGTGTGTCAGCTGTCTAAA
GCTCTGCTCGAACAGGGCACAGAGGCCCAGTTGCCTTGTACACTGACCGG
ACTGTATGTGTCCCTGCTGGGACCTGCCGCTCAAAATTCTCCTCCTGGTG
CTCTGGTGGAACTGGCCAAACTGGCTTGGGAACTCGGAAGAAGGCACCAG
TCTACCCTGCAAGAGACAAGATTCAGCAGCGTGGAAGTGAAAACCTGGGC
CGTGACACAGGGCCTGATGCAGCAGACCCTGGAAACAACAGAAGCTCAGC
TGGCCTTTAGCAGCTTCCTGCTGCAGTGTTTTCTGGGCGCTGTGTGGCTG
GCCCAGTGTAATGAGATCAAGGACAAAGAGCTGCCTCAGTACCTGGCTCT
GACACCTAGAAAGAAGAGGCCCTACGATAACTGGCTGGAAGGGGTGCCCA
GATTCCTGGCTGGACTGGTGTTTCAGCCTAGGGCTCATTGTCTGGGAGCC
CTGGTTGAACCAGCTGTGGCTGCCGTGGCTGACAGAAAGCAGAAAGTGCT
GACCAGATACCTGAAGAGACTGAAACTGGGAACACTGAGAGCCGGCAGAC
TGCTGGAACTCCTGCACTGTGCTCACGAAACACAGCAGCCTGGCATCTGG
GAGCATGTGGCACATCAGCTGCCTGGCCACCTGTCCTTTCTGGGCACAAG
ACTGACACCTCCAGACGTGTACGTGCTGGGCAGAGCACTGGAAACCGCCT
CTCAGGACTTTAGCCTGGATCTGAGACAGACCGGCGTGGAACCTTCTGGA
CTGGGAAATCTCGTGGGCCTGAGCTGCGTGACAAGCTTCAGAGCCTCTCT
GAGCGACACAATGGCCCTGTGGGAATCTCTGCAACAGCAGGGCGAAGCAC
AGCTGCTTCAGGCCGCTGAAGAGAAGTTCACCATCGAGCCCTTCAAGGCC
AAGTCTCCCAAGGACGTTGAGGACCTGGATAGGCTGGTGCAGACTCAGAG
ACTGAGAAACCCTAGCGAGGACGCCGCTAAGGATCTGCCTGCTATCAGGG
ACCTGAAGAAGCTGGAATTCGCTCTGGGACCCATCCTGGGACCTCAGGCT
TTTCCTACACTGGCTAAGATCCTGCCAGCCTTCTCTAGCCTGCAGCATCT
GGATCTGGACTCCCTGAGCGAGAACAAGATCGGCGATAAGGGCGTGTCCA
AGCTGAGCGCTACATTCCCTCAGCTGAAGGCTCTGGAAACACTGAATCTG
TCCCAGAACAACATCACCGACGTGGGCGCCTGTAAACTGGCTGAAGCACT
GCCTGCTCTGGCCAAATCTCTGCTGAGGCTGAGCCTGTACAACAACTGCA
TCTGCGACAAGGGCGCCAAGTCACTGGCTCAGGTTCTGCCTGACATGGTG
TCCCTGAGAGTGATGGACGTGCAGTTCAACAAGTTCACAGCCGCTGGCGC CCAGCAACTGGCATCATCTCTGCAGAAATGTCCCCAGGTGGAAACCCTGG
CTATGTGGACCCCTACAATCCCCTTCGGCGTGCAAGAACATCTCCAGCAG
CTGGACGCCAGAATCTCCCTGAGA[1]CAATTGGCCACCAACTTCAGCCTGC
TGAAGCAGGCCGGCGACGTGGAAGAAAATCCTGGACCT[2]GGTACCATGGA
CGACCAGAGGGACCTGATCAGCAACCACGAGCAGCTGCCCATCCTGGGCA
ACAGACCCCGCGAGCCTGAGAGATGTAGCAGAGGCGCTCTGTACACCGGC
GTGTCCGTGCTGGTGGCTCTGCTGCTGGCTGGCCAGGCTACAACCGCCTA
CTTCCTGTATCAGCAGCAGGGCAGACTGGACAAGCTGACCATCACCAGCC
AGAACCTCCAGCTCGAAAGCCTGAGAATGAAGCTG[3]CCGCGGTGCGGCTC
TCACCTGGTGGAAGCTCTGTACCTCGTGTGCGGCGAGGAAGGCTTCTTCA
AGAGGGCTGTGCGACCCCTGTGGGTCCGAATGGAAAAGAGATGCGGCAGC
CACCTGGTCGAGGCCCTCTATCTCGTGTGTGGGGAGAGAGGCTTTTTCAG
CCTGAAGAAGGGCGCTGCCGCCCTGGGCATCGGCACAGACTCTGTGATCC
TGATCTGCGGAAGCCATCTCGTCGAAGCACTGTATCTGGTCTGCGGAGGC
GAGGGCTTCTTCCGGATGAGCAGACTGAGCAAGGTGGCCCCCGTGATCAA
GGCCAGAATGATGGAATACGGCACCACAATGGTGGAAGGCAGAGGCAGCC
TGCTGACCTGCGGCGACGTGGAAGAGAACCCTGGCCCTGAGGCACTCTAC
CTGGTCTGTGGCGAGCGCGGATTCTTCCTGAGCGTGTACCTCAAGACCAA
CGTGTTCCTGTTCCTG[4]CCCGGGTAG Key for the IET5AIC DNA Sequence Superscript Annotations:

1-CIITA, 2-P2A 3-Ii(1-80), 4-CD4 epitopes, T2A, CD8 epitopes

Peptides Included in IET5AI and IET5BS:

TABLE 3

| | Peptides included i IET5AI and IET5BS: | | | | |
|---|---|---|---|---|---|
| Peptide | Antigen | Sequence | SEQ ID NO | T MHC | cell Mouse/clone/tet |
| B: 9-23 | Ins2 | SHLVEALYLVCGERG | 1 | I-A$^{g7}$ CD4 | Tet |
| B: 9-23 (R22E) | Mimotope | SHLVEALYLVCGEEG | 3 | I-A$^{g7}$ CD4 | BDC12-4.1/Tet |

TABLE 3-continued

Peptides included i IET5AI and IET5BS:

| Peptide | Antigen | Sequence | SEQ ID NO | MHC | T cell | Mouse/clone/tet |
|---|---|---|---|---|---|---|
| B: 9-23 (E21G/R22E) | Mimotope | SHLVEALYLVCGGEG | 64 | I-A$^{g7}$ | CD4 | Tet |
| 1040-79 | Mimotope | AVRPLWVRME | 65 | I-A$^{g7}$ | CD4 | BDC2.5/Tet |
| 286-300 | GAD65 | KKGAAALGIGTDSVI | 7 | I-A$^{g7}$ | CD4 | G286/Tet |
| 524-543 | GAD65 | SRLSKVAPVIKARMMEYGTT | 66 | I-A$^{g7}$ | CD4 | Tet |
| B: 15-23 | Ins2 | LYLVCGERG | 2 | K$^d$ | CD8 | G9C8/Tet |
| 206-214 | IGRP | VYLKTNVFL | 6 | K$^d$ | CD8 | NY8.3/Tet |

All epitopes expressed in IET5 constructs are derived from four beta-cell antigens (Ins, GAD65, ChgA and IGRP). These particular epitopes were chosen because of the existence of TCR-transgenic mice, T cell clones and MHC tetramer reagents that allow specific analysis of antigen-specific T cells in vivo (see FIGS. 2B-D for examples). Most epitopes have been described in a previous review by DiLorenzo et al.[1]. InsB(9-23), GAD65(286-300) and GAD65(524-543) are shown in Table 2 of the DiLorenzo review. InsB(9-15) and IGRP (206-214) are shown in Table 4 of the DiLorenzo review.

All epitopes presented in the DiLorenzo et al. paper have been identified based on evidence of autoimmune reaction against them. There is a great deal of overlap in epitopes between the NOD mouse model and human T1D patients. Epitope binding in human depends on the MHC haplotype, most of those identified are restricted to MHC-II HLA-DR3, HLA-DR4 and HLA-DQ8, which are the most common haplotypes of T1D patients. Most human CD8 epitopes are HLA-A2 restricted, because HLA-A2 is one of the most common MHCI haplotype.

Some of the epitopes used are mimotopes, which allow a better recognition by diabetogenic T cells. The InsB(9-23) mimotopes R22E and E21G/R22E differentially engage different clones of insulin-reactive CD4+ T cells[2]. Such mimotopes may be more efficient to engage T cells for tolerance in vivo[3]. Similar mimotopes have been used to engage human insulin-reactive T cells[4], and T1D patients have more circulating T cells reacting against those mimotopes than against native epitopes[5]. Mimotopes such as the 1040-70 (aka 2.5 mimotope) can also recognize a number of diabetogenic CD4+ T cells and have been discovered by peptide library screening[6,7]. Natural epitopes that are physiological equivalents of these mimotopes were more recently described as hybrid insulin peptides (HIPs) that are fusions between insulin peptides and peptides from other beta-cell antigens, including ChgA, IAPP1, IAPP2 and amylin[8]. Examples of such peptides that can be included in our constructs include GDLQTLWSRMD (SEQ ID NO: 48), LQTLALWSRMD (SEQ ID NO: 49) and LQTLAL-NAARD (SEQ ID NO: 50). Similar HIPs identified from T1D patients include GQVELGGGSSPETLI (SEQ ID NO: 51) and GQVELGGGNAVEVLK[8] (SEQ ID NO: 52). More peptide fusion may be produced between insulin and ChgA by transpeptidation that can stimulate diabetogenic T cell clones[9].

New epitopes not listed in the 2007 DiLorenzo review include ChgA epitopes in mouse[10] and T1D patients[11,12], REGII as autoantigen in NOD mice[13], ZnT8 epitopes in NOD mice[14] and T1D patients[15], and Vitamin D binding protein (VDBP) as new autoantigen in NOD mice and T1D patients[16].

DNA vaccine-based delivery of specific epitopes for tolerance is amenable to personalization. Although many targeted autoantigens are in common between patients, epitope binding depends on HLA haplotype (primarily HLA-DR/DQ for MHCII, HLA-A/B for MHCI). Most epitopes described in T1D have been described to bind HLA-DR3, DR4, DQ8 or A2.

The binding potential of peptides from a particular antigen to a particular MHC may be predicted based on available online prediction algorithms, such as SYFPEITHI (www.syfpeithi.de/), IEDB (tools.immuneepitope.org/mhci/), and NetMHC (www.cbs.dtu.dk/services/NetMHC/). Other methods of predicting peptides from a protein that may bind a particular MHC have been described[17].

Predicted peptides may be validated for a particular patient. For example, peripheral blood mononucleated cells (PBMCs) from T1D patients may be tested ex vivo for response to common and predicted peptides by ELISPOT assay. The same PBMCs may also be screened with existing MHC tetramers (providing MHC compatibility) for the presence of peptide-specific T cells in the circulation.

Targeted autoantigens can also be detected based on autoantibodies. Assuming that autoantibody production required T cell help, epitopes from these targeted antigens (either already described for common HLA haplotypes, or predicted for other HLA haplotypes) can be determined and included in an epitope-based tolerogenic DNA vaccine. Epitopes that are widely shared as targeted epitopes among patients of the same haplotype may be used as treatment for that group. The majority of T1D patients have the HLA-DR3, DR4, DQ8 and/or A2 haplotypes.

References Related to Example 17

1. Di Lorenzo, T P, Peakman, M, and Roep, B O (2007). Translational mini-review series on type 1 diabetes: Systematic analysis of T cell epitopes in autoimmune diabetes. *Clin Exp Immunol* 148: 1-16.
2. Crawford, F, Stadinski, B, Jin, N, Michels, A, Nakayama, M, Pratt, P, et al. (2011). Specificity and detection of insulin-reactive CD4+ T cells in type 1 diabetes in the nonobese diabetic (NOD) mouse. *Proc Natl Acad Sci USA* 108: 16729-16734.
3. Daniel, C, Weigmann, B, Bronson, R, and von Boehmer, H (2011). Prevention of type 1 diabetes in mice by tolerogenic vaccination with a strong agonist insulin mimetope. *J Exp Med* 208: 1501-1510.
4. Serr, I, Furst, R W, Achenbach, P, Scherm, M G, Gokmen, F, Haupt, F, et al. (2016). Type 1 diabetes vaccine candidates promote human Foxp3(+)Treg induction in humanized mice. *Nature communications* 7: 10991.
5. Nakayama, M, McDaniel, K, Fitzgerald-Miller, L, Kiekhaefer, C, Snell-Bergeon, J K, Davidson, H W, et al. (2015). Regulatory vs. inflammatory cytokine T-cell responses to mutated insulin peptides in healthy and type 1 diabetic subjects. *Proc Natl Acad Sci USA* 112: 4429-4434.
6. Judkowski, V, Pinilla, C, Schroder, K, Tucker, L, Sarvetnick, N, and Wilson, D B (2001). Identification of MHC class II-restricted peptide ligands, including a glutamic acid decarboxylase 65 sequence, that stimulate diabetogenic T cells from transgenic BDC2.5 nonobese diabetic mice. *J Immunol* 166: 908-917.
7. You, S, Chen, C, Lee, W H, Wu, C H, Judkowski, V, Pinilla, C, et al. (2003). Detection and characterization of T cells specific for BDC2.5 T cell-stimulating peptides. *J Immunol* 170: 4011-4020.
8. Delong, T, Wiles, T A, Baker, R L, Bradley, B, Barbour, G, Reisdorph, R, et al. (2016). Pathogenic CD4 T cells in type 1 diabetes recognize epitopes formed by peptide fusion. *Science* 351: 711-714.
9. Jin, N, Wang, Y, Crawford, F, White, J, Marrack, P, Dai, S, et al. (2015). N-terminal additions to the WE14 peptide of chromogranin A create strong autoantigen agonists in type 1 diabetes. *Proc Natl Acad Sci USA* 112: 13318-13323.
10. Nikoopour, E, Sandrock, C, Huszarik, K, Krougly, O, Lee-Chan, E, Masteller, E L, et al. (2011). Cutting edge: vasostatin-1-derived peptide ChgA29-42 is an antigenic epitope of diabetogenic BDC2.5 T cells in nonobese diabetic mice. *J Immunol* 186: 3831-3835.
11. Gottlieb, P A, Delong, T, Baker, R L, Fitzgerald-Miller, L, Wagner, R, Cook, G, et al. (2014). Chromogranin A is a T cell antigen in human type 1 diabetes. *J Autoimmun* 50: 38-41.
12. Li, Y, Zhou, L, Li, Y, Zhang, J, Guo, B, Meng, G, et al. (2015). Identification of autoreactive CD8+ T cell responses targeting chromogranin A in humanized NOD mice and type 1 diabetes patients. *Clin Immunol* 159: 63-71.
13. Gurr, W, Shaw, M, Li, Y, and Sherwin, R (2007). RegII is a beta-cell protein and autoantigen in diabetes of NOD mice. *Diabetes* 56: 34-40.
14. Nayak, D K, Calderon, B, Vomund, A N, and Unanue, E R (2014). ZnT8-reactive T cells are weakly pathogenic in NOD mice but can participate in diabetes under inflammatory conditions. *Diabetes* 63: 3438-3448.
15. Xu, X, Gu, Y, Bian, L, Shi, Y, Cai, Y, Chen, Y, et al. (2016). Characterization of immune response to novel HLA-A2-restricted epitopes from zinc transporter 8 in type 1 diabetes. *Vaccine* 34: 854-862.
16. Kodama, K, Zhao, Z, Toda, K, Yip, L, Fuhlbrigge, R, Miao, D, et al. (2016). Expression-Based Genome-Wide Association Study Links Vitamin D-Binding Protein With Autoantigenicity in Type 1 Diabetes. *Diabetes* 65: 1341-1349.
17. Lee, S J, McLachlan, J B, Kurtz, J R, Fan, D, Winter, S E, Baumler, A J, et al. (2012). Temporal expression of bacterial proteins instructs host CD4 T cell expansion and Th17 development. *PLoS Pathog* 8: e1002499.

Example 18: Assessment of Nucleic Acid Constructs In Vitro and In Vivo

Methods

FIG. 19A, in vitro studies:

Bone marrow-derived dendritic cells (DCs) were generated over 6 days by culture of lymphocyte and granulocyte depleted bone marrow cells with GM-CSF and IL-4 (10 ng/ml). At the end of the culture, over 80-90% of cells are CD11c+ CD11b+ DCs. PCRC-5 are immortalized fibroblastic reticular cells from the lymph node of NOD mice (lymph node stromal cells). Both cell types were plated in 96-well plates (50,000 DCs or 2,500 PCRC-5 cells) and transfected 24 hours later with Luciferase-expressing plasmid DNA (pBHT-LUC). To generate polyplexes, the K9 poly-lysine peptide was used as cell-penetrating peptide and 15 uL was added to 10 uL of pDNA (1 ug) (N/P ratio=30), then 15 uL of 100 mM CaCl2 and the mixtures was incubated at 4 C for 20 to 25 minutes to condense. pBHT-LUC (1 ug) was also complexed with lipofectamine (from Invitrogen) and JetPrime (from PolyPlus, 1:2 DNA/JetPrime ratio in presence or serum) following manufacturer's instructions. Naked DNA is 1 ug of non-complexed plasmid. All DNA mixtures were completed to 100 uL with OptiMEM and added to cells for 7 hours, after which the transfection medium was replaced with complete growth medium. After 48 hours, total cellular protein was measured by using BCA Protein Assay Reagent (Thermo Fisher Scientific Inc.). The efficiency of pBHT-LUC transfection was determined by Luciferase Reporter Assay (Promega). The Luciferase expression was measured by a micro-plate reader (BioTek). The transfection efficiency was expressed as relative light units (RLU) per milligram (mg) of cellular protein.

FIGS. 19B-D, in vivo studies:

FIGS. 19B-C: response of adoptively transferred antigen-specific T cells: $1 \times 10^{\wedge}6$ CD4+CD25− T cells from BDC2.5 (Thy1.2+) NOD female mouse were isolated by magnetic beads isolation, stained with a Violet proliferation cell dye (VCPD) and transferred intravenously into congenic NOD-.Thy1.1 female recipients, which were then treated by intradermal injection of 50 ug of IET5AI (AI) or IET5BS (BS) plasmids (see FIG. 18E). Three days later, the response of the transferred cells in the Cervical, Inguinal and Pancreatic lymph-nodes (CLN, ILN, PLN) was analyzed by FACS, including CD25 and Foxp3 expression (FIG. 19B) and cell division (FIG. 19C, % of divided T cells based of VCPD dilution). The CLNs serve as negative control sites. The proliferation seen in the PLNs represent a vigorous response to endogenous presentation of islet antigens, including the BDC2.5 natural antigen, by immunogenic DCs. No CD25/Foxp3 expression is seen in spite of a clear proliferative response. The ILNs are the lymph nodes draining the site of DNA inoculation. There a response is seen to the BDC2.5 epitope expressed by DNA constructs AI and BS, characterized by a more modest proliferative response, but more Foxp3 and CD25 expression, which may indicate a more tolerogenic response.

FIG. 19D: response of endogenous antigen-specific T cells:

Female NOD mice were treated by intradermal injection of 50 ug of IET5AI (AI) or IET5BS (BS) plasmids. The three days later, endogenous T cells responsive to the BDC2.5 epitopes were identified by staining with CD25 and I-A(g7)/2.5 mimotope MHC tetramers (NIH Tetramer Core Facility) using FACS. Clonal expansion, reflective of antigen encounter, was visible in the draining lymph nodes (ILNs) and not in the other lymph nodes. Thus, antigen-specific T cells preexist in those lymph nodes and can be targeted by the DNA vaccine.

Example 19: Assessment of In Vivo Ag-Specific Responses of Nucleic Acid Constructs Experimental Approach:

Two models are used for the assessment of in vivo Ag-specific responses to the 3 forms of DNA vaccines presented above. In the adoptive transfer model, Ag-specific Thy1.2$^+$ T cells recognizing one or several epitopes expressed in the constructs (from BDC2.5, BDC12-4.1.TCRβKO and NY8.3 mice) are injected into recipient Thy1.1$^+$ NOD mice at the time of DNA immunization. The response of these T cell clones to the constructs in vivo has already been validated based on CD25 upregulation and cell proliferation (as in FIGS. 19B-C). The phenotype of the stimulated T cells at various sites, including the pancreatic lymph nodes (PLNs), the lymph nodes draining the inoculation site and cervical lymph nodes as control is assessed by flow cytometry. Ag-specific T cells based on Thy1.2 and cell proliferation dye expression is tracked and surface staining (CD4/CD8, CD25, Lag3/CD49b, CD73/FR4) (Gagliani, N, Magnani, C F, Huber, S, Gianolini, M E, Pala, M, Licona-Limon, P, et al. (2013). Coexpression of CD49b and LAG-3 identifies human and mouse T regulatory type 1 cells. *Nat Med* 19: 739-746; Pauken, K E, Linehan, J L, Spanier, J A, Sahli, N L, Kalekar, L A, Binstadt, B A, et al. (2013). Cutting edge: type 1 diabetes occurs despite robust anergy among endogenous insulin-specific CD4 T cells in NOD mice. *J Immunol* 191: 4913-491; and Kalekar, L A, Schmiel, S E, Nandiwada, S L, Lam, W Y, Barsness, L O, Zhang, N, et al. (2016). CD4(+) T cell anergy prevents autoimmunity and generates regulatory T cell precursors. *Nat Immunol* 17: 304-314), intracellular staining (Foxp3, IL-10, IFN-γ) and/or ex vivo culture with or without peptide restimulation is performed to evaluate their cytokine profile (Cytokine Bead Array, 13-plex panel). Alternatively, NOD.Foxp3-GFP and NOD.IL-10-GFP mice are used as reporter mice that are crossed with BDC2.5 mice for donor T cells. Deletion of CD8$^+$ T cells is determined based on the disappearance of the transferred cells within two weeks after the initial expansion (Lee, J, Epardaud, M, Sun, J, Becker, J, Cheng, A, Yonekura, A, et al. (2007). Peripheral antigen display by lymph node stroma promotes T cell tolerance to intestinal self. *Nat Immunol* 8: 181-190; Nichols, L, Chen, Y, Colella, T, Bennett, C, Clausen, B, and Engelhard, V (2007). Deletional self-tolerance to a melanocyte/melanoma antigen derived from tyrosinase is mediated by a radio-resistant cell in peripheral and mesenteric lymph nodes. *J Immunol* 179: 993-1003; and Gardner, J M, Devoss, J J, Friedman, R S, Wong, D J, Tan, Y X, Zhou, X, et al. (2008). Deletional tolerance mediated by extrathymic Aire-expressing cells. *Science* 321: 843-847). The second model is a direct DNA immunization of female NOD, NOD.Foxp3-GFP or NOD.IL-10-GFP mice followed by ex vivo analysis of Ag-specific T cells by MHC tetramer (as in FIG. 19D). MHC tetramers specific for 5 out of 6 CD4 epitopes and 1 out of 2 CD8 epitopes expressed by the constructs are used. At least two routes of immunization are tested (intradermal on the abdomen and intramuscular in the quadriceps), and multiple lymph nodes are analyzed (pancreatic, inguinal, periaortic, cervical) after 3 days or 2 weeks. The response of non-Ag-specific bystander T cells is measured as control.

It is expected that CD4$^+$ T cells engaged through the DNA vaccine epitopes will have a more regulatory phenotype than those stimulated in PLNs by inflammatory DCs. It is expected that constructs AIC and BS will improve engagement of circulating diabetogenic T cells in non-inflamed lymph nodes, either by more efficient transfer to tolerogenic DCs (BS) or by allowing more stromal cells to present the epitopes to CD4$^+$ T cells (AIC) after MHCII upregulation. The secreted epitope-containing polypeptides from BS are more likely to be presented in draining lymph nodes upon direct lymphatic draining or if acquired by migratory DCs, unless some of the DNA can also directly transfect cells in the lymph nodes. Direct injection of DNA into lymph node is possible and may be preferred for direct transfection of lymph node stromal cells. In this case, constructs such as AIC will be useful to confer stromal cells the ability to upregulate MHCII via the expressed CIITA and present co-expressed CD4 epitopes. The feasibility of intranodal injection into T1D patients has been demonstrated with protein antigens (Ludvigsson J, Wahlberg J, Casas R. Intralymphatic Injection of Autoantigen in Type 1 Diabetes. N Engl J Med. 2017 Feb. 16; 376(7):697-699.).

Example 20 Assessment of Nucleic Acid Constructs Complexed with Polycationic Molecules It is expected that most of the transfected cells are stromal or parenchymal cells at the site of DNA vaccine inoculation, while optimal Ag exposure to T cells likely requires presentation within the draining lymph nodes. Even strictly endogenous epitopes lead to a response in the draining lymph nodes (FIGS. 19B-D), raising the possibilities that 1) some migratory DCs are directly transfected, 2) migratory DCs capture Ag from dying transfected cells, and/or 3) certain transfected non-DC populations can relocate to lymph nodes. Draining of the DNA constructs themselves to the lymph nodes is limited by their large size, which can be substantially reduced with mini-circle DNA technology. The new formulations are expected to improve cell transfection and increase the amount of Ag presented in non-inflamed tissues and lymph nodes. It is also expected that tiny vectors may more efficiently reach the draining lymph nodes and directly transfect LNSCs, which may promote tolerance even in inflamed PLNs. It is also expected minicircle vectors to enhance transfection (possibly into DCs as well) and dramatically prolong Ag expression (weeks) relative to conventional vectors (days) (Chen, Z Y, He, C Y, Ehrhardt, A, and Kay, M A (2003). Minicircle DNA vectors devoid of bacterial DNA result in persistent and high-level transgene expression in vivo. *Mol Ther* 8: 495-500; Dietz, W M, Skinner, N E, Hamilton, S E, Jund, M D, Heitfeld, S M, Litterman, A J, et al. (2013). Minicircle DNA is superior to plasmid DNA in eliciting antigen-specific CD8+ T-cell responses. *Mol Ther* 21: 1526-1535; and Kay, M A, He, C Y, and Chen, Z Y (2010). A robust system for production of minicircle DNA vectors. *Nat Biotechnol* 28: 1287-1289).

Experimental Approach:

First, using the BHT backbone vector expressing an optimized firefly luciferase (Luc2), different formations of DNA for in vivo delivery are tested: soluble 'naked' DNA[7,20], CPP/DNA Polyplexes (Alhakamy, N A, Nigatu, A S, Berkland, C J, and Ramsey, J D (2013). Noncovalently associated cell-penetrating peptides for gene delivery applications. *Therapeutic delivery* 4: 741-757; Alhakamy, N A, Ishiguro, S, Uppalapati, D, Berkland, C J, and Tamura, M (2016). AT2R Gene Delivered by Condensed Polylysine Complexes Attenuates Lewis Lung Carcinoma after Intravenous Injection or Intratracheal Spray. *Mol Cancer Ther* 15: 209-218; and Fang, W B, Yao, M, Brummer, G, Acevedo, D, Alhakamy, N, Berkland, C, et al. (2016). Targeted gene silencing of CCL2 inhibits triple negative breast cancer progression by blocking cancer stem cell renewal and M2 macrophage recruitment. *Oncotarget*), and polyethylenimine (also polycationic)/DNA complexes (Polyplus, polyplus-transfection.com). The level of Luc2 expression at inoculation sites (intradermal and intramuscular) and draining lymph nodes (inguinal, periaortic) will be measured by in vivo and ex vivo bioluminescence imaging (IVIS Spectrum) and compared between formulations (10-50 ug DNA per site). The amplitude and nature of the Ag-specific T cell responses in the draining lymph node is measured and correlated with the level and duration of transgene expression. Second, three minicircle vectors are produced, expressing constructs AI, BS and the mCherry reporter (same small size of ~2.1 kb, compared with 3.6-3.8 kb for the BHT vector), using the commercially available production kits from SBI systembio.com/. The mCherry minicircle is used in conjunction with the fluorescence imaging capability of the IVIS Spectrum to determine how long and where the vector is expressed. Using the Ag-expressing vectors, BDC2.5 and/or NY8.3 T cells are injected at different times (same day, 3 days, 1 week, 1 month) after DNA inoculation to see how long Ags are presented in the draining lymph nodes, compared to the conventional DNA vaccine. The nature of the T cell response is evaluated according to the panels described in Example 19.

It is expected that DNA formulations that improve cell transfection will ultimately result in engagement of diabetogenic T cells for tolerance induction. It is also expected that minicircle vectors will extend the duration of Ag expression, and enable better lymph node drainage and direct transfection of LNSCs by itself or when condensed with CPPs. Further data and validation of the embodiments and teachings herein are provided in Dastagir et al., Mol Ther Methods Clin Dev. 2016 Dec. 24; 4:27-38, which is incorporated herein in its entirety, including supplementary data and information.

As will be apparent to one of ordinary skill in the art from a reading of this disclosure, further embodiments of the present invention can be presented in forms other than those specifically disclosed above. The particular embodiments described above are, therefore, to be considered as illustrative and not restrictive. Those skilled in the art will recognize, or be able to ascertain, using no more than routine experimentation, numerous equivalents to the specific embodiments described herein. Such equivalents are considered to be within the scope of this invention. Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways within the scope and spirit of the invention. The scope of the invention is as set forth in the appended claims and equivalents thereof, rather than being limited to the examples contained in the foregoing description. All publications mentioned herein, are incorporated by reference in their entirety. Nothing herein is to be construed as an admission that the invention is not entitled to antedate such disclosure by virtue of prior invention.

REFERENCES

All publications mentioned herein and listed below are incorporated by reference in their entirety.

Allaart, and Huizinga, Treatment strategies in recent onset rheumatoid arthritis. Curr. Opin. Rheumatol., 23:241-244, 2011.

Ansari et al., The programmed death-1 (PD-1) pathway regulates autoimmune diabetes in nonobese diabetic (NOD) mice. J. Exp. Med. 198:63-69, 2003.

Antigen Express, PCT Patent Application WO1997/049439, filed 1997 Immunotherapy by modulation of antigen presentation.

Apetoh et al., The aryl hydrocarbon receptor interacts with c-Maf to promote the differentiation of type 1 regulatory T cells induced by IL-27. Nat. Immunol. 11:854-861, 2010.

Auger et al., Autoantibodies to PAD4 and BRAF in rheumatoid arthritis. Autoimmun Rev. 11:801-803, 2012.

Badami et al., Defective differentiation of regulatory FoxP3+ T cells by small-intestinal dendritic cells in patients with type 1 diabetes. Diabetes 60:2120-2124, 2011.

Baker et al., CD4 T cells reactive to an islet amyloid polypeptide peptide accumulate in the pancreas and contribute to disease pathogenesis in nonobese diabetic mice. J. Immunol. 2013 191:3990-3994. 2013.

Bar-Or et al., Induction of antigen-specific tolerance in multiple sclerosis after immunization with DNA encoding myelin basic protein in a randomized, placebo-controlled phase ½ trial. Arch. Neurol. 64:1407-1415, 2007.

Benham et al., Citrullinated peptide dendritic cell immunotherapy in HLA risk genotype-positive rheumatoid arthritis patients. Sci. Translat. Med. 7:290ra287, 2015.

Besgen et al., Ezrin, maspin, peroxiredoxin 2, and heat shock protein 27: potential targets of a streptococcal-induced autoimmune response in psoriasis. J. Immunol. 184:5392-5402, 2010.

Beswick et al., Expression of the programmed death ligand 1, B7-H1, on gastric epithelial cells after *Helicobacter pylori* exposure promotes development of CD4+ CD25+ FoxP3+ regulatory T cells. Infect. Immunity 75:4334-4341, 2007.

Bettini et al., Prevention of autoimmune diabetes by ectopic pancreatic beta-cell expression of interleukin-35. Diabetes 61: 1519-1526, 2012.

Boettler & von Herrath, Immunotherapy of type 1 diabetes—how to rationally prioritize combination therapies in T1D. Intl. Immunopharmacol. 10:1491-1495, 2010.

Boks et al., IL-10-generated tolerogenic dendritic cells are optimal for functional regulatory T cell induction—a comparative study of human clinical-applicable DC. Clin. Immunol. 142:332-342, 2012.

Bonasio et al., Clonal deletion of thymocytes by circulating dendritic cells homing to the thymus. Nat. Immunol. 7:1092-1100, 2006.

Bonehill et al., Messenger RNA-electroporated dendritic cells presenting MAGE-A3 simultaneously in HLA class I and class II molecules. J. Immunol. 172: 6649-6657, 2004.

Bonehill et al., Enhancing the T-cell stimulatory capacity of human dendritic cells by co-electroporation with CD40L, CD70 and constitutively active TLR4 encoding mRNA. Mol. Ther. 16:1170-1180, 2008.

Bonehill et al., Single-step antigen loading and activation of dendritic cells by mRNA electroporation for the purpose of therapeutic vaccination in melanoma patients. Clin. Cancer Res. 15:3366-3375, 2009.

Bonifacio et al., Identification of protein tyrosine phosphatase-like IA2 (islet cell antigen 512) as the insulin-dependent diabetes-related 37/40K autoantigen and a target of islet-cell antibodies. J. Immunol. 155:5419-5426. 1995

Bot et al., Plasmid vaccination with insulin B chain prevents autoimmune diabetes in nonobese diabetic mice. J. Immunol. 167:2950-2955, 2001.

Boudaly et al., Altered dendritic cells (DC) might be responsible for regulatory T cell imbalance and autoimmunity in nonobese diabetic (NOD) mice. Eur. Cytokine Network 13:29-37, 2002.

Breckpot et al., Activation of immature monocyte-derived dendritic cells after transduction with high doses of lentiviral vectors. Hum. Gene Ther. 18:536-546, 2007.

Busse et al., ICOS mediates the generation and function of CD4+CD25+Foxp3+ regulatory T cells conveying respiratory tolerance. J. Immunol. 189:1975-1982, 2012.

Carvalho-Pinto et al., Leukocyte attraction through the CCR5 receptor controls progress from insulitis to diabetes in non-obese diabetic mice. Eur. J. Immunol. 34:548557, 2004.

Chee et al., Effector-memory T cells develop in islets and report islet pathology in type 1 diabetes. J. Immunol. 192:572-580, 2014.

Cheever and Higano, PROVENGE (Sipuleucel-T) in prostate cancer: the first FDA-approved therapeutic cancer vaccine. Clin. Cancer Res. 17:3520-3526, 2011.

Chen et al., The epidermolysis bullosa acquisita antigen (type VII collagen) is present in human colon and patients with crohn's disease have autoantibodies to type VII collagen. J. Invest. Dermatol. 118:1059-1064, 2002.

Christen et al., Among CXCR3 chemokines, IFN-gamma-inducible protein of 10 kDa (CXC chemokine ligand (CXCL) 10) but not monokine induced by IFN-gamma (CXCL9) imprints a pattern for the subsequent development of autoimmune disease. J. Immunol. 171:6838-6845, 2003.

Coates et al., Human myeloid dendritic cells transduced with an adenoviral interleukin-10 gene construct inhibit human skin graft rejection in humanized NOD-scid chimeric mice. Gene Ther. 8:1224-1233, 2001.

Collison et al., IL-35-mediated induction of a potent regulatory T cell population. Nat. Immunol. 11:1093-1101, 2010.

Collison et al., The inhibitory cytokine IL-35 contributes to regulatory T-cell function. Nature 450:566-569, 2007.

Conway and Cohen, Combination therapy in multiple sclerosis. Lancet Neurol. 9:299-308, 2010.

Coppieters et al., Demonstration of islet-autoreactive CD8 T cells in insulitic lesions from recent onset and long-term type 1 diabetes patients. J. Exp. Med. 209:51-60, 2012.

Coppieters et al., Trials in type 1 diabetes: Antigen-specific therapies. Clin. Immunol. 149:345-355, 2013.

Crawford et al., Specificity and detection of insulin-reactive CD4+ T cells in type 1 diabetes in the nonobese diabetic (NOD) mouse. P.N.A.S. USA 108:16729-16734, 2011.

Creusot et al., Early commitment of adoptively transferred CD4+ T cells following particle-mediated DNA vaccination: implications for the study of immunomodulation. Vaccine 19:1678-1687, 2001.

Creusot et al., Instruction of naive CD4+ T cells by polarized CD4+ T cells within dendritic cell clusters. Eur. J. Immunol. 33:1686-1696, 2003.

Creusot et al., Local cooperation dominates over competition between CD4+ T cells of different antigen/MHC specificity. J. Immunol. 171:240-246, 2003.

Creusot et al., A short pulse of IL-4 delivered by DCs electroporated with modified mRNA can both prevent and treat autoimmune diabetes in NOD mice. Mol. Ther. 18:2112-2120, 2010.

Creusot et al., Targeted gene therapy of autoimmune diseases: advances and prospects. Exp. Rev. Clin. Immunol. 1:385-404, 2005.

Creusot et al., It's time to bring dendritic cell therapy to type 1 diabetes. Diabetes 63:20-30, 2014.

Creusot et al., Lymphoid-tissue-specific homing of bone-marrow-derived dendritic cells. Blood 113:6638-6647, 2009.

Creusot et al., Tissue-targeted therapy of autoimmune diabetes using dendritic cells transduced to express IL-4 in NOD mice. Clin. Immunol. 127:176-187, 2008.

Dang et al., Human type 1 diabetes is associated with T cell autoimmunity to zinc transporter 8. J. Immunol. 186(10): 6056-6063, 2011.

Daniel et al., Prevention of type 1 diabetes in mice by tolerogenic vaccination with a strong agonist insulin mimetope. J. Exp. Med. 208:1501-1510, 2011.

Delgoffe et al., Stability and function of regulatory T cells is maintained by a neuropilin-1-semaphorin-4a axis. Nature 501:252-256, 2013.

Delong et al., Diabetogenic T-cell clones recognize an altered peptide of chromogranin A. Diabetes 61:3239-3246, 2012.

Di Lorenzo et al., Translational mini-review series on type 1 diabetes: Systematic analysis of T cell epitopes in autoimmune diabetes. Clin. Exp. Immunol. 148:1-16, 2007.

Diebold et al., MHC class II presentation of endogenously expressed antigens by transfected dentritic cells. Gene Ther. 8(6):487, 2001.

Dorrie et al., Introduction of functional chimeric E/L-selectin by RNA electroporation to target dendritic cells from blood to lymph nodes. Cancer Immunol. Immunother. 57:467-477, 2008.

Dullaers et al., Side-by-side comparison of lentivirally transduced and mRNA-electroporated dendritic cells: implications for cancer immunotherapy protocols. Mol. Ther. 10:768-779, 2004.

Fallarino et al., IDO mediates TLR9-driven protection from experimental autoimmune diabetes. J. Immunol. 183: 6303-6312, 2009.

Fernandez et al., Characterization of MHC class II-presented peptides generated from an antigen targeted to different endocytic compartments. Eur. J. Immunol. 30(8):2333, 2000.

Fischbach et al., Cell-based therapeutics: the next pillar of medicine. Science Translational Med. 5:179ps177, 2013.

Fitzgerald et al., Suppression of autoimmune inflammation of the central nervous system by interleukin 10 secreted by interleukin 27-stimulated T cells. Nat. Immunol. 8:1372-1379, 2007.

Fletcher et al., Lymph node stroma broaden the peripheral tolerance paradigm. Trends Immunol. 32:12-18, 2011.

Floess et al., Epigenetic control of the foxp3 locus in regulatory T cells. PLoS Biology 5:e38, 2007.

Francisco et al., PD-L1 regulates the development, maintenance, and function of induced regulatory T cells. J. Exp. Med. 206:3015-3029, 2009.

Fukaya et al., Crucial roles of B7-H1 and B7-DC expressed on mesenteric lymph node dendritic cells in the generation of antigen-specific CD4+Foxp3+ regulatory T cells in the establishment of oral tolerance. Blood 116:2266-2276, 2010.

Gabrysova et al., Integrated T cell receptor and costimulatory signals determine TGF-beta-dependent differentiation and maintenance of Foxp3+ regulatory T cells. Eur. J. Immunol. 41:1242-1248, 2011.

Garrod et al., Targeted lymphoid homing of dendritic cells is required for prolongation of allograft survival. J. Immunol. 177:863-868, 2006.

Gefter et al., U.S. Pat. No. 6,759,234, filed 1994. Compositions and methods for administering to humans, peptides capable of down regulating an antigen specific immune response.

Giannoukakis et al., Phase I (safety) study of autologous tolerogenic dendritic cells in type 1 diabetic patients. Diabetes Care 34:2026-2032, 2011.

Giannoukakis & Trucco, Dendritic cell therapy for Type 1 diabetes suppression. Immunotherapy 4:1063-1074, 2012.

Gordon et al., Regulatory dendritic cells for immunotherapy in immunologic diseases. Frontiers Immunol. 5:7, 2014.

Goronzy et al., Developments in the scientific understanding of rheumatoid arthritis. Arthritis Res Ther. 11:249. 2009.

Gottlieb et al., Chromogranin A is a T cell antigen in human type 1 diabetes. J. Autoimmun 50:38-41. 2014.

Gottlieb et al., Clinical optimization of antigen specific modulation of type 1 diabetes with the plasmid DNA platform. Clin. Immunol. 149:297-306, 2013.

Grinberg-Bleyer et al., IL-2 reverses established type 1 diabetes in NOD mice by a local effect on pancreatic regulatory T cells. J. Exp. Med. 207:1871-1878, 2010.

Guilliams et al., Skin-draining lymph nodes contain dermis-derived CD103(−) dendritic cells that constitutively produce retinoic acid and induce Foxp3(+) regulatory T cells. Blood 115:1958-1968, 2010.

Guleria et al., Mechanisms of PDL1-mediated regulation of autoimmune diabetes. Clin. Immunol. 125:16-25, 2007.

Gurr et al., A Reg family protein is overexpressed in islets from a patient with new-onset type 1 diabetes and acts as T-cell autoantigen in NOD mice. Diabetes. 51:339-346, 2002.

Gurr et al., RegII is a beta-cell protein and autoantigen in diabetes of NOD mice. Diabetes. 56:34-40, 2007.

Hackstein et al., Rapamycin inhibits IL-4—induced dendritic cell maturation in vitro and dendritic cell mobilization and function in vivo. Blood 101:4457-4463, 2003.

Hadeiba et al., CCR9 expression defines tolerogenic plasmacytoid dendritic cells able to suppress acute graft-versus-host disease. Nat. Immunol. 9:1253-1260, 2008.

Hadeiba et al., Plasmacytoid dendritic cells transport peripheral antigens to the thymus to promote central tolerance. Immunity 36:438-450, 2012.

Hanninen et al., Recirculation and homing of lymphocyte subsets: dual homing specificity of beta 7-integrin (high)-lymphocytes in nonobese diabetic mice. Blood 88:934-944, 1996.

Henry et al., Dendritic cells genetically engineered to express IL-10 induce long-lasting antigen-specific tolerance in experimental asthma. J. Immunol. 181:7230-7242, 2008.

Herman et al., CD4+CD25+ T regulatory cells dependent on ICOS promote regulation of effector cells in the prediabetic lesion. J. Exp. Med. 199:1479-1489, 2004.

Hilkens and Isaacs, Tolerogenic dendritic cell therapy for rheumatoid arthritis: where are we now? Clin. Exp. Immunol. 172:148-157, 2013.

Ho et al., An immunomodulatory GpG oligonucleotide for the treatment of autoimmunity via the innate and adaptive immune systems. J. Immunol. 171: 4920-4926, 2003.

Ho et al., A suppressive oligodeoxynucleotide enhances the efficacy of myelin cocktail/IL-4-tolerizing DNA vaccination and treats autoimmune disease. J. Immunol. 175: 6226-6234, 2005.

Huang et al., Plasmacytoid precursor dendritic cells from NOD mice exhibit impaired function: are they a component of diabetes pathogenesis? Diabetes 57:2360-2370, 2008.

Huck et al., Activation and route of administration both determine the ability of bone marrow-derived dendritic cells to accumulate in secondary lymphoid organs and prime CD8+ T cells against tumors. Cancer Immunol. Immunother. 57:63-71, 2008.

Hundorfean et al. Autoimmunity against type VII collagen in inflammatory bowel disease. J. Cell Mol Med. 14:2393-2403, 2010.

Ilarregui et al., Tolerogenic signals delivered by dendritic cells to T cells through a galectin-1-driven immunoregulatory circuit involving interleukin 27 and interleukin 10. Nat. Immunol. 10:981-991, 2009.

Inokuma et al., Autoantibodies against type XVII collagen C-terminal domain in a patient with bullous pemphigoid associated with psoriasis vulgaris. Br. J. Dermatol. 160: 451-454, 2009.

Iversen et al., The autoantigen Pso p27: a post-translational modification of SCCA molecules. Autoimmunity. 44:229-234, 2011.

Ito et al., Plasmacytoid dendritic cells prime IL-10-producing T regulatory cells by inducible costimulator ligand. J. Exp. Med. 204:105-115, 2007.

Jarchum et al., Identification of novel IGRP epitopes targeted in type 1 diabetes patients. Clin Immunol. 127:359-65. 2008.

Jasinski et al., Transgenic insulin (B:923) T-cell receptor mice develop autoimmune diabetes dependent upon RAG genotype, H-2g7 homozygosity, and insulin 2 gene knockout. Diabetes 55:1978-1984, 2006.

Jensen-Jarolim et al., Anti-Galectin-3 IgG autoantibodies in patients with Crohn's disease characterized by means of phage display peptide libraries. J. Clin Immunol. 21:348-356, 2001.

Jiang et al., Disruption of E-cadherin-mediated adhesion induces a functionally distinct pathway of dendritic cell maturation. Immunity 27:610-624, 2007.

Johnson et al., Genetic vaccination for re-establishing T-cell tolerance in type 1 diabetes. Hum. Vaccines 7:27-36, 2011.

Jones et al., Identification of autoantigens in psoriatic plaques using expression cloning. J. Invest. Dermatol. 123:93-100, 2004.

Josefowicz et al., Regulatory T cells: mechanisms of differentiation and function. Annu. Rev. Immunol. 30:531-564, 2012.

Judkowski et al., Identification of MHC class II-restricted peptide ligands, including a glutamic acid decarboxylase 65 sequence, that stimulate diabetogenic T cells from transgenic BDC2.5 nonobese diabetic mice. J. Immunol. 166:908-917, 2001.

Kang et al., De novo induction of antigen-specific CD4+ CD25+Foxp3+ regulatory T cells in vivo following systemic antigen administration accompanied by blockade of mTOR. J. Leukoc. Biol. 83:1230-1239, 2008.

Kleijwegt et al., Tolerogenic dendritic cells impede priming of naive CD8(+) T cells and deplete memory CD8(+) T cells. Eur. J. Immunol. 43:85-92, 2013.

Kleijwegt et al., Transfer of regulatory properties from tolerogenic to proinflammatory dendritic cells via induced autoreactive regulatory T cells. J. Immunol. 187:6357-6364, 2011.

Komorowski et al., Autoantibodies against exocrine pancreas in Crohn's disease are directed against two antigens: the glycoproteins CUZD1 and GP2. J. Crohns Colitis. 7:780-790, 2013.

Kornete et al., ICOS-dependent homeostasis and function of Foxp3+ regulatory T cells in islets of nonobese diabetic mice. J. Immunol. 188:1064-1074, 2012.

Kriegel et al., Pancreatic islet expression of chemokine CCL2 suppresses autoimmune diabetes via tolerogenic CD11c+ CD11b+ dendritic cells. Proc. Natl. Acad. Sci. USA 109:3457-3462, 2012.

Kriegel et al., Naturally transmitted segmented filamentous bacteria segregate with diabetes protection in nonobese diabetic mice. P.N.A.S. USA 108:11548-11553, 2011.

Kristensen et al., B7-H4-Ig treatment of normal mice changes lymphocyte homeostasis and increases the potential of regulatory T cells. Immunopharmacol. Immunotoxicol. 35:505-513, 2013.

Kyte & Gaudernack, Immuno-gene therapy of cancer with tumour-mRNA transfected dendritic cells. Cancer Immunol. Immunother. 55:1432-1442, 2006.

Lande et al., The antimicrobial peptide LL37 is a T-cell autoantigen in psoriasis. Nat Commun. 5:5621, 2014.

Larche and Wraith, Peptide-based therapeutic vaccines for allergic and autoimmune diseases. Nat. Med. 11:S69-76, 2005.

Latchman et al., PD-L2 is a second ligand for PD-1 and inhibits T cell activation. Nat. Immunol. 2:261-268, 2001.

Lernmark et al., Immune therapy in type 1 diabetes mellitus. Nat Rev Endocrinol. 9:92-103. 2013.

Li et al., Identification of autoreactive CD8+ T cell responses targeting chromogranin A in humanized NOD mice and type 1 diabetes patients. Clin Immunol. 159: 63-71. 2015.

Li et al., Isolation and characteristics of autoreactive T cells specific to aggrecan G1 domain from rheumatoid arthritis patients. Cell Res. 10:39-49, 2000.

Lueking et al., Profiling of alopecia areata autoantigens based on protein microarray technology. Mol Cell Proteomics. 4:1382-1390, 2005.

Lukacs-Kornek et al., Self-antigen presentation by dendritic cells and lymphoid stroma and its implications for autoimmunity. Curr Opin Immunol. 23:138-145. 2011.

Lundgren et al., Identification of complement C3 as an autoantigen in inflammatory bowel disease. Eur J. Gastroenterol Hepatol. 22:429-436.

Luo et al., Dendritic cells with TGF-beta1 differentiate naive CD4+CD25− T cells into islet-protective Foxp3+ regulatory T cells. Proc. Natl. Acad. Sci. USA 104:2821-2826, 2007.

Lutz, Therapeutic potential of semi-mature dendritic cells for tolerance induction. Frontiers Immunol. 3:123, 2012.

Macedo et al., Immunoregulatory properties of rapamycin-conditioned monocyte-derived dendritic cells and their role in transplantation. Transplantation Res. 1:16, 2012.

Manicassamy and Pulendran, Dendritic cell control of tolerogenic responses Immunological Rev. 241:206-227, 2011.

Markle et al., Sex differences in the gut microbiome drive hormone-dependent regulation of autoimmunity. Science 339:1084-1088, 2013.

Mascanfroni et al., IL-27 acts on DCs to suppress the T cell response and autoimmunity by inducing expression of the immunoregulatory molecule CD39. Nat. Immunol. 14:1054-1063, 2013.

Mays et al., Modified Foxp3 mRNA protects against asthma through an IL-10-dependent mechanism. J. Clin. Invest. 123:1216-1228, 2013.

McFadden et al., A review on the potential role of basement membrane laminin in the pathogenesis of psoriasis. Scand J. Immunol. 10.1111-12384, 2015.

Michels et al., 2011 Update: antigen-specific therapy in type 1 diabetes. Curr Opin Endocrinol Diabetes Obes. 18:235-240. 2011.

Michiels et al., Electroporation of immature and mature dendritic cells: implications for dendritic cell-based vaccines. Gene Ther. 12:772-782, 2005.

Moreau et al., Tolerogenic dendritic cells and negative vaccination in transplantation: from rodents to clinical trials. Front. Immunol. 3:218, 2012.

Morimoto et al., CXC chemokine ligand 10 neutralization suppresses the occurrence of diabetes in nonobese diabetic mice through enhanced beta cell proliferation without affecting insulitis. J. Immunol. 173:7017-7024, 2004.

Morin et al., Granulocyte-dendritic cell unbalance in the non-obese diabetic mice. Cell. Immunol. 223:13-25, 2003.

Nair et al., "Isolation and Generation of Human Dendritic Cells," Cur. Protoc. Immunol. 99:7.32.1-7.32.23, 2012.

Nakayama et al., Regulatory vs. inflammatory cytokine T-cell responses to mutated insulin peptides in healthy and type 1 diabetic subjects. P.N.A.S. USA 112:4429-4434, 2015.

Nakayama et al., Prime role for an insulin epitope in the development of type 1 diabetes in NOD mice. Nature 435:220-223, 2005.

Nakayama, Insulin as a key autoantigen in the development of type 1 diabetes. Diabetes/Metabolism Res. Rev. 27:773-777, 2011.

Naranjo-Gomez et al., Comparative study of clinical grade human tolerogenic dendritic cells. J. Transl. Med. 9:89, 2011.

Natarajan & Thomson, Tolerogenic dendritic cells and myeloid-derived suppressor cells: potential for regulation and therapy of liver auto- and alloimmunity Immunobiology 215:698-703, 2010.

Nava et al., "An optimized method for manufacturing a clinical scale dendritic cell-based vaccine for the treatment of glioblastoma. PloS ONE 7(12):e52301. Doi10.1371/journal.pone.052301, 2012.

Nayak et al., ZnT8-reactive T cells are weakly pathogenic in NOD mice but can participate in diabetes under inflammatory conditions. Diabetes. 63:3438-3448, 2014.

Nishimoto et al., Th17 cells carrying TCR recognizing epidermal autoantigen induce psoriasis-like skin inflammation. J. Immunol. 191:3065-3072, 2013.

Norian et al., Tumor-infiltrating regulatory dendritic cells inhibit CD8+ T cell function via L-arginine metabolism. Cancer Res. 69:3086-3094, 2009.

Northern Sydney and Central Co., European Patent Application EP-0960119, filed 1997. T cell antigen receptor peptides.

Okada et al., Augmentation of the migratory ability of DCbased vaccine into regional lymph nodes by efficient CCR7 gene transduction. Gene Ther. 12:129-139, 2005.

Palucka and Banchereau, Cancer immunotherapy via dendritic cells. Nat. Rev. Cancer 12:265-277, 2012.

Paronen et al., Glutamate decarboxylase-reactive peripheral blood lymphocytes from patients with IDDM express gutspecific homing receptor alpha4beta7-integrin. Diabetes 46:583-588, 1997.

Peakman et al., Naturally processed and presented epitopes of the islet cell autoantigen IA-2 eluted from HLA-DR4. J. Clin Invest. 104:1449-1457, 1999.

Pedersen et al., Dendritic cells modified by vitamin D: future immunotherapy for autoimmune diseases. Vitamins Hormones 86:63-82, 2011.

Pen et al., Modulation of regulatory T cell function by monocyte-derived dendritic cells matured through electroporation with mRNA encoding CD40 ligand, constitutively active TLR4, and CD70. J. Immunol. 191:1976-1983, 2013.

Peng et al., Dendritic cells transfected with PD-L1 recombinant adenovirus induces T cell suppression and long-term acceptance of allograft transplantation. Cell. Immunol. 271:73-77, 2011.

Penna & Adorini, 1 Alpha,25-dihydroxyvitamin D3 inhibits differentiation, maturation, activation, and survival of dendritic cells leading to impaired alloreactive T cell activation. J. Immunol. 164:2405-2411, 2000.

Perone et al., Dendritic cells expressing transgenic galectin-1 delay onset of autoimmune diabetes in mice. J. Immunol. 177:5278-5289, 2006.

Plaisier et al., Anti-glomerular basement membrane nephritis and bullous pemphigoid caused by distinct anti-alpha 3(IV)NC1 and anti-BP180 antibodies in a patient with Crohn's disease. Am J. Kidney Dis. 40:649-654, 2002.

Podojil et al., B7-H4Ig inhibits mouse and human T-cell function and treats EAE via IL-10/Treg-dependent mechanisms. J. Autoimmun 44:71-81, 2013.

Pop et al., Single cell analysis shows decreasing FoxP3 and TGFbeta1 coexpressing CD4+CD25+ regulatory T cells during autoimmune diabetes. J. Exp. Med. 201:1333-1346, 2005.

Pot et al., Type 1 regulatory T cells (Tr1) in autoimmunity. Sem. Immunology 23:202-208, 2011.

Pujol-Autonell et al., Use of autoantigen-loaded phosphatidylserine-liposomes to arrest autoimmunity in type 1 diabetes. PloS one 10:e0127057, 2015.

Qiao et al., T cell activation threshold regulated by E3 ubiquitin ligase Cbl-b determines fate of inducible regulatory T cells. J. Immunol. 191:632-639, 2013.

Robert et al., Gene therapy to target dendritic cells from blood to lymph nodes. Gene Ther. 10:1479-1486, 2003.

Roep et al., Islet inflammation and CXCL10 in recent-onset type 1 diabetes. Clin. Exp. Immunol. 159:338-343, 2010.

Roep et al., Plasmid-encoded proinsulin preserves C-peptide while specifically reducing proinsulin-specific CD8(+) T cells in type 1 diabetes. Science Translational Med. 5:191-182, 2013.

Roggenbuck et al., Identification of GP2, the major zymogen granule membrane glycoprotein, as the autoantigen of pancreatic antibodies in Crohn's disease. Gut. 58:1620-1628, 2009.

Rondas et al., Citrullinated glucose-regulated protein 78 is an autoantigen in type 1 diabetes. Diabetes. 64:573-586, 2015.

Roozendaal et al., Catalase and alpha-enolase: two novel granulocyte autoantigens in inflammatory bowel disease (IBD). Clin Exp Immunol. 112:10-16, 1998.

Roozendaal et al., Prevalence and clinical significance of anti-lactoferrin autoantibodies in inflammatory bowel diseases and primary sclerosing cholangitis. Adv Exp Med Biol. 443:313-319, 1998.

Rydén et al., Non-antigenic and antigenic interventions in type 1 diabetes. Hum Vaccin Immunother. 10:838-846. 2014.

Sakkas et al., Anti-citrullinated peptides as autoantigens in rheumatoid arthritis-relevance to treatment. Autoimmun Rev. 13:1114-1120, 2014.

Sakiyama et al., Autoantibodies against ubiquitination factor E4A (UBE4A) are associated with severity of Crohn's disease. Inflamm Bowel Dis. 14:310-317, 2008.

Sanderson et al., Expression of endogenous peptide-major histocompatibility complex class II complexes derived from in variant chain-antigen fusion proteins. P.N.A.S. USA 92(16):7217-7221, 1995.

Sasaki et al., Adjuvant formulations and delivery systems for DNA vaccines. Methods. 31:243-254. 2003.

Saxena et al., The counterveiling actions of myeloid and plasmacytoid dendritic cells control autoimmune diabetes in the nonobese diabetic mouse. J. Immunol. 179:5041-5053, 2007.

Shi et al., Carbamylation and antibodies against carbamylated proteins in autoimmunity and other pathologies. Autoimmun Rev. 13:225-230, 2014.

Shurin et al., Genetically modified dendritic cells in cancer immunotherapy: a better tomorrow? Expert Opin. Biol. Ther. 10:1539-1553, 2010.

Skyler et al., Effects of oral insulin in relatives of patients with type 1 diabetes: The Diabetes Prevention Trial—Type 1. Diabetes care 28:1068-1076, 2005.

Solvason et al., Improved efficacy of a tolerizing DNA vaccine for reversal of hyperglycemia through enhancement of gene expression and localization to intracellular sites. J. Immunol. 181:8298-8307, 2008.

Soroosh et al., Lung-resident tissue macrophages generate Foxp3+ regulatory T cells and promote airway tolerance. J. Exp. Med. 2013.

Stadinski et al., Chromogranin A is an autoantigen in type 1 diabetes. Nat. Immunol. 11:225-231, 2010.

Stadinski et al., Diabetogenic T cells recognize insulin bound to IAg7 in an unexpected, weakly binding register. Proc. Natl. Acad. Sci. USA 107:10978-10983, 2010.

Steinbrink et al., Induction of tolerance by IL-10-treated dendritic cells. Journal of immunology 159:4772-4780, 1997.

Takayama et al., Retroviral delivery of viral interleukin-10 into myeloid dendritic cells markedly inhibits their allostimulatory activity and promotes the induction of T-cell hyporesponsiveness. Transplantation 66:1567-1574, 1998.

Tang et al., Central role of defective interleukin-2 production in the triggering of islet autoimmune destruction. Immunity 28:687-697, 2008.

Tarbell et al., CD4(+) T cells from glutamic acid decarboxylase (GAD)65-specific T cell receptor transgenic mice are not diabetogenic and can delay diabetes transfer. J. Exp. Med. 196: 481-492, 2002.

Targan et al., Antibodies to CBir1 flagellin define a unique response that is associated independently with complicated Crohn's disease. Gastroenterology. 128:2020-2028. 2005.

Tatura et al., Quantification of regulatory T cells in septic patients by real-time PCR-based methylation assay and flow cytometry. PloS one 7, e49962, 2012.

Thomas, Dendritic cells and the promise of antigen-specific therapy in rheumatoid arthritis, Arthr. Res. Ther. 15:204, 2013.

Thurner et al., Progranulin antibodies in autoimmune diseases. J. Autoimmun 42:29-38, 2013.

Todd, Etiology of type 1 diabetes. Immunity 32, 457-467, 2010.

Torisu et al., Protective role of interleukin-10-producing regulatory dendritic cells against murine autoimmune gastritis. J. Gastroenterol. 43:100-107, 2008.

Torres-Aguilar et al., IL-10/TGF-beta-treated dendritic cells, pulsed with insulin, specifically reduce the response to insulin of CD4+ effector/memory T cells from type 1 diabetic individuals. J. Clin. Immunol. 30:659-668, 2010.

Turley et al., Endocrine self and gut non-self intersect in the pancreatic lymph nodes. P.N.A.S. USA 102:17729-17733, 2005.

Turner et al., Low TCR signal strength induces combined expansion of Th2 and regulatory T cell populations that protect mice from the development of type 1 diabetes. Diabetologia 57:1428-1436, 2014.

Turner et al., Dominant role of antigen dose in CD4+Foxp3+ regulatory T cell induction and expansion. J. Immunol. 183:4895-4903, 2009.

Ueno et al., Transient upregulation of indoleamine 2,3-dioxygenase in dendritic cells by human chorionic gonadotropin downregulates autoimmune diabetes. Diabetes 56:1686-1693, 2007.

Uniyal et al., Leukocytes utilize both alpha4 and alpha5 integrins for intraislet infiltration in non-obese diabetic mice. J. Autoimmun 12:167-176, 1999.

Uno et al., Expression of chemokines, CXC chemokine ligand 10 (CXCL10) and CXCR3 in the inflamed islets of patients with recent-onset autoimmune type 1 diabetes. Endocrine J. 57:991-996, 2010.

Van Lint et al., mRNA: From a chemical blueprint for protein production to an off-the-shelf therapeutic. Hum. Vaccines Immunother. 9:265-274, 2013.

van Lummel et al., Changing faces, unmasking the beta-cell: post-translational modification of antigens in type 1 diabetes. Curr. Opin. Endocrinol. Diabetes Obesity 20:299-306 (2013).

Van Meirvenne et al., Efficient genetic modification of murine dendritic cells by electroporation with mRNA. Cancer Gene Ther. 9:787-797, 2002.

Van Nuffel et al., Immunotherapy of cancer with dendritic cells loaded with tumor antigens and activated through mRNA electroporation. Meth. Mol. Biol. 629:405-452, 2010.

Vasquez et al., Qualitative and quantitative abnormalities in splenic dendritic cell populations in NOD mice. Clin. Exp. Immunol. 135:209-218, 2004.

Verdaguer et al., Spontaneous autoimmune diabetes in monoclonal T cell nonobese diabetic mice. J. Exp. Med. 186:1663-1676, 1997.

Verhagen et al., Extra-thymically induced T regulatory cell subsets: the optimal target for antigen-specific immunotherapy. Immunol. 145:171-181, 2015.

Verheijden et al., Human cartilage glycoprotein-39 as a candidate autoantigen in rheumatoid arthritis. Arthritis Rheum. 40:1115-1125, 1997.

Vermeulen et al., Identification of a novel autoantigen in inflammatory bowel disease by protein microarray. Inflamm Bowel Dis. 17:1291-1300, 2011.

Wagner et al., Identification of anticitrullinated protein antibody reactivities in a subset of anti-CCP-negative rheumatoid arthritis: association with cigarette smoking and HLA-DRB1 'shared epitope' alleles. Ann. Rheum. Dis. 74:579-586, 2015.

Walker & von Herrath, CD4 T cell differentiation in Type 1 Diabetes. Clin. Exp. Immunol., 2015.

Wang et al., Programmed death 1 ligand signaling regulates the generation of adaptive Foxp3+CD4+ regulatory T cells. Proc. Natl. Acad. Sci. USA 105:9331-9336, 2008.

Wang et al., Early treatment of NOD mice with B7-H4 reduces the incidence of autoimmune diabetes. Diabetes 60:3246-3255, 2011.

Wei et al., Tissue-specific expression of B7x protects from CD4 T cell-mediated autoimmunity. J. Exp. Med. 208:1683-1694, 2011.

Weiss et al., Neuropilin 1 is expressed on thymus-derived natural regulatory T cells, but not mucosa-generated induced Foxp3+ T reg cells. J. Exp. Med. 209:1723-1742, 51721, 2012.

Witsch et al., ICOS and CD28 reversely regulate IL-10 on re-activation of human effector T cells with mature dendritic cells. Eur. J. Immunol. 32:2680-2686, 2002.

Wong et al., Activation of insulin reactive CD8 T-cells for development of autoimmune diabetes. Diabetes 58:1156-1164, 2009.

Yadav et al., Neuropilin-1 distinguishes natural and inducible regulatory T cells among regulatory T cell subsets in vivo. J. Exp. Med. 209:1713-1722, S1711-1719, 2012.

Yang et al., A predominant role of integrin alpha 4 in the spontaneous development of autoimmune diabetes in nonobese diabetic mice. Proc. Natl. Acad. Sci. USA 91:12604-12608, 1994.

Yip, et al., Deaf1 isoforms control the expression of genes encoding peripheral tissue antigens in the pancreatic lymph nodes during type 1 diabetes. Nat. Immunol. 10:1026-1033, 2009.

You et al., Detection and characterization of T cells specific for BDC2.5 T cell-stimulating peptides. J. Immunol. 170:4011-4020, 2003.

Zhao et al., Tolerogenic dendritic cells and rheumatoid arthritis: current status and perspectives. Rheumatol. Intl. 32:837-844, 2012.

Zheng et al., A noncytolytic IL-10/Fc fusion protein prevents diabetes, blocks autoimmunity, and promotes suppressor phenomena in NOD mice. J. Immunol. 158:4507-4513, 1997.

Zhu et al., IL-10 gene modified dendritic cells inhibit T helper type 1-mediated alloimmune responses and promote immunological tolerance in diabetes. Cell. Mol. Immunol. 5:41-46, 2008.

Ziegler and Nepom, Prediction and pathogenesis in type 1 diabetes. Immunity 32:468-478, 2010.

What is claimed is:

1. An isolated nucleic acid construct that encodes a polypeptide wherein the polypeptide comprises:
    (a) a first peptide sequence comprising a major histocompatibility complex (MHC) class II targeting sequence and one or more different epitope sequences that are processed in endosomes for presentation to CD4+ T cells, wherein the MHC class II targeting sequence is operably linked to the one or more different epitope sequences intended for processing in endosomes;

(b) a second peptide sequence comprising one or more different epitope sequences that are processed by cytoplasmic proteasomes for presentation to CD8+ T cells; and (c) a peptide cytosolic protease cleavage site located between the first and second sequences, wherein the cleavage site is recognized and cleaved by a cytosolic protease.

2. The nucleic acid construct of claim 1, wherein the polypeptide further comprises:
(a) one or more endosomal proteolytic cleavage sites flanking the one or more epitope sequences of the first sequence;
(b) one or more cytoplasmic proteolytic cleavage sites flanking the one or more epitope sequences of the second sequence; or
(c) both (a) and (b).

3. The nucleic acid construct of claim 2, wherein the one or more endosomal proteolytic cleavage sites are naturally occurring.

4. The nucleic acid construct of claim 1, which is DNA.

5. The nucleic acid construct of claim 1, which is mRNA.

6. The nucleic acid construct of claim 1, wherein the sequences are in the order, from 5' to 3':
(a) the first sequence;
(b) the cytosolic protease cleavage site; and
(c) the second sequence.

7. The nucleic acid construct of claim 1, wherein the cytosolic protease cleavage site is selected from the group consisting of a T2A cleavage site, a P2A cleavage site, an E2A cleavage site, and an F2A cleavage site.

8. The nucleic acid construct of claim 1, wherein the MHC class II targeting sequence is selected from the group consisting of an upstream transferrin receptor domain; an upstream invariant chain domain; an upstream invariant chain domain; an upstream CD16 domain 1-23 and a downstream LAMP-1 domain; a downstream LIMP-2 domain; downstream a CD1a-d cytoplasmic tail; and a downstream PMEL domain.

9. The nucleic acid construct of claim 1, wherein at least one epitope in the first sequence or the second sequence is from a self antigen.

10. The nucleic acid construct of claim 9, wherein the self antigen is recognized in an autoimmune disease condition.

11. The nucleic acid construct of claim 10, wherein the autoimmune disease condition is selected from the group consisting of type 1 diabetes, rheumatoid arthritis, multiple sclerosis, psoriasis, Crohn's disease and ulcerative colitis.

12. The nucleic acid construct of claim 1, wherein at least one epitope in the first sequence or the second sequences is from a non-self antigen.

13. The nucleic acid construct of claim 1, wherein at least one of the epitopes in the first sequence, the second sequence or both is a mimotope.

14. The nucleic acid construct of claim 1, which is codon-optimized.

15. An isolated nucleic acid construct that encodes a polypeptide wherein the polypeptide comprises:
(a) a first peptide sequence comprising an MHC class II targeting sequence and one or more different epitope sequences that are processed in endosomes for presentation to CD4+ T cells, wherein the MHC class II targeting sequence is operably linked to the one or more different epitope sequences intended for processing in endosomes;
(b) a second peptide sequence comprising one or more different epitope sequences that are processed by cytoplasmic proteasomes for presentation to CD8+ T cells;
(c) a third peptide sequence comprising a MHC class II expression activator sequence; and
(d) an additional sequence comprising a first cytosolic protease cleavage site located between the first and second sequences and a second additional sequence comprising a second cytosolic protease cleavage site located between the third sequence and either the first sequence or the second sequence.

16. The nucleic acid construct of claim 15, wherein the nucleic acid construct further comprises at least one polycationic molecule complexed therewith.

17. The nucleic acid construct of claim 16, wherein the polycationic molecule is a positively charged cell-penetrating peptide (CPP).

18. The nucleic acid construct of claim 17, wherein the CPP is polylysine, polyarginine or Tat peptide.

19. The nucleic acid construct of claim 16, wherein the polycationic molecule is a polycationic polymer.

20. The nucleic acid construct of claim 19, wherein the polycationic polymer is polyethylenimine.

21. The nucleic acid construct of claim 15, wherein the MHC class II expression activator is a Class II TransActivator (CIITA) sequence.

22. The nucleic acid construct of claim 15, wherein the nucleic acid construct is a minicircle DNA.

23. The nucleic acid construct of claim 15, wherein the third sequence is located upstream or downstream of the first and second sequences, or in between the first and second sequences with the first and second cytosolic protease cleavage site on either side of the third sequence.

24. The nucleic acid construct of claim 15, wherein one or more of the cytosolic protease cleavage sites, are selected from the group consisting of a T2A cleavage site, a P2A cleavage site, an E2A cleavage site, and an F2A cleavage site.

25. The nucleic acid construct of claim 15, wherein at least one epitope in the first sequence or the second sequence of claim 15 is from a self antigen.

26. The nucleic acid construct of claim 25, wherein the self antigen is recognized by autoreactive T cells in an autoimmune disease condition.

27. The nucleic acid construct of claim 26, wherein the autoimmune disease condition is selected from the group consisting of type 1 diabetes, rheumatoid arthritis, multiple sclerosis, lupus, psoriasis, Crohn's disease and ulcerative colitis.

28. The nucleic acid construct of claim 15, wherein at least one of the epitopes in the first sequence, the second sequence or both of claim 15 is a mimotope.

29. The nucleic acid construct of claim 15, which is codon-optimized.

* * * * *

UNITED STATES PATENT AND TRADEMARK OFFICE
CERTIFICATE OF CORRECTION

PATENT NO. : 10,238,741 B2
APPLICATION NO. : 15/483889
DATED : March 26, 2019
INVENTOR(S) : Creusot It is certified that error appears in the above-identified patent and that said Letters Patent is hereby corrected as shown below:

In the Specification

Column 1, Line 22: after DK063608 add --and AI110812--

Signed and Sealed this
Fourteenth Day of November, 2023

Katherine Kelly Vidal
*Director of the United States Patent and Trademark Office*